US012672972B2

(12) United States Patent
Gurovich et al.

(10) Patent No.: US 12,672,972 B2
(45) Date of Patent: Jul. 7, 2026

(54) DOCKING STATION FOR PROSTHETIC IMPLANT

(71) Applicant: EDWARDS LIFESCIENCES CORPORATION, Irvine, CA (US)

(72) Inventors: Nikolai Gurovich, Hadera (IL); Boaz Manash, Givat Ada (IL); Adi Carmi, Ganei Tikva (IL); Eran Goldberg, Nesher (IL); Khen Perlmutter, Binyamina (IL)

(73) Assignee: Edwards Lifesciences Corporation, Irvine, CA (US)

( * ) Notice: Subject to any disclaimer, the term of this patent is extended or adjusted under 35 U.S.C. 154(b) by 610 days.

(21) Appl. No.: 18/171,187

(22) Filed: Feb. 17, 2023

(65) Prior Publication Data

US 2023/0201015 A1     Jun. 29, 2023

Related U.S. Application Data

(63) Continuation of application No. PCT/US2021/046207, filed on Aug. 17, 2021.

(Continued)

(51) Int. Cl.
*A61F 2/24*          (2006.01)
*A61F 2/95*          (2013.01)

(52) U.S. Cl.
CPC .......... *A61F 2/9522* (2020.05); *A61F 2/2418* (2013.01)

(58) Field of Classification Search
CPC ........ A61F 2/24; A61F 2/2418; A61F 2/2427; A61F 2/243; A61F 2/2433; A61F 2/2436;

(Continued)

(56) References Cited

U.S. PATENT DOCUMENTS 519,297 A      5/1894   Bauer
4,035,849 A    7/1977   Angell et al.
               (Continued)

FOREIGN PATENT DOCUMENTS

DE      19532846 A1    3/1997
DE      19907646 A1    8/2000
        (Continued)

OTHER PUBLICATIONS

Walther, et al., "Trans-catheter valve-in-valve implantation: in vitro hydrodynamic performance of the Sapien + cloth trans-catheter heart valve in the Carpentier-Edwards Perimount valves," European Journal of Cardio-thoracic Surgery, 40 (2011) 1120-1126, Sep. 23, 2010.

*Primary Examiner* — Seema Mathew
(74) *Attorney, Agent, or Firm* — Klarquist Sparkman LLP

(57)          ABSTRACT

A docking station for a prosthetic heart valve includes a radially expandable and collapsible frame with a first plurality of struts, an inflow end portion, an outflow end portion, and a longitudinal axis. A sealing member is disposed on the outflow end portion and configured to form a seal between the docking station and a body lumen. The docking station further includes a valve seat coupled to the frame and configured to receive an expandable prosthetic valve. The valve seat includes a second plurality of struts coupled to the frame and extending in a downstream direction and angled inwardly toward the longitudinal axis of the frame.

21 Claims, 61 Drawing Sheets

Related U.S. Application Data

(60) Provisional application No. 63/073,643, filed on Sep. 2, 2020, provisional application No. 63/066,688, filed on Aug. 17, 2020.

(58) Field of Classification Search
CPC .......... A61F 2/90; A61F 2/9522; A61F 2/966; A61F 2002/9505; A61F 2002/9511; A61F 2002/9534; A61F 2002/9665; A61F 2/82
See application file for complete search history.

(56) References Cited

U.S. PATENT DOCUMENTS

| | | | |
|---|---|---|---|
| 4,592,340 A | 6/1986 | Boyles | |
| 4,790,843 A | 12/1988 | Carpentier et al. | |
| 4,955,895 A | 9/1990 | Sugiyama et al. | |
| 4,994,077 A | 2/1991 | Dobben | |
| 5,059,177 A | 10/1991 | Towne et al. | |
| 5,176,698 A | 1/1993 | Burns et al. | |
| 5,192,297 A | 3/1993 | Hull | |
| 5,266,073 A | 11/1993 | Wall | |
| 5,325,845 A | 7/1994 | Adair | |
| 5,358,496 A | 10/1994 | Ortiz et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,419,696 B1 | 7/2002 | Ortiz et al. | |
| 6,425,916 B1 | 7/2002 | Garrison et al. | |
| 6,432,134 B1 | 8/2002 | Anson et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,797,002 B2 | 9/2004 | Spence et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,445,632 B2 | 11/2008 | McGuckin, Jr. et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,637,946 B2 | 12/2009 | Solem et al. | |
| 7,708,775 B2 | 5/2010 | Rowe et al. | |
| 7,737,060 B2 | 6/2010 | Strickler et al. | |
| 7,780,723 B2 | 8/2010 | Taylor | |
| 7,785,366 B2 | 8/2010 | Maurer et al. | |
| 7,951,195 B2 | 5/2011 | Antonsson et al. | |
| 7,959,661 B2 | 6/2011 | Hijlkema et al. | |
| 8,029,556 B2 | 10/2011 | Rowe | |
| 8,142,492 B2 | 3/2012 | Forster et al. | |
| 8,167,932 B2 | 5/2012 | Bourang et al. | |
| 8,236,049 B2 | 8/2012 | Rowe et al. | |
| RE43,882 E | 12/2012 | Hopkins et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,605 B2 | 5/2013 | Lichtenstein et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,685,086 B2 | 4/2014 | Navia et al. | |
| 8,734,507 B2 | 5/2014 | Keranen | |
| 8,801,776 B2 | 8/2014 | House et al. | |
| 9,061,119 B2 | 6/2015 | Le et al. | |
| 9,078,747 B2 | 7/2015 | Conklin | |
| 9,095,434 B2 | 8/2015 | Rowe | |
| 9,119,716 B2 | 9/2015 | Lee et al. | |
| 9,119,718 B2 | 9/2015 | Keranen | |
| 9,192,471 B2 | 11/2015 | Bolling | |
| 9,237,886 B2 | 1/2016 | Seguin et al. | |
| 9,314,335 B2 | 4/2016 | Konno | |
| 9,364,326 B2 | 6/2016 | Yaron | |
| 9,463,268 B2 | 10/2016 | Spence | |
| 9,474,599 B2 | 10/2016 | Keranen | |
| 9,526,572 B2 | 12/2016 | Kunis | |
| 9,597,205 B2 | 3/2017 | Tuval | |
| 9,622,863 B2 | 4/2017 | Karapetian et al. | |
| 9,795,477 B2 | 10/2017 | Tran et al. | |
| 10,413,401 B2* | 9/2019 | Eberhardt | A61F 2/2409 |
| 11,045,313 B2* | 6/2021 | Ratz | A61F 2/2445 |
| 11,273,038 B2 | 3/2022 | Tang et al. | |
| 12,285,331 B2* | 4/2025 | Johnson | A61F 2/2415 |
| 12,318,290 B2* | 6/2025 | Quadri | A61F 2/2436 |
| 12,376,960 B2* | 8/2025 | Agreli | A61F 2/90 |
| 12,539,209 B2* | 2/2026 | Noe | A61F 2/2418 |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0107535 A1 | 8/2002 | Wei et al. | |
| 2002/0151970 A1 | 10/2002 | Garrison et al. | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2003/0225420 A1 | 12/2003 | Wardle | |
| 2004/0093061 A1 | 5/2004 | Acosta et al. | |
| 2004/0111006 A1 | 6/2004 | Alferness et al. | |

(56)                References Cited

U.S. PATENT DOCUMENTS

| | | |
|---|---|---|
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137689 A1 | 6/2005 | Salahieh et al. |
| 2005/0137691 A1 | 6/2005 | Salahieh et al. |
| 2005/0149160 A1 | 7/2005 | McFerran |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0195134 A1 | 8/2006 | Crittenden |
| 2006/0271172 A1 | 11/2006 | Tehrani |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2007/0293808 A1 | 12/2007 | Williams et al. |
| 2008/0033542 A1 | 2/2008 | Antonsson et al. |
| 2008/0065011 A1 | 3/2008 | Marchand et al. |
| 2008/0077235 A1 | 3/2008 | Kirson |
| 2008/0103520 A1 | 5/2008 | Selkee |
| 2008/0125853 A1 | 5/2008 | Bailey et al. |
| 2008/0208330 A1 | 8/2008 | Keranen |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0192601 A1 | 7/2009 | Rafiee et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0036484 A1 | 2/2010 | Hariton et al. |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0145440 A1 | 6/2010 | Keranen |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0312333 A1 | 12/2010 | Navia et al. |
| 2010/0318184 A1 | 12/2010 | Spence |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0059458 A1 | 3/2012 | Buchbinder et al. |
| 2012/0078347 A1 * | 3/2012 | Braido ................... A61F 2/915 |
| | | 623/1.26 |
| 2012/0123529 A1 | 5/2012 | Levi et al. |
| 2012/0239142 A1 | 9/2012 | Liu et al. |
| 2012/0283820 A1 | 11/2012 | Tseng et al. |
| 2013/0023984 A1 * | 1/2013 | Conklin ................ A61F 2/2418 |
| | | 623/2.14 |
| 2013/0030519 A1 | 1/2013 | Tran et al. |
| 2013/0190865 A1 | 7/2013 | Anderson |
| 2013/0204311 A1 | 8/2013 | Kunis |
| 2013/0317598 A1 | 11/2013 | Rowe et al. |
| 2014/0074299 A1 | 3/2014 | Endou et al. |
| 2014/0081394 A1 | 3/2014 | Keranen et al. |
| 2014/0163669 A1 | 6/2014 | Ben-Zvi et al. |
| 2014/0172070 A1 | 6/2014 | Seguin |
| 2014/0296962 A1 | 10/2014 | Cartledge et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0157455 A1 * | 6/2015 | Hoang .................. A61F 2/2418 |
| | | 264/269 |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0351904 A1 * | 12/2015 | Cooper ................. A61F 2/2418 |
| | | 623/2.1 |
| 2015/0374493 A1 | 12/2015 | Yaron et al. |
| 2016/0015514 A1 | 1/2016 | Lashinski et al. |
| 2016/0038281 A1 * | 2/2016 | Delaloye .............. A61F 2/2412 |
| | | 623/2.18 |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0065415 A1 | 3/2017 | Rupp et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2017/0325945 A1 * | 11/2017 | Dale ...................... A61F 2/2412 |
| 2017/0360426 A1 | 12/2017 | Hacohen et al. |
| 2018/0000580 A1 | 1/2018 | Wallace et al. |
| 2018/0085217 A1 | 3/2018 | Lashinski et al. |
| 2018/0153689 A1 | 6/2018 | Maimon et al. |
| 2018/0206074 A1 | 7/2018 | Tanasa et al. |
| 2018/0221143 A1 * | 8/2018 | Ratz ...................... A61F 2/2409 |
| 2018/0250130 A1 * | 9/2018 | Hariton ................. A61F 2/2418 |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2018/0344456 A1 | 12/2018 | Barash et al. |
| 2019/0000615 A1 * | 1/2019 | Tayeb .................. A61F 2/9522 |
| 2019/0142588 A1 * | 5/2019 | Kovalsky ............. A61F 2/2445 |
| | | 623/2.38 |

FOREIGN PATENT DOCUMENTS

| | | |
|---|---|---|
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |

(56)  References Cited

FOREIGN PATENT DOCUMENTS

| | | | |
|---|---|---|---|
| WO | 0154625 | A1 | 8/2001 |
| WO | 0176510 | A2 | 10/2001 |
| WO | 0222054 | | 3/2002 |
| WO | 0236048 | A1 | 5/2002 |
| WO | 0247575 | A2 | 6/2002 |
| WO | 02060352 | | 8/2002 |
| WO | 03028558 | A2 | 4/2003 |
| WO | 03030776 | A2 | 4/2003 |
| WO | 03047468 | | 6/2003 |
| WO | 2004019825 | A1 | 3/2004 |
| WO | 2005084595 | A1 | 9/2005 |
| WO | 2005102015 | A2 | 11/2005 |
| WO | 2006011127 | A2 | 2/2006 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2009155561 | A2 | 12/2009 |
| WO | 2010121076 | A2 | 10/2010 |
| WO | 2012063228 | A1 | 5/2012 |
| WO | 2013110722 | A2 | 8/2013 |
| WO | 2013114214 | A2 | 8/2013 |
| WO | 2015023579 | A1 | 2/2015 |
| WO | 2015023862 | A2 | 2/2015 |
| WO | 2015127264 | A1 | 8/2015 |
| WO | 2015198125 | A1 | 12/2015 |
| WO | 2016038017 | A1 | 3/2016 |
| WO | 2016040881 | A1 | 3/2016 |
| WO | 2016130820 | A1 | 8/2016 |
| WO | 2017103833 | A1 | 6/2017 |

* cited by examiner

SEE FIG. 5A

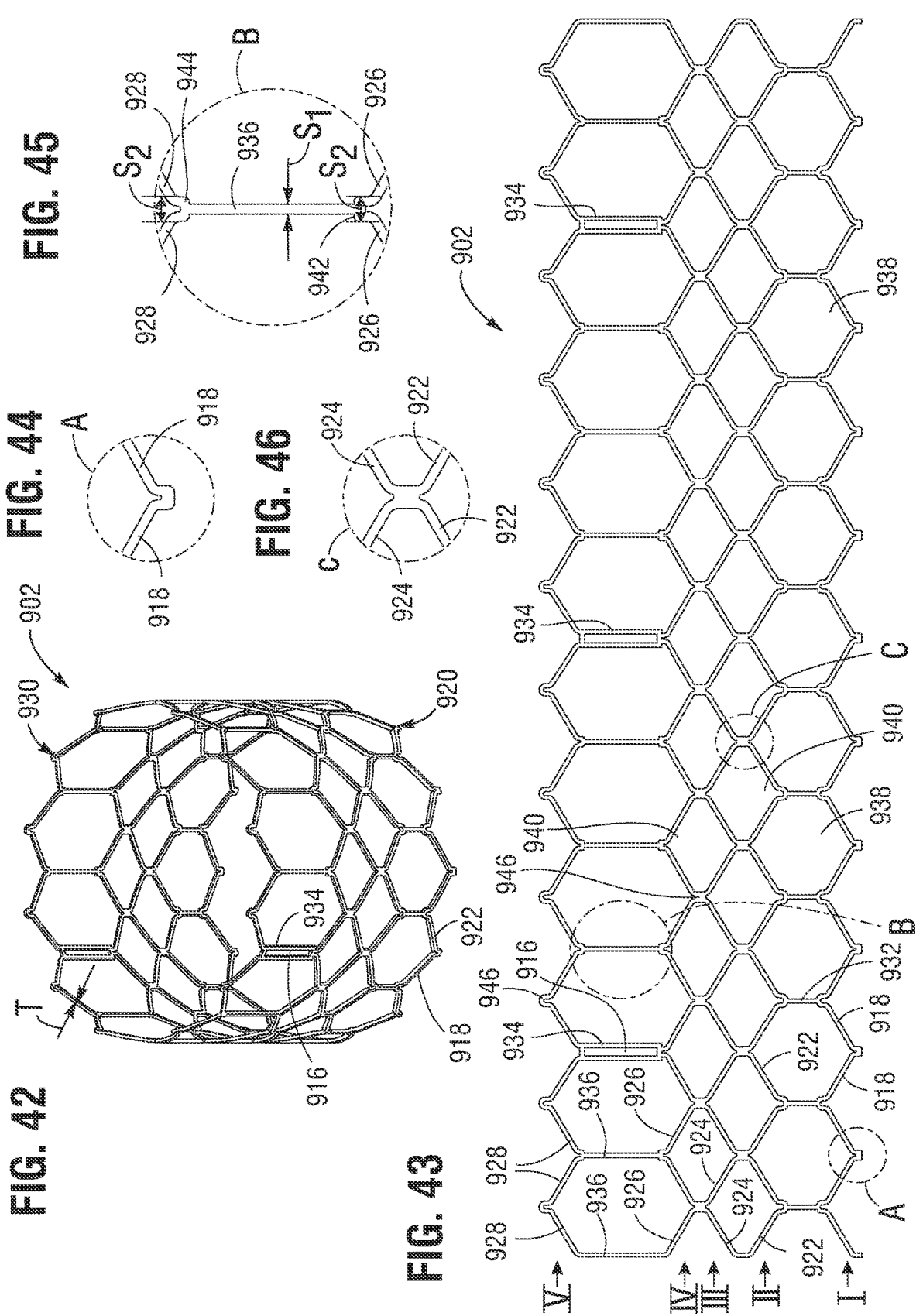

406    402

420

456

462

61

450

404

408

410          410

420

456          457

459          462

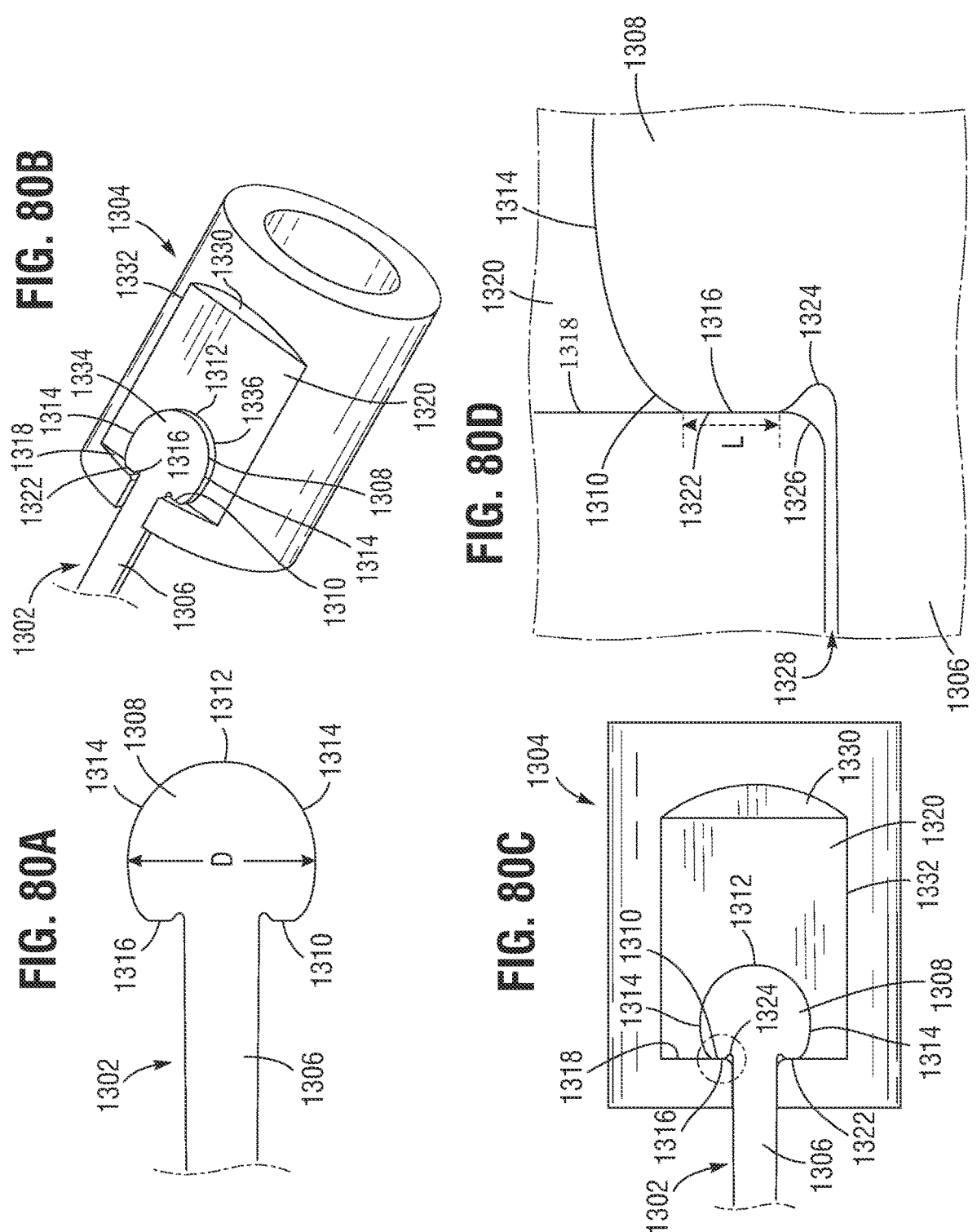

DOCKING STATION FOR PROSTHETIC IMPLANT

CROSS-REFERENCE TO RELATED APPLICATIONS

The present application is a continuation of International Patent Application No. PCT/US2021/046207, filed Aug. 17, 2021, which application claims the benefit of U.S. Provisional Application No. 63/073,643, filed Sep. 2, 2020, and claims the benefit of U.S. Provisional Application No. 63/066,688, filed Aug. 17, 2020. Each of International Patent Application No. PCT/US2021/046207, U.S. Provisional Application No. 63/073,643, and U.S. Provisional Application No. 63/066,688 is incorporated herein by reference in its entirety.

FIELD

The present disclosure relates to implantable adaptor systems for engaging and retaining a prosthetic implant such as a prosthetic heart valve in a lumen of the body, such as a blood vessel or valve of the heart, which has a diameter greater than the functional diameter of the prosthetic heart valve.

BACKGROUND

Prosthetic heart valves can be used to treat cardiac valvular disorders. The native heart valves (the aortic, pulmonary, tricuspid and mitral valves) function to prevent backward flow or regurgitation, while allowing forward flow. These heart valves can be rendered less effective by congenital, inflammatory, infectious conditions, etc. Such conditions can eventually lead to serious cardiovascular compromise or death. For many years, doctors attempted to treat such disorders with surgical repair or replacement of the valve during open heart surgery.

A transcatheter technique for introducing and implanting a prosthetic heart valve using a catheter in a manner that is less invasive than open heart surgery can reduce complications associated with open heart surgery. In this technique, a prosthetic valve can be mounted in a crimped state on the end portion of a catheter and advanced through a blood vessel of the patient until the valve reaches the implantation site. The valve at the catheter tip can then be expanded to its functional size at the site of the defective native valve, such as by inflating a balloon on which the valve is mounted or, for example, the valve can have a resilient, self-expanding stent or frame that expands the valve to its functional size when it is advanced from a delivery sheath at the distal end of the catheter. Optionally, the valve can have a balloon-expandable frame, self-expanding frame, a mechanically-expandable frame, and/or a frame expandable in multiple or a combination of ways.

Transcatheter heart valves (THVs) may be appropriately sized for placement inside many native cardiac valves or orifices. However, with larger native valves, blood vessels (e.g., an enlarged aorta), grafts, etc., aortic transcatheter valves might be too small to secure into the larger implantation or deployment site. In this case, the transcatheter valve may not be large enough to sufficiently expand inside the native valve or other implantation or deployment site or the implantation/deployment site may not provide a good seat for the THV to be secured in place. As one example, aortic insufficiency can be associated with difficulty securely implanting a THV in the aorta and/or aortic valve. Accordingly, there exists a need for improved systems and methods of securing a THV in a relatively large diameter blood vessel or annulus.

SUMMARY

Certain embodiments of the disclosure pertain to docking stations, frame adaptors, presents, and the like for engaging and retaining a prosthetic implant such as a prosthetic heart valve in a lumen of the body, such as a blood vessel or valve of the heart. In a representative embodiment, a docking station comprises a radially expandable and collapsible frame comprising a first plurality of struts, the frame comprising an inflow end portion and an outflow end portion, and defining a longitudinal axis, a sealing member disposed on the outflow end portion and configured to form a seal between the docking station and a body lumen, and a valve seat coupled to the frame and configured to receive an expandable prosthetic valve, the valve seat comprising a second plurality of struts coupled to the frame extending in a downstream direction and angled inwardly toward the longitudinal axis of the frame.

In another representative embodiment, method comprises advancing the docking station of any of the disclosed embodiments to a treatment site in a radially collapsed state, expanding the docking station to anchor the docking station at the treatment site, and deploying a prosthetic valve in the valve seat of the docking station such that the prosthetic valve regulates blood flow through the docking station.

In another representative embodiment, a system comprises a delivery apparatus comprising a first shaft comprising a delivery capsule at a distal end portion of the first shaft. The system further comprises a second shaft disposed within the first shaft and comprising a retaining member at a distal end portion of the second shaft, and the docking station of any of the disclosed embodiments disposed within the delivery capsule and coupled to the retaining member.

In another representative embodiment, a docking station for a prosthetic valve comprises a radially expandable and collapsible frame comprising a plurality of struts, the frame comprising an inflow end portion and an outflow end portion and defining a longitudinal axis, and a valve seat coupled to the frame and configured to receive an expandable prosthetic valve. The valve seat is at least partially defined by a plurality of valve seat struts coupled to the frame at frame junctions and comprising free end portions, the valve seat struts being angled radially inwardly from the frame of the docking station toward the longitudinal axis such that the free end portions are offset from the frame junctions in a downstream direction along the longitudinal axis.

In another representative embodiment, a docking station for a prosthetic valve comprises a radially expandable and collapsible frame comprising a plurality of longitudinally-extending first struts circumferentially arranged about a longitudinal axis of the frame and extending between an inflow end portion and an outflow end portion of the frame, a plurality of angled second struts extending between adjacent first struts, and a valve seat coupled to the frame and configured to receive an expandable prosthetic valve.

In another representative embodiment, a docking station for a prosthetic valve comprises a radially expandable and collapsible frame comprising a plurality of struts, the frame comprising an inflow end portion and an outflow end portion, and defining a longitudinal axis, a sealing member disposed on the outflow end portion and configured to form a seal between the docking station and a body lumen, and a valve seat coupled to the frame and configured to receive an expandable prosthetic valve, wherein the struts of the frame define a plurality of free apices offset circumferentially from each other around a circumference of the frame and configured to resist movement of the docking station within a body lumen.

In another representative embodiment, a docking station for a prosthetic valve comprises a radially expandable and collapsible frame comprising a plurality of struts, the frame comprising an inflow end portion and an outflow end portion and defining a longitudinal axis, a sealing member disposed on the outflow end portion and configured to form a seal between the docking station and a body lumen, and a valve seat within the frame and configured to receive an expandable prosthetic valve, the valve seat comprising an inflow end portion coupled to the frame and a free outflow end portion, the free outflow end portion being downstream of the inflow end portion of the valve seat and upstream of the outflow end of the frame of the docking station.

In another representative embodiment, a docking station for a prosthetic valve comprises a radially expandable and collapsible frame comprising a first plurality of struts, the frame comprising an inflow end portion and an outflow end portion, the outflow end portion of the frame comprising a plurality of supports defined by struts of the first plurality of struts, the frame defining a longitudinal axis. The docking station further comprises a sealing member disposed on the outflow end portion and configured to form a seal between the docking station and a body lumen, the sealing member being engaged by the plurality of supports of the outflow end of the frame, and a valve seat within the frame and configured to receive an expandable prosthetic valve, the valve seat comprising a second plurality of struts coupled to the frame and defining a plurality of supports, wherein the outflow end portion of the frame comprises more supports than the valve seat.

In another representative embodiment, a docking station for a prosthetic valve comprises a radially expandable and collapsible frame comprising a plurality of struts, the frame comprising an inflow end portion and an outflow end portion, and defining a longitudinal axis, a sealing member disposed on the outflow end portion and configured to form a seal between the docking station and a body lumen, and a valve seat coupled to the frame and configured to receive an expandable prosthetic valve, wherein at least an outflow edge of the sealing member is disposed at an angle to the longitudinal axis of the frame to align with an outlet of the body lumen.

In another representative embodiment, a docking station for a prosthetic valve comprises a radially expandable and collapsible frame comprising a plurality of longitudinal struts extending between an inflow end portion and an outflow end portion of the frame, the frame further comprising a plurality of angled struts arranged circumferentially to form a plurality of cylindrical, spaced apart frame portions interconnected by the longitudinal struts, and a valve seat at the outflow end portion of the frame.

In another representative embodiment, a sealing member comprises a first tubular portion which tapers along a longitudinal axis from a first diameter to a second diameter less than the first diameter, a second tubular portion coupled to the first tubular portion and comprising the second diameter, and a third tubular portion coupled to the second tubular portion such that the second tubular portion is between the first tubular portion and the third tubular portion, the third tubular portion having a diameter which increases from the second diameter toward the first diameter in a direction along the longitudinal axis.

In another representative embodiment, a docking station comprises a radially expandable and collapsible frame comprising a first plurality of struts, the frame comprising an inflow end portion and an outflow end portion, and defining a longitudinal axis, a sealing member disposed on the outflow end portion and configured to form a seal between the docking station and a body lumen, and a valve seat within the frame and configured to receive an expandable prosthetic valve, the valve seat comprising a second plurality of struts coupled to the frame and angled inwardly toward the longitudinal axis of the frame.

The foregoing and other objects, features, and advantages of the described technology will become more apparent from the following detailed description, which proceeds with reference to the accompanying figures.

BRIEF DESCRIPTION OF THE DRAWINGS

FIGS. 42-46 illustrate an exemplary frame of the prosthetic heart valve of FIG. 39.

FIGS. 80A-80D illustrate another embodiment of a coupling member of a frame and its engagement with a retaining member of a delivery assembly.

DETAILED DESCRIPTION

Explanation of Terms

Figure 1A:
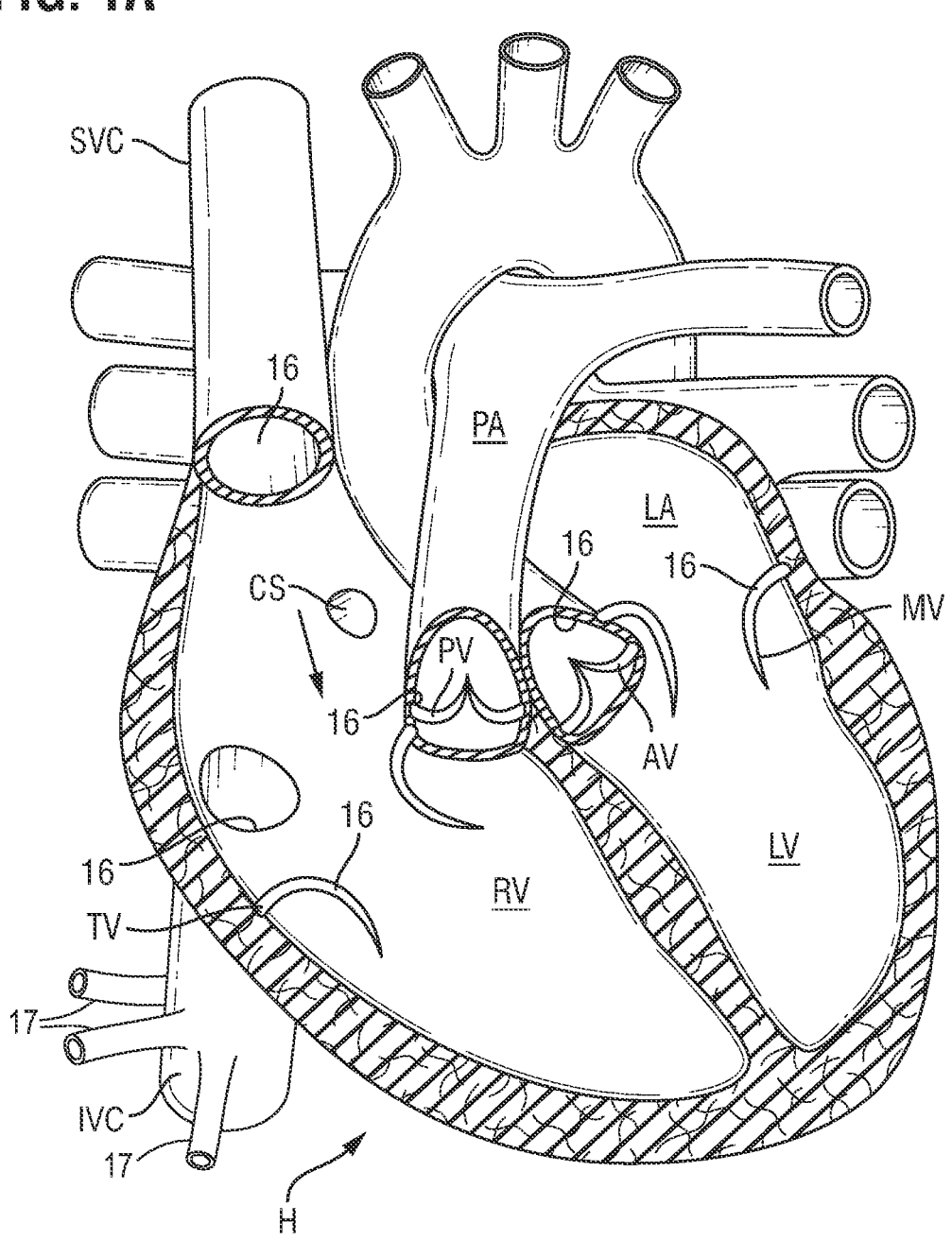
FIG. 1A is a cutaway view of the human heart in a diastolic phase.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

It should be understood that the disclosed embodiments can be adapted for delivery and implantation in any of the native annuluses and blood vessels of the heart (e.g., the pulmonary, mitral, and tricuspid annuluses, the inferior and superior vena cava, etc.), and can be used with any of various delivery approaches (e.g., retrograde, antegrade, transseptal, transventricular, transatrial, etc.).

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, the sealing member 436 shown in FIGS. 62-66B can be used in combination with any of the docking station embodiments disclosed herein.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language. As used herein, the term "and/or" used between the last two of a list of elements means any one or more of the listed elements. For example, the phrase "A, B, and/or C" means "A", "B,", "C", "A and B", "A and C", "B and C", or "A, B, and C."

In the context of the present application, the terms "lower" and "upper" are used interchangeably with the terms "inflow" and "outflow", respectively. Thus, for example, typically the lower end of a valve or docking station as depicted in the figures is its inflow end and the upper end of the valve or docking station is its outflow end.

As used herein, the term "proximal" refers to a position, direction, or portion of a device that is closer to the user and further away from the implantation site and/or body lumen orifice. As used herein, the term "distal" refers to a position, direction, or portion of a device that is further away from the user and closer to the implantation site and/or body lumen orifice. Thus, for example, proximal motion of a device is motion of the device toward the user, while distal motion of the device is motion of the device away from the user.

The terms "longitudinal" and "axial" refer to an axis extending in the upstream and downstream directions, or in the proximal and distal directions, unless otherwise expressly defined.

Although there are alternatives for various components, features, parameters, operating conditions, etc., set forth herein, that does not mean that those alternatives are necessarily equivalent and/or perform equally well. Nor does it mean that the alternatives are listed in a preferred order unless stated otherwise.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

As used herein, the terms "integrally formed" and "unitary construction" refer to a construction that does not require any sutures, fasteners, or other securing means to attach two portions of the construction together.

Examples of Disclosed Technology

The present disclosure pertains to valve adapter/docking station/landing zone/prestent technology for implanting a prosthetic heart valve, such as a transcatheter heart valve, in a lumen or valve of the heart where the diameter of the lumen or valve is significantly greater than the functional diameter of the prosthetic valve. In certain examples, the docking station can comprise a radially expandable and collapsible frame formed from a plurality of struts, and including a valve seat within the frame configured to receive an expandable prosthetic valve. In certain embodiments, the valve seat can comprise a plurality of struts coupled to the frame and angled inwardly toward the longitudinal axis of the frame. The valve seat can be configured to engage and retain prosthetic valves of a variety of types and sizes. The outer aspect of the docking station frame can engage the surrounding tissue of the native lumen and form a seal, and the valve seat can engage and retain the prosthetic heart valve within the docking station. In certain embodiments, the frame can comprise a sealing member configured to form a seal between the frame and the surrounding anatomy without substantially interfering with blood flow entering the upstream portions of the frame, such as adjacent the ostia of the hepatic veins when implanted in the inferior vena cava.

In certain embodiments, the struts of the valve seat can form valve seat frame cells of the frame. In certain embodiments, struts and/or cells of the valve seat can comprise free end portions/apices, which can be disposed within the lumen of the docking station frame and define a reduced diameter portion configured to engage and retain a prosthetic heart valve. In certain embodiments, the struts of the valve seat can be coupled to the docking station frame at frame junctions, and the free end portions/apices of the valve seat can be offset from the frame junctions in a downstream direction toward the outflow end of the frame. This reduce or minimize the length of the prosthetic valve that protrudes or extends distally or in the downstream direction from the docking station. In certain embodiments, the struts of the valve seat can be wholly disposed within the docking station frame, or the free end portions/apices of the valve seat can define a downstream-most end of the docking station frame.

In certain embodiments, the docking station frame can comprise a plurality of circumferentially-arranged longitudinal struts. The longitudinal struts can reduce or prevent foreshortening of the frame between the collapsed and expanded configuration. This can facilitate more accurate and/or predictable deployment of the docking station from the collapsed delivery configuration. The longitudinal struts can also facilitate recapture of the docking station frame from a partially deployed state by limiting an angle formed by the flared, partially deployed portion of the frame and the longitudinal axis of the delivery apparatus. The longitudinal struts can also strengthen the frame and reduce or eliminate infolding or invagination of the frame during recapture.

In certain embodiments, the docking station frame can comprise a plurality of free end portions or apices arranged circumferentially around the frame. In certain embodiments, the free apices can be located between pairs of adjacent longitudinal struts. In certain embodiments, the free apices can be proximal and/or distal apices of frame cells defined between pairs of longitudinal frame struts. In certain embodiments, the frame cells can be axially spaced apart from each other. The free apices can be configured to engage the surrounding tissue of a body lumen in which the docking station frame is implanted to prevent frame movement/migration/rotation relative to the body lumen.

In some exemplary embodiments, docking stations/devices for prosthetic valves or THVs are illustrated as being used within the superior vena cava (SVC), inferior vena cava (IVC), or both the SVC and the IVC, although the docking stations/devices (e.g., docking station/device 10, other docking stations/devices described herein, modified versions of the docking stations, etc.) can be used in other areas of the anatomy, heart, or vasculature, such as the tricuspid valve, the pulmonary valve, the pulmonary artery, the aortic valve, the aorta, the mitral valve, or other locations. The docking stations/devices described herein can be configured to compensate for the deployed transcatheter valve or THV being smaller and/or having a different geometrical shape than the space (e.g., anatomy/heart/vasculature/etc.) in which it is to be placed. For example, the native anatomy (e.g., the IVC) can be oval, egg shaped, or another shape, while the prosthetic valve or THV can be cylindrical.

Various embodiments of docking stations/devices and examples of prosthetic valves or transcatheter valves are disclosed herein, and any combination of these options can be made unless specifically excluded. For example, any of the docking stations/devices disclosed, can be used with any type of valve, and/or any delivery system, even if a specific combination is not explicitly described. Likewise, the different constructions and features of docking stations/devices and valves can be mixed and matched, such as by combining any docking station type/feature, valve type/feature, covering/sealing element, etc., even if not explicitly disclosed. In short, individual components of the disclosed systems can be combined unless mutually exclusive or physically impossible.

For the sake of uniformity, in the present disclosure the docking stations are typically depicted such that the right atrium end (e.g., the outflow end) is up, while the ventricular end or IVC end (e.g., the inflow end) is down unless otherwise indicated.

First Representative Embodiment

Figure 1B:
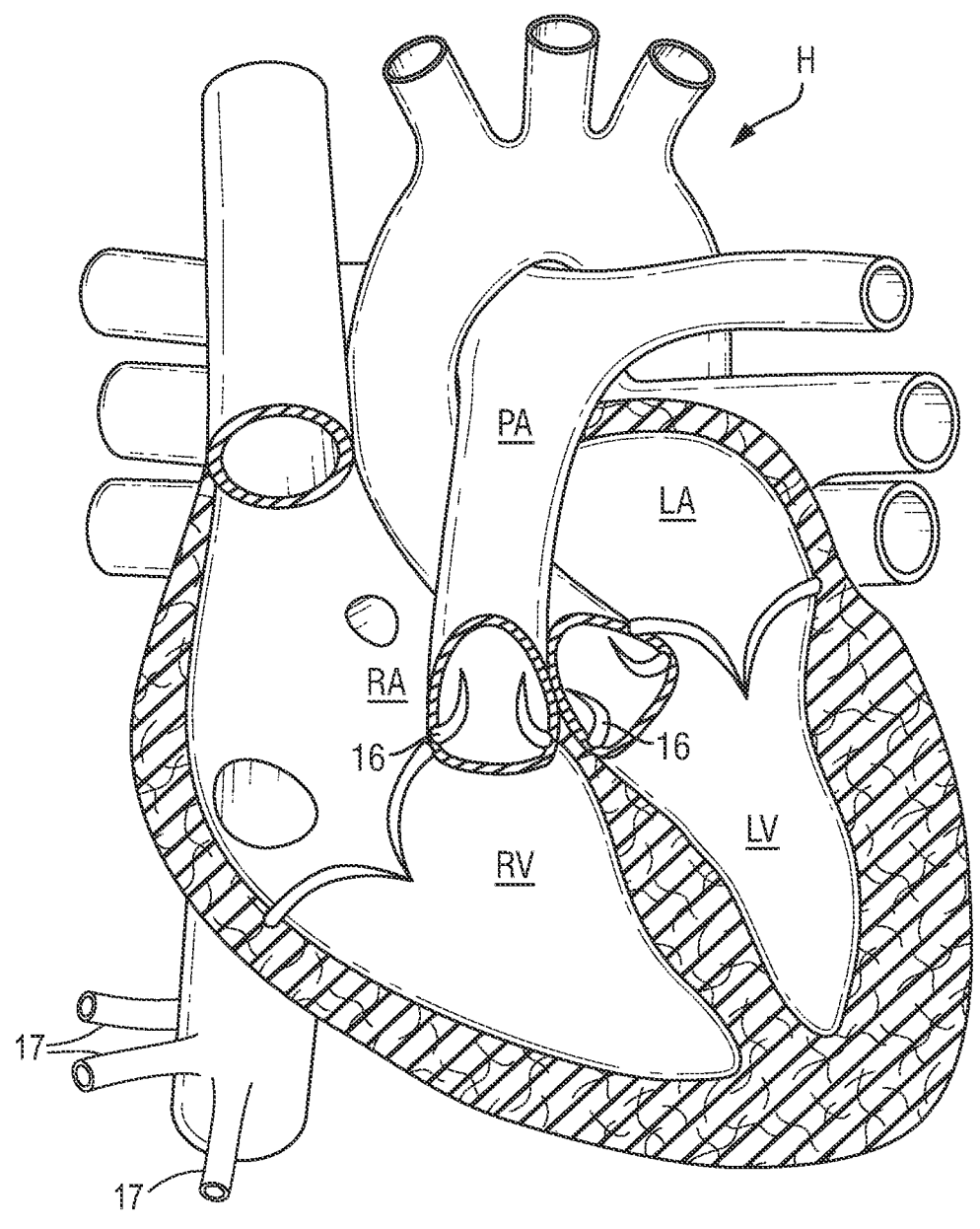
FIG. 1B is a cutaway view of the human heart in a systolic phase.

FIGS. 1A and 1B are cutaway views of the human heart H in diastolic and systolic phases, respectively. The right ventricle RV and left ventricle LV are separated from the right atrium RA and left atrium LA, respectively, by the tricuspid valve TV and the mitral valve MV; i.e., the atrioventricular valves. Additionally, the aortic valve AV separates the left ventricle LV from the ascending aorta (not identified) and the pulmonary valve PV separates the right ventricle from the pulmonary artery PA. Each of these valves has flexible leaflets extending inward across the respective orifices that come together or "coapt" in the flowstream to form one-way, fluid-occluding surfaces. The docking stations and valves of the present application are described, for illustration, primarily with respect to the inferior vena cava IVC, superior vena cava SVC, and aorta/aortic valve. A defective aortic valve, for example, can be a stenotic aortic valve and/or suffer from insufficiency and/or regurgitation. The blood vessels, such as the aorta, IVC, SVC, pulmonary artery, may be healthy or may be dilated, distorted, enlarged, have an aneurysm, or be otherwise impaired. Anatomical structures of the right atrium RA, right ventricle RV, left atrium LA, and left ventricle LV will be explained in greater detail. The devices described herein can be used in various areas whether explicitly described herein or not, e.g., in the IVC and/or SVC, in the aorta (e.g., an enlarged aorta) as treatment for a defective aortic valve, in other areas of the heart or vasculature, in grafts, etc.

The right atrium RA receives deoxygenated blood from the venous system through the superior vena cava SVC and the inferior vena cava IVC, the former entering the right atrium from above, and the latter from below. The hepatic veins 17 carry blood from the liver to the inferior vena cava IVC. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the deoxygenated blood from the IVC, SVC, and CS that has collected in the right atrium RA passes through the tricuspid valve TV and into the RV as the right ventricle RV expands. In the systolic phase, or systole, seen in FIG. 1B, the right ventricle RV contracts to force the deoxygenated blood collected in the RV through the pulmonary valve PV and pulmonary artery into the lungs.

The devices described herein can be used to supplement the function of a defective tricuspid valve and/or to prevent too much pressure from building up in the RA. During systole, the leaflets of a normally functioning tricuspid valve TV close to prevent the venous blood from regurgitating back into the right atrium RA. When the tricuspid valve does not operate normally, blood can backflow or regurgitate into the right atrium RA, the inferior vena cava IVC, the superior vena cava SVC, and/or other vessels in the systolic phase. Blood regurgitating backward into the right atrium increases the volume of blood in the atrium and the blood vessels that direct blood to the heart. This can cause the right atrium to enlarge and cause blood pressure to increase in the right atrium and blood vessels, which can cause damage to and/or swelling of the liver, kidneys, legs, other organs, etc. A transcatheter valve or THV implanted in the inferior vena cave IVC and/or the superior vena cava SVC can prevent or inhibit blood from backflowing into the inferior vena cava IVC and/or the superior vena cava SVC during the systolic phase.

The length L, diameter D, and curvature or contour may vary greatly between the superior vena cava SVC and inferior vena cava IVC of different patients. The relative orientation and location of the IVC and/or SVC can also vary between patients. Further, the size or diameter D can vary significantly along the length L of an individual IVC and/or SVC. Also, the anatomy of the IVC and/or SVC is soft, flexible, and dynamic as compared to other cardiac vessels, such as the aorta. This softer, more flexible, and/or more dynamic (moving and/or shape changing) characteristic of the IVC and SVC make it more difficult for a transcatheter valve frame or a docking station that supports a transcatheter valve to anchor in the IVC and/or the SVC than in the aorta. Further, other regions or other vasculature in other areas of the body and across patients where docking stations could be used can also vary significantly in shape and size.

The left atrium LA receives oxygenated blood from the left and right pulmonary veins, which then travels through the mitral valve to the left ventricle. During the diastolic phase, or diastole, seen in FIG. 1A, the oxygen rich blood that collects in the left atrium LA passes through the mitral valve MV and into the left ventricle LV as the left ventricle LV expands. In the systolic phase, or systole, seen in FIG. 1B, the left ventricle LV contracts to force the oxygen rich blood through the aortic valve AV and aorta into the body through the circulatory system. In certain embodiments, the devices described herein can be used to supplement or replace the function of a defective aortic valve. For example, the devices herein can be particularly effective for treating aortic insufficiency. During diastole, the leaflets of a normally functioning aortic valve AV close to prevent the oxygen rich blood from regurgitating back into the left ventricle LV. When the aortic valve does not operate normally, blood backflows or regurgitates into the left ventricle LV. A THV implanted in the aortic valve helps prevent or inhibit blood from back-flowing into the left ventricle LV during the diastole phase. The length L, diameter, D, and curvature or contour of the aortic root may vary greatly between different patients, especially if the aorta is a dilated, distorted, or enlarged. Further, the size or diameter D may vary significantly along the length L of an individual aorta.

Referring to FIGS. 2A, 3A, 3B, and 3C, in one exemplary embodiment an expandable docking station/device/valve adapter/landing zone/prestent 10 includes one or more sealing portions 12, a valve seat 18, and one or more retaining portions 14. The sealing portion(s) 12 provide a seal between the docking station 10 and an interior surface 16 (see FIG. 2A) of the circulatory system. The valve seat 18 provides a supporting surface for implanting or deploying a valve 29 in the docking station 10 after the docking station 10 is implanted in the circulatory system. Optionally, the docking station 10 and the valve 29 can be integrally formed, for example, in one embodiment, the valve seat 18 can be omitted. When integrally formed, the docking station 10 and the valve 29 can be deployed as a single device, rather than first deploying the docking station 10 and then deploying the valve 29 into the docking station. Any of the docking stations and/or valve seats 18 described herein can be provided or formed with an integrated valve 29.

The retaining portion 14 helps retain the docking station 10 and the valve 29 at the implantation position or deployment site in the circulatory system. The retaining portion 14 can take a wide variety of different forms. In one exemplary embodiment, the retaining portion 14 includes friction enhancing features that reduce or eliminate migration of the docking station 10. The friction enhancing features can take a wide variety of different forms. For example, the friction enhancing features can comprise barbs, spikes, texturing, adhesive, and/or a cloth or polymer cover with high friction properties on the retaining portions 14. Such friction enhancing features can also be used on any of the various docking stations or retaining portions described herein.

Expandable docking station 10 and valve 29 as described in the various embodiments herein are also representative of a variety of docking stations and/or valves described herein or that might be known or developed, e.g., a variety of different types of valves could be substituted for and/or used as valve 29 in the various docking stations.

Figure 2A:
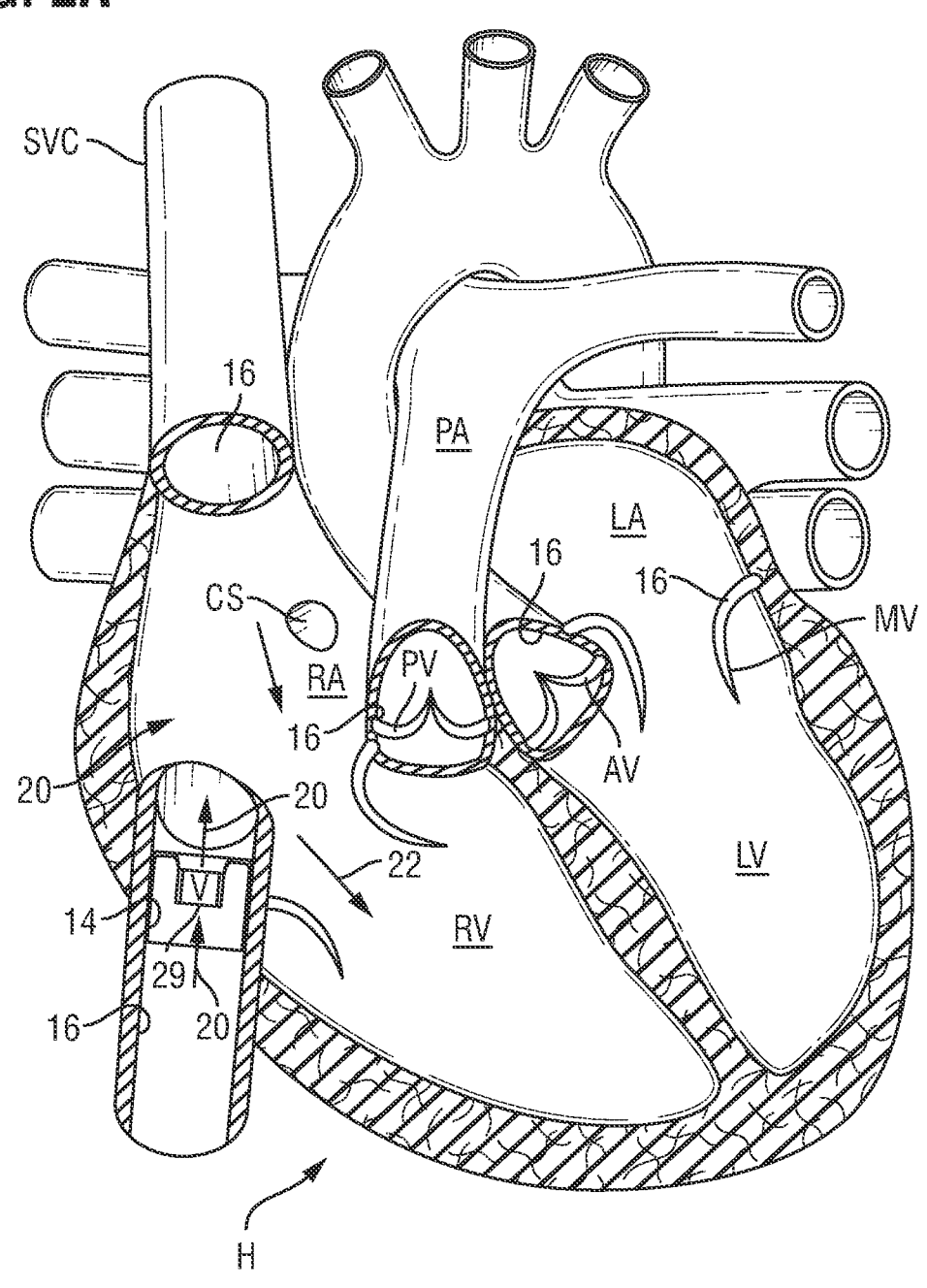
FIG. 2A is a cutaway view of the human heart with an exemplary embodiment of an exemplary docking station positioned in a blood vessel, the inferior vena cava IVC.
Figures 2B, 2C:
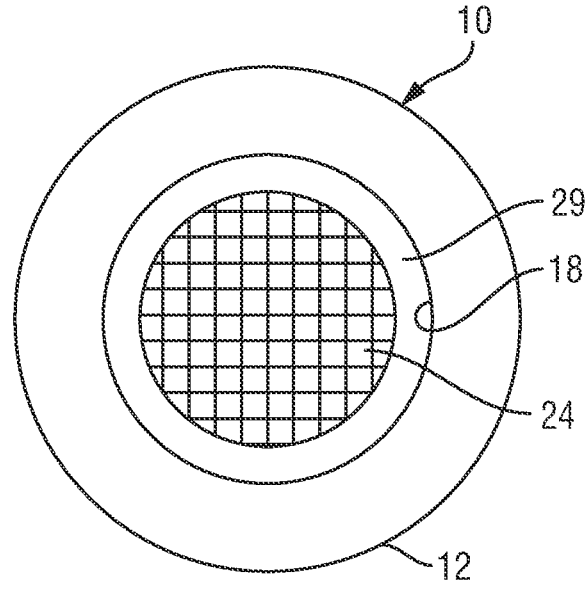
FIG. 2B is an end view of an exemplary docking station and valve showing the valve in an open configuration such that blood can flow through the valve, e.g., when the heart is in a diastolic phase.
FIG. 2C is an end view of the docking station and valve of FIG. 2B showing the valve in a closed configuration, e.g., when the heart is in a systolic phase.

FIGS. 2A, 2B, and 2C illustrate a representative example of the operation of the docking stations 10 and valves 29 disclosed herein. In the example of FIGS. 2A, 2B, and 2C, the docking station 10 and valve 29 are deployed in the inferior vena cava IVC. However, the docking station 10 and valve 29 can be deployed in any interior surface within the heart or a lumen of the body. For example, the various docking stations and valves described herein can be deployed in the superior vena cava SVC, the tricuspid valve TV, the pulmonary valve PV, pulmonary artery, the mitral valve MV, the aortic valve AV, aorta, or other vasculature/ lumens in the body.

FIGS. 2A and 2B illustrate the valve 29, docking station 10 and heart H, when implanted in the IVC and the heart H is in the diastolic phase. When the heart is in the diastolic phase, the valve 29 opens. Blood flows from the inferior vena cava IVC and the superior vena cava SVC, into the right atrium RA. The blood that flows from the inferior vena cava IVC flows through the docking station 10 and valve 29 as indicated by arrows 20. Also, while in the diastolic phase, blood in the right atrium flows through the tricuspid valve TV, and into the right ventricle RV and valve as indicated by arrows 22. FIG. 2B illustrates space 24 that represents the valve 29 being open when the heart is in the diastolic phase. A variety of types of valves can be used that may open and close in a variety of ways (e.g., including valves with leaflets of tissue that open then coapt to close), so the drawings are meant to be representative of a variety of valves that can operate in different ways. FIG. 2B does not show the interface between the docking station 10 and the inferior vena cava to simplify the drawing. The cross-hatching in FIG. 2B represents blood flow through the valve 29. In an exemplary embodiment, blood is prevented or inhibited from flowing between the inferior vena cava IVC and the docking station 10 by the seal 12 and blood is prevented or inhibited from flowing between the docking station 10 and the valve by implanting or seating the valve in the seat 18 of the docking station 10. In this example, blood only substantially flows or is only able to flow through the valve 29 when the valve is open (e.g., in certain embodiments, only when the heart is in the diastolic phase).

FIG. 2C illustrates the valve 29 and docking station 10, when the valve 29 is closed (e.g., when implanted in the IVC and the heart H is in the systolic phase). When implanted in the IVC and the heart is in the systolic phase, the valve 29 closes. Blood is prevented from flowing from the right atrium RA into the inferior vena cava IVC by the valve 29 being closed. As such, the closed valve 29 prevents any blood that regurgitates through the tricuspid valve TV during the systolic phase from being forced into the inferior vena cava IVC. The solid area 26 in FIG. 2C represents the valve 29 being closed (e.g., in certain embodiments, when the heart is in the systolic phase). FIG. 2C is meant to be representative of a variety of valves, even though those valves may close in different ways.

In one exemplary embodiment, the docking station 10 acts as an isolator that prevents or substantially prevents radial outward forces of the valve 29 from being transferred to the inner surface 16 of the circulatory system. In one embodiment, the docking station 10 includes a valve seat 18 that resists expansion, e.g., is not expanded radially outwardly (e.g., the diameter of the valve seat does not increase) or is not substantially expanded radially outward (e.g., the diameter of the valve seat increases by less than 4 mm) by the radially outward force of the transcatheter valve or valve 29. The valve seat can be configured such that expansion of a THV/valve 29 increases the diameter of the valve seat only to a diameter less than an outer diameter of the docking station 10 when the docking station is implanted. Retaining portions 14 and sealing portions 12 can be configured to impart only relatively small radially outward forces on the inner surface 16 of the circulatory system (as compared to the radially outward force applied to the valve seat 18 by the valve 29). Having a valve seat 18 that is stiffer or less radially expansive than the outer portions of the docking station (e.g., retaining portions 14 and sealing portions 12), as in the various docking stations described herein, provides many benefits, including allowing a THV/valve 29 to be implanted in vasculature or tissue of varying strengths, sizes, and/or shapes. The outer portions of the docking station can better conform to the anatomy (e.g., vasculature, tissue, heart, etc.) without putting too much pressure on the anatomy, while the THV/valve 29 can be firmly and securely implanted in the valve seat 18 with forces that will prevent or mitigate the risk of migration or slipping.

The docking station 10 can include any combination of one or more than one different types of valve seats 18, retaining portions 14, and/or sealing portions 12. For example, the valve seat 18 can be a separate component that is attached to the frame 28 of the docking station 10, while the sealing portion is integrally formed with the frame 28 of the docking station. Also, the valve seat 18 can be a separate component that is attached to the frame 28 of the docking station 10, while the sealing portion 12 is a separate component that is also attached to the frame 28 of the docking station. Optionally, the valve seat 18 can be integrally formed with the frame 28 of the docking station 10, while the sealing portion is integrally formed with the frame 28 of the docking station. Further, the valve seat 18 can be integrally formed with the frame 28 of the docking station 10, while the sealing portion is a separate component that is attached to the frame 28 of the docking station 10.

Figures 3A, 3B, 3C:
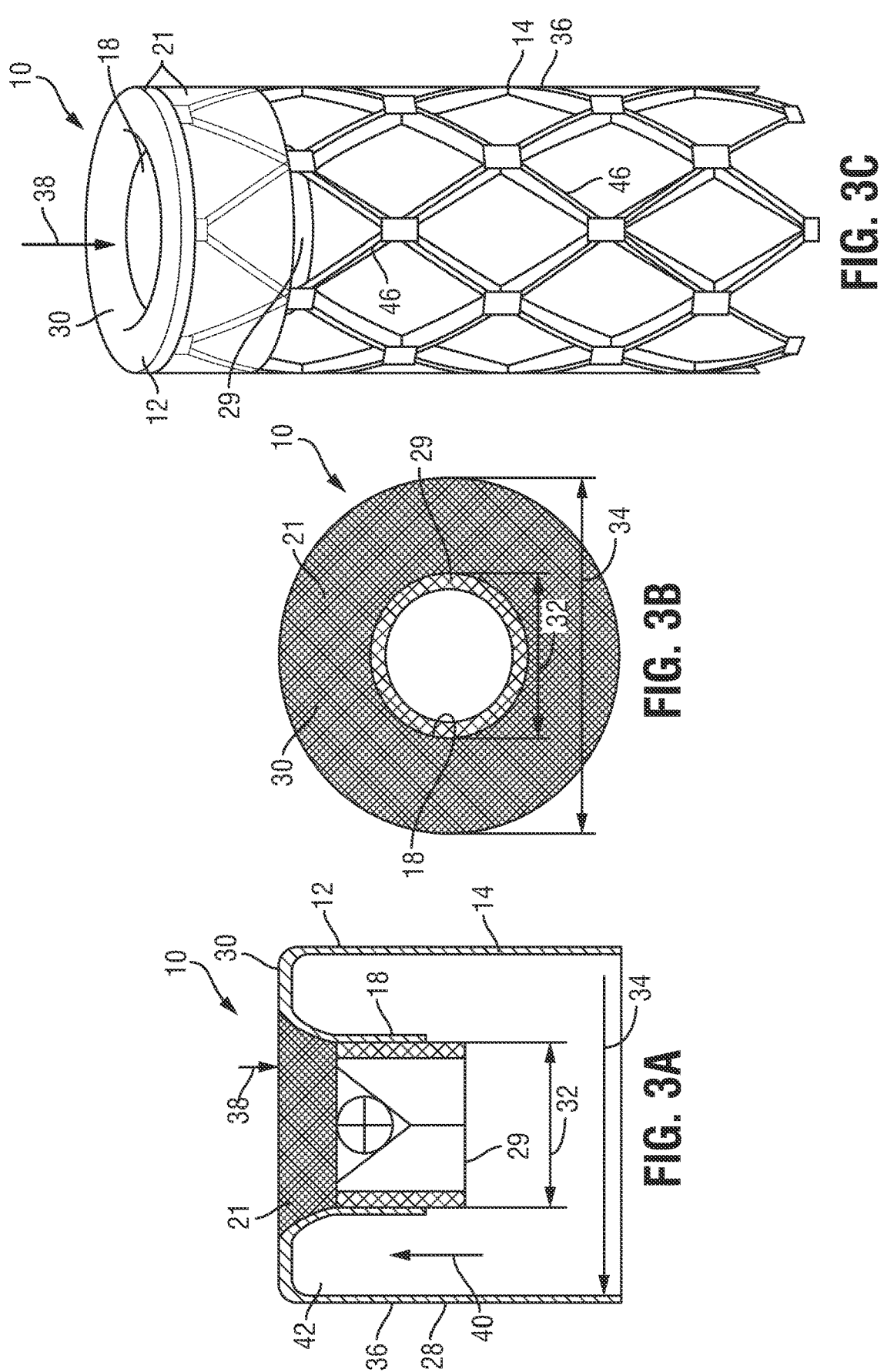
FIG. 3A is a sectional view of an exemplary embodiment of a docking station with an exemplary transcatheter valve disposed inside the docking station.
FIG. 3B is a top view of the docking station and valve illustrated by FIG. 3A.
FIG. 3C is a perspective view of an exemplary embodiment of a docking station that illustrates an example of a frame portion that can be used in the docking station of FIGS. 3A-3B.

The sealing portion 12, the valve seat 18, and one or more retaining portions 14 of the various docking stations herein can take a variety of different forms and characteristics. In FIGS. 3A-3C, an expandable frame 28 provides the shape of the sealing portion 12, the valve seat 18, and the retaining portion 14. The expandable frame 28 can take a wide variety of different forms. The illustrated expandable frame 28 in FIGS. 3A-3C has an end 30 having an inside diameter 32 and an outside diameter 34. An annular or cylindrical outer portion or wall 36 extends downward from the outside diameter 34 of the end 30. An annular or cylindrical valve seat or wall 18 extends downward from the inside diameter 32 of the end 30. In the illustrated example, the expandable frame 28 is an expandable lattice. The expandable lattice can be made in a variety of ways, e.g., with individual wires connected to form the lattice, braiding, cut from a sheet and then rolled or otherwise formed into the shape of the expandable frame, molded, cut from a cylindrical tube (e.g., cut from a nitinol tube), other ways, or a combination of these.

The frame 28 can be made from a highly flexible metal, metal alloy, or polymer. Examples of metals and metal alloys that can be used include, but are not limited to, nitinol and other shape memory alloys, elgiloy, and stainless steel, but other metals and highly resilient or compliant non-metal materials can be used to make the frame 28. These materials can allow the frame to be compressed to a small size, and then when the compression force is released, the frame will self-expand back to its pre-compressed diameter and/or the frame can be expanded by inflation of a device positioned inside the frame. The frame 28 can also be made of other materials and be expandable and collapsible in different ways, e.g., mechanically-expandable, balloon-expandable, self-expandable, or a combination of these.

The sealing portions can take a wide variety of different forms. In the example of FIGS. 3A-3C, a covering/material 21 is attached to a portion of the frame 28 to form the sealing portion 12. However, the sealing portion 12 can be formed in a wide variety of other ways. The covering/material 21 can be a fabric material, polymer material, or other material. The sealing portion 12 can take any form that prevents or inhibits the flow of blood from flowing around the outside surface of the valve 29 and through the docking station. In the example of FIGS. 3A, 3B, and 3C, the sealing portion 12 comprises a covering/material 21 (e.g., a fabric or other covering material that can be the same as or similar to other coverings/materials described herein) that extends up to the valve seat 18. The covering/material 21 can be shaped and positioned in a variety of ways, e.g., the covering/material can be configured to partially cover the valve seat 18, entirely cover the valve seat 18, or not cover the valve seat 18 when the frame 28 is expanded. The covering/material 21 (e.g., fabric or other covering material) that forms the sealing portion 12 can also extend radially outward, covering the end 30 of the frame 28, and can optionally extend (e.g., longitudinally, downward, etc.) to cover at least a portion of the annular outer portion or wall 36. The sealing portion 12 provides a seal between the docking station 10 and an interior surface 16 (see FIG. 2) of the circulatory system. That is, the sealing portion 12 and the closed valve 29 prevent or inhibit blood from flowing in the direction indicated by arrow 38. In the example of FIGS. 3A and 3B, blood is not inhibited from flowing in the direction indicated by arrow 40 into the area 42 between the valve seat 18 and the annular outer portion or wall 36.

Figure 3D:
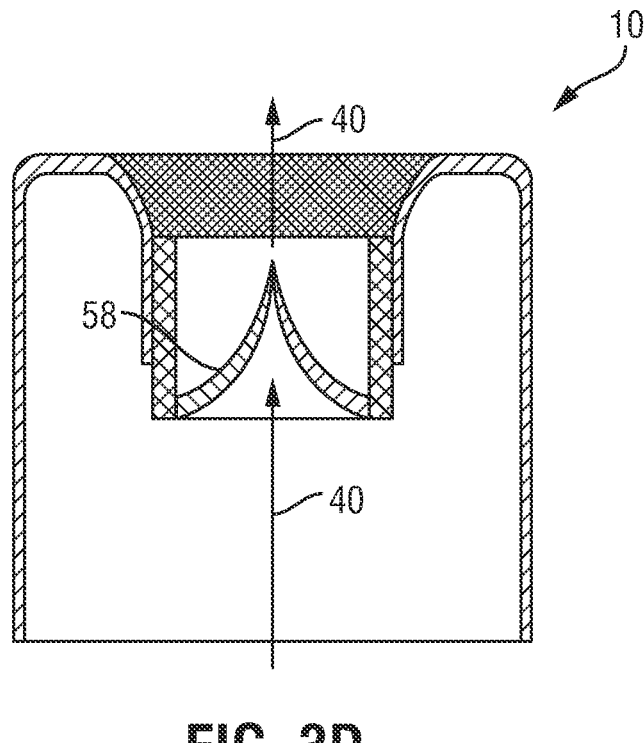
FIG. 3D is a sectional view of the docking station illustrated by FIG. 3A where the transcatheter valve shown is representative of a leaflet type transcatheter valve.

The valve seat can take a wide variety of different forms. The valve seat 18 is a portion of the frame 28 in the example of FIGS. 3A-3C. However, the valve seat 18 can be formed separately from the frame 28. The valve seat 18 can take any form that provides a supporting surface for implanting or deploying a valve 29 in the docking station 10 after the docking station 10 is implanted in the circulatory system. The valve seat can optionally be reinforced with a reinforcing material (e.g., a suture, wire, band, collar, etc. that can circumscribe the valve seat or a portion of the valve seat). The valve 29 is schematically illustrated in FIG. 3A to indicate that the valve 29 can take a wide variety of different forms. FIG. 3D illustrates the more specific example where the valve 29 is a leaflet type THV, such as the SAPIEN® 3 valve available from Edwards Lifesciences Corporation, including a plurality of leaflets 58. In one exemplary embodiment, a valve 29 is integrated with or replaces the valve seat 18, such that docking station 10 is configured as a transcatheter valve that is delivered as a single unit in the same step (as opposed to first implanting a docking stations and subsequently implanting a separate valve/THV in the docking station). Optionally, any of the docking stations described herein can be formed as a valve or THV, e.g., with valve tissue or other valve material integrated into the docking station.

The retaining portions 14 can take a wide variety of different forms. For example, the retaining portion(s) 14 can be any structure that sets the position of the docking station 10 in the circulatory system. For example, the retaining portion(s) 14 can press against or into the inside surface 16 or contour/extend around anatomical structures of the circulatory system to set and maintain the position of the docking station 10. The retaining portion(s) 14 can be part of or define a portion of the body and/or sealing portion of the docking station 10 or the retaining portion(s) 14 can be a separate component that is attached to the body of the docking station. The docking station 10 can include a single retaining portion 14 or two, or more than two retaining portions. The retaining portion(s) 14 can include friction enhancing features as discussed above.

In the example of FIGS. 3A-3C, the retaining portion 14 comprises the annular outer portion or wall 36 of the frame 28. A shape set (e.g., a programmed shape of a shape memory material) of annular outer portion or wall 36 can bias the annular outer portion or wall 36 radially outward and into contact with/against the interior surface 16 of the circulatory system to retain the docking station 10 and the valve 29 at the implantation position. In the illustrated embodiment, the retaining portion 14 is elongated to allow a relatively small force to be applied to a large area of the interior surface 16, while the valve 29 can apply a relatively large force to the valve seat 18. For example, the length of the retaining portion 14 can be twice, three times, four times, five times, or greater than five times the outside diameter of the transcatheter valve. Applying a small radially outward force over a larger area can be sufficient to securely hold the docking station in place, and this design/configuration can allow the docking station to conform to the unique shape/ size of the anatomy and avoid/reduce the likelihood of damaging relatively weaker native tissue. Thereby the valve 29 can be securely held in a variety of locations and anatomies (e.g., the docking station of FIGS. 3A-D is usable in the IVC, SVC, aorta, etc.).

In certain examples, the retaining portion 14 can comprise the annular outer portion or wall 36 of the frame 28. A shape set (e.g., a programmed shape of a shape memory material) of annular outer portion or wall 36 can bias the annular outer portion or wall 36 radially outward and into contact with/ against the interior surface 16 of the aorta to retain the docking station 10 and the valve 29 at the implantation position. In certain examples, the shape set can also be selected to substantially match the shape of a portion of the aorta. The retaining portion 14 can be elongated to allow a relatively small force to be applied to a large area of the interior surface 16, while the valve 29 can apply a relatively large force to the valve seat 18, as discussed above. Further details regarding such configurations can be found in U.S. Publication No. 2019/0000615, which is incorporated herein by reference.

Figure 4A:
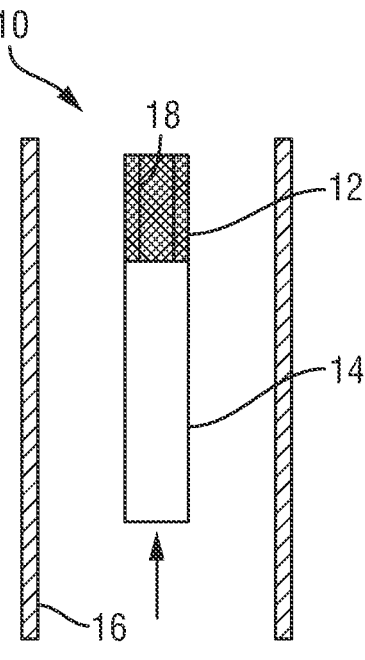
FIGS. 4A and 4B schematically illustrate deployment of a docking station.
Figure 4B:
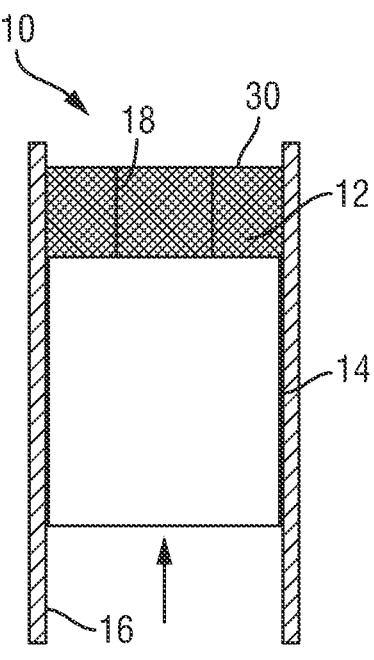
Figure 4C:
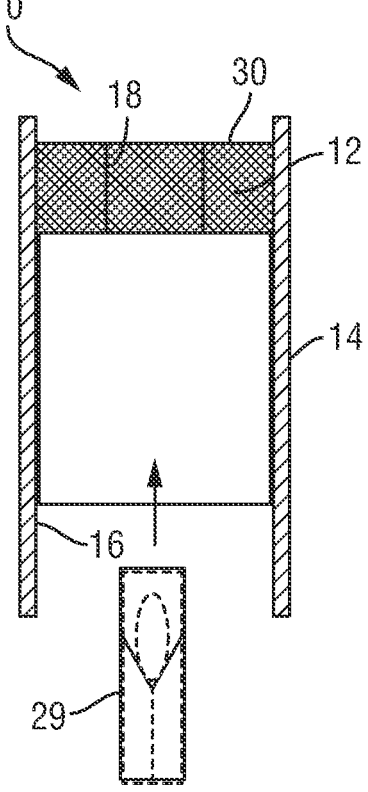
FIGS. 4C and 4D schematically illustrate deployment of a valve in the docking station.
Figure 4D:
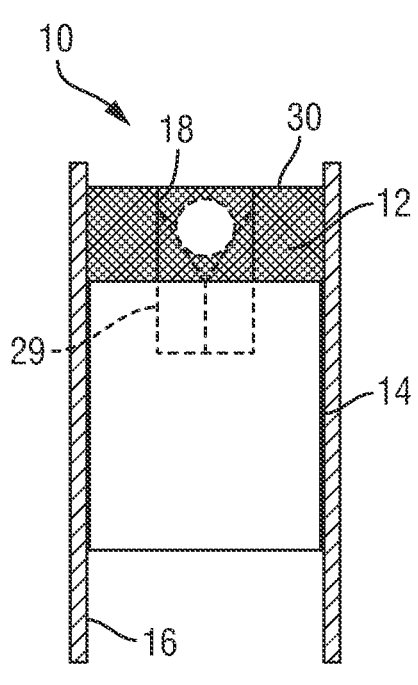

FIGS. 4A-4D schematically illustrate an exemplary deployment of the docking station 10 and valve 29 in the circulatory system. Referring to FIG. 4A, the docking station 10 is in a compressed form/configuration and is introduced to a deployment site in the circulatory system. For example, the docking station 10, can be positioned at a deployment site in a SVC, IVC, aorta, or other location. Referring to FIG. 4B, the docking station 10 is expanded in the circulatory system such that the sealing portion(s) 12 and the retaining portion(s) 14 engage the inside surface 16 of a portion of the circulatory system. The docking station can be self-expanding, and can be advanced from a delivery capsule into the expanded state, or plastically expandable such that it can be expanded using a balloon or other expansion device. Referring to FIG. 4C, after the docking station 10 is deployed, the valve 29 is in a compressed form and is introduced into the valve seat 18 of the docking station 10. Referring to FIG. 4D, the valve 29 is expanded in the docking station, such that the valve 29 engages the valve seat 18 and the seat 18 of the docking station supports the valve. The docking station 10 allows the valve 29 to operate within the expansion diameter range for which it is designed. In the examples depicted herein, the docking station 10 is longer than the valve. However, in some embodiments the docking station 10 can be the same length or shorter than the length of the valve 29. Similarly, the valve seat 18 can be longer, shorter, or the same length as the length of the valve 29. Any of the docking station embodiments described herein can be deployed in the manner described above.

Figure 4E:
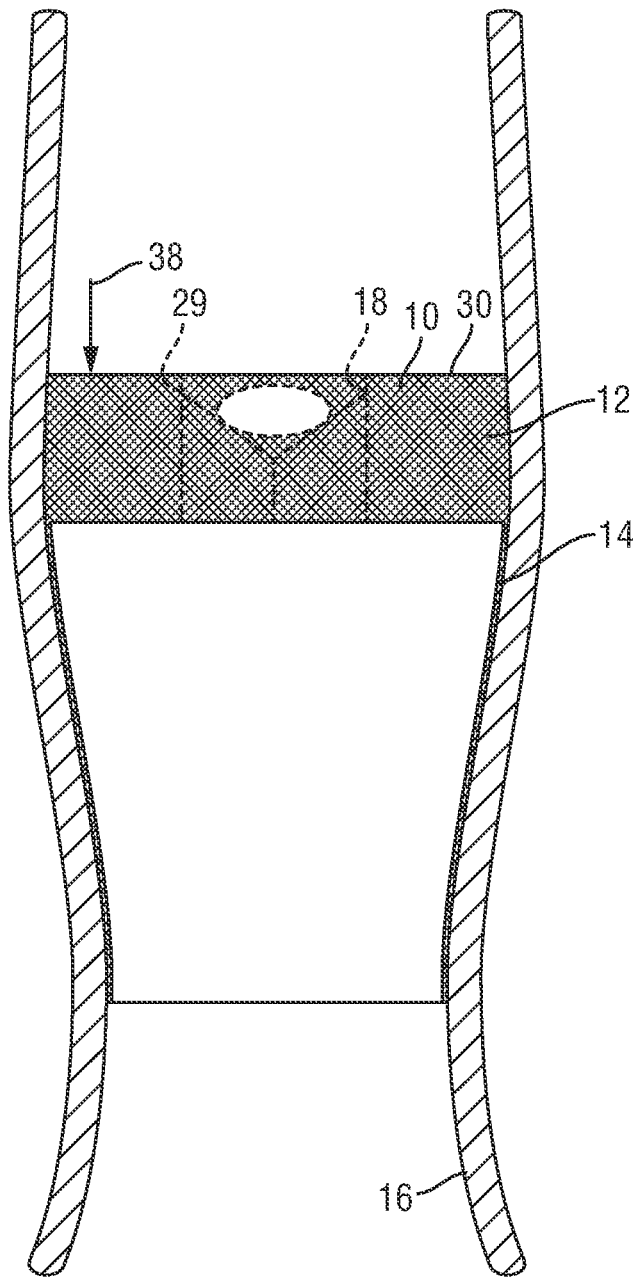
FIG. 4E schematically illustrates conformance of a docking station to an inner surface having a varying size.

FIG. 4E illustrates that the inner surface 16 of the circulatory system, such as the inner surface of a blood vessel or anatomy of the heart can vary in cross-section size and/or shape along its length. In an exemplary embodiment, the docking station 10 is configured such that it can expand radially outwardly to varying degrees along its length L to conform to shape of the inner surface 16. In one exemplary embodiment, the docking station 10 is configured such that the sealing portion(s) 12 and/or the retaining portion(s) 14 engage the inner surface 16, even though the shape of the blood vessel or anatomy of the heart vary significantly along the length L of the docking station. The docking station can be made from a very resilient or compliant material to accommodate large variations in the anatomy.

Figures 5A, 5B, 5C:
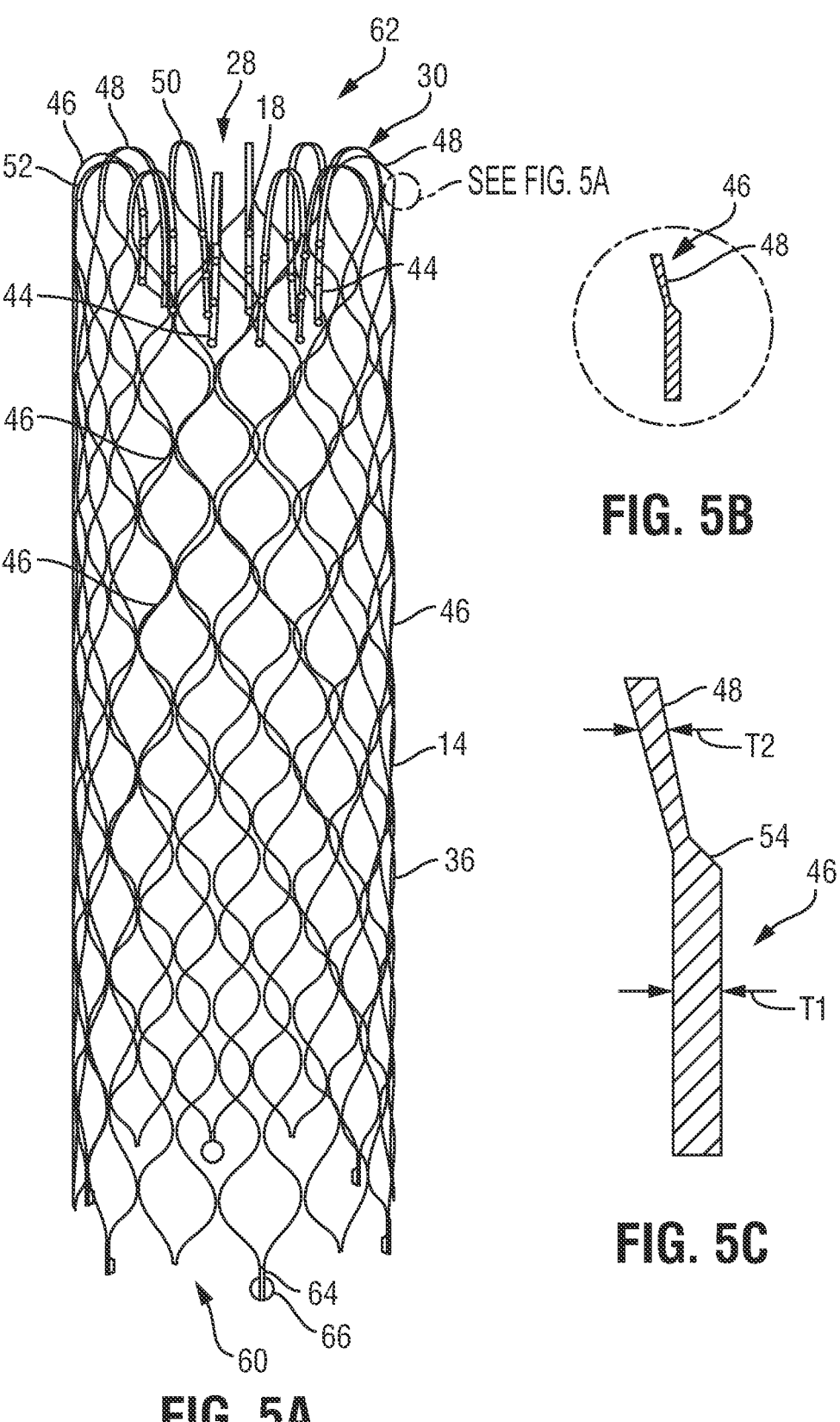
FIG. 5A is a perspective view of an exemplary embodiment of a docking station frame.
FIGS. 5B and 5C illustrate enlarged portions of FIG. 5A.
Figure 6:
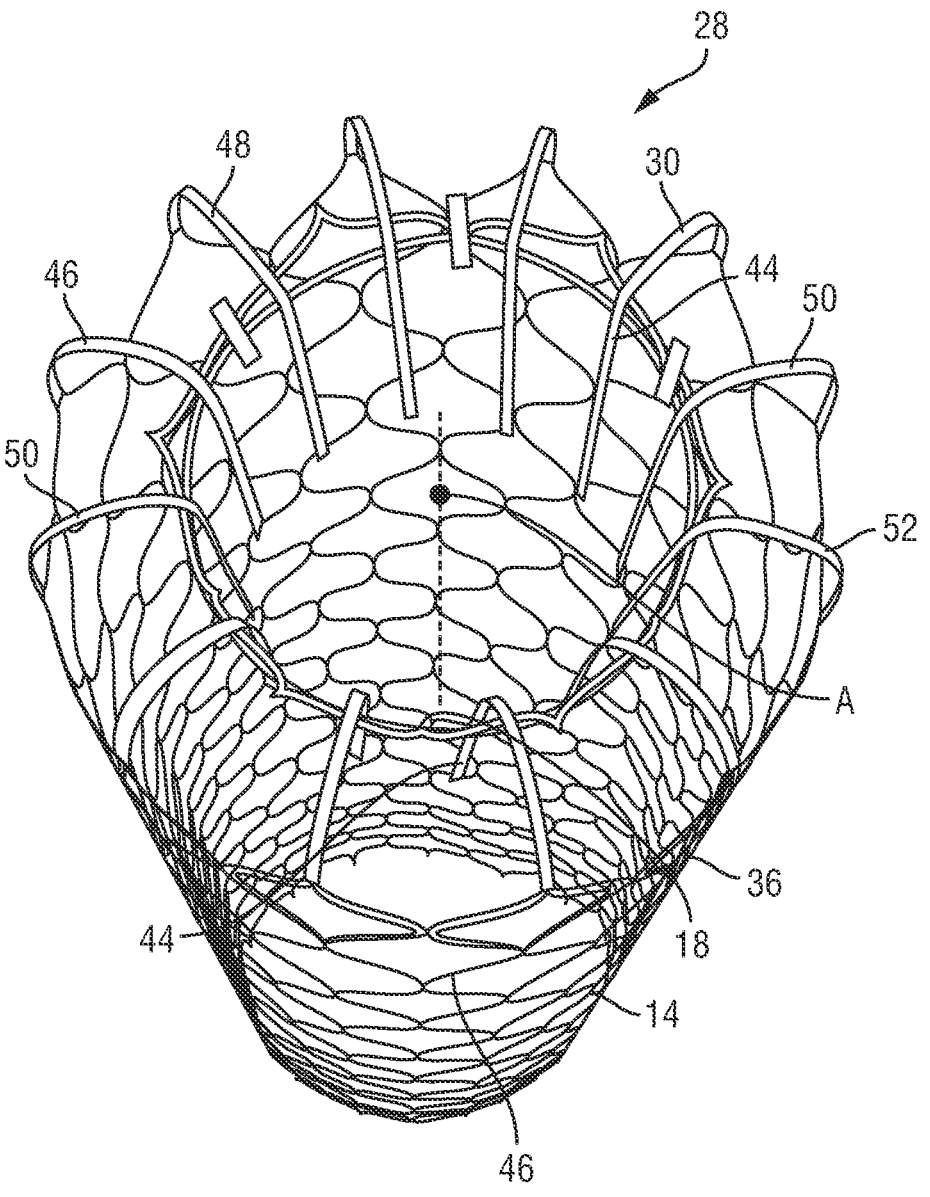
FIG. 6 is a perspective view of the docking station frame illustrated by FIG. 5A.
Figure 7:
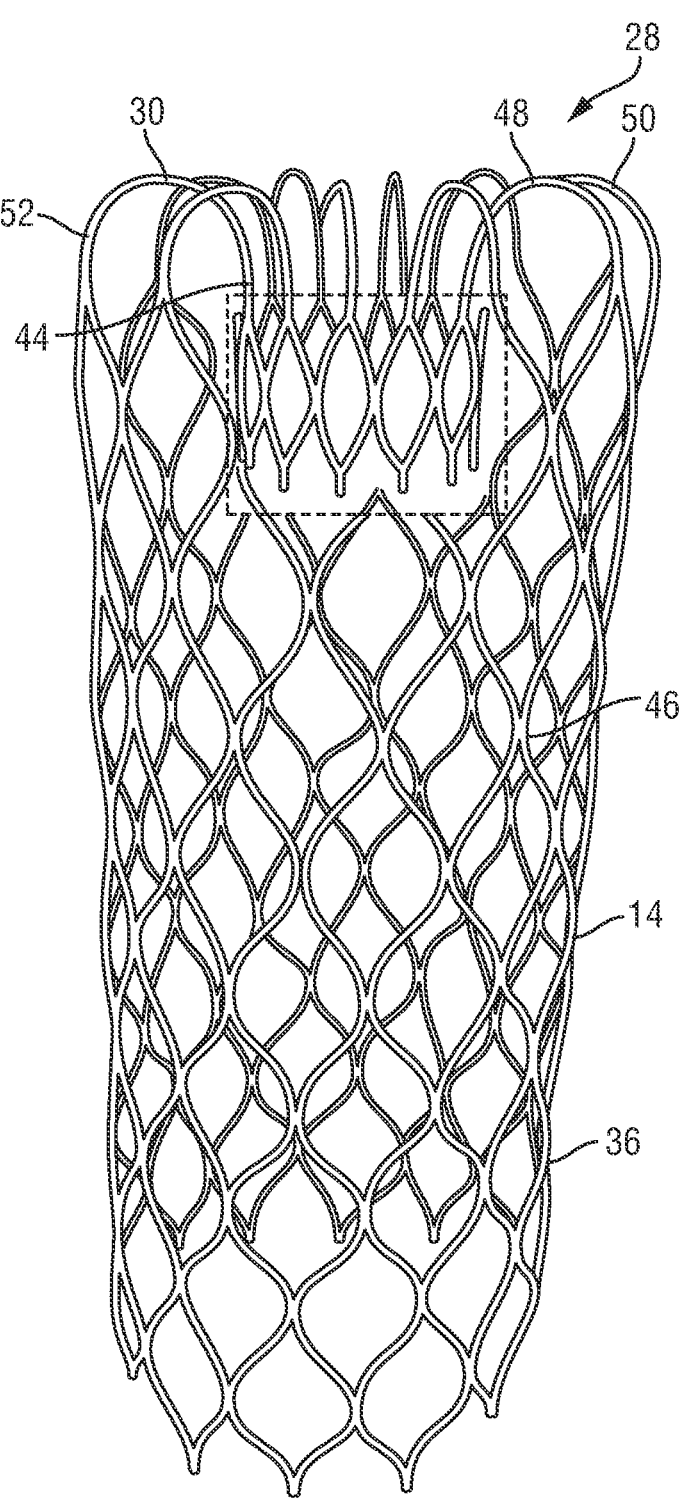
FIG. 7 is a perspective view of an exemplary embodiment of a docking station frame.
Figure 8A:
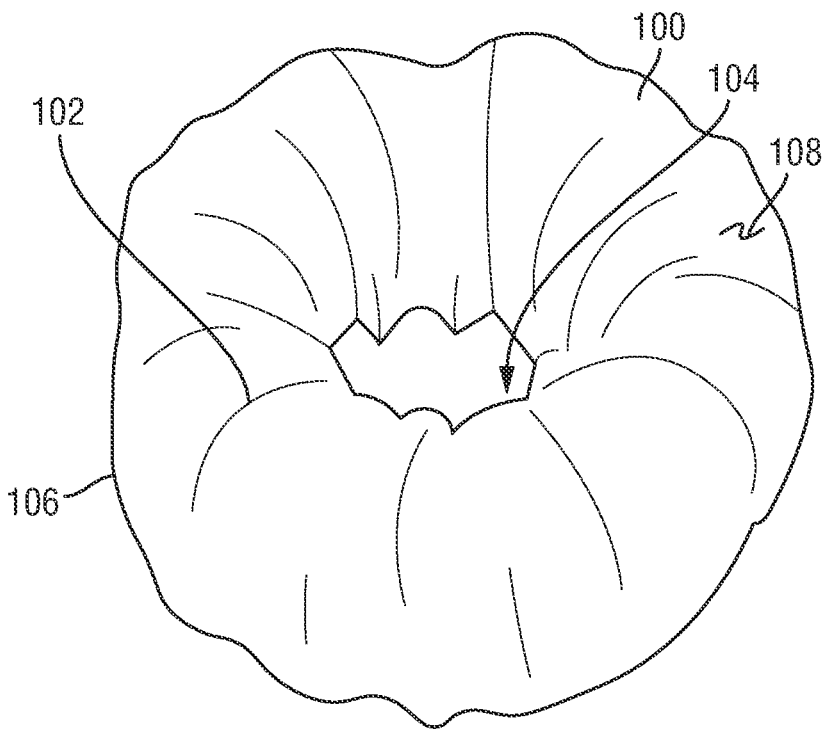
FIG. 8A is a perspective view of an exemplary cover for a docking station frame.
Figure 8B:
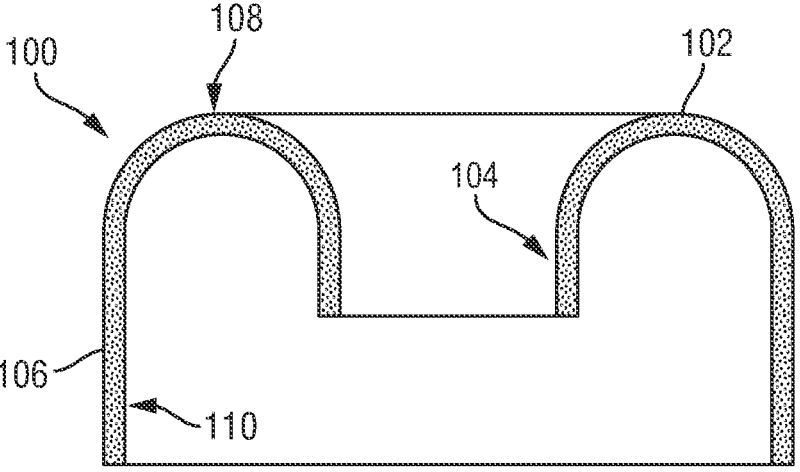
FIG. 8B is a sectional view of an exemplary cover for a docking station frame.

The docking station frame 28 can take a wide variety of different forms. FIGS. 5A-5C, 6 and 7 illustrate exemplary embodiments of docking station frames. The frames can include a first or inflow end generally indicated at 60 and a second or outflow end indicated at 62. In FIG. 5A, a portion of the valve seat 18 is omitted, but the frame includes legs 44 for supporting a valve seat 18 or forming a portion of a valve seat. In FIGS. 6 and 7 two examples of valve seats 18 are shown connected to the legs 44. In FIG. 6, the valve seat 18 comprises a separate valve seat component attached to the legs 44. In FIG. 7, the valve seat 18 is integrally formed with the legs 44. In other embodiments, the valve seat 18 is replaced/integrated with a valve/THV 29 and the docking station 10 and valve/THV are configured and deployed as a single unit. In FIG. 7, a portion of the annular outer wall 36 is removed to show the integrally formed valve seat 18. In the illustrated embodiments, the docking station frame 28 can include one or a plurality of elongated legs/extensions/ members 64 including end portions 66 configured for attachment to a delivery apparatus, as described further in U.S. Publication No. 2019/0000615 incorporated by reference above.

In one exemplary embodiment, a thickness of struts 46 of the frame varies. A wide variety of different portions of the struts 46 can vary and the struts can vary in different ways. Referring to FIGS. 7A and 7B, in one exemplary embodiment a strut 46 has a first thickness T1 and a second thickness T2. In the illustrated example, the struts 46 of the annular wall portion 14 have the first thickness T1 and strut portions or links 48 of the struts 46 that form the end 30 have the second thickness T2. In this example, the thickness T2 is less than the thickness T1. This reduced thickness allows the end 30 to bend or flex more easily and connect the annular outer portion or wall 36 to the valve seat 18. In the illustrated example, the thicknesses T1, T2 are measured in the radial outward direction (e.g., measured from an inside surface of the frame 28 to the outside surface). In one exemplary embodiment, the width of the struts 46 is also reduced with the thickness reduction or, optionally, the width of the strut portions can be reduced instead of the thickness reduction. The thickness T2 can be 90% or less of the thickness T1, the thickness T2 can be 80% or less of the thickness T1, thickness T2 can be 70% or less of the thickness T1, thickness T2 can be 60% or less of the thickness T1, thickness T2 can be half or less of the thickness T1, thickness T2 can be 40% or less of the thickness T1, thickness T2 can be 30% or less of the thickness T1, thickness T2 can be ¼ or less of the thickness T1, or the thickness T2 can be 20% or less of the thickness T1.

In the illustrated example, the entirety of the strut portions or links 48 of the struts 46 that form the end 30 have the second thickness T2. However, in other embodiments, only part of the portions/links 48 that form the end 30 have the reduced thickness. For example, the thickness of the portions/links 48 can have the thickness T2 at the top or apex 50 of the illustrated bend 52 while another part(s) can have the thickness T1. In one embodiment, a taper 54 transitions the struts 46 or strut portions/links 48 from the thickness T1 to the thickness T2. In one embodiment, the taper is more gradual (e.g., occurs over a longer distance or length) and extends into the bend of the links 52. The thickness can also increase (e.g., taper) in the area from the top or apex 50 to the valve seat 18 or area where the valve seat will be attached.

The length of the retaining portion 14 in FIGS. 5A-7B shows as being many times both the length/height of the valve seat and diameter of the valve seat. As discussed previously, this configuration applies a relatively small radially outward force over a larger area to the interior surface of the circulatory system and is sufficient to secure the docking station in place against the interior surface. Further, this design/configuration allows the docking station to conform to the unique shape/size of the anatomy expanding more or less in many different locations to adjust to the contours (e.g., bulges, narrowed regions, contractions, etc.) of the interior surface of the circulatory system (e.g., blood vessel) and contact more of the interior surface. In one embodiment, the docking station and frame are configured such that, when implanted, all or most of the outer surface of the docking station or frame contacts the interior surface of the circulatory system (even when irregular or varied in shape). This also helps avoid/reduce the likelihood of damaging relatively weaker native tissue (e.g., by having too much localized force and/or pressure in one, two, or more particular locations). Thereby the valve 29 can be securely held in a variety of locations and anatomies.

For example, the frame shown in FIGS. 5, 6, and 7 is configured such that a docking station incorporating this frame can conform to an interior shape of circulatory system when expanded inside the blood vessel such that the expandable frame can expand in multiple locations (e.g., 2, 3, 4, 5, 6, 7, 8, or more) to conform to multiple bulges of the circulatory system and/or can contracts (e.g., is less expanded, has a smaller diameter, etc.) in multiple locations (e.g., 2, 3, 4, 5, 6, 7, 8, or more) to conform to multiple narrowed regions of the circulatory system. Further, whether the native anatomy is varied or more uniform, the frame is configured such that, when a docking station incorporating the frame is expanded in the circulatory system, the majority (e.g., more than 50%), more than 60%, more than 70%, more than 80%, 50-90%, or more of an outer surface of the docking station contacts an interior surface of the circulatory system and distributes the pressure and force exerted on the interior surface by the docking station over the portion or length of the outer surface of the docking station in contact with the interior surface. Additional details regarding the frames shown in FIGS. 5A-7B can be found in U.S. Publication No. 2019/0000615 incorporated by reference above.

Referring now to FIGS. 8A through 10B, the frame 28 can include a sealing material or cover/covering 100 disposed on the end 30 of the frame 28 to effectuate a seal between the valve 29 and interior surface 16 of the circulatory system when the valve 29 is disposed in the valve seat 18 of the frame 28 and the frame 28 is radially expanded and placed in the body. The cover 100 can be a cylinder or substantially a cylinder rolled partially backward on itself and can have an end 102 having an inside diameter 104, an outside diameter 106, a distal surface 108, and a proximal surface 110. The cover 100 can comprise a single sheet of PET (Polyethylene terephthalate), PTFE, ePTFE, another polymer, or other biocompatible material which can provide an effective seal. In one embodiment, the cover 100 can comprise a woven ribbon or fabric, such as a woven ribbon or fabric that comprises PET, PTFE, ePTFE, another polymer, or other biocompatible material.

Figures 9A, 9B:
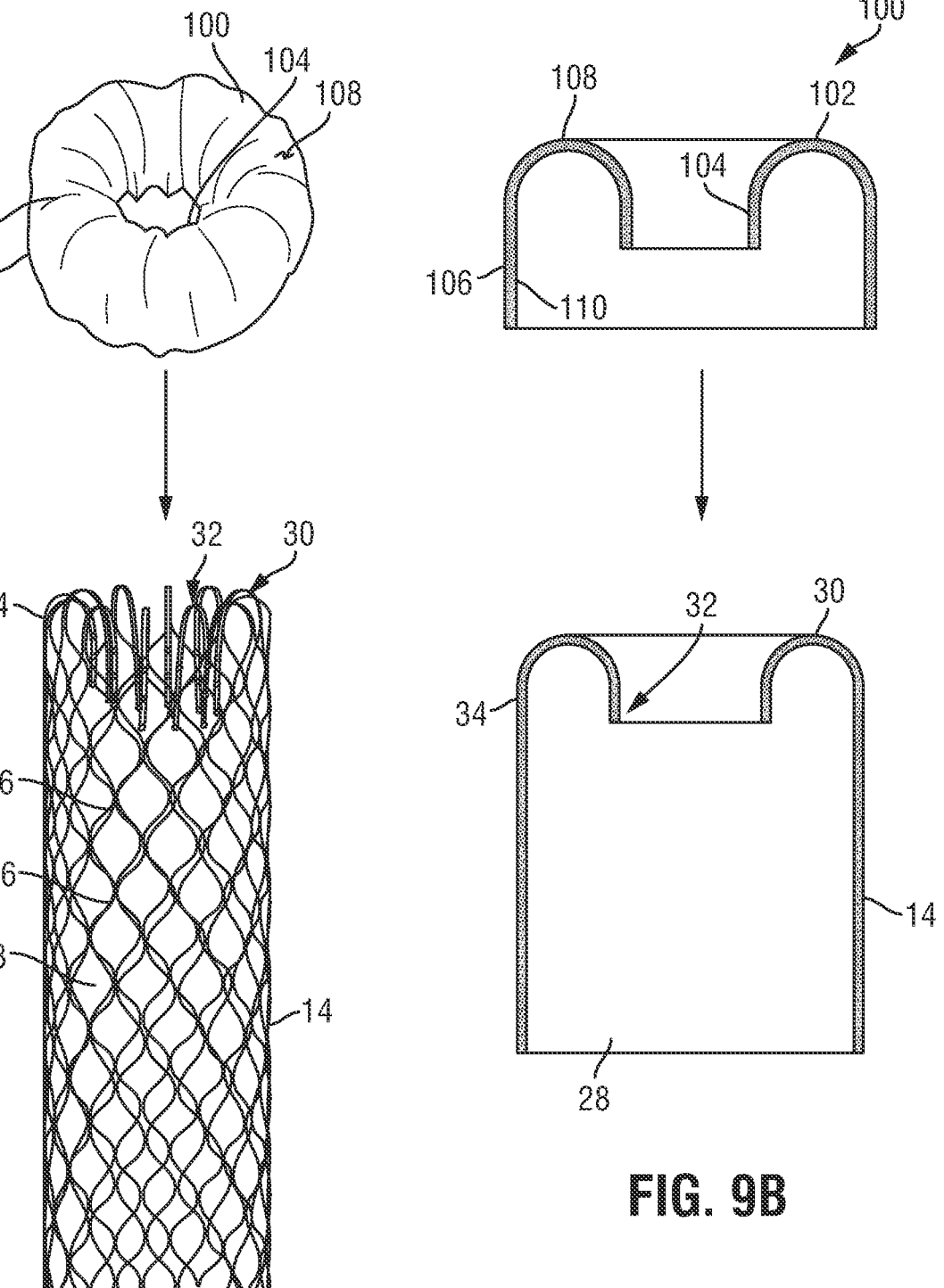
FIGS. 9A and 9B illustrate an exemplary installation of an exemplary cover on a docking station.

As shown in FIGS. 9A through 10B, the cover 100 can be disposed over the end 30 of the frame 28. The cover 100 can be secured to the frame 28 in a wide variety of different ways. For example, the cover 100 can be attached to the frame with sutures, adhered, tied, fused, etc. Turning to FIGS. 9A and 9B, the cover 100 can be placed onto the end 30 of the frame 28. In one embodiment, the end 102 of the cover 100 abuts the end 30 of the frame 28. The inside diameter 104 of the cover 100 is radially inward of and adjacent to the inside diameter 32 of the frame 28. The outside diameter 106 the cover 100 is radially outward of and adjacent to the outside diameter 34 of the frame 28. The proximal surface 110 of the cover 100 can extend around a portion of the retaining portions 14 of the frame 28. In one embodiment, the outside diameter 106 of the cover provides a secure fit and/or seal between the frame 28 and the interior surface 16 of the circulatory system.

Figure 10A:
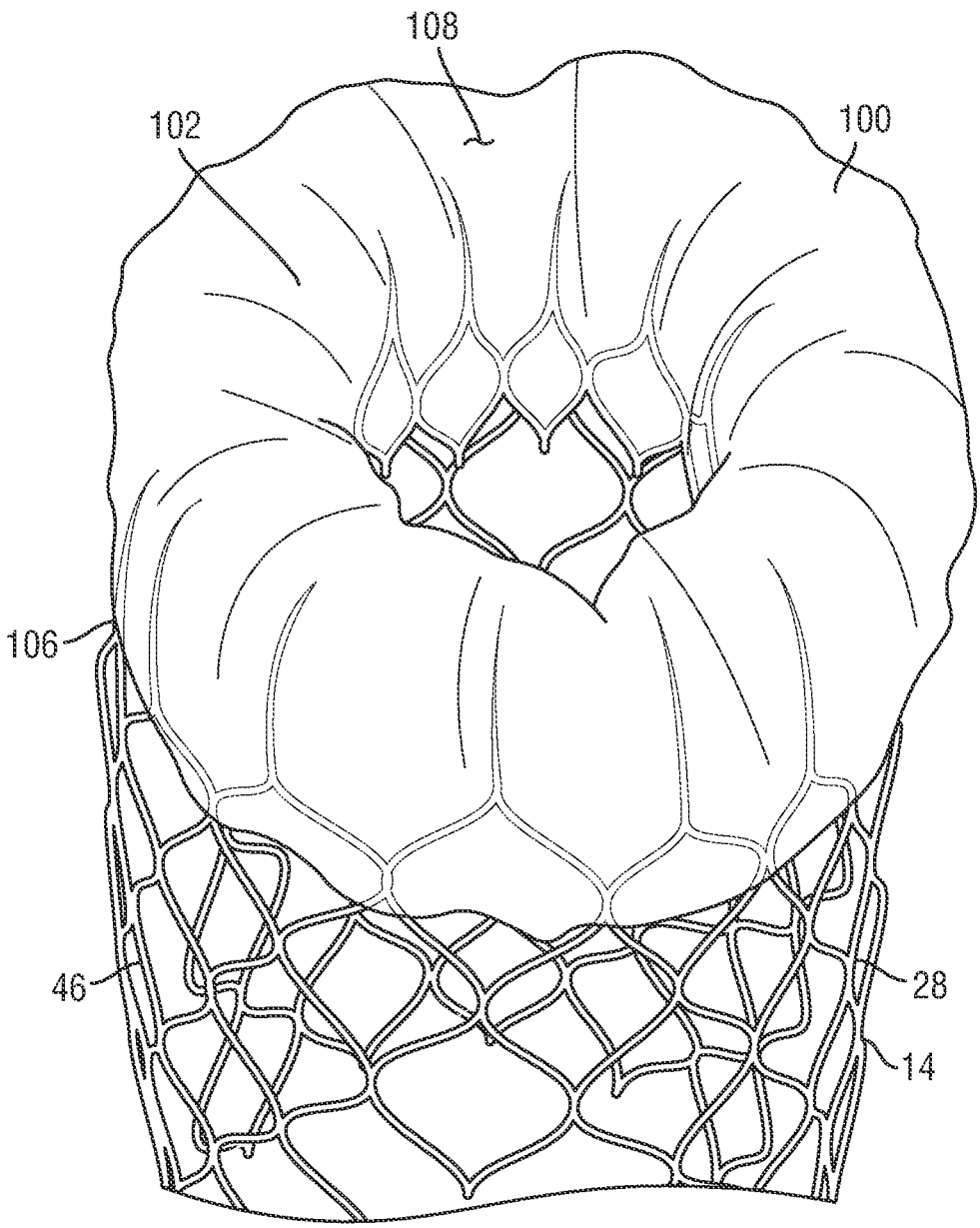
FIG. 10A is a perspective view of an exemplary cover disposed on a frame.
Figure 10B:
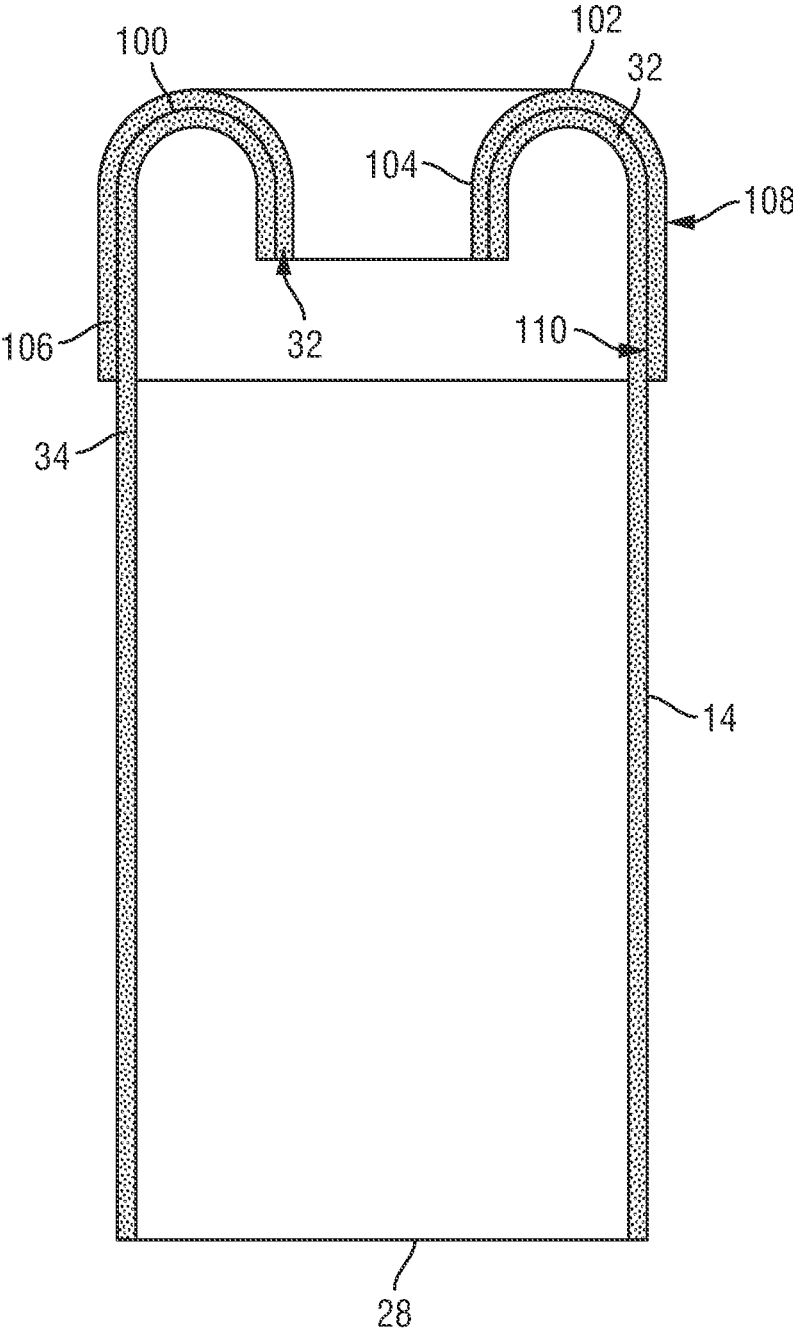
FIG. 10B is a sectional view of an exemplary cover disposed on a docking station frame.

Referring to FIGS. 10A and 10B, the cover 100 can be draped or otherwise disposed entirely around the end 32 of the frame 28. The cover 100 can have contours or otherwise undulate between the struts 46 of the frame 28 (FIG. 10A) or the cover 100 can be flush with the end 32 of the frame 28 (FIG. 10B). A valve 29 (such as any of the valves described herein) can be inserted into the valve seat 18 defined by the inside diameter 32 of the frame 28 and the inside diameter 104 of the cover 100. In such a configuration, the cover 100 can effectuate a continuous seal between the outside diameter 34 of the frame 28 and the interior surface 16 of the circulatory system, around the end 32 of the frame 28, and between the inside diameter 34 of the frame 28 and the valve 29. For example, when the valve 29 is in the closed position, the valve 29 and the cover 100 provide a seal against blood flow.

Second Representative Embodiment

Figure 11:
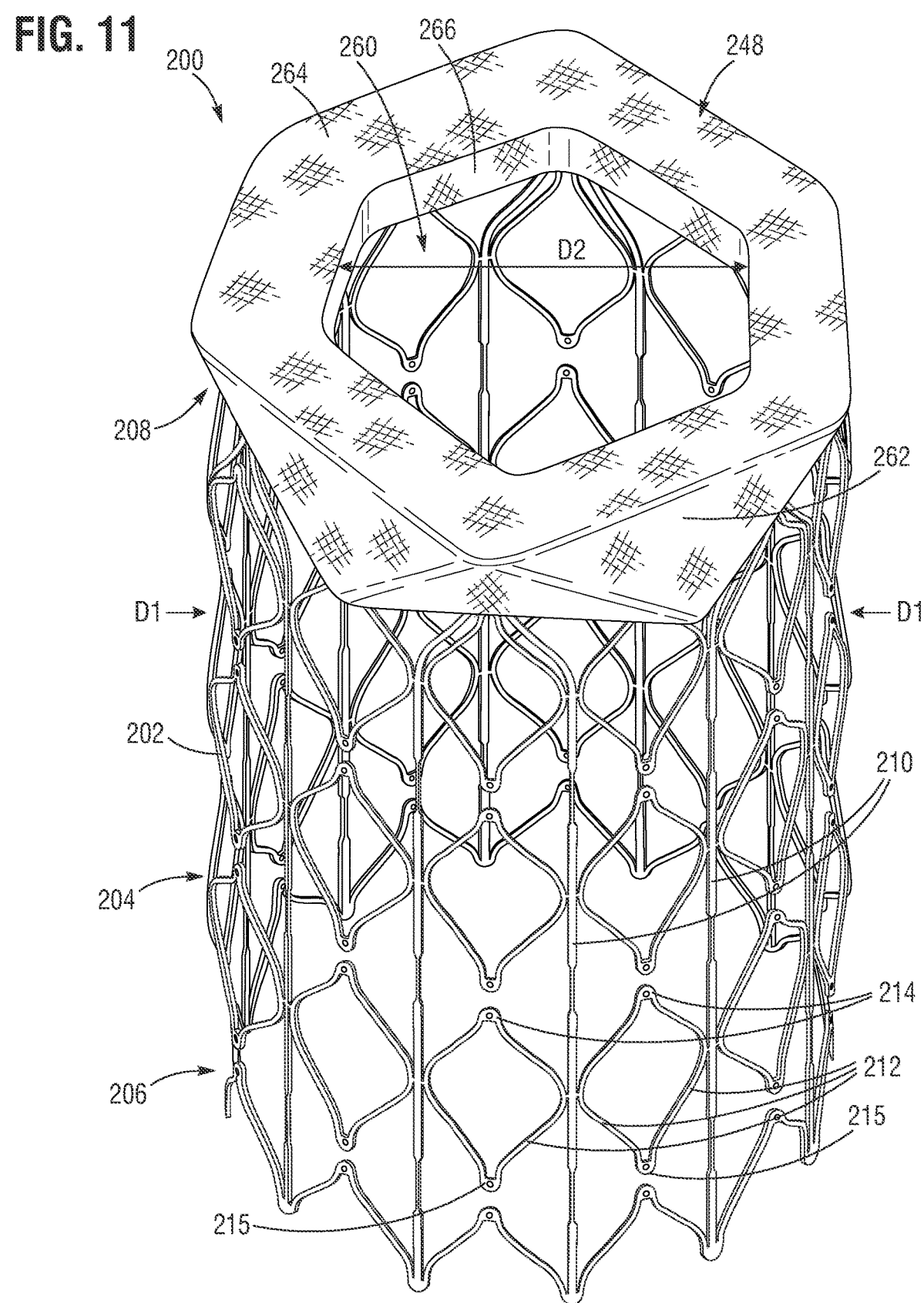
FIG. 11 is a perspective view of another embodiment of a docking station frame.
Figure 12:
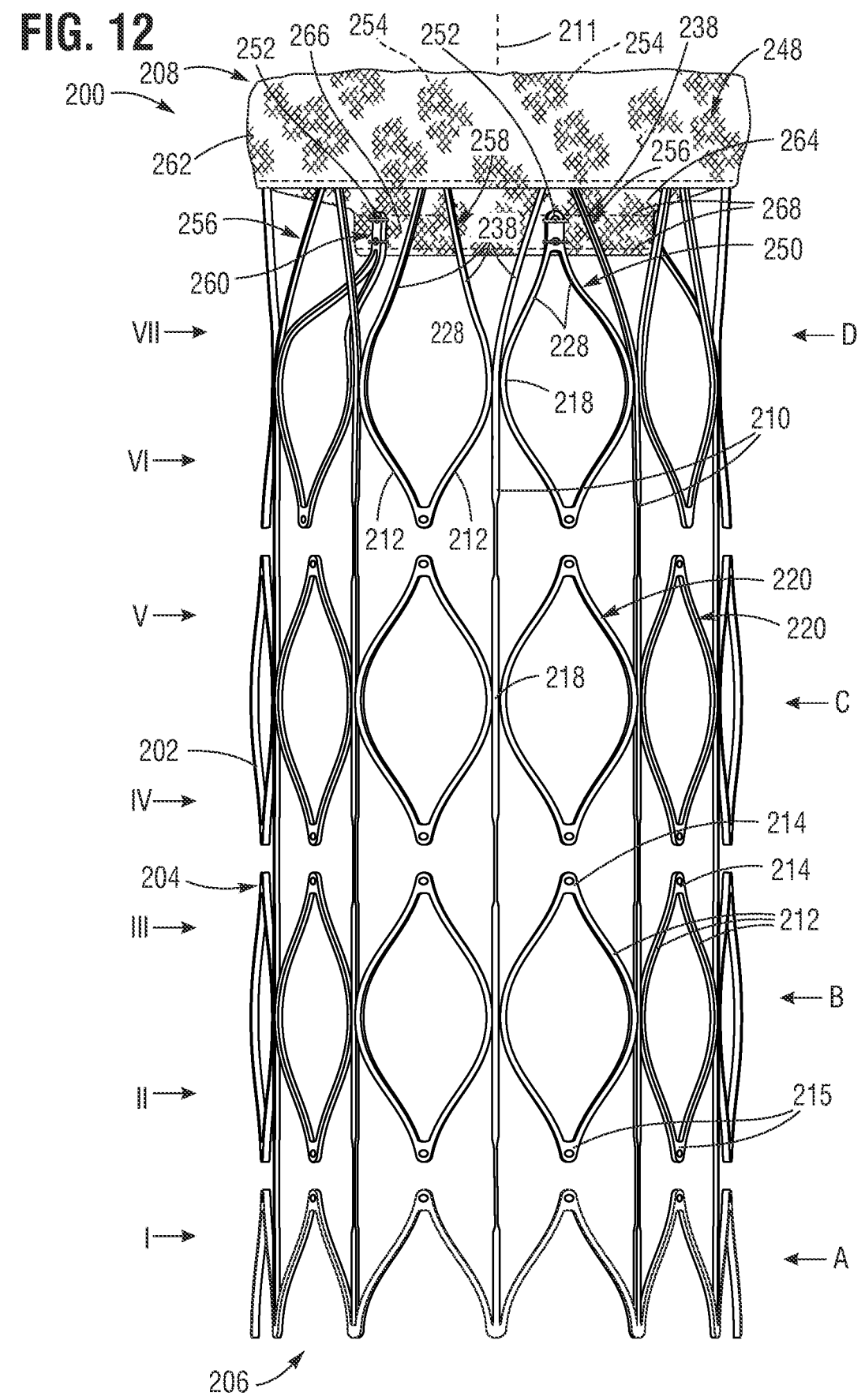
FIG. 12 is a side elevation view of the docking station frame of FIG. 11.

FIGS. 11 and 12 illustrate another embodiment of a docking station/device/valve adapter/landing zone/prestent 200. The docking station 200 can comprise a frame 202 comprising a plurality of interconnected strut members forming a main body 204, and having an inflow end portion 206 and an outflow end portion 208. A sealing member 248 can be disposed around the outflow end portion, as described in greater detail below. The frame 202 can comprise a plurality of longitudinally-extending strut members referred to herein as longitudinal struts 210 angularly spaced apart from each other around the circumference of the frame and extending generally along a longitudinal axis 211 (FIG. 12) of the frame. In certain embodiments, the longitudinal struts 210 can be configured to reduce or substantially eliminate foreshortening of the frame when it is crimped for delivery, as discussed in greater detail below. Referring to FIG. 12, the frame can further comprise a plurality of rows or tiers of angled strut members, such as strut members 212, arranged circumferentially around the frame. The struts 212 can be joined to the longitudinal struts 210 at one end, and can extend toward and be joined to an adjacent strut 212 at the opposite end to form first, distal, or outflow apices 214 and second, proximal, or inflow apices 215 disposed between adjacent longitudinal struts 210.

Figure 13:
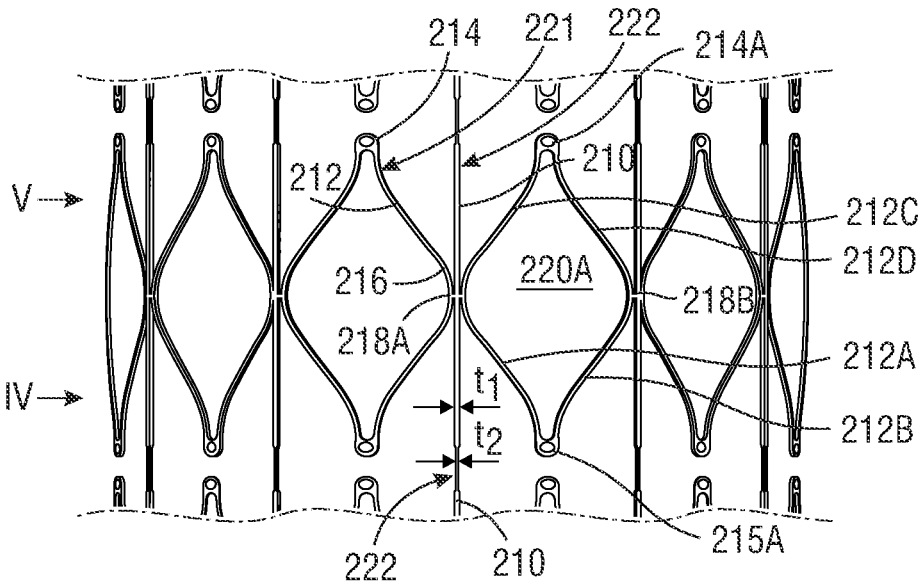
FIG. 13 is a magnified view of a portion of the docking station frame of FIG. 11.

For example, referring to FIG. 13, the struts 212 can comprise first end portions 216 coupled to the respective longitudinal strut members 210 at junctions 218, and second end portions 221. The struts 212 can extend circumferentially and/or longitudinally away from the junctions 218. Adjacent struts 212 that are between sequential/adjacent longitudinal struts 210, and which are at the same position along the longitudinal axis 211 of the frame, can be joined together at respective apices 214.

Returning to FIG. 12, in the illustrated embodiment the frame 202 comprises seven rows I-VII of struts such as the struts 212, although in other embodiments the frame can comprise any number of rows depending upon the size of the struts and the particular application. Moving in a direction along the longitudinal axis 211 from the inflow end portion 206 toward the outflow end portion 208, the strut members 212 of each sequential row can be oriented in the opposite direction of the rows above and below it (or proximal and distal to the row). For example, beginning at row I at the inflow end portion 206, the struts 212 can be oriented in the direction of the outflow end portion 208 such that the apices 214 are offset from the junctions 218 in a direction toward the outflow end. At row II, the struts 212 can be oriented toward the inflow end portion 206 such that the apices 215 are offset from the junctions 218 toward the inflow end. This pattern can be repeated along at least a portion of the length of the frame 202.

This pattern can also result in the formation of substantially diamond-shaped enclosed areas or cells 220 defined by the intersection of four adjacent struts 212 located between two adjacent longitudinal struts 210. For example, referring again to FIG. 13, the representative cell indicated at 220A can be formed by the intersection of struts 212A and 212B of the strut row IV, and by the intersection of struts 212C and 212D of the strut row V. Thus, the cell 220A can be defined by the struts 220A-220D, the respective apices 214A and 215A, and the junctions 218A and 218B.

The frame 202 can comprise multiple tiers or arcades of such cells or partial cells along its length. Each tier can comprise a plurality of cells or partial cells positioned around the circumference of the frame. For example, in the illustrated embodiment the frame can include a tier A of partial cells 220 at the inflow end portion 206 of the frame, and two tiers B, C of complete cells 220. The frame can further comprise a fourth tier D of cells 250 (FIG. 12) located at the outflow end portion 208 and elongated in the downstream direction as compared to the cells 220. In the illustrated embodiment, the cells 250 can at least partially define a valve seat described in greater detail below, and are referred to as valve seat frame cells. The cells of each tier can be coupled together circumferentially at the junctions 218.

In certain embodiments, the frame 202 can further comprise one or a plurality of bend/flex/buckle/deformation-inducing features or means between the tiers A-D of cells 220/250. For example, referring again to FIG. 13, in the illustrated embodiment the longitudinal strut members 210 can comprise thinned, narrowed, or reduced thickness portions referred to herein as flex-inducing portions 222 about which the struts 210 are configured to flex/bend when subjected to, for example, off-axis forces. For example, the longitudinal struts 210 can comprise a first thickness $t_1$ in the circumferential direction, and the flex-inducing portions 222 can have a second thickness $t_2$ that is less than the thickness $t_1$. The longitudinal struts 210, and thus the frame 202, can be configured to bend/flex at the flex-inducing portions 222 to change the shape of the frame (e.g., in order to approximate the curvature of a body lumen). In certain embodiments, the flex-inducing portions 222 can be thinned in the circumferential direction but not in the radial direction such that the flex-inducing portions resist radial deformation in order to avoid reducing the diameter of the lumen.

In other embodiments, the thickness of the longitudinal struts at the flex-inducing portions can be reduced in one or both of the circumferential and radial directions, depending upon the particular application. In other embodiments, the flex-inducing portions 222 can be located at any location along the length of the longitudinal struts 210. The flex-inducing portions 222 can also be configured in a variety of other ways, such as springs (see FIG. 36).

The outflow end portion 208 can be configured to receive and retain a prosthetic valve, such as a prosthetic heart valve, as in the configurations described above. For example, in certain embodiments the struts at the outflow end can form a reduced diameter portion or valve seat configured to receive a prosthetic valve having a diameter smaller than the outer diameter of the docking station 200. For example, in the illustrated configuration the outflow end portion 208 can comprise a plurality of enclosed areas or cells of different shape and/or size nested within each other. The struts of the different cells can be oriented at various angles relative to each other and/or relative to the longitudinal axis of the frame to form structures having different diameters. In certain embodiments, such nested cells can be defined by a plurality of sets of nested or partially nested struts at the level of the row VII of struts (FIG. 12).

For example, in the embodiment of FIG. 12, the seventh row VII of struts can comprise a first plurality or set of strut members 228 and a second plurality or set of strut members 238. The struts 228 and 238, along with the struts 212, can form cells of two different sizes and shapes at the outflow end of the frame. For example, the struts 228 can be coupled at their first or inflow end portions to junctions 218. The struts 228 can extend generally in the downstream direction toward the outflow end of the frame. In the illustrated embodiment, the struts 228 can have a curved shape similarly to the struts 212, but can be longer than the struts 212. Struts 228 between pairs of longitudinal struts 210 can be coupled together at their second or downstream end portions to form apices 252. Thus, the struts 212 of the sixth row VI, the junctions 218 between the strut rows VI and VII, and the struts 228 can define inner frame cells referred to herein as valve seat frame cells 250. The valve seat frame struts 250 can have curved or tapered lobes extending in the inflow direction (e.g., defined by the struts 212) and lobes extending in the outflow direction (e.g., defined by the struts 228), with the widest point at the level of the junctions 218.

The struts 238 can form two types of cells alternatingly offset from each other and from the valve seat frame cells 250 around the circumference of the frame. More particularly, at the location of valve seat frame cells 250, pairs of struts 238 can extend from respective junctions 218 in the downstream direction, and can be joined together at apices 254 (indicated in phantom in FIG. 12). The struts 238 can be disposed circumferentially outward of the struts 228 on the junctions 218 such that the struts 228 are nested within the struts 238. Accordingly, at the location of valve seat frame cells 250, the struts 238 can define enclosed areas or cells 256 defined by the struts 238, the respective junctions 218, and the apices 254. The inner cells or valve seat frame cells 250 can be nested within the outer frame cells 256.

Valve seat frame cells 250 can be located between each pair of longitudinal struts 210, or between selected pairs of longitudinal struts. Stated differently, pairs of struts 228 can be located between each pair of longitudinal struts 210, or between selected pairs of longitudinal struts. For example, in the embodiment illustrated in FIG. 12, pairs of struts 228 are located between every other pair of longitudinal struts 210. Between pairs of longitudinal struts 210 without struts 228, the struts 238 are coupled to the struts 212 at the junctions 218 to define cells 258. The cells 258 can include the associated struts 238 and corresponding apex 254, and the upstream-extending struts 212 where those struts are coupled to the struts 238 instead of to struts 228. Accordingly, the cells 250 and 258 are angularly offset from each other around the circumference of the frame.

There can also be a pair of struts 238 for each pair of longitudinal struts 210, and a corresponding apex 254 between the longitudinal struts. Thus, in the embodiment illustrated in FIG. 12 there are more apices 254 than apices 252 (e.g., twice as many), and the angular spacing between apices 252 is greater than the angular spacing between apices 254. However, in other embodiments the number, position, and/or angular spacing between pairs of struts 228 and/or struts 238 can be varied depending upon the particular application. For example, in certain embodiments a valve seat frame cell 250 can be nested between each pair of struts 238 such that there are the same number of outer frame cells 256 and inner valve seat frame cells 250.

In certain embodiments, the struts of the different cells at the outflow end of the frame can be angled inwardly or outwardly relative to the longitudinal axis of the frame, and/or relative to the struts of the other cells. For example, with reference to FIG. 11, the frame 202 can define a first or outer diameter D1, and a second or inner diameter D2. The main body 204 of the frame 202 can have the outer diameter D1. For example, the inflow end portion 206, the outflow end portion 208, and the portion of the main body extending between the inflow end portion and the outflow end portion can each comprise the first diameter D1. Referring again to FIG. 12, the struts 228 of the valve seat frame cells 250 can be angled inwardly toward the longitudinal axis 211 such that the apices 252 can define the inner diameter D2. The reduced diameter structure formed by the struts 228 and their free apices 252 can be configured to receive an expandable prosthetic/transcatheter valve, such as any of the prosthetic/transcatheter heart valves described herein, and is referred to herein as a valve-receiving portion or valve seat 260. In certain embodiments, the free apices 252 can define a free outflow end portion of the valve seat 260, and the junctions 218 can be an inflow end portion of the valve seat.

In certain embodiments, the valve seat 260 can be coaxial with the frame 202, and the apices 252 of the valve seat 260 can be offset from the apices 254 along the longitudinal axis 211. For example, in the illustrated embodiment the apices 252 of the struts 228 can be offset from the apices 254 in the upstream direction such that the valve seat 260 is at least partially or wholly within the lumen of the frame 202. Where the apices 254 form the downstream-most end or outflow end of the frame, the free apices 252 can be offset from the downstream-most end in an upstream direction along the longitudinal axis 211 in a direction toward the inflow end portion 206. The distance between the valve seat 260 and the downstream end of the frame (e.g., as defined by the apices 254) can be selected to limit or minimize the amount or distance by which a prosthetic valve received in the valve seat extends beyond the outflow end of the frame once expanded in the valve seat 260. This, in turn, can minimize the amount by which the prosthetic valve extends into the right atrium RA when the docking station is implanted in the inferior vena cava IVC.

The sealing member 248 can be disposed on the outflow end portion 208 of the frame. Referring to FIGS. 11 and 12, in certain embodiments, the sealing member 248 can be a three-dimensional structure comprising a first or outer portion 262, a second or intermediate portion 264, and a third or inner portion 266, in which the inner portion is disposed radially inwardly of the outer portion and connected to the outer portion by the intermediate portion. The outer portion 262 can be disposed around the outer surface of the outflow end portion 208, and can be configured to seal against the native anatomy when the docking station is implanted in a patient. In certain embodiments, the apices 254 of the struts 238 can be disposed within a pocket, fold, or cuff defined by the outer portion 262, the intermediate portion 264, and/or the inner portion 266. In certain embodiments, the outer portion 262 can be sutured to the struts 238 and/or to the apices 254. In certain embodiments, the diameter of the outer portion 262 can be equal to, or substantially equal to, the diameter D1 of the frame when expanded to its functional size.

The inner portion 266 of the sealing member can be disposed at least partially within the lumen of the valve seat 260. For example, in certain embodiments the inner portion 266 can be positioned against the radially inward surfaces of the apices 252 of the struts 228. The inner portion 266 can be configured to form a seal between the valve seat 260 and a prosthetic valve received in the valve seat. In certain embodiments, the inner portion 266 can be secured to the struts 228, such as by suturing along the suture lines 268 shown in FIG. 12. In certain embodiments, any or all of the apices 252 and/or 254 can define openings, for example, to receive sutures or other attachments. In certain embodiments, the diameter of the inner portion 266 can be equal to, or substantially equal to, the diameter D2 of the valve seat 260.

The intermediate portion 264 can extend between the outer portion 262 and the inner portion 266. In certain embodiments, the intermediate portion 264 can be angled or flared relative to the longitudinal axis 211. For example, in the illustrated embodiment the diameter of the intermediate portion 264 can increase from the valve seat 260 in a downstream direction along the longitudinal axis 211 toward the outer portion 262. The angle of the intermediate portion 264 relative to the longitudinal axis 211 can depend on, for example, the longitudinal and radial positions of the apices 252 of the valve seat 260 relative to the apices 254 of the main body.

In certain embodiments, the sealing member 248 can comprise any of various woven fabrics, such as gauze, polyethylene terephthalate (PET) fabric (e.g., Dacron), polyester fabric, polyamide fabric, or any of various non-woven fabrics, such as felt, non-woven cotton or silk fibers, or any other material, woven or non-woven, having sealing properties.

In certain embodiments, a length of the sealing member 248 (e.g., of the exterior or outer portion 262) can be sized so that the sealing member seals the space between the docking station and the surrounding anatomy of the IVC (or the SVC) without obstructing blood flow into the IVC from the hepatic veins 17 (FIG. 1A). In certain embodiments, at least the portion of the frame 202 positioned adjacent the ostia of the hepatic veins and/or the renal vein can be free of sealing members, coverings, or other barriers so that blood can flow through the open, unobstructed cells of the frame into the interior of the docking station, and from there into the right atrium RA through a prosthetic valve received in the docking station as described in greater detail below.

In certain embodiments, the frame 200 can be made from a highly flexible metal, metal alloy, or polymer, such as a shape-memory material such that the frame is self-expandable. Examples of metals and metal alloys that can be used include, but are not limited to, nitinol and other shape memory alloys, elgiloy, stainless steel, etc. In certain embodiments, the frame 200 can be crimped for delivery in a delivery cylinder in a manner similar to that described below with reference to FIGS. 30-33. In other embodiments, the frame 200 can be formed from plastically-expandable materials such as nickel-chromium alloys, and can be expanded at the treatment site using a balloon or other expansion device. In yet other embodiments, the frame 200 can be mechanically-expandable.

Figure 14:
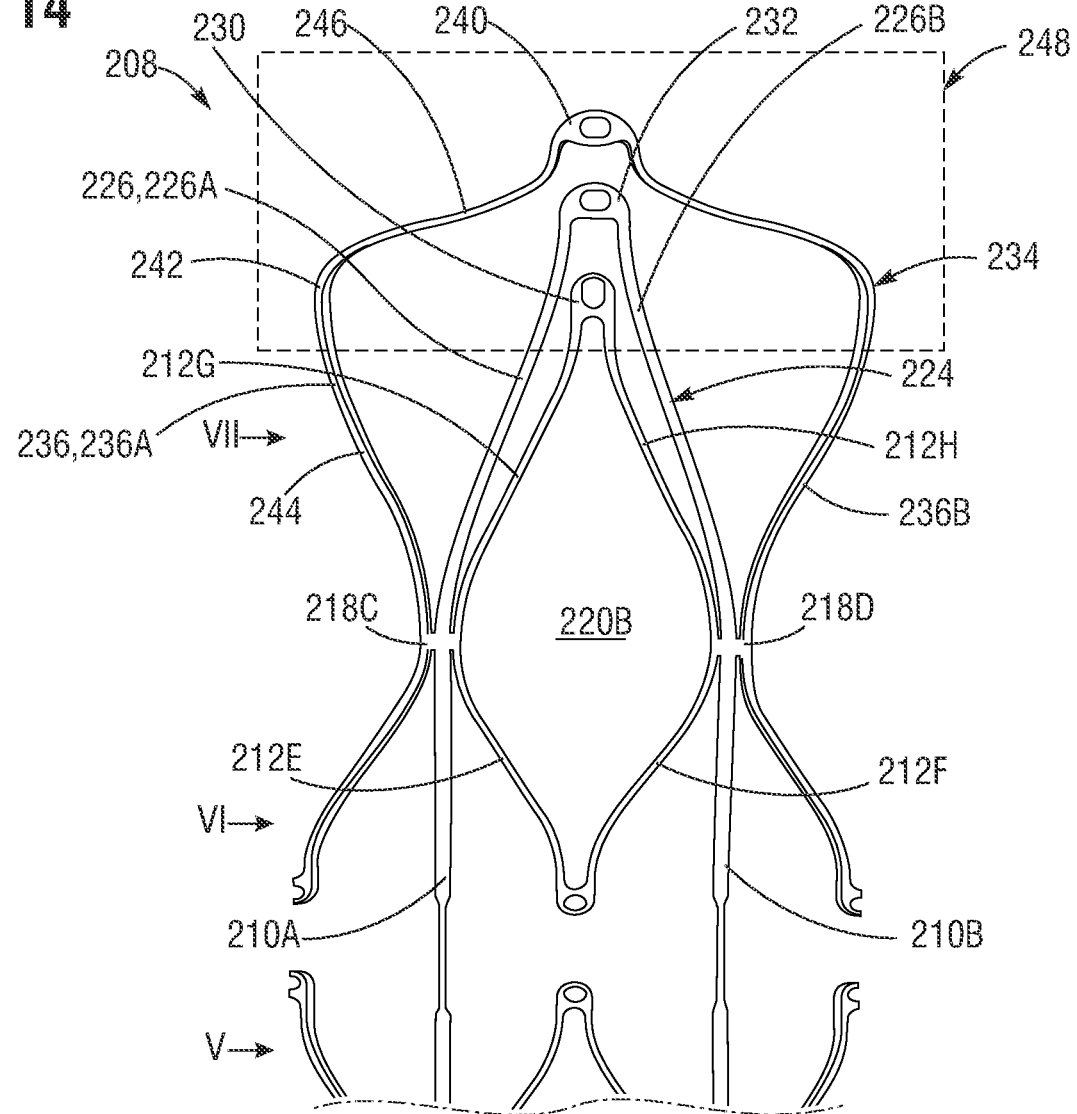
FIG. 14 is a magnified side elevation view of a portion of a docking station frame, according to another embodiment.
Figure 15:
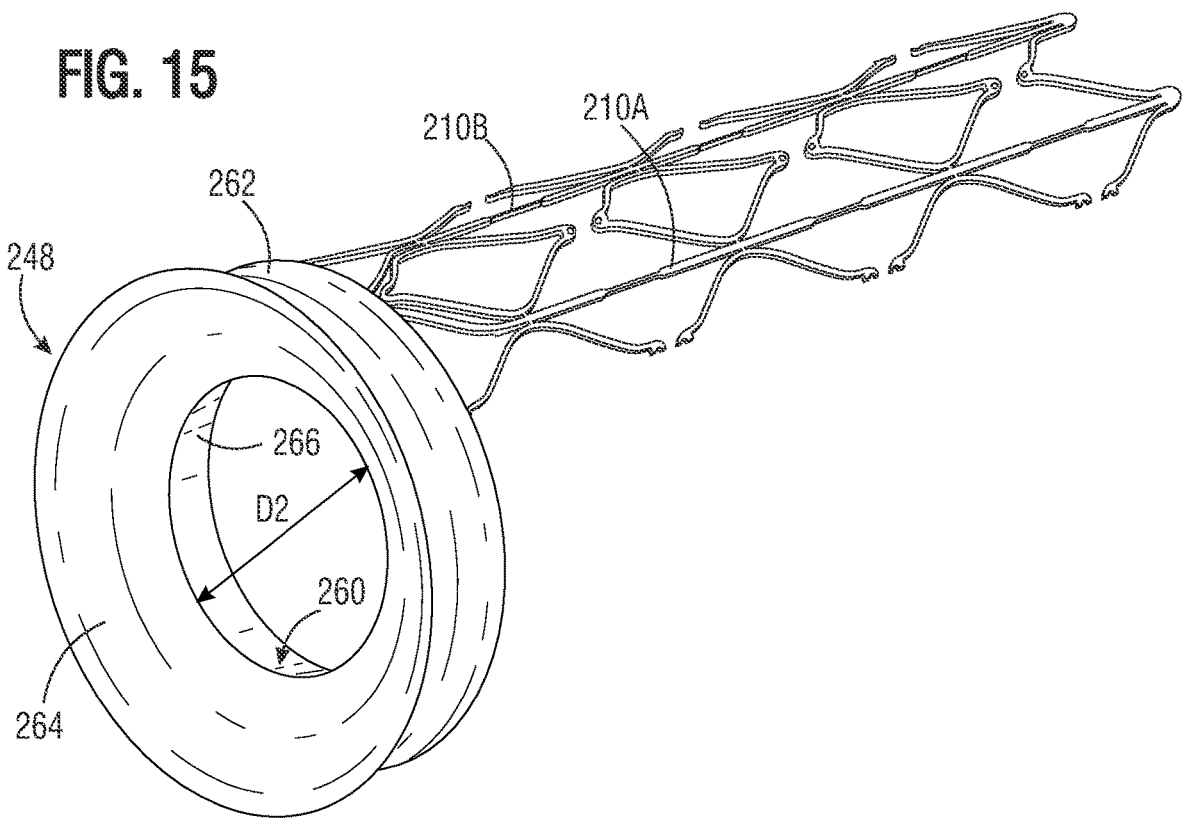
FIGS. 15 and 16 are perspective views of a representative portion of the frame of FIG. 14.
Figure 16:
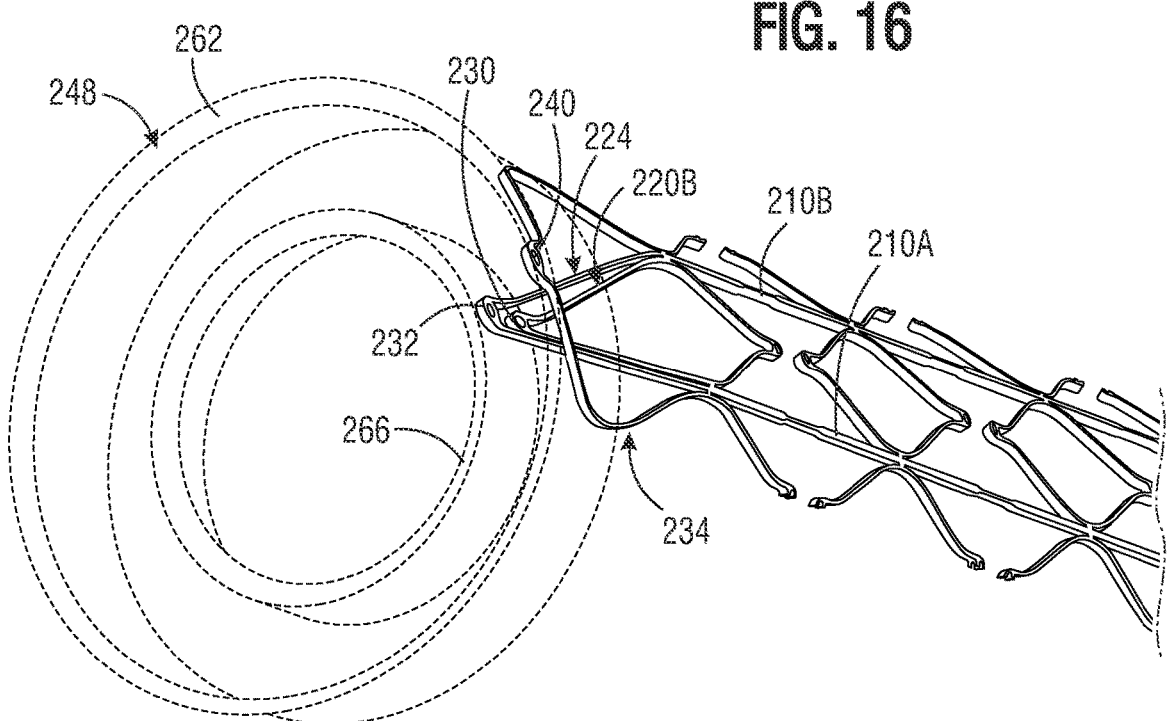

FIGS. 14-16 illustrate another configuration of the frame 202 in which the seventh strut row VII includes three nested pairs of struts at or between each pair of longitudinal struts 210. In FIGS. 14-16, only two longitudinal struts 210 and the associated cells are shown for purposes of illustration. FIG. 14 illustrates a portion of the outflow end portion 208. In FIG. 14, the struts 212E-212H define a valve seat frame cell 220B similar to the valve seat frame cells 250 and/or the cells 220 described above. In the illustrated embodiment, the struts 212G and 212H are longer than the struts 212E and 212F, although in other embodiments they may be the same length, longer, or shorter than the struts 212E and 212F. The struts 212E and 212G can be coupled to the longitudinal strut 210A at a junction 218C, and the struts 212F and 212H can be coupled to the longitudinal strut 210B at a junction 218D. The struts 212G and 212H can extend in the direction of the outflow end of the frame, and can be joined at an apex 230.

The valve seat frame cell 220B can be a first cell, inner cell, or valve seat frame cell nested at least partially within a second or intermediate cell 224 defined by a strut member 226A and a strut member 226B, part of a plurality or set of struts 226 disposed around the circumference of the outflow end portion 208 at the seventh row VII. For example, the strut 226A can extend from the junction 218C generally in the direction of the outflow end of the frame, and the strut 226B can extend from the junction 218D generally in the direction of the outflow end. The struts 226A and 226B can be joined together at an apex 232. Thus, the cell 224 can be defined by the struts 226A and 226B, the apex 232, the junctions 218C and 218D, and the struts 212G and 212H. In certain embodiments, the cells 224 can also be configured as valve seat frame cells as described below.

The frame can further comprise a set of third or outer cells disposed circumferentially around the frame at the seventh row VII (or at the outflow end portion, depending on the number of strut rows). An exemplary third or outer cell is shown at 234, and is defined by a strut 236A extending from the junction 218C and a strut 236B extending from the junction 218D. The struts 236A and 236B can be part of a plurality or set of struts 236 disposed around the circumference of the outflow end portion 208 at the seventh row VII. The struts 236A and 236B can be joined at an apex 240 located downstream or distally of the apices 230 and 232. Thus, the cell 234 can be defined by the struts 236A and 236B, the apex 240, the junctions 218C and 218D, and the struts 226A and 226B. Accordingly, the cells 224 can be disposed or nested within the cells 234, and the cells 220 such as 220B can be nested within the cells 224.

In some embodiments, the struts 236A and 236B can form a generally teardrop-shaped profile similar to the struts 226A and 226B, as in FIGS. 11 and 12. In other embodiments, the struts 236A and 236B can be curved, and can define shoulders or apices circumferentially offset from the apex 240, as in FIG. 14. For example, referring to FIG. 14 and beginning at the junction 218C, the strut 236A can comprise a curved first portion 244 that extends circumferentially and longitudinally away from the junction 218C. At an apex 242, a second portion 246 of the strut 236A curves circumferentially in the opposite direction, and continues to extend in the longitudinal direction to the apex 240. In the illustrated embodiment, the strut 236B can be configured in a similar manner. In certain embodiments, the apices 242 can comprise junctions where struts 236 are joined to adjacent struts 236 (see, e.g., FIG. 20). In certain embodiments, the struts 236A and/or 236B can be shaped similarly to the struts 226A and 226B forming a generally teardrop-shaped profile, as in the embodiment of FIGS. 11-13. In the illustrated embodiment, the apices/junctions 242 can be located closer to the apices 240 than to the junctions 218, although the apices 242 can be located at any longitudinal position between the junctions 218 and the apices 240.

Figures 17, 18:
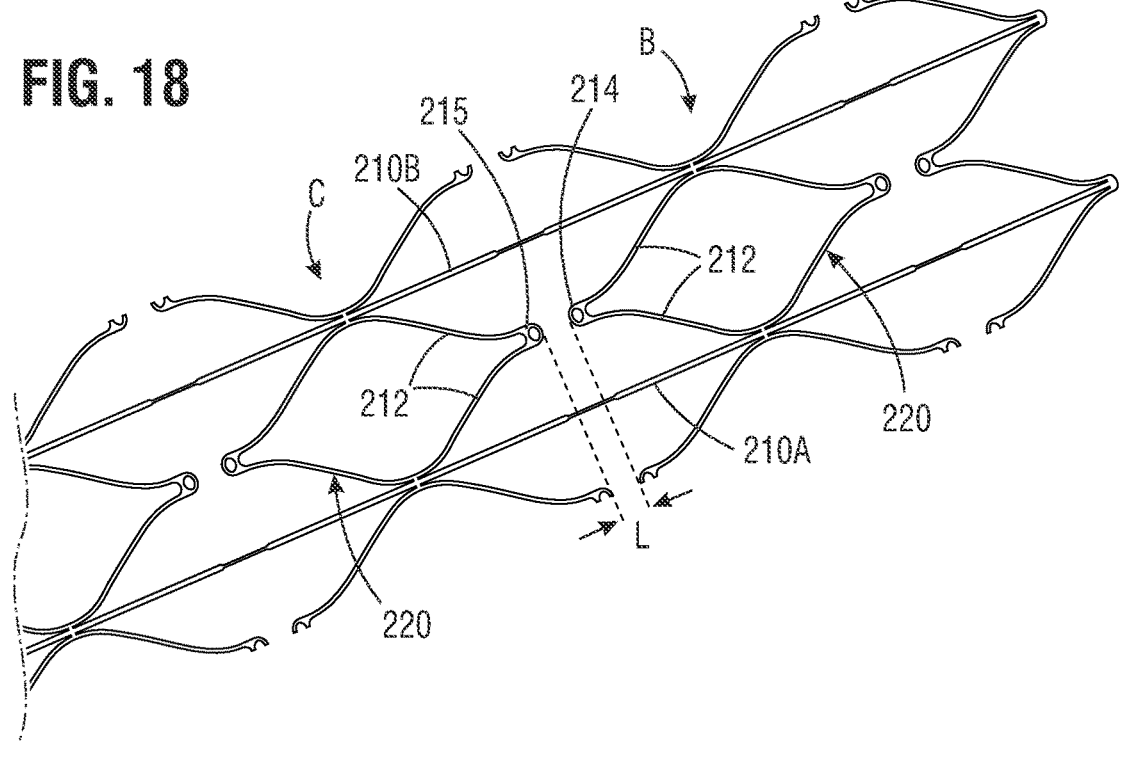
FIG. 17 is a perspective end view of a portion of the frame of FIG. 14.
FIG. 18 is a magnified perspective view of a portion of the frame of FIG. 14.

In certain embodiments, the struts of one or more of the different cells 220B, 224, and/or 234 at the outflow end of the frame can be angled inwardly relative to the longitudinal axis of the frame and/or relative to the other cells, similar to the embodiment of FIGS. 11-13 above. For example, with reference to FIGS. 15-17, the struts of the valve seat frame cells 220 of the seventh row VII and the struts of the valve seat frame cells 224 can be angled inwardly relative to the struts 236A/236B of the outer frame cells 234. FIG. 15 illustrates the portion of the frame shown in FIG. 14 coupled to the sealing member 248, and FIGS. 16 and 17 illustrate the outline of the sealing member 248 for purposes of illustration. Referring to FIGS. 16 and 17, the apices 230 and 232, and/or portions of the respective struts of the valve seat frame cells 220B and 224, can be positioned against the radially outward surface of the portion 266 of the sealing member 248, and can at least partially define the valve seat 260 and the inner diameter D2. The apices 240 of the outer frame cells 234 can be disposed outwardly of the apices 230 and 232, for example, against the radially interior surface of the outer portion 262 of the sealing member 248. In certain embodiments, the two sets of apices of the valve seat frame cells 220B and the cells 224 defining the inner diameter can provide additional retention force when a prosthetic heart valve is deployed in the valve seat. In other embodiments, the struts any of the cells 220B, 224, and/or 234 can also be angled outwardly relative to the longitudinal axis of the frame, or can extend parallel to the longitudinal axis, depending upon the particular characteristics desired.

As in the embodiment of FIGS. 11 and 12, the struts of the valve seat frame cells 220B and 224 of FIGS. 15-17 are configured such that the respective apices 230 and 232 are offset from the apices 240 of the outer frame cells 234 in the upstream direction (e.g., toward the inflow end 206) along the longitudinal axis of the frame. The location of the inner apices 230 and 232 can be configured according to the particular prosthetic valve to be implanted in the docking station such that the prosthetic valve extends beyond the outflow end portion 208 of the frame 202 by a specified amount or less, or is fully or substantially fully within the lumen of the docking station when expanded to its functional size. The angle and length of the struts can be selected to provide an inner diameter D2 of the valve seat 260 that will sufficiently frictionally retain the type and size of prosthetic valve to be implanted in the docking station. In certain embodiments, the valve seat 260 can be configured to accommodate any of a variety of sizes of prosthetic heart valve, such as by being configured to flex or bend radially outwardly to accommodate valves having different diameters.

In certain embodiments, elements of the frame 202 can be configured to reduce or prevent movement, translation, and/or rotation of the docking station once implanted in a body lumen. For example, referring again to FIGS. 11 and 12 any or all of the inflow apices 215 and/or the outflow apices 214 of the struts 212 can be configured to engage the tissue surrounding the docking station to prevent movement of the docking station. Referring to FIG. 18, in certain embodiments the struts 212, cells 220, and/or longitudinal struts 210 can be configured such that the outflow apices of one tier or arcade of cells 220 are spaced apart from the inflow apices of the subsequent tier or arcade of cells 220 in the downstream direction. For example, in FIG. 18 the outflow apices 214 of the cells 220 of tier B are axially offset from the inflow apices 215 of the cells 220 of tier C by a distance L. Accordingly, the tiers or arcades of cells 220 are also axially offset/spaced apart from each other along the longitudinal axis of the frame. Once implanted, the outflow apices 214 can engage the tissue of the body lumen to reduce or prevent downstream motion and/or rotation of the frame in the body lumen, and the inflow apices 215 can engage the surrounding tissue to reduce or prevent upstream motion and/or rotation of the frame in the body lumen. In certain embodiments, any, all, or select struts of the cells 220 can be angled radially outwardly such that the respective apices are positioned radially outwardly of the main body of the frame to engage the surrounding tissue when the frame is expanded to its function size.

The distance L can be specified according to any of various parameters, such as the body lumen in which the docking station is to be implanted, the size of the frame, the particular anatomy of the patient, etc. In particular embodiments, the length L can be from 0.1 mm to 20 mm, such 0.1 mm to 10 mm, 0.1 mm to 5 mm, 1 mm to 10 mm, 20 mm or less, 10 mm or less, 5 mm or less, etc. Free apices axially separated by a distance L within the ranges given herein can facilitate frame-tissue interaction/contact/engagement to reduce or prevent relative frame movement within the blood vessel. In certain embodiments, any of the prosthetic heart valve frame configurations described herein can also include axially-spaced cells and/or free apices configured as described above.

FIGS. 19-22 illustrate another embodiment of the frame 202 similar to the configuration illustrated in FIGS. 14-17.

Figures 19, 20:
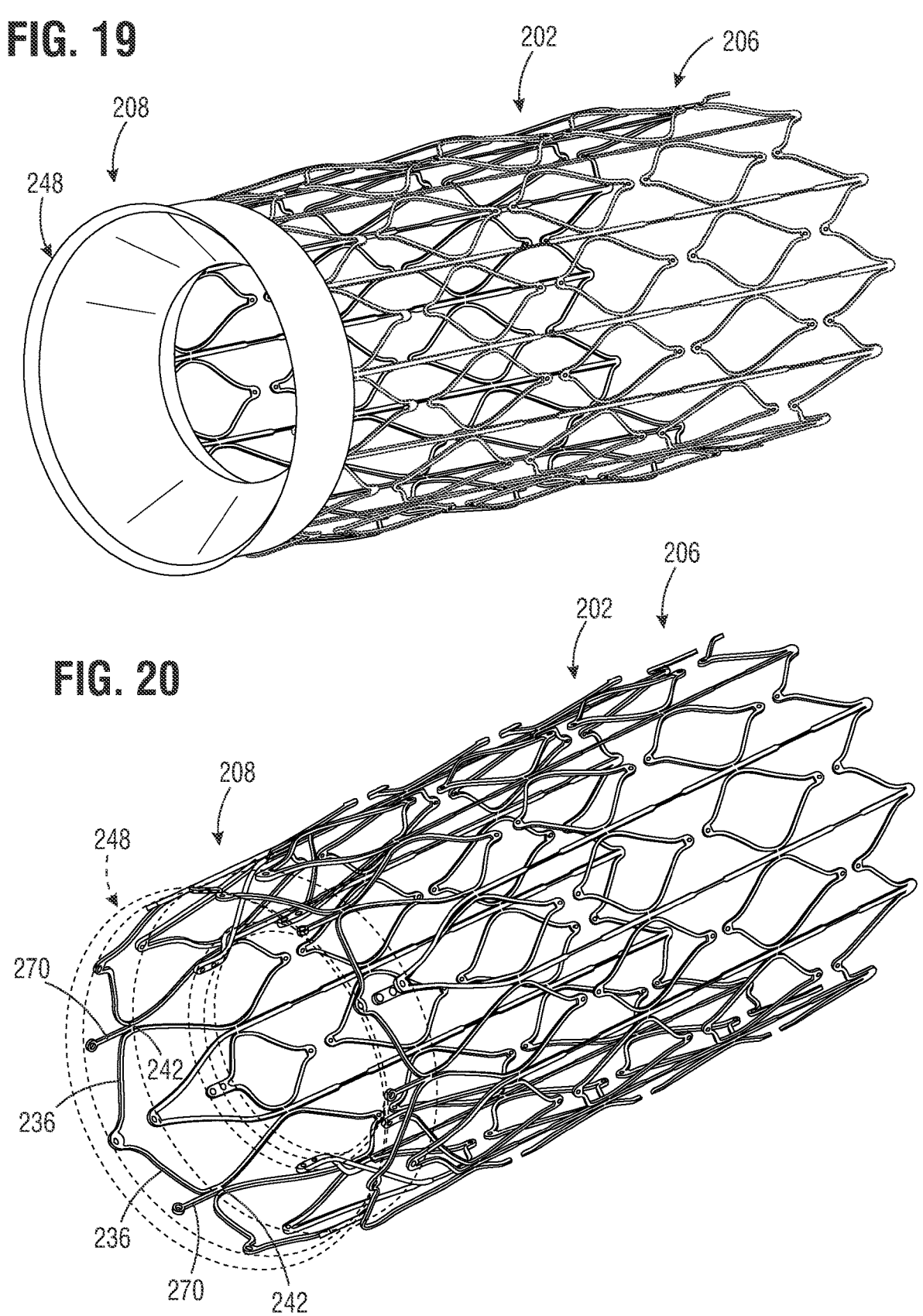
FIGS. 19 and 20 are perspective views of another embodiment of a docking station frame.
Figures 21, 22:
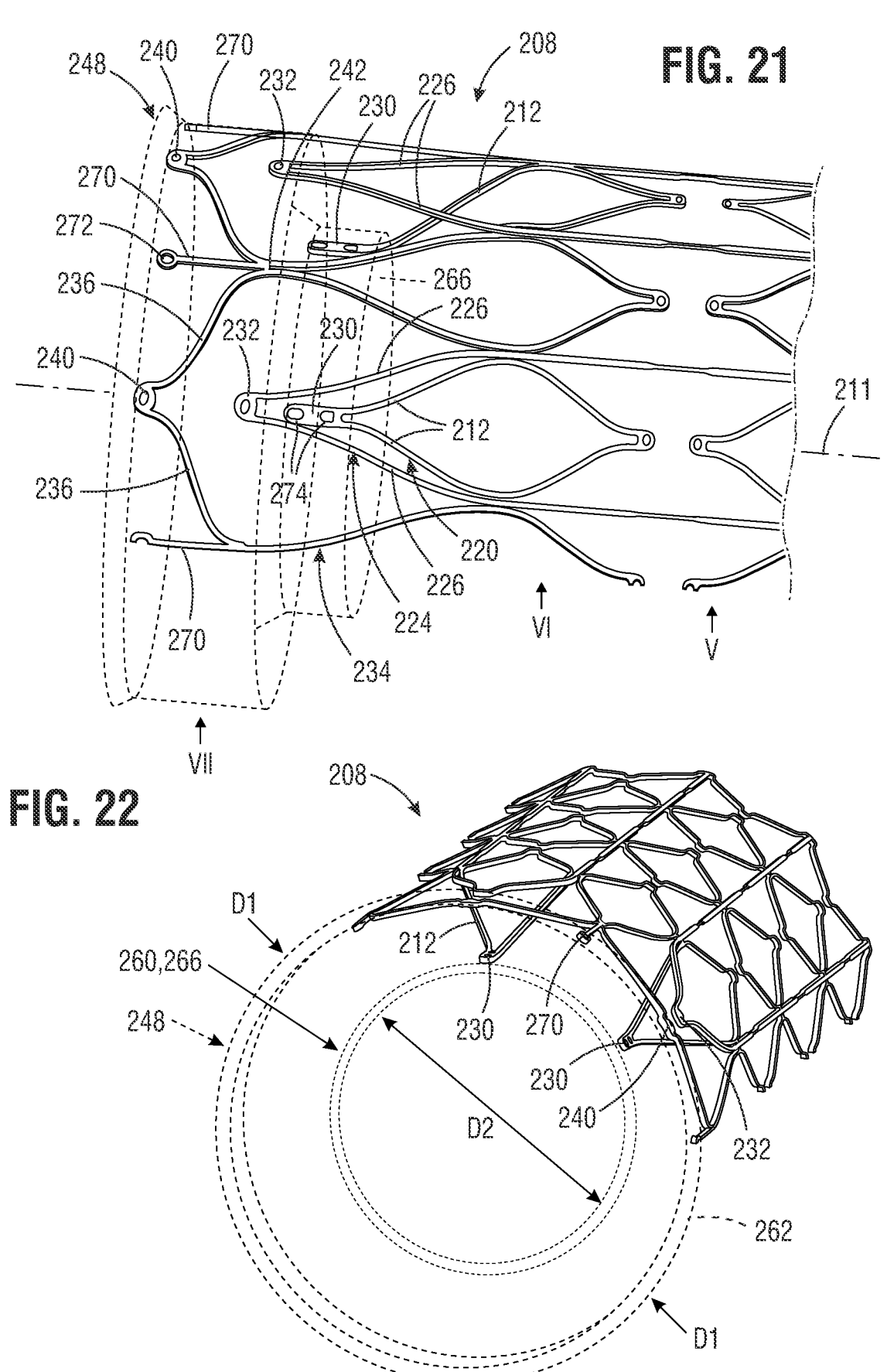
FIG. 21 is a magnified view of the outflow end portion of a representative portion of the frame of FIG. 19.
FIG. 22 is a perspective end view of the outflow end portion of the frame of FIG. 21.

FIG. 19 illustrates the complete frame 202 with the sealing member 248, and FIG. 20 illustrates the complete frame with the sealing member 248 rendered in dashed lines to better illustrate the outflow end portion 208. In the embodiment of FIGS. 19-22, the frame further includes struts/members/extension portions 270 extending in the downstream direction from the junctions 242 between struts 236. Referring to FIG. 21, which illustrates a portion of the outflow end portion 208, the struts 270 can have a length configured such that end portions 272 of the struts 270 are located at the same or nearly the same longitudinal/axial position as the apices 240 of the struts 236. This can increase the number of supports at the outflow end portion 208 of the frame for retaining the docking station in the native anatomy once deployed, and/or increase the number of attachment points for the sealing member 248.

For example, in the illustrated embodiment a strut member 270 can extend from each of the junctions 242 of the seventh row VII of struts, resulting in double the number of supports/attachment points/apices at the outflow end as the number of apices 230 and/or 232 of the valve seat 260. In certain embodiments, this can aid in retaining the docking station frame in place in the inferior vena cava IVC, where only a small length of the lumen may be available for anchoring (see FIGS. 37 and 38). In certain embodiments, this additional support can avoid the need to implant a separate, second frame at the outlet of the IVC to receive the prosthetic valve, as in certain existing systems. In other embodiments, struts 270 can extend from a selected number of junctions 242 at, for example, a specified angular spacing (e.g., two struts 270 angularly spaced by 180°, three struts 270 angularly spaced by 120°, four struts 270 angularly spaced by 90°, etc.).

Additionally, in the embodiment of FIGS. 19-22, the struts 212 of the seventh row VII are angled inwardly toward the longitudinal axis 211 as in the previous embodiments, but the struts 226 can extend generally parallel to the longitudinal axis such that they are disposed at the outer diameter D1. Accordingly, in certain embodiments the diameter D2 and the valve seat 260 (FIG. 22) can be defined by the outflow apices 230 of the struts 212 of the seventh row VII of the struts, while the struts 226 and the corresponding apices 232 remain at the outer diameter D1. As best shown in FIG. 21, in certain embodiments, the apices 230 of the struts 212 of the seventh row VII can be elongated relative to the embodiment of FIG. 13, and can define a plurality of apertures or openings 274 to facilitate, for example, attachment (e.g., by suturing) of the inner portion 266 of the sealing member 248. In certain embodiments, the struts 270, the junctions 242, and/or the apices 232 can provide points of contact or engagement between the frame 202 and the surrounding anatomy (e.g., in the relatively narrow portion of the IVC between the ostium and the hepatic veins), helping to anchor the docking station in the IVC and prevent movement of the docking station in the IVC once expanded. In the embodiment of FIGS. 19-22 in particular, the apices 232 and the junctions 242 can provide the same number of contact points between the frame and the surrounding tissue as the apices 240 and the struts 270. The apices 240 and the struts 270 can thus provide a first circumferential series of supports or contact points, and the apices 232 and the junctions 242 can provide a second series of supports or contact points offset axially from the first set in the upstream direction toward the inflow end.

As noted above, the apices 232 of the struts 226 can be disposed at or near the outer diameter D1 of the main body of the frame such that the valve seat 260 is defined by the valve seat frame cells 220 at the seventh strut row VII. In certain embodiments, the apices 232 can be attached to the outer skirt portion 262 of the sealing member 248. Referring again to FIG. 21, as noted above in certain embodiments the apices 232 can be located at or near the same axial position as the junctions 242 of strut members 236, increasing (e.g., doubling) the number of support or contact points between the frame and the surrounding anatomy at the axial position of the apices 232 and the junctions 242. Thus, in the embodiment of FIGS. 19-22 the frame 202 can comprise a total of twelve support/engagement/contact elements or points at the outflow end or edge of the frame in the form of the apices 240 and the end portions 272 of the struts 270. The frame can further comprise a total of twelve support/engagement/contact elements or points proximal or upstream of the outflow edge in the form of the apices 232 and the junctions 242. In certain embodiments, this structure can improve the anchoring of the outflow end portion 208 of the frame 202 in the ostium of the IVC. In certain embodiments, the outer diameter aspect of the outflow end portion can comprise a greater number of supports or contact points than the valve seat. In other embodiments, the frame can include any number of apices/junctions/contact points at the outflow edge and/or offset axially from the outflow edge, depending upon the particular characteristics desired.

Figure 23:
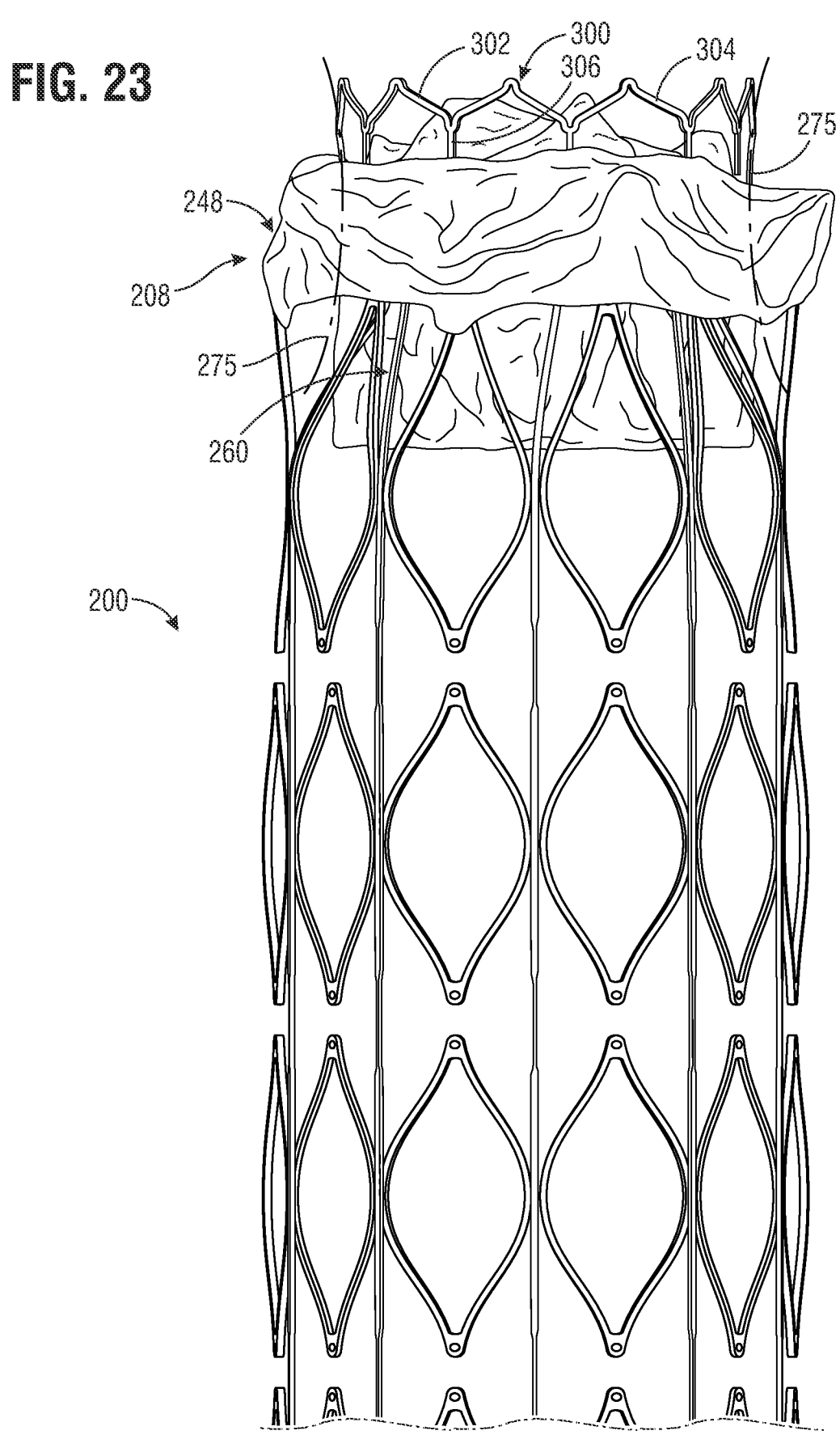
FIG. 23 is a side elevation view illustrating a prosthetic heart valve received in the docking station frame of FIG. 11.
Figure 24:
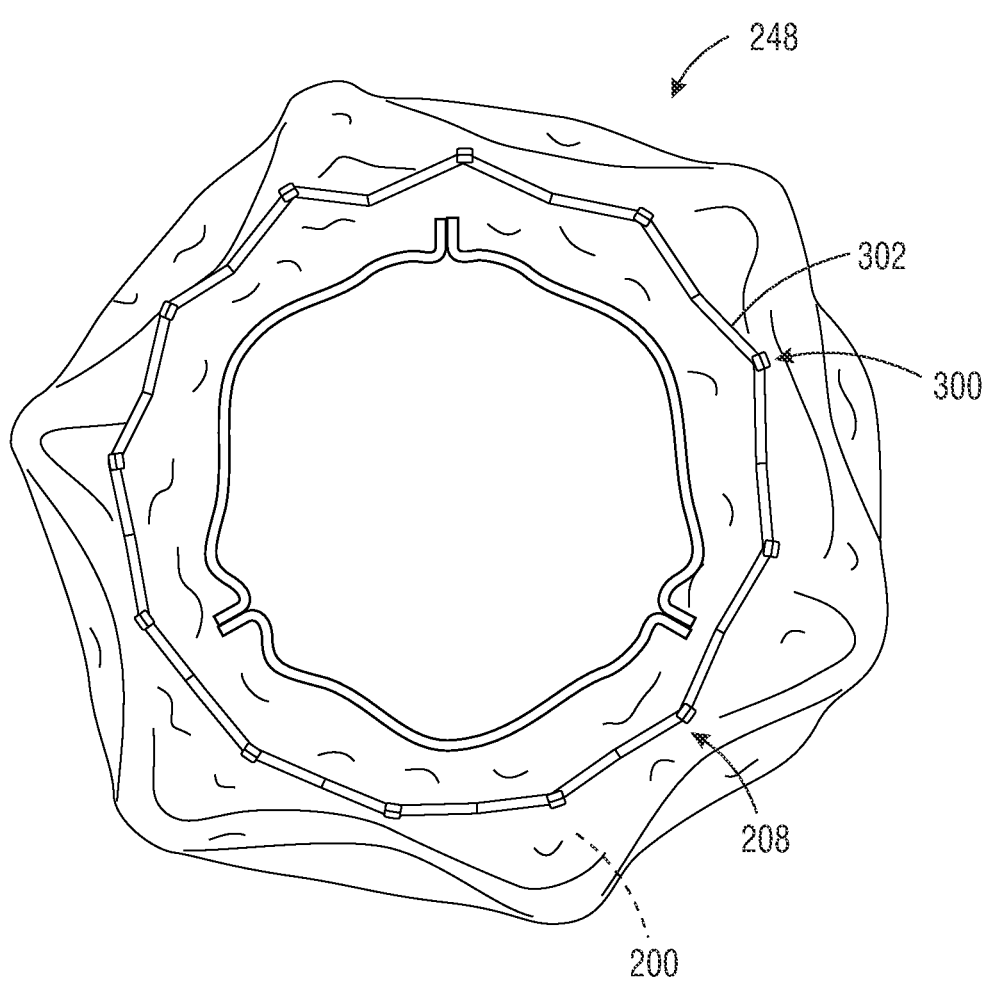
FIG. 24 is a top plan view of the docking station frame and prosthetic heart valve of FIG. 23.

The docking station embodiments described herein can be configured to receive any of a variety of prosthetic valves, including any of the prosthetic heart valves described herein. By way of example and without limitation, FIGS. 23 and 24 illustrate a prosthetic heart valve 300 received in the outflow end portion 208 of the docking station 200 as configured in FIGS. 11-13. In the illustrated embodiment, the prosthetic heart valve 300 is configured similarly to the balloon-expandable SAPIEN® 3 transcatheter heart valve available from Edwards Lifesciences Corporation, which is described in greater detail with reference to FIGS. 39-46.

In certain embodiments, the valve seat 260 and the constituent struts of the frame 202 can be configured to receive and engage the frame 302 of the prosthetic heart valve 300 such that it forms an hourglass-shaped profile when expanded to its functional size in the valve seat. For example, in certain embodiments the apices 252 of the valve seat frame cells 250 can be configured to contact/engage the prosthetic heart valve 300 between the first row I of valve frame struts (FIG. 43) and the fourth row IV of valve frame struts, which can constrain expansion of the middle portion of the prosthetic valve frame 302. The inflow and outflow struts of the frame 302, being longitudinally displaced from the apices 252, can expand to at or near the wider diameter D1 of the main body of the frame 202, or more. Thus, the mid-portion of the prosthetic valve frame 302 adjacent the valve seat 260 can have a smaller diameter than the inflow and outflow ends, resulting in the hourglass profile of the frame 302 indicated in FIG. 23 by dashed lines 275. In certain embodiments, the apices 252 can be positioned at or near the apex or inflection point of the curved hourglass profile of the THV frame 302. In certain embodiments, the prosthetic heart valve can be positioned in this manner relative to the struts/apices defining the valve seat 260 of any of the docking station embodiments described herein.

In certain embodiments, the hourglass shape of the prosthetic valve frame 302 can help to secure the prosthetic heart valve in the docking station and prevent the prosthetic heart valve from moving or becoming dislodged. For example, in one embodiment a SAPIEN® 3 prosthetic heart valve expanded within a docking station configured according to the embodiment of FIGS. 19-22 withstood an axially-applied force of 17 N (equivalent to 240 mm Hg, far higher than the physiological pressure of the right side of the human heart) without downstream displacement of the valve relative to the docking station.

In certain embodiments, the prosthetic heart valve 300 can be disposed entirely within the lumen of the docking station 200. In certain embodiments, a relatively small portion of the prosthetic heart valve 300 can extend beyond (e.g., downstream of) the outflow edge of the docking station frame 202. For example, referring to FIGS. 23, the struts 304 of the fifth row V of valve struts and portions of the struts 306 of the prosthetic valve extend beyond the outflow edge of the frame (see also FIG. 43), but this may vary in practice depending upon factors such as the type of valve, the size of the valve, the particulars of a patient's anatomy, the surgeon's preferred placement, etc.

Figure 25:
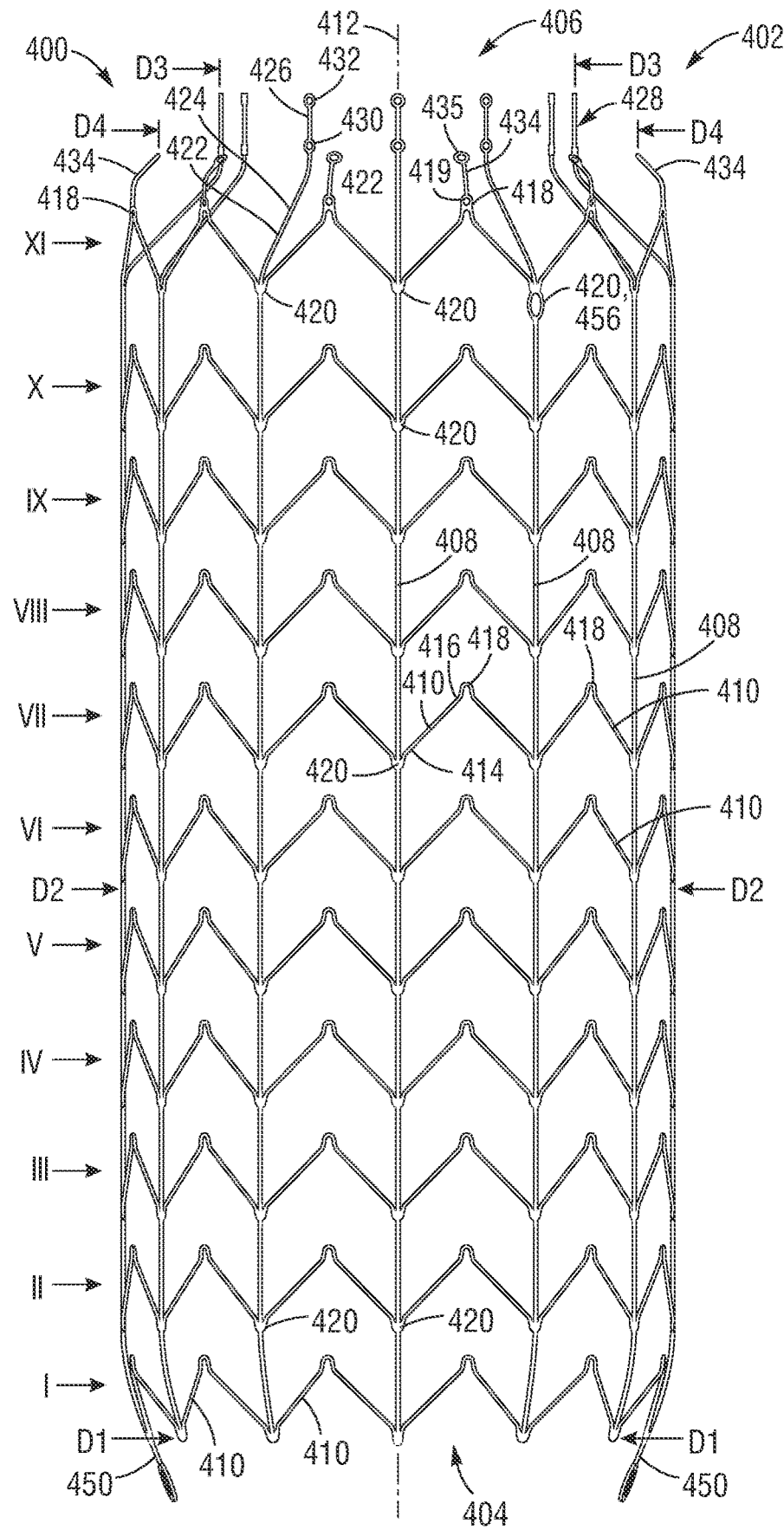
FIG. 25 is a side elevation view of another embodiment of a docking station frame.

FIG. 25 illustrates another embodiment of a radially collapsible and expandable frame 402 of a docking station 400 configured for implantation in a body lumen, such as in the inferior vena cava or the superior vena cava of the human heart. Only half of the total circumference of the frame is illustrated in FIG. 25 for clarity. The frame 402 can comprise an inflow end portion 404 and an outflow end portion 406. The frame 402 can comprise a plurality of longitudinal strut members 408 circumferentially spaced apart from each other around the frame 402. The frame can further comprise a plurality of circumferentially extending rows of struts 410 arranged alternatingly in a zig-zag pattern. The rows of struts 410 can be axially spaced apart from each other along the longitudinal axis 412 of the frame. For example, in the illustrated embodiment the frame 402 can comprise eleven rows I-XI of struts 410, with the first row I located at the inflow end portion 404 and the eleventh row XI located at the outflow end portion 406. The remaining rows can be axially spaced apart between the inflow end portion 404 and the outflow end portion 406. In the illustrated embodiment, the rows I-XI are equally spaced along the longitudinal axis 412, but the number of rows and/or the spacing between rows may be varied according to the particular characteristics desired.

The struts 410 are arranged such that first end portions 414 of the struts are coupled to longitudinal strut members 408 at junctions 420, and second end portions 416 of the struts are coupled to second end portions of adjacent struts 410 to form "free" apices 418. The free apices 418 can be arranged in circumferential rows, each row spaced apart longitudinal from the preceding and succeeding rows along the longitudinal axis 412. In the illustrated embodiment, the free apices 418 are oriented in the direction of the outflow end portion 406, but the apices can also be oriented toward the inflow end portion 404. When oriented in the downstream/outflow direction, the free apices 418 of the struts 410 can engage the tissue of the IVC and reduce or prevent downstream displacement or migration of the frame 402 post-implantation. In certain embodiments, the orientation of the free apices 418 in the downstream direction (and the lack of apices oriented in the upstream direction) can also facilitate proximal/upstream motion of the frame through the IVC, allowing recapture of the frame and/or retrieval/removal of the docking station from the patient in certain embodiments. In yet other embodiments, the frame 402 can include cells similar to the cells 220 of FIG. 12 formed from the struts 410.

In the illustrated embodiment, the struts 410 of the first row I at the inflow end 404 and associated portions of the longitudinal struts 408 are angled inwardly toward the longitudinal axis 412 such that the diameter D1 of the inflow end is less than the diameter D2 of the main body of the frame. In the illustrated embodiment, beginning at the junctions 420 of the second row II, the longitudinal struts 408 can begin curving radially inwardly moving in an upstream direction toward the inflow end 404. The struts 410 of the first row I coupled to the angled portions of the longitudinal struts 408 can thus be angled inwardly as well. In certain embodiments, angling the struts inwardly toward the longitudinal axis at the inflow end and/or the outflow end can reduce the force applied to the surrounding anatomy by the struts and/or their apices, thereby reducing the risk of tissue damage and injury.

The outflow end portion 406 can comprise a plurality of struts 422 coupled to the junctions 420 of the eleventh row XI of struts. The struts 422 can extend in a downstream direction, and can be angled radially inwardly toward the longitudinal axis 412. More particularly, the struts 422 can comprise first portions 424 coupled to the junctions 420 and angled inwardly toward the longitudinal axis, and second portions 426 extending from the first portions 424 parallel, or substantially parallel, to the longitudinal axis 412. The second portions 426 of the struts 422 can thereby define a valve-receiving portion or valve seat generally indicated at 428, which can be coaxial with the frame 402 and configured to receive a prosthetic valve. The valve seat 428 can have a diameter D3 less than the diameter D2 of the main body of the frame 402. The second portions 426 of the struts 422 can further comprise one or a plurality of apertures and/or openings, such as openings 430 and 432 spaced apart along the portions 426. In certain embodiments, the free end portions (e.g., at 432) of the struts 422 can define a downstream-most end of the frame.

Figure 27:
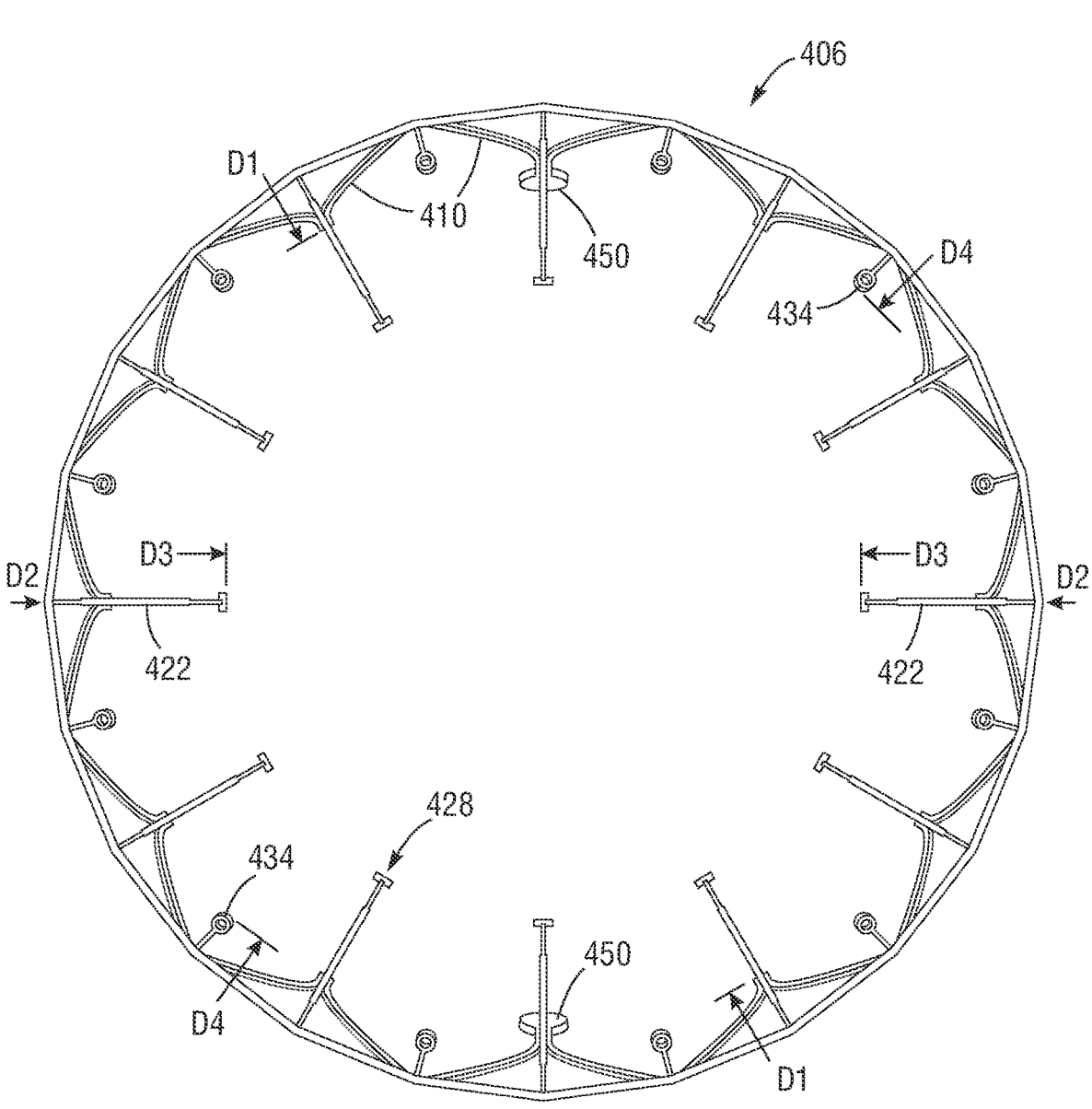
FIG. 27 is a top plan view of the docking station frame of FIG. 25.

In certain embodiments, the struts 410 of the eleventh row XI can further comprise struts 434 extending from the apices 418 and curving radially inwardly. The end portions of the struts 434 can comprise openings 435, and can define a diameter D4 that is less than the diameter D2 and greater than the diameter D3. FIG. 27 is an end view of the outflow end portion 406 illustrating the various diameters formed by the inwardly curved struts 410 at the inflow end, the main body of the frame 402, the struts 422, and the struts 434.

Figure 26:
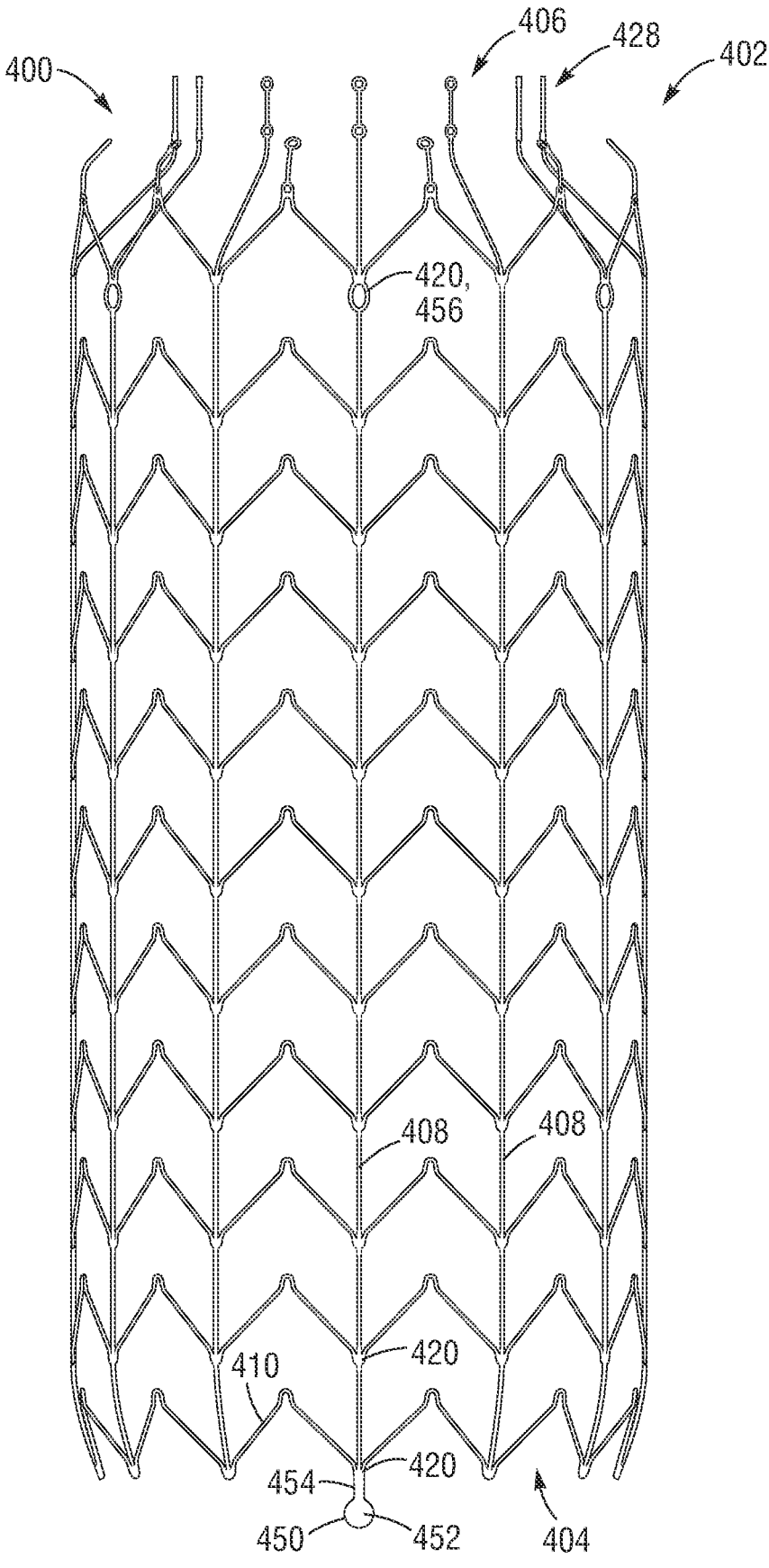
FIG. 26 is a side elevation view of the docking station frame of FIG. 25 rotated by 90°.
Figure 79:
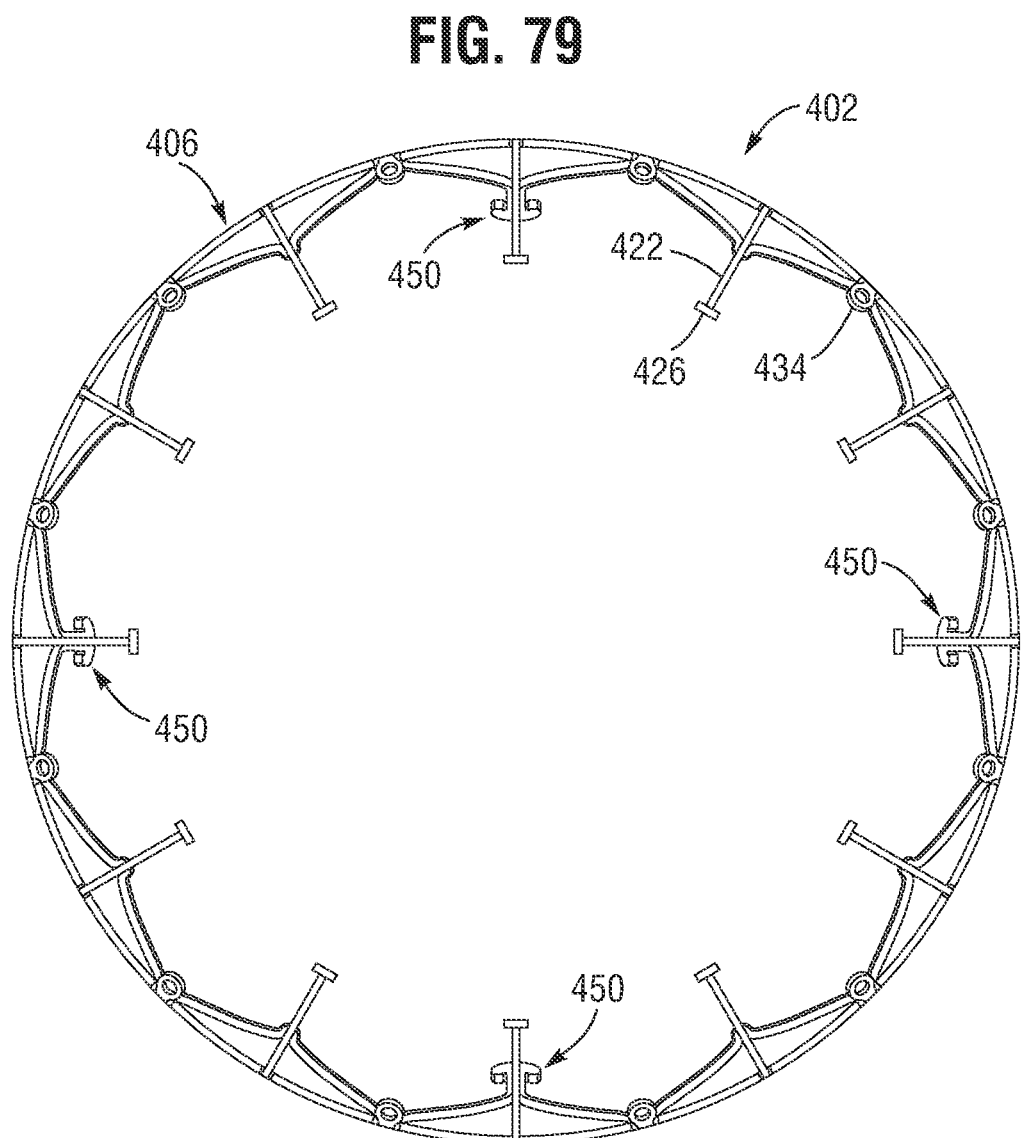
FIG. 79 illustrates another configuration of the frame of FIG. 50 including four coupling members.

Referring to FIGS. 25 and 26, in certain embodiments the frame can comprise one or a plurality of coupling members 450 extending from junctions 420 of the first strut row I in the upstream direction away from the junctions. As best shown in FIG. 26, in the illustrated embodiment the coupling members 450 can comprise round, circular, and/or substantially circular members/portions/tabs/plates/pedals 452 coupled at the ends of respective members or struts 454. As shown in FIGS. 25 and 26, the struts 454 and the round portions 452 can be angled radially inwardly similar to the struts 410 at the first row I and the inflow end portions of the longitudinal struts 408. The struts 454 and the round portions 452 can extend beyond the struts 410 at the inflow end of the frame, and can be configured for coupling to a delivery system such as the delivery apparatus 500 of FIG. 30. In the illustrated embodiment, the frame 402 can comprise two coupling members 450 angularly spaced apart from each other around the circumference of the frame by 180°. However, the frame can include any number of coupling members (e.g., three, four, six, eight, 12, etc.) spaced at any angular spacing. For example, FIG. 79 illustrates another configuration of the frame 402 including four coupling members 450 circumferentially spaced apart from each other by 90°.

Figure 28:
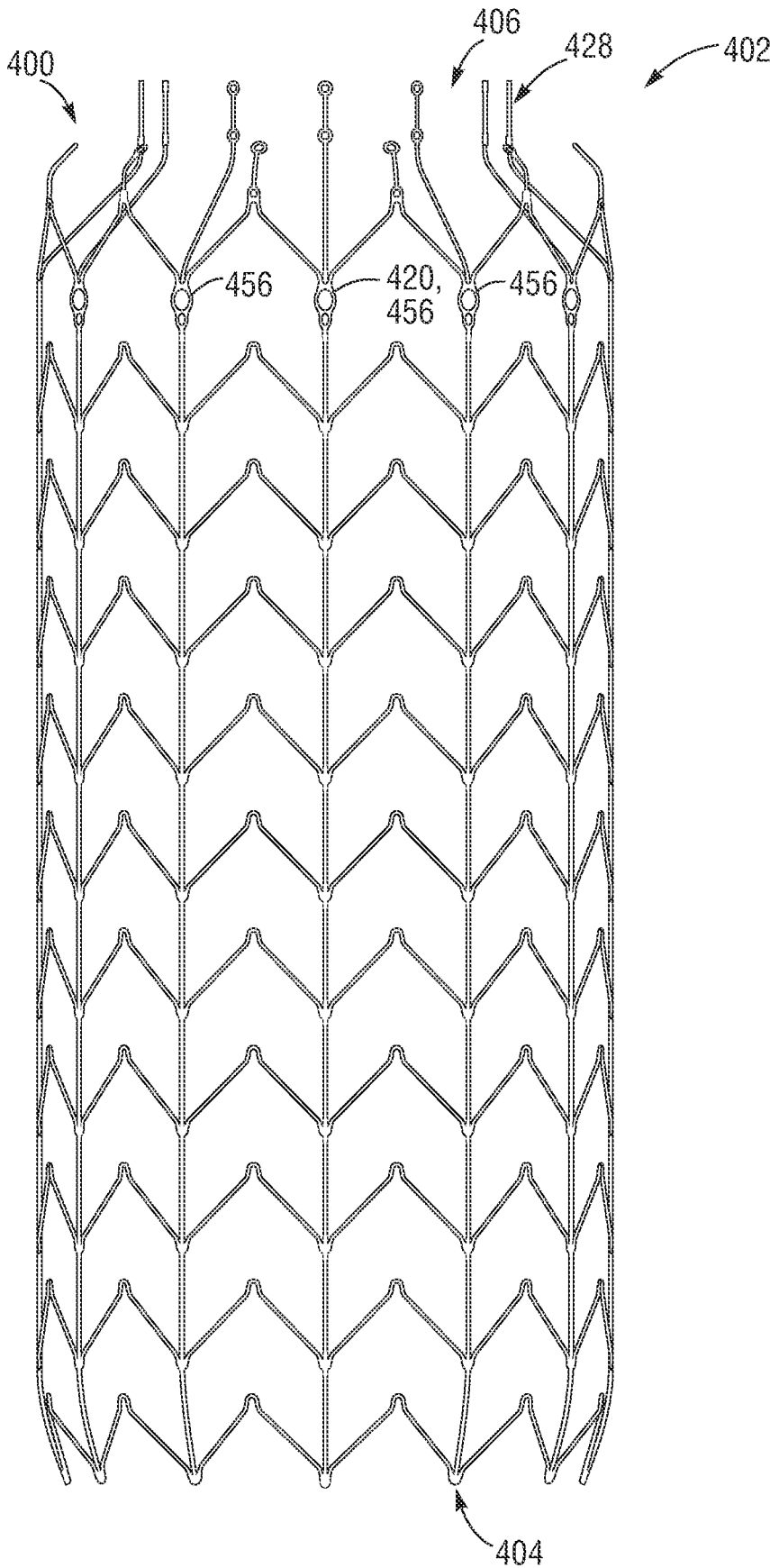
FIGS. 28 and 29 are side elevation views of embodiments of docking station frames including radiopaque markers.
Figure 29:
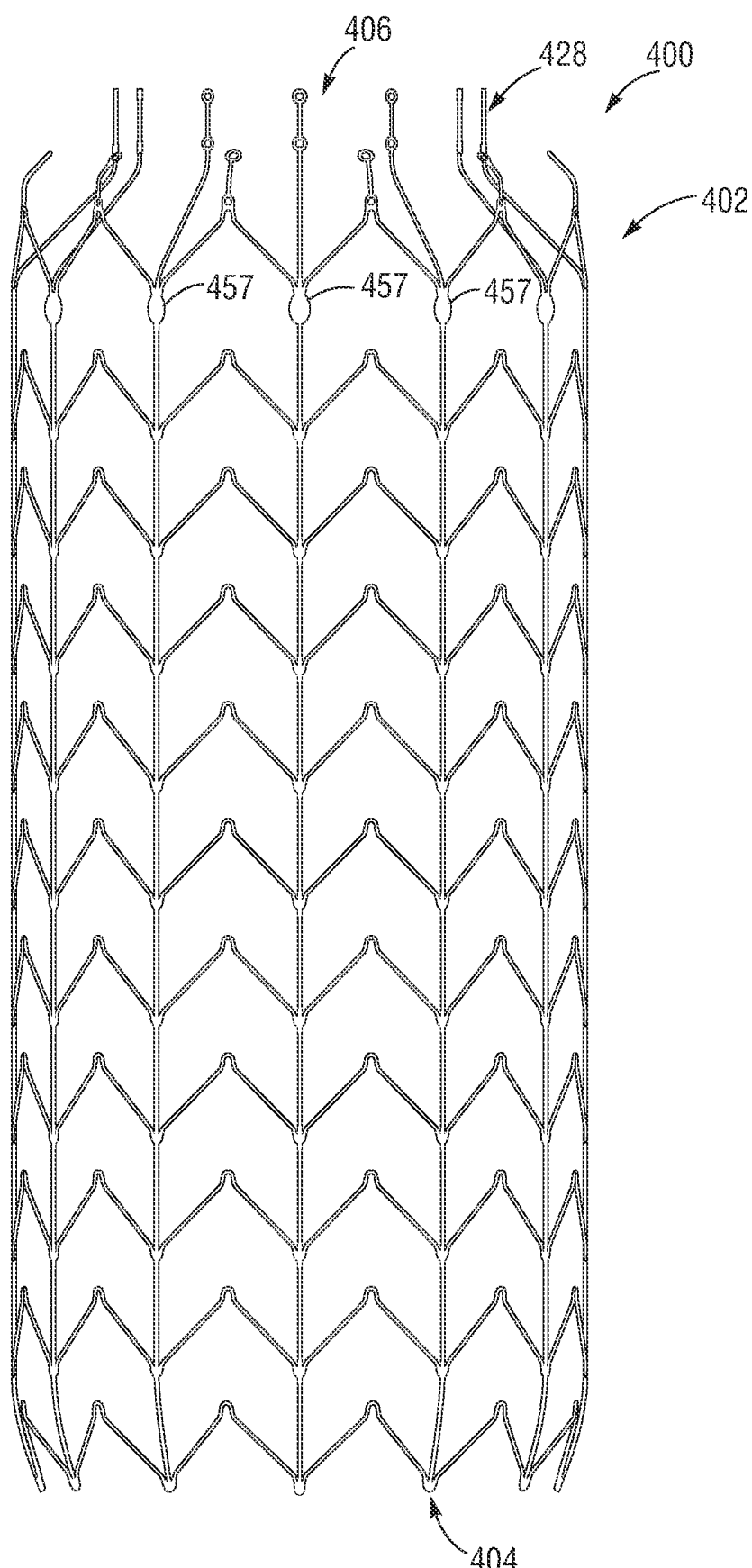

The frame 402 can also include one or a plurality of markers or indicators configured to indicate the rotational position of the frame in vivo when imaged fluoroscopically, radiographically, echocardiographically, etc. For example, certain of the junctions 420 of the frame can include marker features configured as openings, rings, or solid (e.g., metallic) regions configured to be readily discernable using any of a variety of imaging or diagnostic tools. In the embodiment illustrated in FIGS. 25-27, certain of the junctions 420 at or near the outflow end portion 406 (e.g., of the eleventh strut row XI) can comprise openings/rings/hoops 456 (FIG. 26) configured to function as, or incorporate, indicators/markers. The openings 456 can be spaced apart circumferentially around the frame at any interval. For example, the frame can include a plurality of openings 456 circumferentially spaced apart by 180°, 120°, 90°, 30° (as in the embodiment of FIGS. 25-27), 15° (in which each of the 24 junctions 420 comprises an opening 456, as illustrated in FIG. 28), or any other angular spacing.

In certain embodiments, the indicators can be configured as solid regions, as noted above. For example, FIG. 28 illustrates another embodiment of the frame 402 in which the indicators are solid disks/plates/medallions 457 integrally formed or separately attached to the frame at junctions 420. The indicators can also be positioned at any other location on the frame, including at different or multiple locations along the longitudinal axis 412 (FIG. 25), including at the inflow end portion 404.

Figure 33:
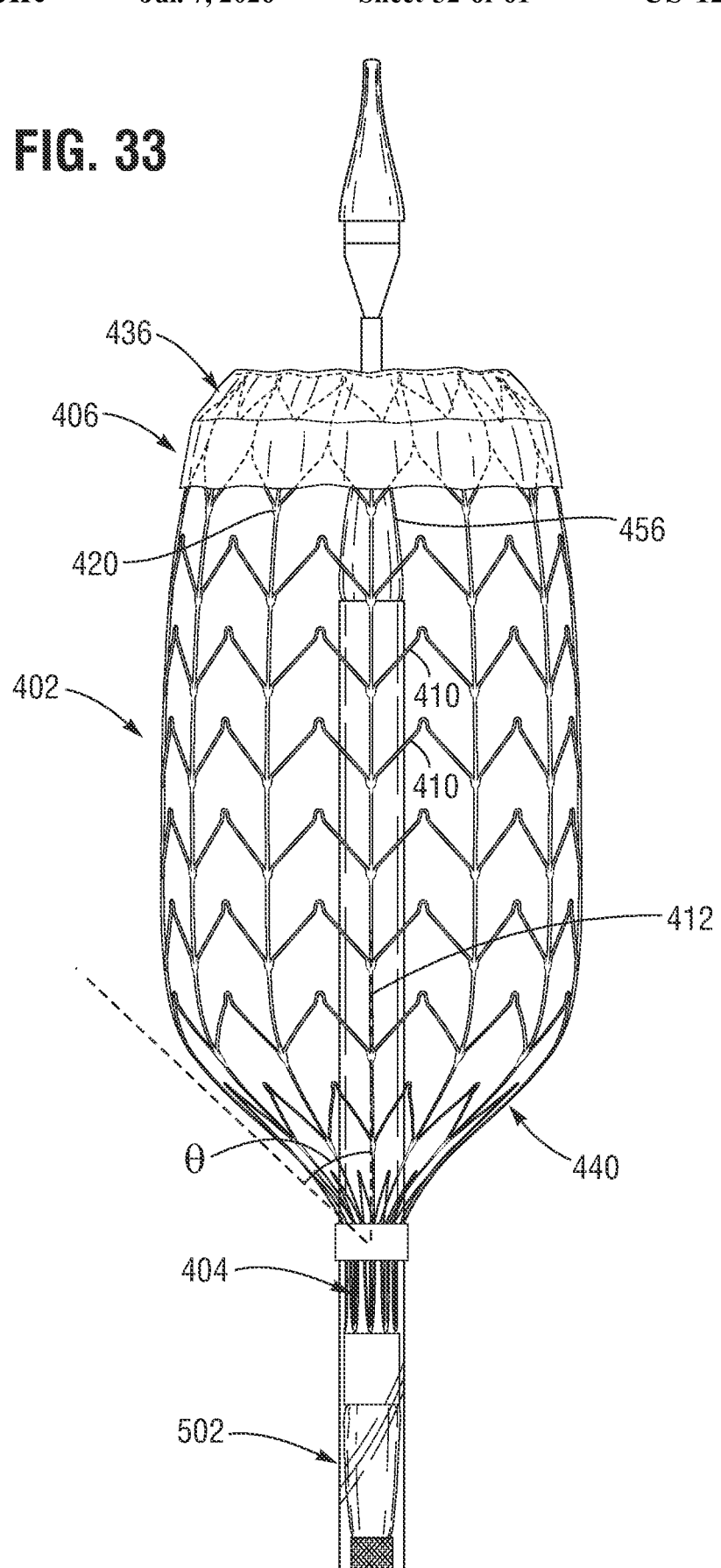
FIG. 33 illustrates the docking station frame of FIG. 25 in a partially deployed state.

In certain embodiments, a sealing member can be disposed on the outflow end portion 406, such as the representative sealing member 436 shown in FIG. 33. In certain embodiments, the sealing member 436 can cover at least a portion of the exterior surfaces of struts 422, the struts 410 of the eleventh row XI, and the struts 434. In certain embodiments, the sealing member 436 can comprise an inner portion disposed radially inwardly of the struts 422 and coupled to the struts 422 (e.g., by suturing), an outer portion covering outer surfaces of the struts 422, the struts 410 of the eleventh row XI, and the struts 434, and an intermediate portion extending between the inner portion and the outer portion similar to the embodiments described above, although the sealing member may have any configuration that facilitates sealing between a prosthetic valve and the valve seat 428, and/or between the outer surface of the frame 402 and the surrounding anatomy at the outflow end portion of the frame. The sealing member 436 can be coupled/secured/attached to the frame for example, by suturing through the various strut openings 435, 430, 432, and/or the openings 419 in the apices 418 of the struts of the eleventh row XI (FIG. 25).

Figures 30, 31:
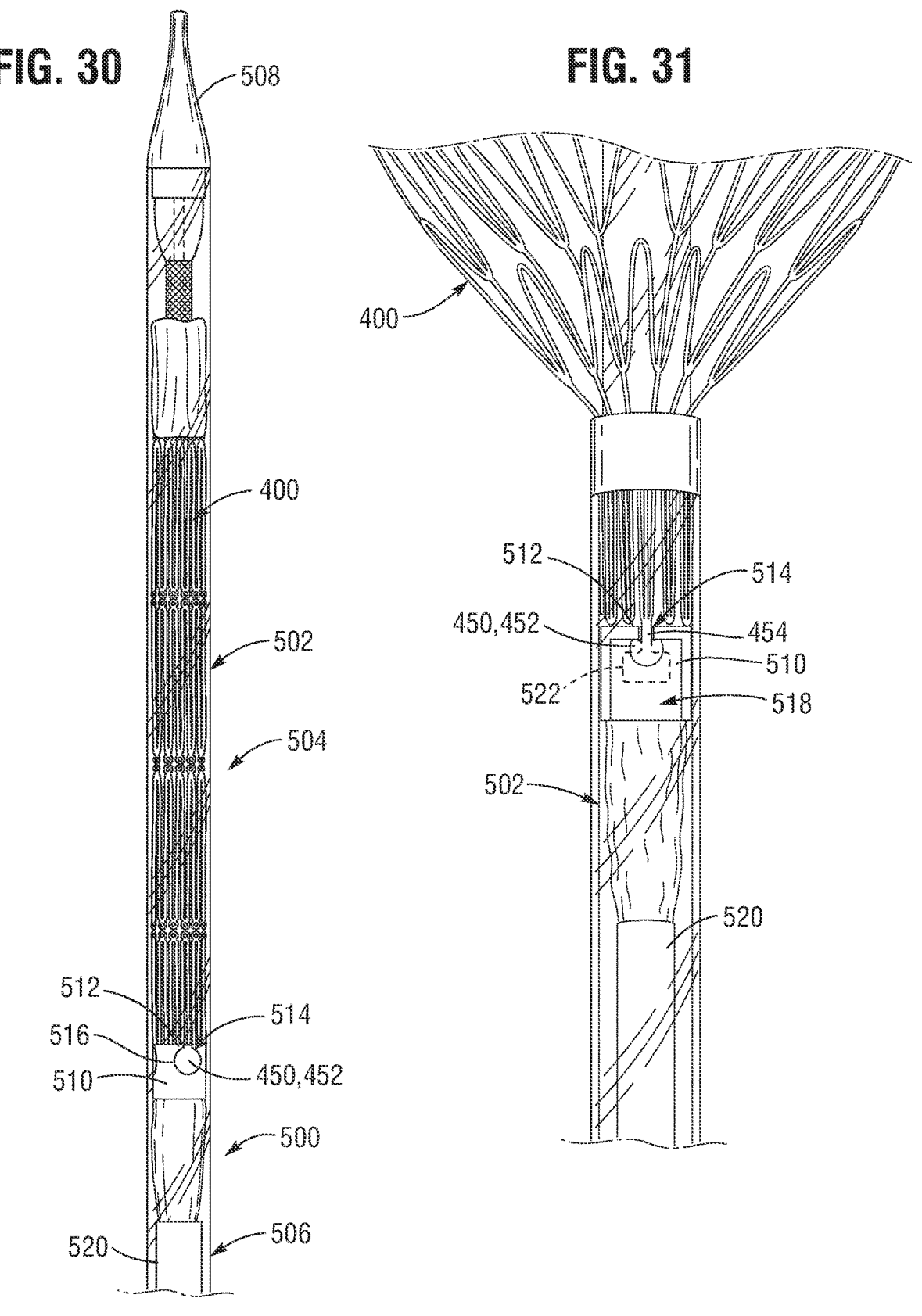
FIG. 30 is a top plan view of a distal end portion of a delivery apparatus including the docking station frame of FIG. 25 retained in a radially collapsed state in a delivery capsule.
FIG. 31 is a magnified view of the distal end portion of the delivery apparatus of FIG. 30 showing the docking station frame in a partially deployed state.

As noted above, the docking station embodiments described herein can be radially collapsed to a collapsed or crimped configuration for delivery to the treatment site through a patient's vasculature. In certain embodiments, the docking station frame embodiments described herein can be made of a shape memory material, such as the nickel titanium alloy known as Nitinol, Elgiloy, or stainless steel, or combinations thereof, that allows the frame to be compressed to a reduced diameter for delivery in a delivery apparatus and then causes the frame to expand to its functional size inside the patient's body when deployed from the delivery apparatus. FIG. 30 illustrates the docking station 400 in the collapsed delivery configuration inside a sheath or capsule 502 at the distal end 504 of a delivery apparatus 500. The delivery capsule 502 can be coupled to the distal end of a first catheter or shaft 506, and can comprise a nosecone 508 positioned at the distal end of the delivery capsule 502.

Figure 32:
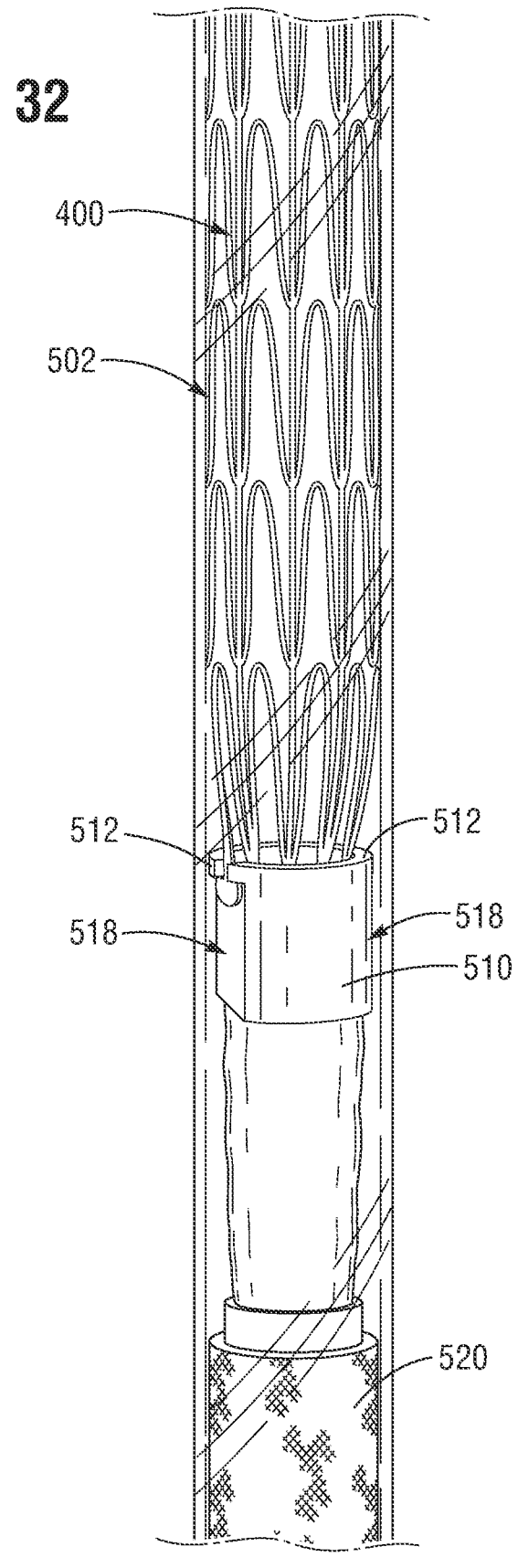
FIG. 32 is a magnified view of a portion of the delivery capsule of FIG. 30 illustrating coupling of docking station frame to the delivery apparatus.

In the illustrated embodiment, the delivery apparatus 500 can comprise a coupling or retaining member or coupling assembly generally indicated at 510 configured to engage and retain the coupling members 450. For example, in the illustrated embodiment the retaining member 510 can be coupled to a distal end of an inner or second catheter or shaft 520 disposed coaxially within the shaft 506 and/or the delivery capsule 502. The retaining member 510 can comprise a lip, projection, or flange 512 extending radially outwardly relative to the longitudinal axis of the shaft 506. In certain embodiments, the flange 512 can define a groove or recess 514 configured to receive the strut portion 454 of the coupling member 450 (see also FIG. 26). The round portion 452 of the coupling member 450 can be received in a corresponding recess or opening 516 defined in the exterior of the retaining member 510. The round portion 452 of the coupling member 450 can be wider than the recess 514, and can contact the flange 512, thereby preventing distal motion of the docking station 400. In the embodiment illustrated in FIG. 30, the retaining member 510 is cylindrical, and comprises three or more flanges 512, grooves 514, and openings 516 corresponding to the number of coupling members 450 of the frame, although other configurations are possible. FIGS. 31 and 32 illustrate another embodiment in which the retaining member 510 comprises a cylindrical member having two flat surfaces 518 on opposite sides of the member 510 configured to receive two coupling members 450. The flanges 512 can be located at the distal ends of the flat surfaces 518, and the recesses 514 can be defined in the respective flanges 512.

In certain embodiments, because the coupling members 450 are angled radially inwardly relative to the longitudinal axis 412 of the docking station, the coupling members can be biased radially inwardly against the retaining member 510 of the delivery apparatus. Thus, the coupling members 450 can be restrained from moving in the radial direction by the delivery capsule 502 and the retaining member 510. At least distal motion along the longitudinal axis of the delivery apparatus can be restrained by the members 450 contacting the flanges 512.

In certain embodiments, the delivery capsule 502 can be at least partially transparent. This can allow the physician to directly view the docking station 400, and the engagement between the coupling members 450 and the retaining members 510 in particular, during loading as the docking station is retracted into the delivery capsule and crimped to the delivery configuration. In certain embodiments, the delivery capsule 502 can be made from polymeric materials such as polymethylmethacrylate, polycarbonate, polystyrene, polyethylene terephthalate (PET), polyethylene such as high-density polyethylene (HDPE), low-density polyethylene, or any other biocompatible transparent or translucent natural or polymeric material. This can eliminate the need to view the docking station by x-ray radiography during the loading process, as is commonly required with many existing systems which use opaque delivery capsules. Transparent capsules similar to capsule 502 can also be used in combination with other types of stents and/or prosthetic valves, such as self-expanding stents and valves.

In certain embodiments, the coupling members 450 can be received in and/or retracted into recesses or recessed portions of the capsule configured to accommodate the coupling members. When loaded into the capsule, the coupling members 450 can be disposed or pressed between the retaining member 510 and the interior surface of the delivery capsule 502. Referring to FIG. 31, in certain embodiments, the delivery capsule 502 can comprise recesses, recessed portions, or cavities 522 defined in the walls, which can be configured to at least partially receive or accommodate the coupling members 450 and/or round portions 452. The recesses 522 can be open or uncovered, or can be partially enclosed. In certain embodiments, the number of flat portions 518 and recesses 514 of the retaining member 510 can correspond to the number of coupling members 450 of the frame 402 (e.g., two, four, six, etc.).

In certain embodiments, the docking station frames can be configured as plastically-expandable or balloon-expandable frames adapted to be crimped onto an inflatable balloon or other expansion mechanism of a delivery apparatus and expanded to their functional size by. Such plastically expandable or ductile materials include nickel-chromium alloys, stainless steel, etc.

Any or all of the frame embodiments described herein can provide improved performance related to frame positioning during deployment, and/or the ability to stably and repeatably deploy and recapture the frame from a delivery capsule. For example, in certain embodiments the longitudinal struts of the frame embodiments described herein can reduce foreshortening of the frame during expansion from the collapsed state. With reference to the embodiment of FIG. 25, when the frame 402 is collapsed in the delivery configuration, the space between the longitudinal struts 408 can be reduced because the pairs of struts 410 between respective pairs of longitudinal struts 408 pivot or angularly move/collapse together. Thus, in the collapsed state, the struts 410 can extend parallel, or substantially parallel, to the longitudinal axis 412 and/or the longitudinal struts 408. However, lengthening and foreshortening of the frame between the collapsed and expanded states can be significantly reduced or eliminated due to the longitudinal struts 408, which do not change angular orientation during frame collapse and expansion. This can allow the frame to be expanded in a smooth, predictable, accurate, and stable manner during deployment, and can reduce the need to reposition the frame mid-procedure because of foreshortening associated with frame expansion.

In certain embodiments, frames including longitudinal struts such as the longitudinal struts 408 (and 210) can also improve the ability to at least partially deploy and recapture the frame from a delivery capsule. For example, in certain embodiments the longitudinal struts 408 can reduce or limit the angle formed between the partially expanded frame emerging from the delivery capsule and the longitudinal axis of the frame/delivery capsule. FIG. 33 illustrates the frame 402 in a partially deployed state. In FIG. 33, the outflow end portion 406 is fully deployed and expanded, and a transition portion indicated generally at 440 is distal of the delivery capsule 502, and in a partially expanded state. The inflow end portion 404 remains in the collapsed state inside the delivery capsule 502. The diameter of the transition portion 440 increases in the distal/downstream direction from substantially the inner diameter of the delivery capsule to the outer diameter D2 (FIGS. 25 and 27).

During deployment and/or recapture, the walls or perimeter of the frame at the transition portion 440 can define an angle θ with the longitudinal axis 412 of the frame. In certain embodiments, the angle θ can be 0° to 90°, such as 15° to 60°, 30° to 50°, etc. In particular embodiments, an angle θ within any of these ranges can facilitate withdrawing/re-collapsing/recapturing the frame 402 back into the delivery capsule 502 after partial deployment of the docking station. For example, in particular embodiments an angle θ within the ranges above can reduce the stresses and/or strains experienced by the frame attendant to crimping or collapsing the frame before initial delivery, and/or returning the frame to the collapsed state after partial deployment (e.g., without a funnel or other guide). An angle θ within the ranges above can also reduce or prevent infolding or invagination of the frame during recapture of the frame and/or during deployment.

In certain embodiments, values of the angle θ above can be facilitated by, for example, the strut width of the struts (e.g., measured circumferentially between circumferential edges of the struts) in relation to the strut thickness (e.g., measured radially from the inner surface of the struts to the outer surface of the struts) and/or the angle between the struts in the expanded or pre-crimped configuration. For example, in certain embodiments the strut width of the frame struts can be 1.1 to 2.0 times smaller than the wall thickness of the struts (e.g., a ratio of the strut width to the strut thickness can be 0.5 to 0.9. In particular embodiments, the strut width can be 1.5 times smaller than the wall thickness (e.g., a ratio of the strut width to the strut thickness can be ⅔ or 0.67). In certain embodiments, the length of the struts can be configured such that adjacent struts form an angle of 120° or less in the pre-crimped state, such as 90° or less.

Figure 34:
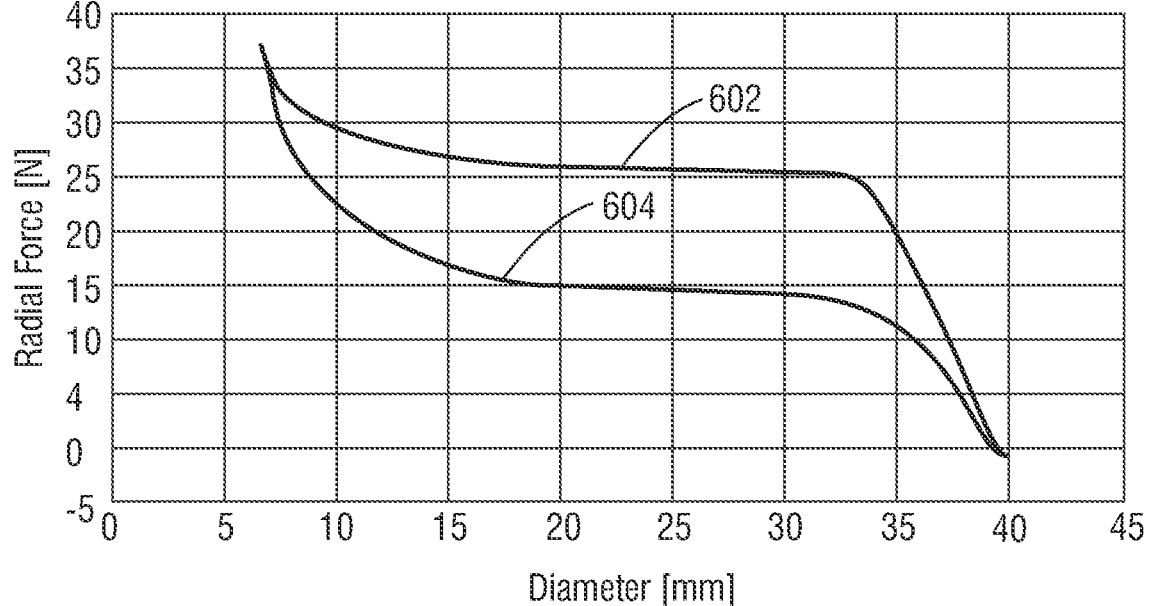
FIG. 34 is a graph illustrating the radial force applied by a docking station frame as a function of diameter during crimping and during expansion.

In addition to improving the ability to recapture the frame, the frame embodiments described herein also meet specified values for parameters including the radial force applied by the frame against the surrounding tissue post-implantation (also known as the "chronic outward force"). FIG. 34 illustrates a curve of force as a function of frame diameter for a frame configured to be expanded to a functional diameter of 28 mm to 35 mm and configured as shown in FIG. 25. The natural, unconstrained diameter of the frame prior to crimping is about 40 mm. As the frame is crimped, the diameter and the force follow the upper curve indicated at 602 to a minimum diameter of 7-8 mm. At this diameter, the radial force exerted by the frame against the delivery cylinder (e.g., the force required to keep the frame radially constrained) is about 36 N. As the frame expands, the force/diameter relation follows the lower curve 604. Between diameters of 28 mm to 35 mm, the frame exerts a chronic outward radial force of 15 N±5 N, such as 15 N or less, which can be sufficient to retain the frame in a vessel such as the inferior or superior vena cava without damaging the tissue.

In certain embodiments, the radial force exerted on the surrounding tissue by the docking station frame can be 0.01 N/mm of length and 0.5 N/mm of length, such as 0.05 N/mm of length and 0.3 N/mm of length. In particular embodiments, the frame can exert 15 N of radial force at the working diameter and can have a frame length of 100 mm, resulting in a radial force of 0.15 N/mm of length.

In certain embodiments, the pressure exerted by the docking station frame against the surrounding tissue can be 0.1 N/cm² to 8 N/cm², such as 0.5 N/cm² to 4 N/cm². In particular embodiments, the frame can exert 15 N of radial force at the working diameter and can have an outer surface area of 6.83 cm², resulting in a pressure of 2.2 N/cm² of frame area.

Figure 35:
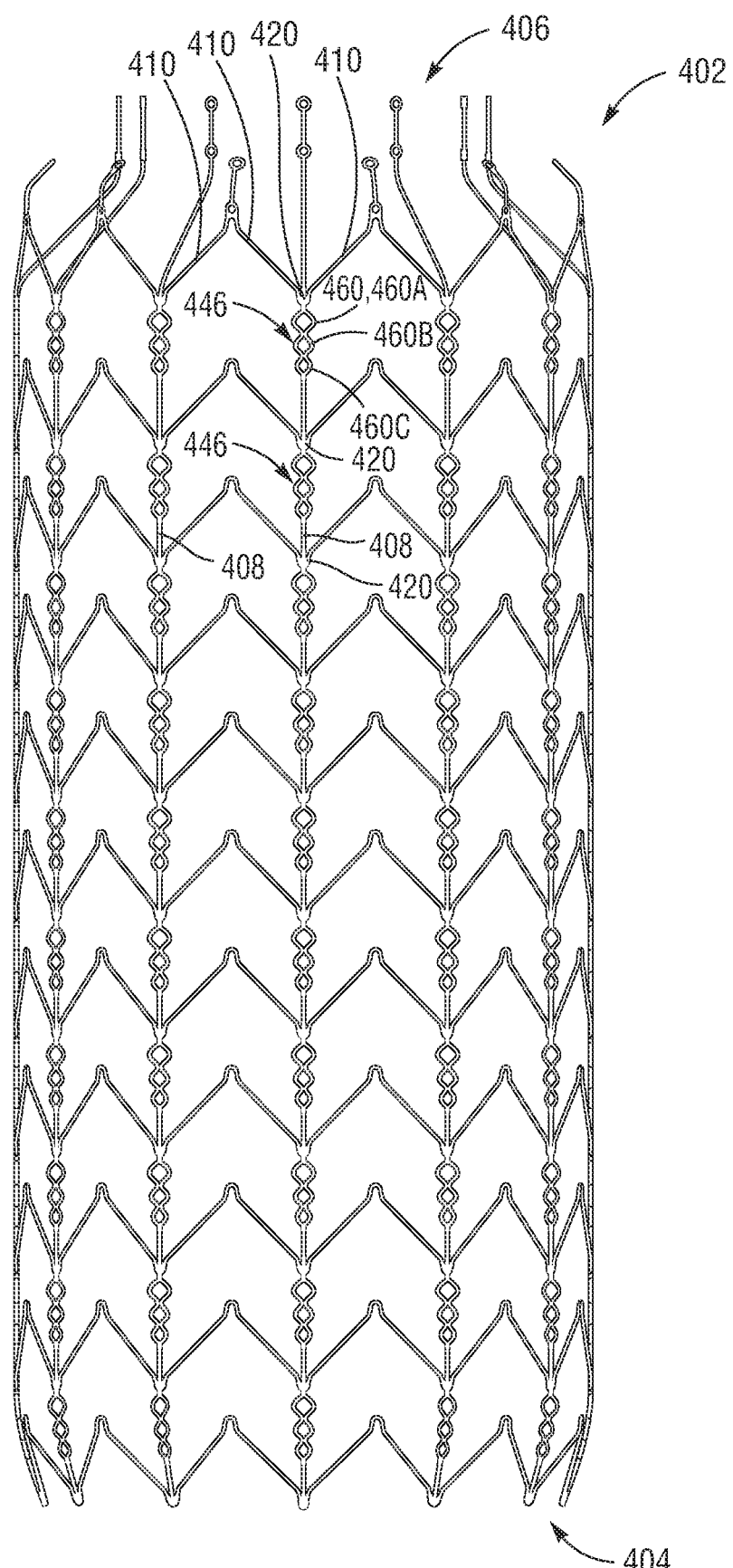
FIG. 35 is a side elevation view of another embodiment of a docking station frame.

FIG. 35 illustrates another embodiment of the frame 402, wherein the longitudinal struts 408 comprise portions 446 located between rows of struts 410. In the illustrated embodiment, the portions 446 can comprise one or a series of cells arranged axially along the struts 408. For example, in the illustrated embodiment the portions 446 can comprise three cells 460A, 460B, and 460C. In certain embodiments, any or all of the cells 460A-460C can be diamond-shaped as shown, or can be other shapes such as round, circular, polygonal, etc. In certain embodiments, the cells can be configured to reduce or prevent collapse or buckling of the frame, such as in curved anatomy, by allowing one side of the frame to elongate (e.g., by making the cells longer in the axial dimension) while the other side contracts or foreshortens (e.g., by compressing the cells in the axial dimension). In certain embodiments, the cells 460A and 460B can be the same size, and the cells 460C can be smaller than the cells 460A and 460B, although in other embodiments the cells can have any size. For example, in certain embodiments, each of the cells 460A-460C can be the same size, or each of the cells can be a different size. In yet other embodiments, the cells 460B and 460C can be the same size, and the cells 460A can be larger or smaller. Further details regarding buckling or kink-resistance can be found in U.S. Provisional Application No. 63/024,386, which is incorporated herein by reference.

In the illustrated embodiment, each of the longitudinal struts 408 comprises a series of cells 460A-460C between each junction 420. The cells 460A-460C are closer to the next junction 420 in the outflow direction than the adjacent junction in the inflow direction, although the cells may be centrally positioned between respective junctions 420, or located closer to the inflow junctions. In other embodiments, the longitudinal struts 408 can comprise cells 460A-460C between selected junction 420 (e.g., between certain rows of struts 410). The frame 402 can also comprise cells at any angular spacing. For example, in certain examples a subset of the longitudinal struts 408 can comprise cells while others do not. The portions 446 can also include more or fewer cells 460, such as one cell, two cells, four cells, etc. The portions 446 can also comprise multiple strut segments coupled together and oriented at different angles (e.g., in a zig-zag arrangement), similar to the embodiment shown in FIG. 36.

Figure 36:
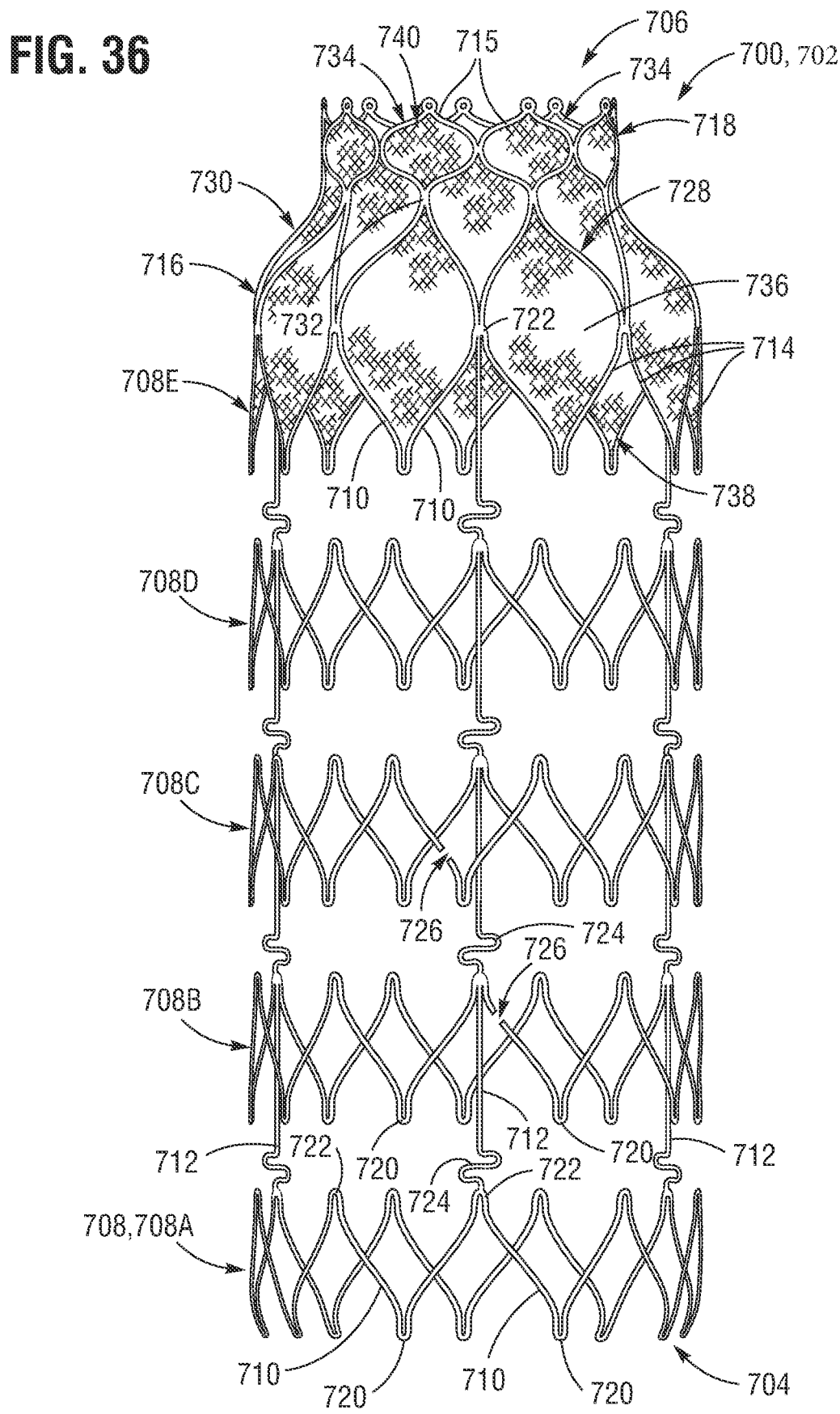
FIG. 36 is a side elevation view of another embodiment of a docking station frame.

FIG. 36 illustrates another embodiment of a docking station 700 comprising a frame 702 having an inflow end 704 and an outflow end 706. The frame 702 can comprise a series of portions generally indicated at 708 formed by rows of angled strut members 710 coupled together in a circumferential arrangement. The portions 708 can be interconnected in the longitudinal direction by longitudinal strut members 712. The outflow end portion 706 can comprise a plurality of struts 714 arranged to form a first portion 716, and a plurality of struts 715 arranged to form a second portion 718 having a diameter different from (e.g., less than) the first portion 716.

The struts 710 can be curved or serpentine members arranged end to end to form a series of inflow peaks or apices 720 and a series of outflow peaks or apices 722. In the illustrated embodiment, the frame 702 includes five portions 708A-708E, although in other embodiments the frame can include more or fewer portions depending upon the particular application and/or a patient's anatomy. The longitudinal struts 712 can extend between selected outflow apices 722 of one portion 708 to corresponding (e.g., circumferentially aligned) outflow apices of the next portion 708 in the outflow direction. In certain embodiments, the longitudinal struts 712 can be integrally formed with the apices 722, or may be separately formed and coupled or secured to the apices (e.g., by laser welding). In other embodiments, the longitudinal struts 712 can extend between outflow apices 722 of one portion 708 to circumferentially aligned inflow apices 720 of the next sequential portion 708.

In the illustrated embodiment, the longitudinal struts 712 can comprise resilient or flexible features configured as zigzagged, undulating, or sinusoidally curved portions 724 comprising one or a plurality of circumferentially offset peaks and valleys. In certain embodiments, the portions 724 can act as springs or flexible portions, and can allow the frame to bend or flex about the portions 724. In certain embodiments, the portions 724 can also be configured to engage the tissue of the IVC or other body lumen in which the docking station is deployed to anchor the docking station in place. In the illustrated embodiment, the portions 724 are closer to the outflow apices 722 of the adjacent portion 708 in the inflow direction than the outflow apices of the next adjacent portion 708 in the outflow direction, but may be located anywhere along the length of the struts 712. In other embodiments, the features can be configured as one or a plurality of cells as in FIG. 35. Additional configurations of flexible portions are described in U.S. Publication No. 2019/0000615 incorporated by reference above.

In certain embodiments, the struts 710 may be discontinuous, and can comprise a gap such as the gaps indicated at 726. The size and location of the gaps can be chosen such that they facilitate bending or curving of the frame (e.g., in curved anatomy) without buckling or kinking. Such gaps can be incorporated into any of the frame embodiments described herein.

The struts 714 of the first portion 716 of the outflow end portion 706 and the struts 710 of the portion 708E can together define a series of relatively large cells 728 arranged circumferentially around the frame at the outflow end portion. The struts 714 can be angled radially inwardly midway along their lengths such that the struts 714 define a shoulder portion 730. In the illustrated embodiment, the struts 714 are coupled to the outflow apices 722 of the struts 710 of the fifth portion 708E, although other configurations are possible.

The struts 715 can be coupled to outflow apices 732 of the struts 714. The apices 732 can be arrayed circumferentially around and can at least partially define the reduced diameter portion 718. In certain embodiments, the struts 715 can define cells 734 arrayed circumferentially around and at least partially defining the portion 718. In certain embodiments, the portion 718 can be configured as a valve seat that is coaxial with the frame 702, and can be configured to receive and retain a prosthetic heart valve expanded within the portion 718 similar to the embodiments described above. The portion 718 can configured to accommodate prosthetic heart valves of any of a variety of functional sizes.

In certain embodiments, the docking station 700 can comprise a sealing member 736 disposed on or in the portion 708E, the shoulder portion 730, and/or the portion 718. In certain embodiments, the sealing member 736 can be a woven or non-woven fabric, and can be disposed around the interior surface and/or the exterior surface of the frame. In the illustrated embodiment, the inflow and outflow edges of the sealing member 736 can be shaped to correspond to the shape of the struts. For example, in the illustrated embodiment the inflow edge portion 738 of the sealing member can be shaped to match the shape of the struts 710 of the cells 728, and the outflow edge 740 of the sealing member can be shaped to match the shape of the outflow edge defined by the struts 715 of the cells 734. In certain embodiments, the remainder of the frame 702 can be uncovered to allow blood flow from the IVC and various communicating blood vessels into the frame. The portion of the sealing member 736 disposed in or on the outflow portion 718 can form a seal with a prosthetic heart valve deployed within the portion 718, and the portion of the sealing member 736 disposed in or on the first portion 716 can form a seal with the surrounding anatomy such as the ostium of the IVC.

Figure 37:
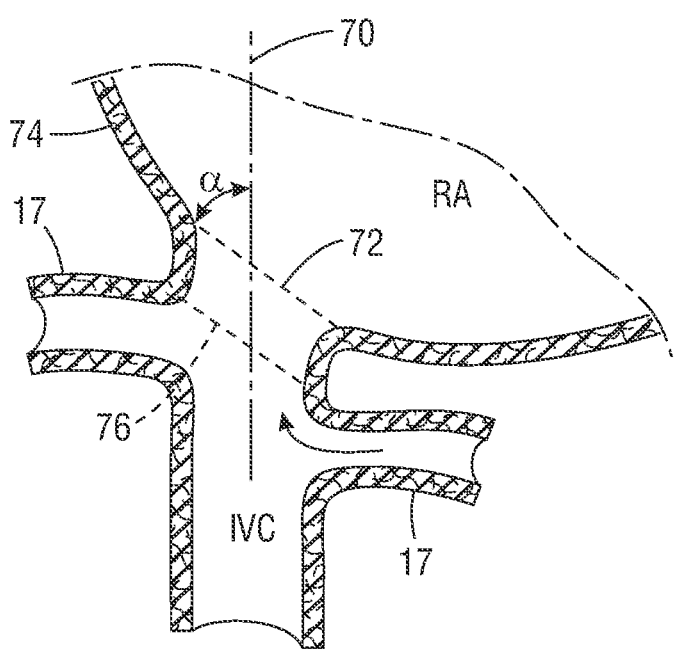
FIG. 37 is a cross-sectional view of a portion of the inferior vena cava and the right atrium of the heart.

In certain embodiments, the ostium of the inferior vena cava IVC can be at an angle to the longitudinal axis of the inferior vena cava IVC (e.g., due to the shape or orientation of the wall of the right atrium RA). FIG. 37 is a schematic cross-sectional view of the outflow portion of the inferior vena cava IVC into the right atrium RA, and illustrates two of the three hepatic veins 17. In certain embodiments, the plane 72 of the annulus or ostium of the inferior vena cava IVC can form an angle α with the longitudinal axis 70 of the IVC (e.g., as measured relative to the upper wall 74 of the right atrium RA), which can be at least 10°, at least 20°, at least 30°, etc. In certain individuals, the ostia of the hepatic veins 17 can be located at different locations along the axis 70 of the inferior vena cava IVC. Thus, in certain embodiments the region generally indicated at 76 can be the portion of the interior wall of the inferior vena cava IVC available for forming a seal between the IVC and an implant, such as the docking station embodiments described herein.

Figure 38:
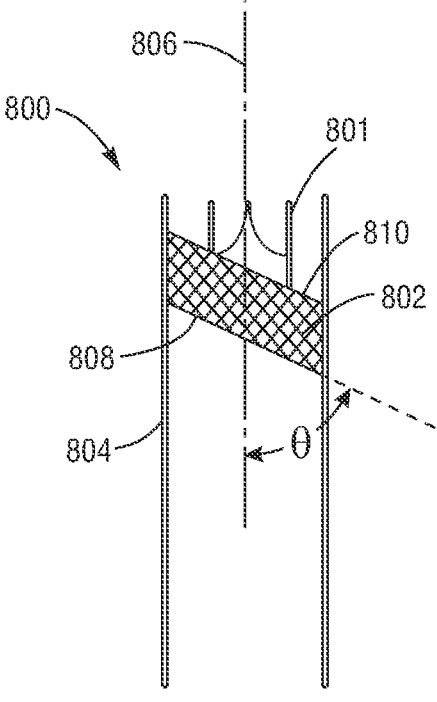
FIG. 38 is a schematic side elevation view of a docking station frame including an angled sealing member.

Accordingly, in certain embodiments it can be advantageous to position the sealing member at an angle on the docking station to approximate or correspond to the angle α. FIG. 38 schematically illustrates a docking station 800 with a prosthetic valve 801 deployed within it, and a cylindrical sealing member 802 with straight inflow and outflow edges 808, 810 disposed around the outflow end of the frame 804. The sealing member 802 can form an angle θ with the longitudinal axis 806 of the frame 804. In certain embodiments, the angle θ can be the same or nearly the same as the angle α so that the sealing member 802 occupies the space 76 (FIG. 37) when implanted in the IVC and all or substantially all of the circumference of the skirt member can form a seal between the docking station 800 and the IVC without obstructing the hepatic veins 17 and/or extending into the right atrium. In particular embodiments, the angle θ can be 0° to 45°, 5° to 40°, 10° to 35°, 45° or less, 40° or less, 35° or less, etc., which can correspond to typical angles of the orientation of the annulus of the IVC. In other embodiments, one of the inflow or outflow edges 808, 810 of the sealing member 802 can be angled relative to the axis 806 to correspond to the angle α, while the other edge can be at a right angle (or another angle) to the axis 806. In yet other embodiments, one or both of the inflow edge 808 and/or the outflow edge can comprise a curved shape, or any other shape depending, for example, on a patient's anatomy.

In certain embodiments, portions of the sealing member 802 can comprise radiopaque materials and/or markings/indicia to enhance visibility on fluoroscopic or other imaging systems, enabling the physician to determine the location and/or orientation of the sealing member relative to the surrounding anatomy. For example, in certain embodiments the base of the sealing member such as the inflow edge portion can comprise threads, yarns, or sutures, woven into the sealing member, which can comprise radiopaque properties or features. In certain embodiments, the sealing member 802 can comprise a radiopaque cloth or other woven or non-woven fabric construction. In certain embodiments, the sealing member 802 can be sutured or attached to the frame 804 by radiopaque sutures. The radiopacity of the sealing material, markers, and/or suture can be provided by, for example, radiopaque inks and/or adhesives applied by coating, screen printing, roller printing, dipping, etc. Radiopaque markers can also comprise small pieces of radiopaque materials, such as metals, incorporated into the sealing member and/or strings/threads/yarns/sutures.

Such radiopaque materials and/or markings can aid the physician in positioning the docking station in the IVC, such as in the region 76 between the ostium and hepatic veins, and/or facilitate accurate placement of the prosthetic valve 801 within the docking station. Radiopaque materials that can be used in combination with the sealing member 802 include, for example, biocompatible metals such as gold, platinum, tantalum, tungsten, platinum iridium alloys, palladium, etc., or alloys including any of these. Such indicia, markings, and/or radiopaque materials can be incorporated into any of the sealing member embodiments described herein.

Figure 47:
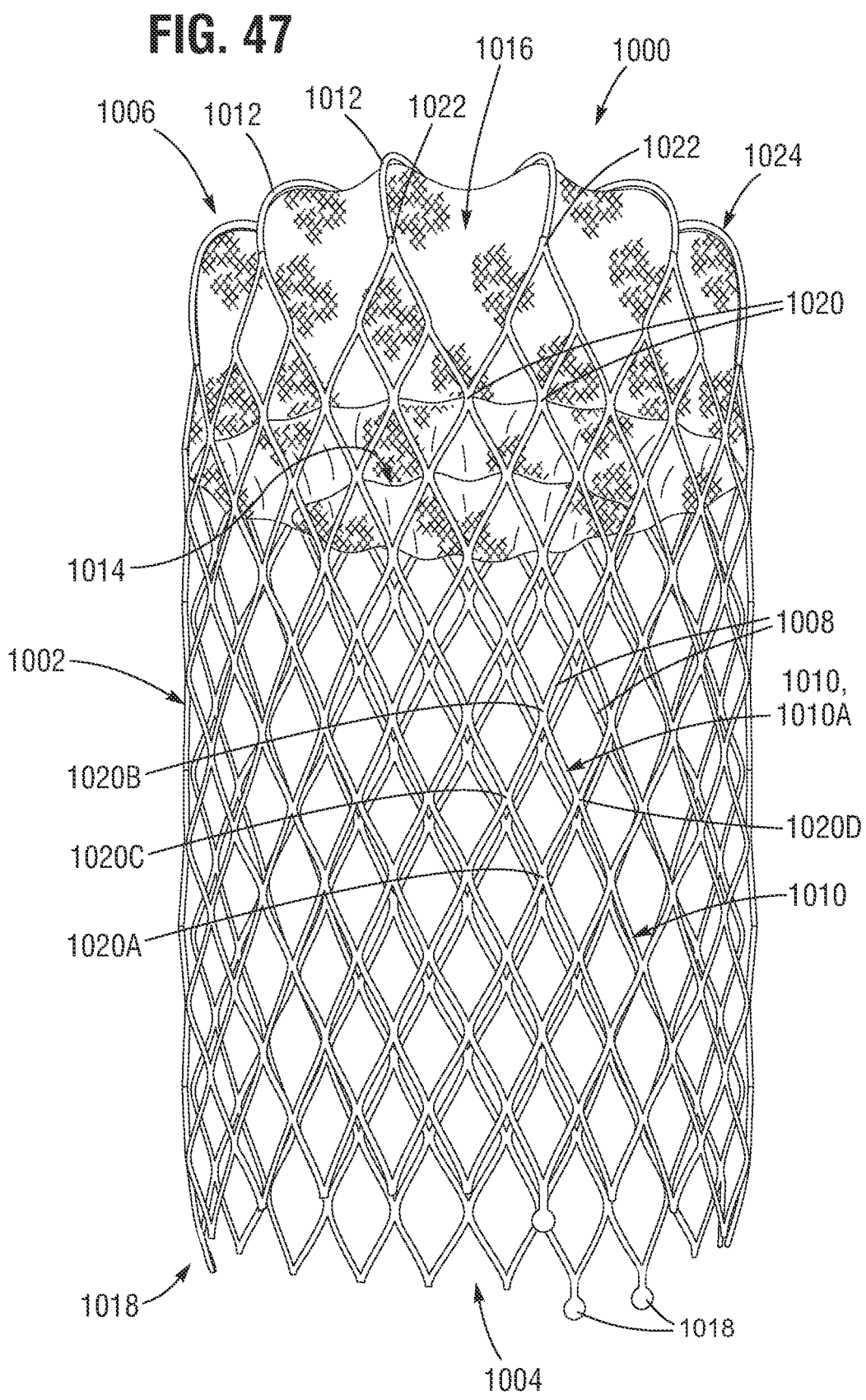
FIG. 47 is a perspective view of another embodiment of a docking station.

FIG. 47 illustrates another embodiment of a docking station 1000 including a frame 1002 configured similarly to the frame 14 of FIG. 5A and including an inflow end portion 1004 and an outflow end portion 1006. The main body of the frame 1002 can be formed by a plurality of struts 1008 arranged to form rows of diamond-shaped cells 1010. The cells 1010 can be joined together at junctions 1020. In most cell/strut rows (e.g., exclusive of the downstream-most row), the cells can be joined to the adjacent cells at each junction 1020. For example, with reference to a representative cell 1010A, the cell 1010A can be coupled to each of the adjacent cells by a proximal or upstream junction 1020A, a distal or downstream junction 1020B, a first circumferential junction 1020C, and a second circumferential junction 1020D.

In the illustrated embodiment the downstream-most row of cells 1010 can be circumferentially spaced apart from each other and can define circumferentially spaced apices 1022. The outflow end portion 1006 can further comprise struts 1012 referred to herein as valve seat struts that extend from the apices 1022 of the struts 1008/cells 1010 of the downstream-most row of cells in the downstream direction. The valve seat struts 1012 can curve inwardly to form arches, and can then extend in the upstream direction within the lumen of the frame 1002 to form the valve seat 1014. The valve seat struts 1012 can thereby form a U-shaped or curved transition portion 1024 between the diameter of the expanded main body of the frame and the smaller diameter of the valve seat 1014 within the frame. As with other embodiments described herein, the valve seat 1014 can be located coaxially within the lumen of the frame 1002 and offset from the outflow edge of the frame in the upstream direction such that a prosthetic valve expanded within the valve seat is wholly or nearly wholly located within the frame 1002 and only minimally protrudes distally from the frame 1002, if at all.

A sealing member 1016 can be disposed within the frame 1002 and coupled to the inside surfaces of the frame struts (e.g., the struts 1008 and/or the valve seat struts 1012) at the outflow end portion 1006 (e.g., by suturing). The sealing member 1016 can also extend along the interior surfaces of the curved valve seat struts 1012 to the valve seat 1014, and can be coupled to the radially outward surfaces of the struts forming the valve seat. The portion of the sealing member 1016 coupled to the outflow portion of the frame (e.g., to the struts radially outward of the valve seat 1014) can be configured to seal against the native anatomy such as the interior vena cava IVC. In certain embodiments, the sealing member 1016 can cover the first or downstream-most row of cells 1010 and all or a portion (e.g., half) of the next row of cells in the upstream direction in order to maintain flow into the frame from the hepatic veins, although the sealing member can extend along any suitable portion of the frame. In certain embodiments, the frame can also include one or a plurality of coupling members 1018 at the inflow end portion 1004, which can be configured similarly to the coupling members 450 of FIG. 25.

In a representative method of use, a docking station configured according to any of the embodiments described herein can be advanced through a patient's body to a treatment site such as the IVC (or the SVC) in a radially compressed or collapsed state, such as with the delivery apparatus 500 of FIG. 30. In certain embodiments, the surgeon can adjust the position of the docking station frame prior to full deployment relative to other blood vessels such as the hepatic veins and/or the renal vein to avoid obstructing the blood vessels. The docking station can then be deployed, such as by advancing the docking station from the delivery capsule 502 (or retracting the delivery capsule from over the docking station) such that the docking station frame expands to its functional size, and such that the outflow end portion is positioned adjacent the ostium of the IVC to anchor the docking station at the treatment site. In certain embodiments, the coupling members 450 of the docking station can be released from the retaining member 510 of the delivery apparatus when the retaining member is exposed from the delivery capsule, or can be released by a separate control action. A prosthetic heart valve, such as any of the prosthetic heart valve embodiments described herein, can then be advanced into the docking station (e.g., from the upstream direction or the downstream direction) and positioned relative to/adjacent the valve seat. In embodiments in which the prosthetic valve is advanced in the downstream direction (e.g., through the lumen of the docking station frame), the prosthetic valve can be crimped on its delivery catheter with the outflow end portion towards the distal end of the delivery apparatus or vice versa. The prosthetic heart valve can then be deployed or expanded in the docking station (e.g., by inflating a balloon onto which the prosthetic valve is crimped) such that the prosthetic valve expands to its functional size and is engaged by/anchored in the valve seat of the docking station and regulates blood flow through the docking station. The docking station embodiments described herein can also be implanted in diseased or enlarged native heart valves, such as the aortic valve, using substantially a similar process.

Prosthetic Heart Valve

Figures 39, 40, 41:
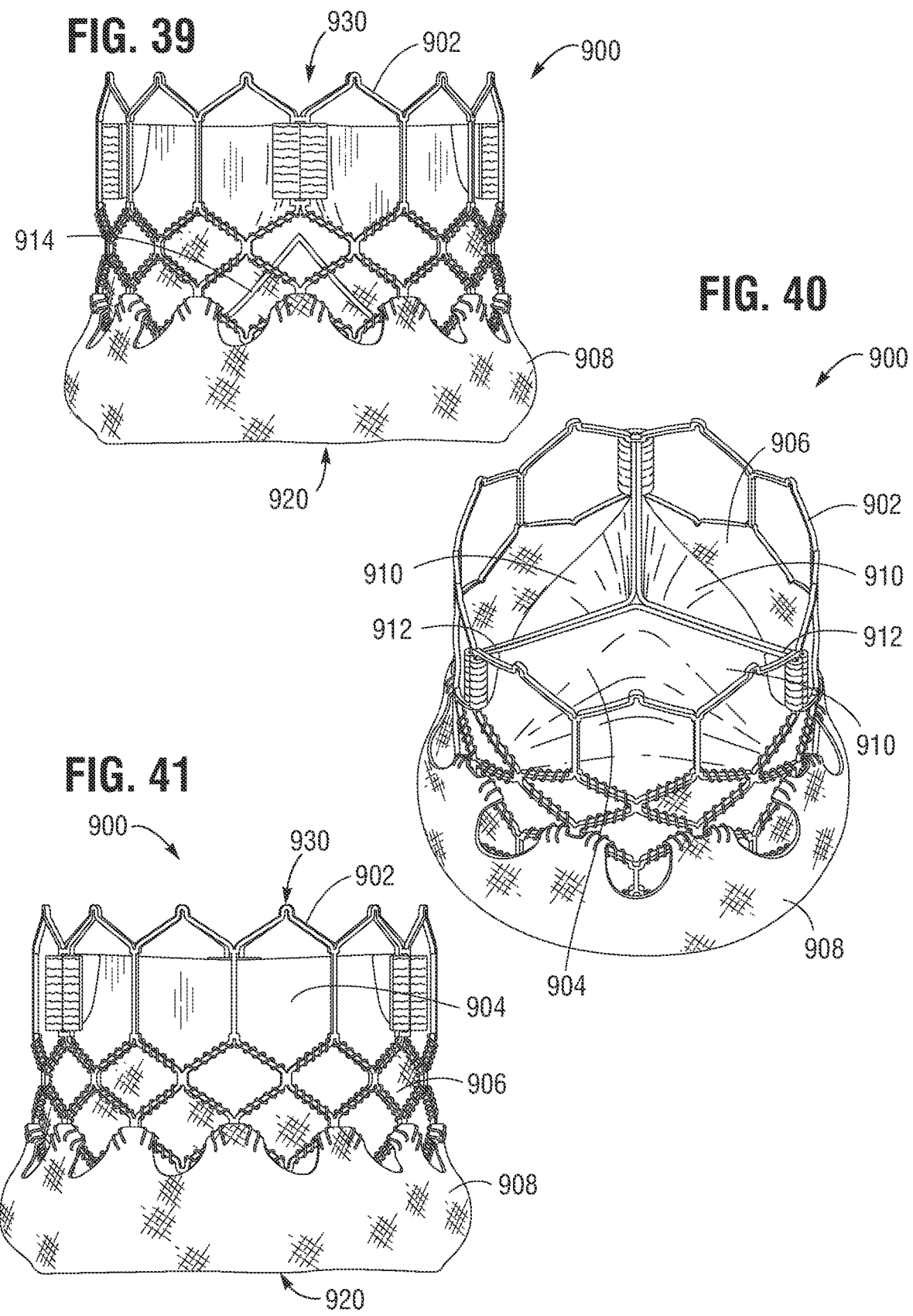
FIGS. 39-41 illustrate an exemplary embodiment of a prosthetic heart valve.

The docking station embodiments described herein can be used in combination with any of a variety of prosthetic valves, such as self-expandable prosthetic heart valves, balloon expandable prosthetic heart valves, and/or mechanically-expandable prosthetic heart valves. FIGS. 39-41 show various views of a balloon-expandable prosthetic heart valve 900 configured as the Edwards Lifesciences SAPIEN® 3 prosthetic heart valve, according to one embodiment. In certain embodiments, the illustrated valve is adapted to be implanted in the native aortic annulus or other native annuluses of the heart, although it can also be adapted to be implanted in any of the docking station embodiments described herein. The valve 900 can have four main components: a stent, or frame, 902, a valvular structure 904, an inner skirt 906, and an outer skirt 908.

The valvular structure 904 can comprise three leaflets 910, collectively forming a leaflet structure, which can be arranged to collapse in a tricuspid arrangement including commissures 912, as best shown in FIG. 40. The lower edge of leaflet structure 904 desirably has an undulating, curved scalloped shape (suture line 914 shown in FIG. 39 tracks the scalloped shape of the leaflet structure). By forming the leaflets with this scalloped geometry, stresses on the leaflets are reduced which, in turn, improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 910 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 902 is shown in FIG. 42. The frame 902 can be formed with a plurality of circumferentially spaced slots, or commissure windows, 916 (three in the illustrated embodiment) that are adapted to mount the commissures of the valvular structure 904 to the frame, as described in greater detail below. The frame 902 can be made of any of various suitable plastically-expandable materials (e.g., stainless steel, etc.) or self-expanding materials (e.g., Nitinol) as known in the art. When constructed of a plastically-expandable material, the frame 902 (and thus the valve 900) can be crimped to a radially compressed state on a delivery catheter and then expanded inside a patient by an inflatable balloon or equivalent expansion mechanism. When constructed of a self-expandable material, the frame 902 (and thus the valve 900) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 902 include, without limitation, stainless steel, a nickel based alloy (e.g., a cobalt-chromium or a nickel-cobalt-chromium alloy), polymers, or combinations thereof. In particular embodiments, frame 902 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 902 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring to FIGS. 42 and 43, the frame 902 in the illustrated embodiment comprises a first, lower row I of angled struts 918 arranged end-to-end and extending circumferentially at the inflow end 920 of the frame; a second row II of circumferentially extending, angled struts 922; a third row III of circumferentially extending, angled struts 924; a fourth row IV of circumferentially extending, angled struts 926; and a fifth row V of circumferentially extending, angled struts 928 at the outflow end 930 of the frame. A plurality of substantially straight axially extending struts 932 (FIG. 43) can be used to interconnect the struts 918 of the first row I with the struts 922 of the second row II. The fifth row V of angled struts 928 are connected to the fourth row IV of angled struts 926 by a plurality of axially extending window frame portions 934 (which define the commissure windows 916) and a plurality of axially extending struts 936. Each axial strut 936 and each frame portion 934 extends from a location defined by the convergence of the lower ends of two angled struts 928 to another location defined by the convergence of the upper ends of two angled struts 926. FIGS. 44, 45, and 46 are enlarged views of the portions of the frame 902 identified by letters A, B, and C, respectively, in FIG. 43.

Each commissure window frame portion 934 mounts a respective commissure of the leaflet structure 904. As can be seen each frame portion 934 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 902 (FIG. 42) measured between the inner diameter and outer diameter is about 0.55 mm, or about 0.48 mm or less.

The struts and frame portions of the frame collectively define a plurality of open cells of the frame. At the inflow end of the frame 902, struts 918, struts 922, and struts 932 define a lower row of cells defining openings 938. The second, third, and fourth rows of struts 922, 924, and 926 define two intermediate rows of cells defining openings 940.

As best shown in FIG. 45, the lower end of the strut 936 is connected to two struts 926 at a node or junction 942, and the upper end of the strut 936 is connected to two struts 928 at a node or junction 944. The strut 936 can have a thickness S1 that is less than the thicknesses S2 of the junctions 942, 944. The geometry of the struts and junctions can assist in creating enough space in openings between frame members in the crimped state to allow portions of the leaflets to protrude (e.g., bulge) outwardly through openings. This allows the valve to be crimped to a relatively smaller diameter than if all of the leaflet material is constrained within the crimped frame. The lower ends of struts 926 are coupled at junctions 946.

Further details regarding the prosthetic heart valve 900 can be found in U.S. Pat. No. 9,393,110, which is incorporated herein by reference.

Additional embodiments of balloon expandable prosthetic heart valves that can be used in combination with the docking systems described herein can be found in U.S. Publication No. 2018/0028310, which is incorporated herein by reference. The docking systems can also be used in combination with mechanically-expandable prosthetic valves. Representative examples of mechanically-expandable prosthetic valves can be found in U.S. Publication No. 2018/0153689 and U.S. Publication No. 2019/0105153, which are incorporated herein by reference. The docking stations can also be used in combination with self-expandable prosthetic valves. Representative examples of self-expanding prosthetic valves can be found in U.S. Pat. Nos. 8,652,202, 9,155,619, and 9,867,700, which are incorporated herein by reference.

Third Representative Embodiment

Figure 48:
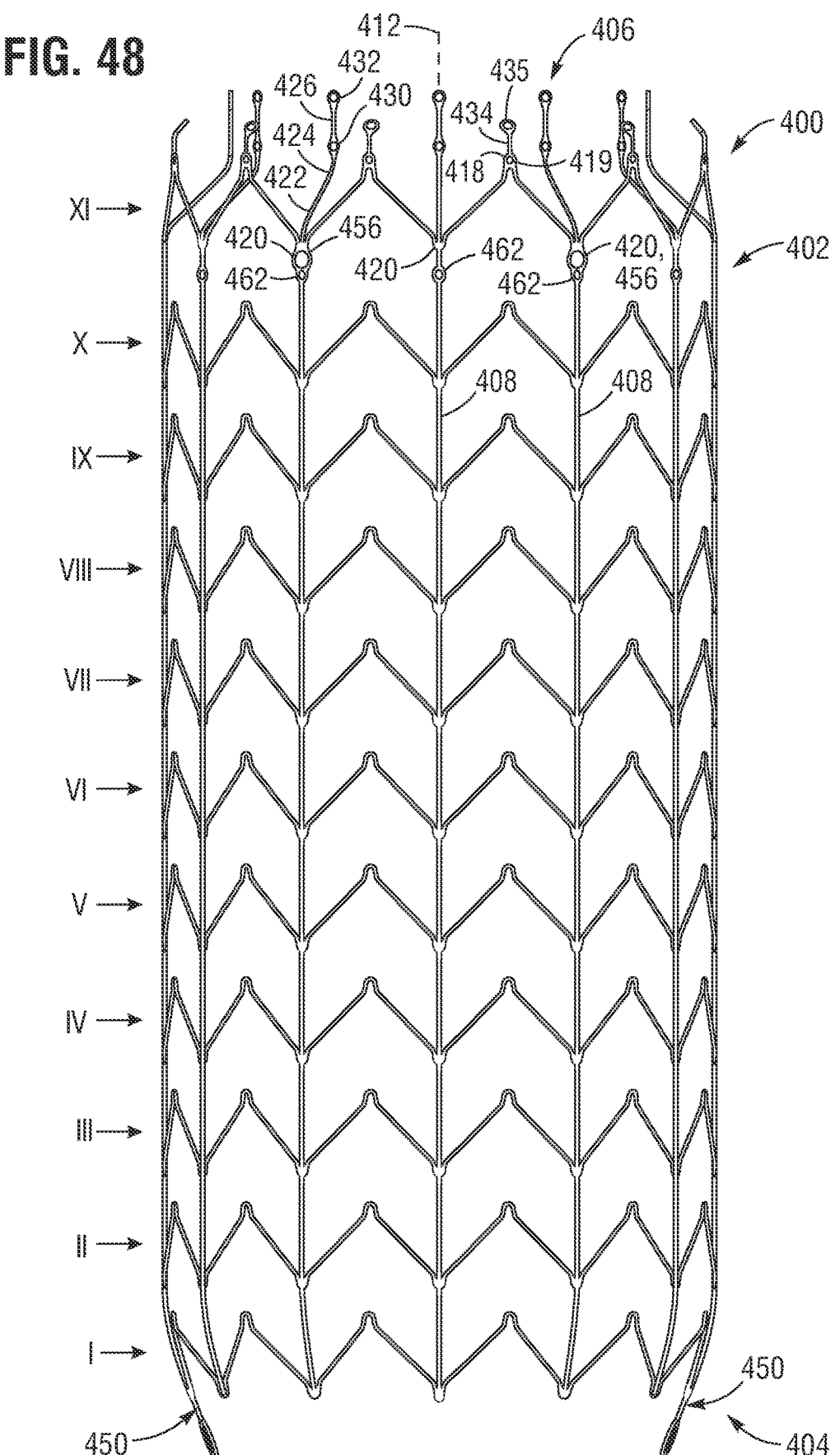
FIGS. 48 and 49 are side elevation views of a frame of a docking station, according to another embodiment.
Figure 49:
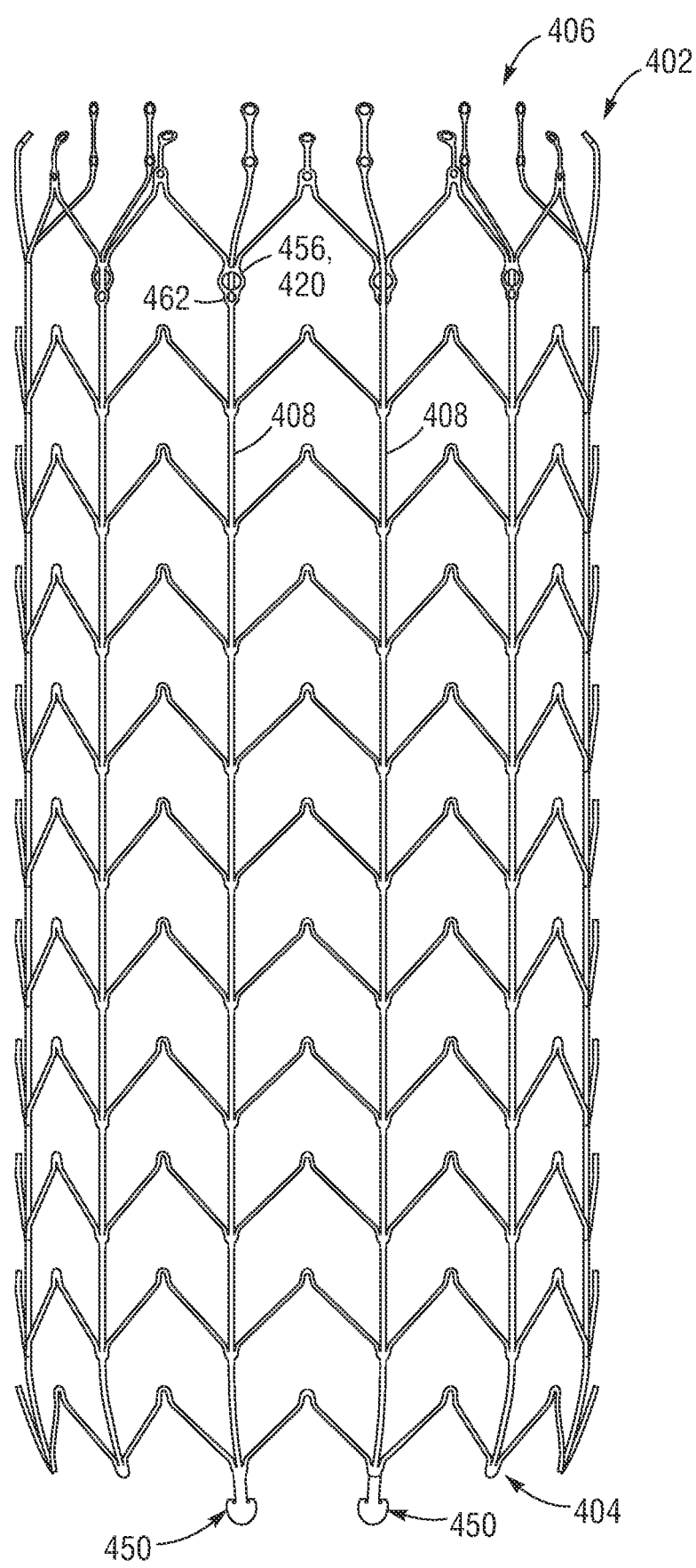
Figure 50:
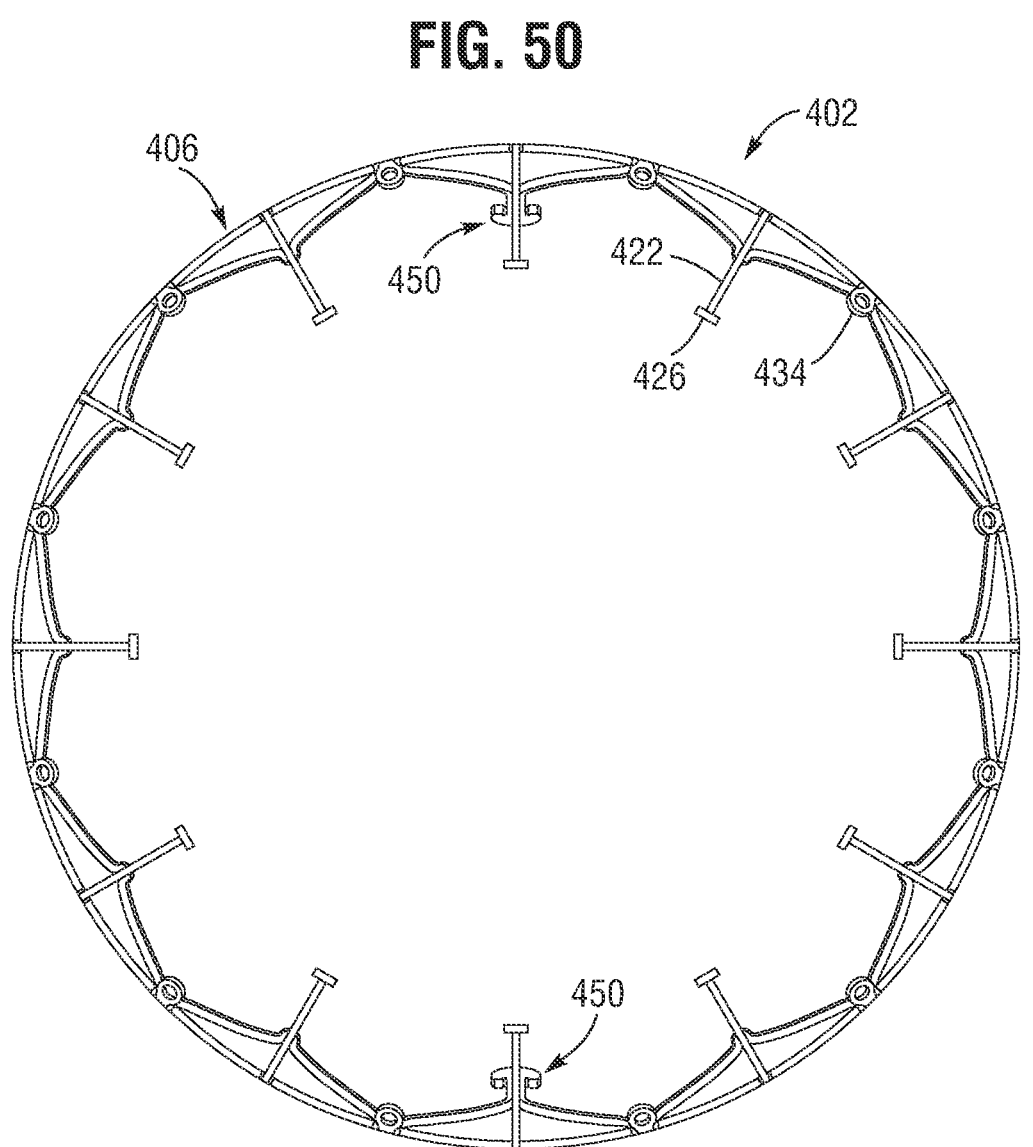
FIG. 50 is a top plan view of the frame of FIG. 48.

FIGS. 48-50 illustrate another embodiment of the docking station/device/valve adaptor/landing zone/prestent frame 402 in which the longitudinal struts (e.g., first struts) 408 comprise a row or rung of openings 462 arrayed circumferentially around the frame between the tenth row X of struts (e.g., second struts) 410 and the eleventh row XI. The openings 462 can be proximate and/or incorporated into the junctions 420 of the eleventh row XI. For example, for longitudinal struts 408 including openings 456 in the junctions 420, the openings 456 can also be incorporated in the junctions 420 and positioned upstream or proximal of the openings 456. For longitudinal struts 408 without openings 456, the openings 462 can be offset from the junctions 420 in the upstream direction, but generally aligned with the openings 462 of adjacent longitudinal struts 408. In the illustrated embodiment, each longitudinal strut 408 includes an opening 462. However, in other embodiments subsets of longitudinal struts 408 can include openings 462 (e.g., every second strut 408), and the openings 462 can be located at any location along the longitudinal struts 408 (e.g., downstream of the openings 456). The longitudinal struts 408 can also include more than one opening 462, such as two openings, three openings, or more. The openings 462 can also be at different longitudinal positions on different struts, depending upon the particular design (e.g., depending on the size and shape of the sealing member). Frames including different numbers of openings 456, such as openings at each junction 420 as shown in FIG. 28, can also include the openings 462 (e.g., incorporated into the junctions 420 as in FIG. 48).

FIG. 49 is another view of the configuration of FIG. 48 in which the frame 402 is rotated about its axis such that the longitudinal struts 408 with junctions 420 including openings 456 are offset from those which do not have the openings 456, resulting in certain of the openings 456 being visible in the background behind struts 408 in the foreground and vice versa. FIG. 50 is a plan view of the outflow end portion 406 of the frame 402 configured as shown in FIGS. 48 and 49.

Figure 51:
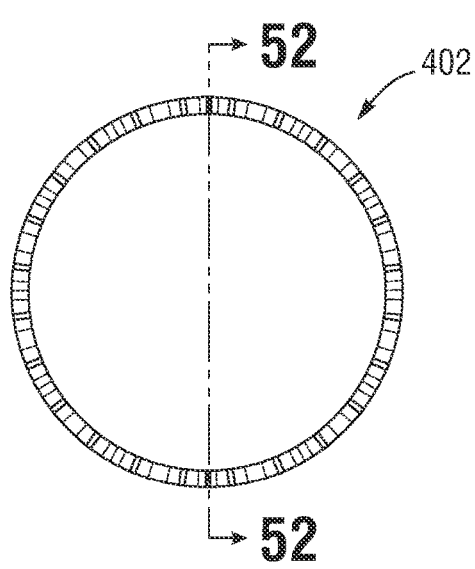
FIG. 51 is a top plan view of the frame of FIG. 48 in a radially collapsed state before shape setting.
Figure 52:
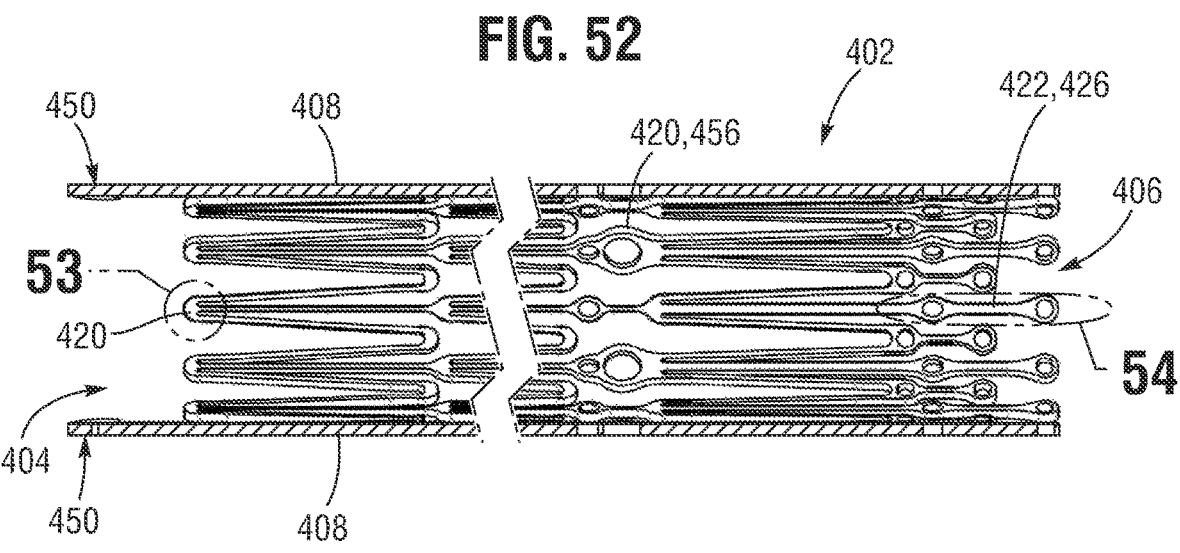
FIG. 52 is a cross-sectional side view of the frame of FIG. 51.
Figure 53:
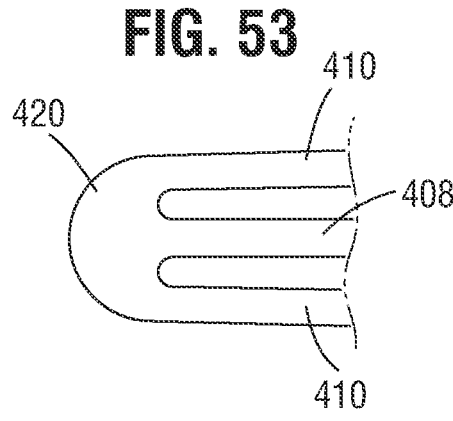
FIG. 53 is a magnified view of a junction between struts at the inflow end of the frame of FIG. 52.

FIGS. 51 and 52 illustrate the frame 402 of FIG. 48 in a radially collapsed state before shape-setting of the end portions of the struts to establish the radially inward curvature. FIG. 53 illustrates a representative example of a junction 420 between the struts 408 and 410 at the inflow end 404 of the frame.

Figure 54:
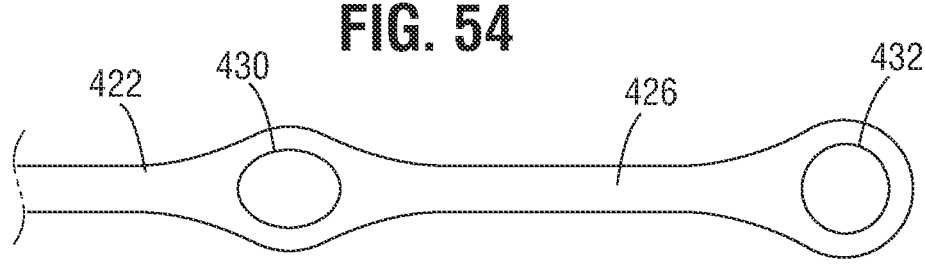
FIG. 54 is a magnified view of a portion of a strut member at the outflow end portion of the frame of FIG. 52.

FIG. 54 illustrates a representative example of a second/distal/outflow end portion 426 of a strut 422. In the illustrated embodiment, the width/diameter of the second portion 426 of the strut 422 can taper or decrease in the upstream direction proximally of the opening 430 and can also taper/decrease in the downstream direction distally of the opening 430. The width/diameter of the second portion 426 can also increase in the upstream direction proximally of the opening 432, while at least a portion of the strut portion 426 between the openings 430 and 432 can have a constant or substantially constant width/diameter.

Still referring still to FIG. 54, in certain embodiments the openings 430 and 432 can also have different shapes. For example, in the illustrated embodiment the opening 430 can comprise an elongated or oval shape in which the long axis of the opening is oriented along the longitudinal axis of the second portion 426, while the opening 432 can be circular or substantially circular (although this configuration may be reversed). In other embodiments both openings 430 and 432 can be circular, or both can be elongated/oval, or can have any other shape.

Figure 55:
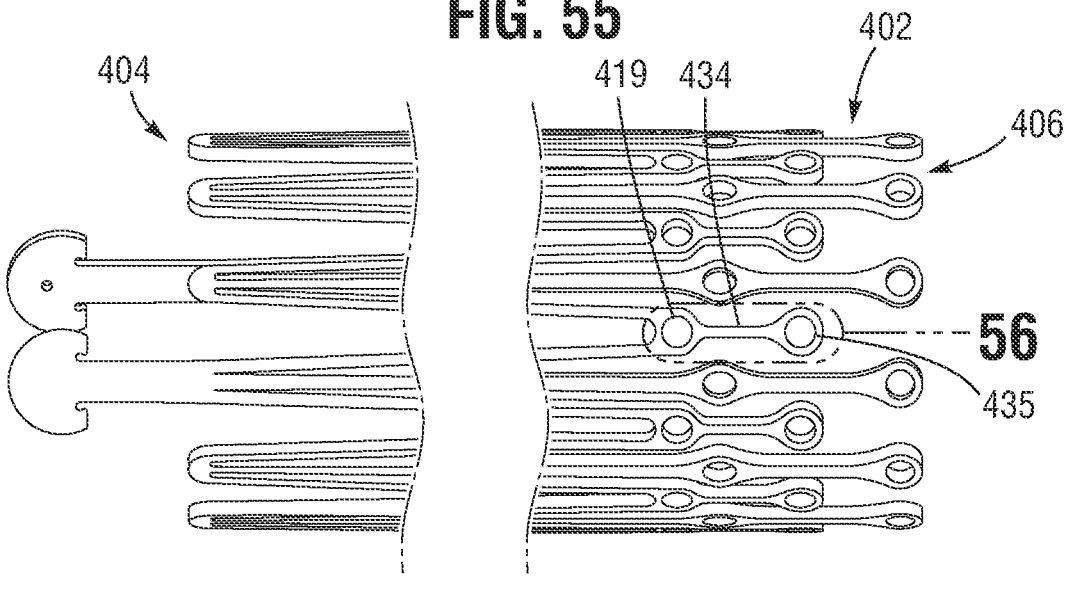
FIG. 55 is a side view of the inflow and outflow end portions of the frame of FIG. 51.

FIG. 55 illustrates the inflow and outflow end portions 404, 406 of the collapsed frame 402 rotated about its longitudinal axis relative to FIG. 52.

Figure 56:
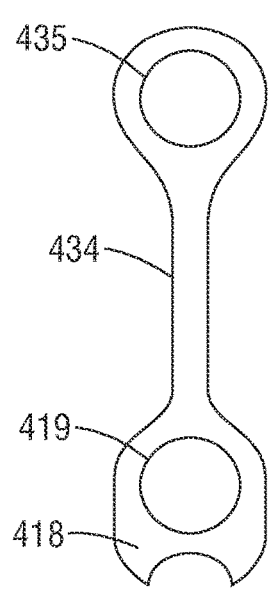
FIG. 56 is a magnified view of a portion of another strut member at the outflow end portion of the frame of FIG. 55.

FIG. 56 illustrates a magnified view of a representative strut 434. In the illustrated embodiment, the openings 419 in the apices 418 and the openings 435 at the free end portions of the struts 434 can be circular or substantially circular, although one or both of the openings 419 and/or 435 can be elongated or oval as described above.

Figure 57:
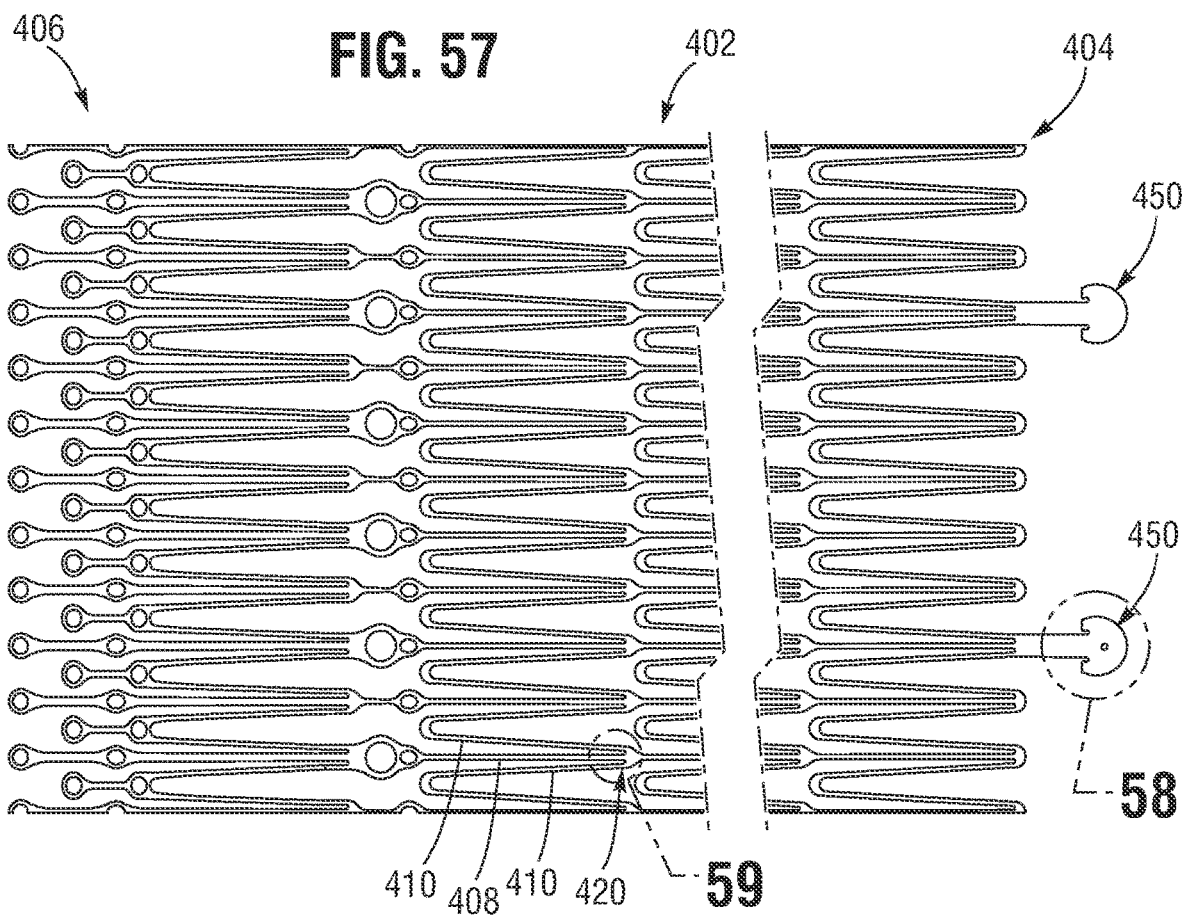
FIG. 57 is a top plan view of the frame of FIG. 51 in an unrolled or laid-flat state.

FIG. 57 illustrates the inflow and outflow end portions 404, 406 of the frame 402 in an unrolled or laid-flat configuration.

Figure 58:
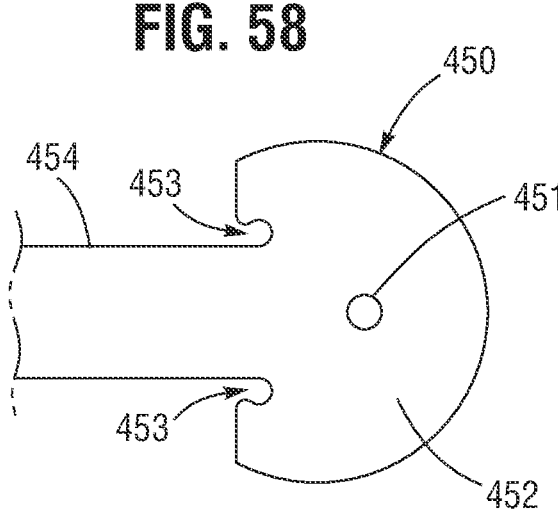
FIG. 58 is a magnified view of a coupling portion of the frame of FIG. 57.

FIG. 58 illustrates a representative coupling member 450 in more detail. In certain embodiments, one or both of the coupling members 450 can define openings 451 in the round member or paddle portion 452. The coupling member 450 can also comprise notches or recesses 453 defined between the strut portion 454 and the round member 452, which can aid in engaging the delivery apparatus as described above.

Figure 59:
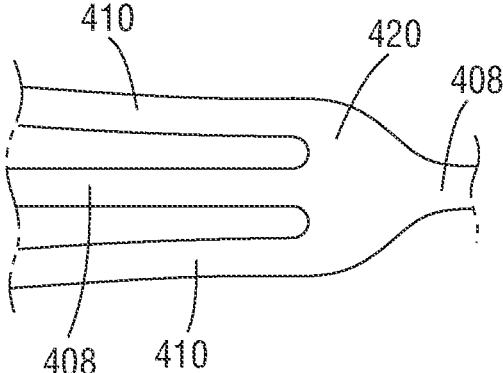
FIG. 59 is a magnified view of a portion of a junction between struts at the outflow end portion of the frame of FIG. 57.

FIG. 59 illustrates a magnified view of a representative junction 420 between the longitudinal struts 408 and struts 410 of the tenth row X of struts 410.

Figure 60:
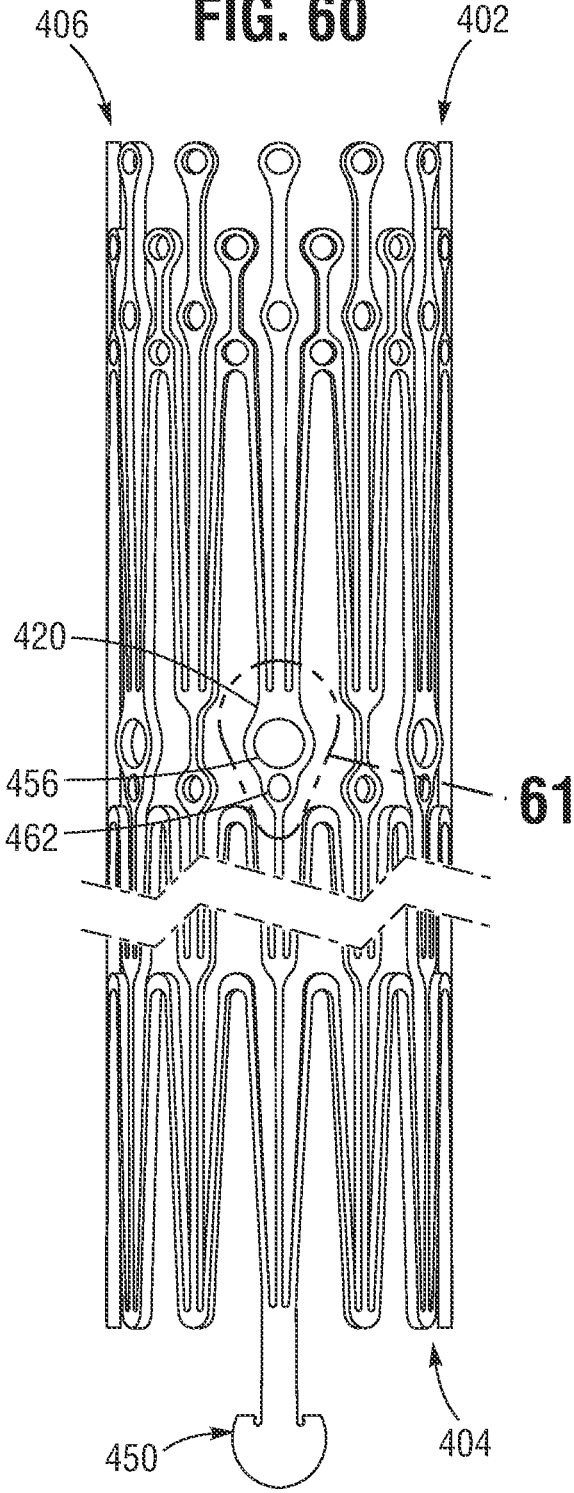
FIG. 60 is another side elevation view of the inflow and outflow end portions of the frame of FIG. 51.

FIG. 60 illustrates the inflow and outflow end portions 404, 406 of the collapsed frame 402 in yet another rotational orientation.

Figure 61:
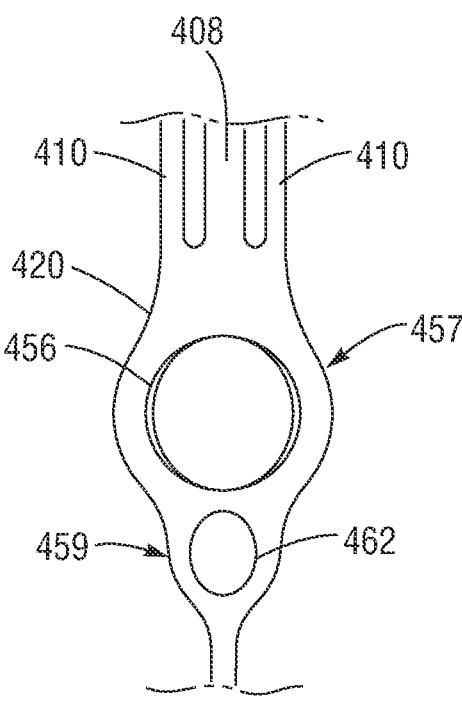
FIG. 61 is a magnified view of a strut junction at the outflow end portion of the frame including a plurality of openings.

FIG. 61 is a magnified view of a representative junction 420 at the eleventh strut row XI (FIG. 48) including an integrated opening 456 and an integrated opening 462. In the illustrated embodiment, the opening 456 can be circular or substantially circular, and can be located in a first portion 457 of the junction 420 that is larger/wider than a second portion 459 including the opening 462. In certain embodiments, the opening 462 can be elongated or ovoid with its long axis oriented along the axis of the longitudinal strut 408, although in other embodiments the opening 462 can be circular or substantially circular similar to the opening 456.

Figure 67:
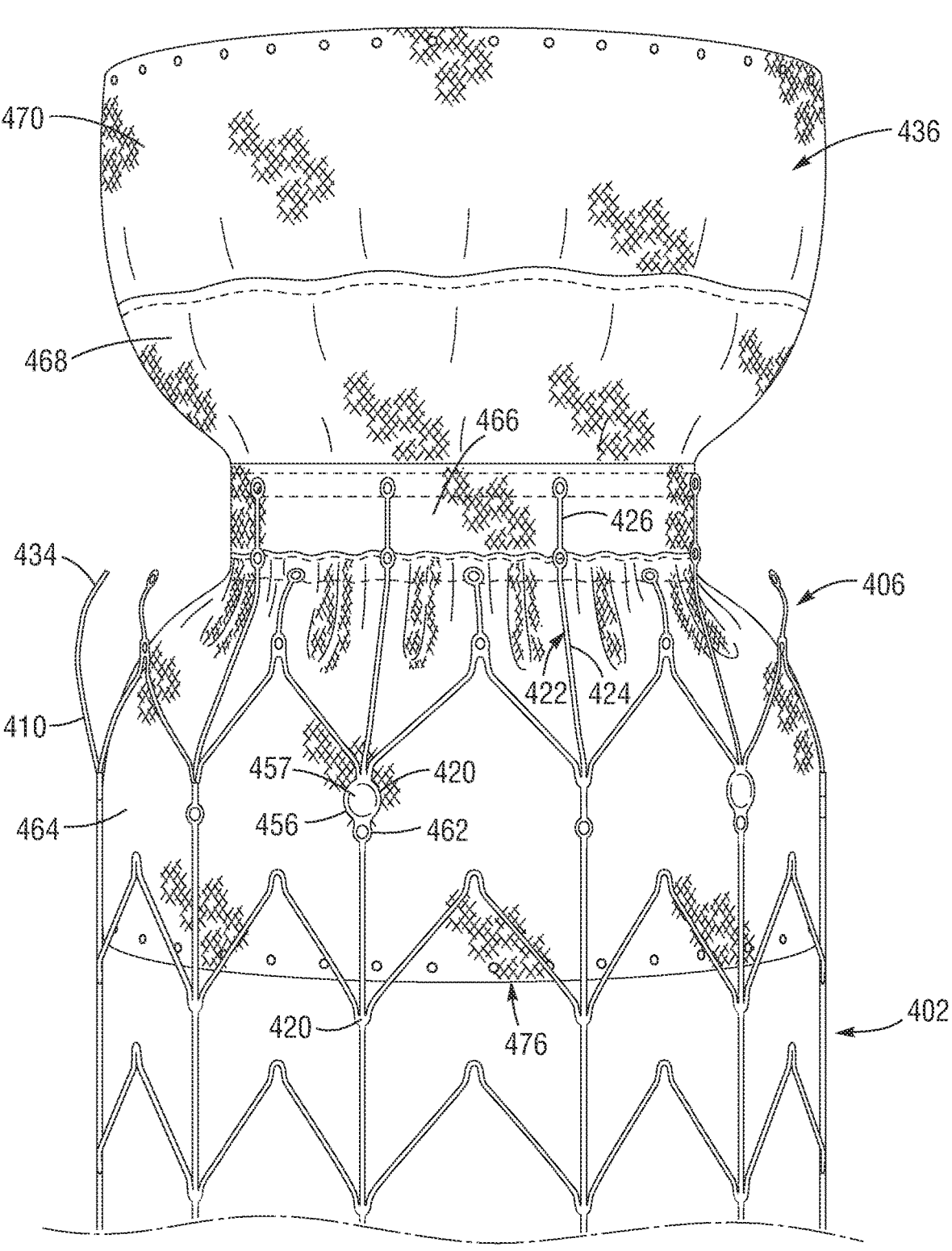
FIG. 67 is a side elevation view illustrating the sealing member of FIG. 62 partially assembled on the docking station frame of FIG. 48.

In certain embodiments, the frames described herein such as the frame 402 can be laser cut from a tube, or patterned and etched in a lithography process. In embodiments in which one or more struts are curved inwardly relative to the central axis of the frame, after the frame is formed from the stock material the various strut members can be shape set. For example, referring to FIGS. 48-50, the end portions of the longitudinal struts 408 and the associated first row I of struts 410 at the inflow end portion 404, along with the coupling members 450, can be shape set such that they are curved or angled radially inwardly toward the longitudinal axis 412 of the frame. At the outflow end portion 406, the struts 410 of the eleventh row XI can be shape set to curve radially outwardly as best shown in FIGS. 49 and 67, and the struts 434 can be shape set to curve radially inwardly from the apices 418. However, the struts 410 of the eleventh row XI can also extend longitudinally without curving, or can curve inwardly. The first portions 424 of the struts 422 can be shape set to extend radially inwardly such that the second portions 426 are offset inwardly from the outer diameter of the frame, as shown in FIGS. 48-50 and other embodiments herein.

Figures 62, 63A, 63B, 63C, 63D:
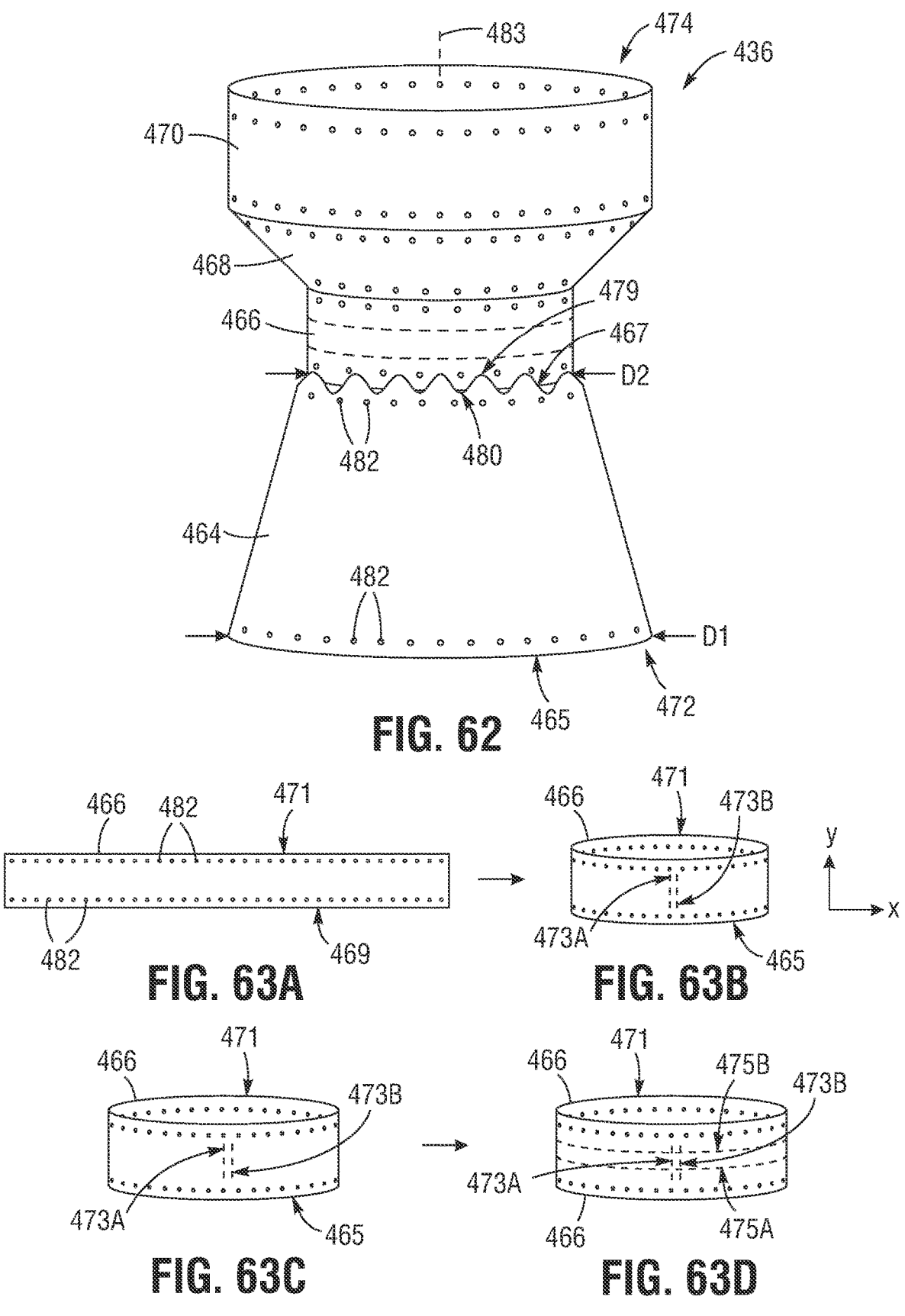
FIG. 62 is a perspective view of a sealing member, according to one embodiment.
FIGS. 63A-63D illustrate assembly of a central portion of the sealing member of FIG. 62.

FIG. 62 illustrates a representative embodiment of the sealing member 436, which can be used in combination with any of the frame embodiments described herein, and with the frames of FIGS. 25-35 and 48-61 in particular. The sealing member 436 can comprise a tubular main body having a first end portion 472 and a second end portion 474. The sealing member 436 can comprise a series of members, elements, sections, or portions having different diameters, and/or diameters that vary along their length. For example, in the illustrated embodiment the sealing member can include a first or inflow portion 464, a second or central portion 466, a third portion 468, and a fourth or outflow portion 470. The first portion 464 can be tapered/conical/frustoconical, with a first diameter D1 at its first or inflow end portion 465. The inflow end portion 465 can correspond to the first end portion 472 of the sealing member overall. The first portion 464 can further comprise a second diameter D2 at a second or outflow end portion 467. The outflow end portion 467 of the first portion 464 can comprise a scalloped edge including a plurality of extension portions 479 having peaks/apices spaced apart by recesses or recessed portions 480. The extension portions 479 and the recesses 480 can have any specified height, depth, and/or width or circumferential length (e.g., at their base).

The second portion 466 can comprise substantially the second diameter D2 along its length. The third portion 468 can increase in diameter moving in a direction toward the second end portion 474 from the second diameter D2 to substantially the first diameter D1, although the diameter of the upper portion of the third portion 468 can also be greater than or less than the diameter D1. The fourth portion 470 can comprise substantially the first diameter D1 along its length (or the diameter of the upper portion of the third portion 468). Thus, prior to attachment to a frame, the sealing member 436 can comprise an hourglass-shaped outer profile in which the diameter of the central portion 466 is less than the diameter of the first end portion 472 of the sealing member and less than the diameter of the second end portion 474 of the sealing member.

Some or all of the portions 464-470 of the sealing member 436 can comprise rows of openings extending along one or both edge portions of the portions 464-470. For example, in the illustrated embodiment the first portion 464 can comprise a row of openings 482 extending circumferentially along the inflow end portion 465, and a row of openings 482 extending circumferentially along the scalloped outflow end portion 467. In certain embodiments, the openings 482 at the outflow end portion 467 can be aligned with the recesses 480, aligned with the extension portions 479, or at any other circumferential location relative to the recesses and/or the extension portions. Each of the other portions 466, 468, and 470 can also include rows of openings 482 located along the inflow and/or outflow end portions. In certain embodiments, the row of openings 482 along an edge portion of one portion of the sealing member can be aligned with the openings 482 of the edge portion of the adjacent portion. For example, in the illustrated embodiment the row of openings 482 at the outflow end portion 467 of the first portion 464 are aligned along the longitudinal axis 483 of the sealing member with the openings 482 of the inflow edge portion of the central portion 466. In other embodiments, one or more of the portions 466, 468, and/or 470 may include one row of openings, no openings, or more than two rows of openings located anywhere on the portions.

Figures 64A, 64B, 65A, 65B, 66A, 66B:
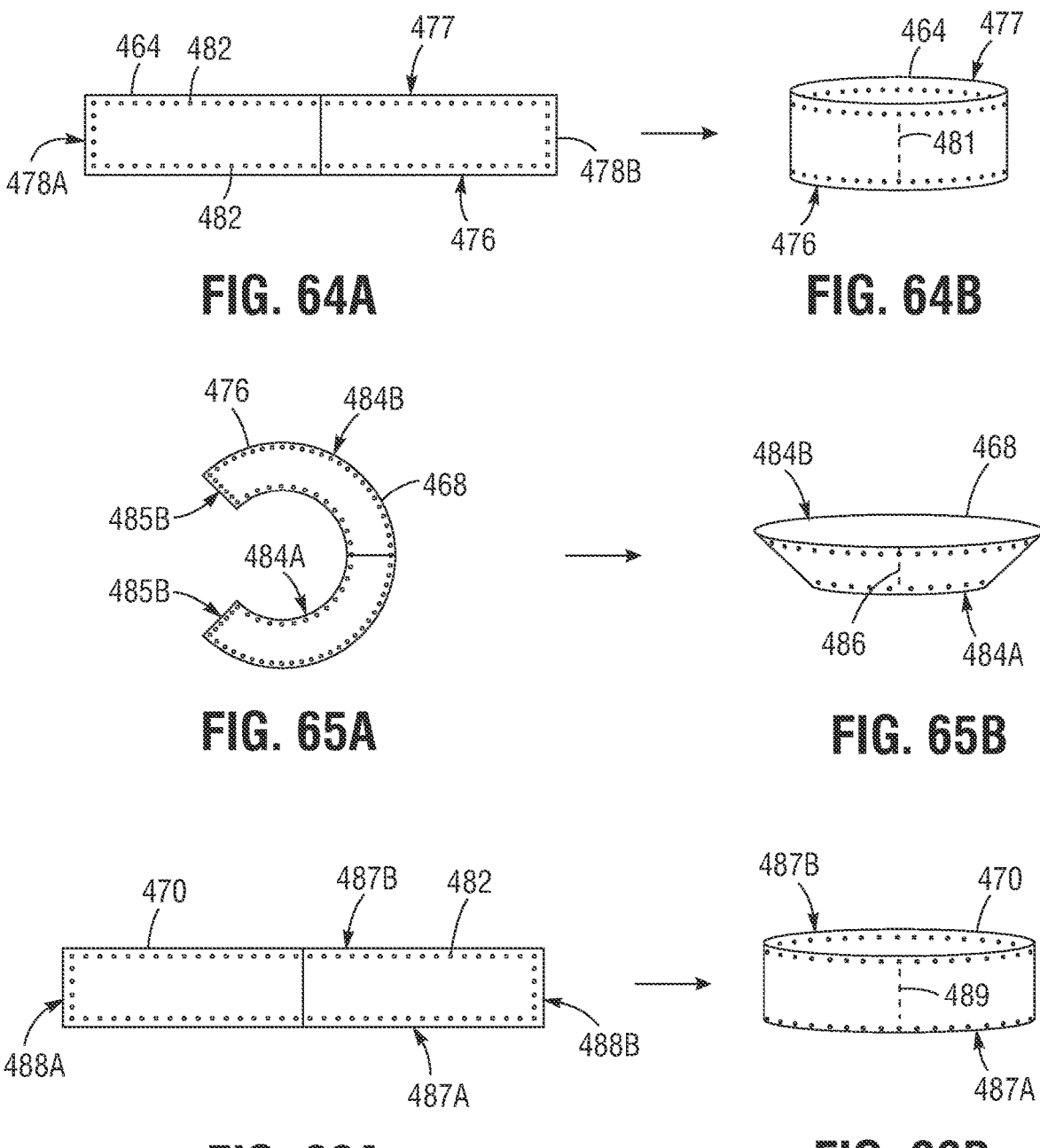
FIGS. 64A and 64B illustrate a first or inflow portion of the sealing member of FIG. 62.
FIGS. 65A and 65B illustrate a third portion of the sealing member of FIG. 62.
FIGS. 66A and 66B illustrate a fourth or outflow portion of the sealing member of FIG. 62.

As described in greater detail below, in certain embodiments the sealing member 436 can be a unitary construction (e.g., a unitary woven tubular member), or can be assembled from a plurality of individual members/elements/swatches. FIGS. 63A-66B illustrate the individual portions of a sealing member 436 formed from discrete members, according to one embodiment. FIGS. 63A-63D illustrate exemplary steps of forming the second portion 466. FIG. 63A illustrates the second portion 466 in a laid-flat state as a rectangular member. Referring to FIG. 63A, a first row of openings 482 can be formed along one longitudinal/circumferential edge portion 469, and a second row of openings 482 can be formed along the other longitudinal/circumferential edge portion 471. In certain embodiments, the second portion 466 can also include columns of openings extending along the end portions between the longitudinal edge portions 469 and 471, similar to the first portion 464 as shown in FIG. 64A. In the illustrated embodiment, the openings 482 are configured as round holes, but the openings may be configured in a variety of ways, such as in the form of slits, knife cuts, or openings extending in two axes (e.g., square, rectangular, etc.). Referring to FIGS. 63B and 63C, the ends of the second portion 466 can be folded together and secured to each other, such as by suturing, to form a tubular member or construction. Two adjacent suture lines 473A and 473B are shown extending along the y-axis to attach the end portions together. Referring to FIG. 63D, two horizontal rows of sutures 475A and 475B can be formed extending circumferentially around the second member 466. In other embodiments, the second portion 466 can include any number of rows of openings 482 and/or suture lines located anywhere on the second portion, having any shape or configuration, and extending in any direction.

FIG. 64A illustrates the first portion 464 in a laid-flat configuration. The first portion 464 can comprise two rows of openings 482 along a first longitudinal edge portion 476 and a second longitudinal edge portion 477. In the illustrated embodiment, the openings 482 are configured as round holes, but may have any shape. Columns of openings 482 can extend along the end portions 478A and 478B, respectively, such that openings 482 extend along the entire perimeter of the first portion 464. Referring to FIG. 64B, the end portions 478A and 478B of the first portion 464 can be folded and secured together at a suture line 481 extending between the first and second edge portions 476, 477 to form a tubular member. In certain embodiments, the suture(s) of the suture line 481 can extend through the openings 482 of the (e.g., overlapping) end portions 478A and 478B. In other embodiments, the openings 482 can have any size and/or configuration/shape, and can extend along any portion or direction of the first portion 464.

In certain embodiments, the scalloped outflow end portion 467 can be formed in the longitudinal edge portion 477, for example, by laser cutting or other cutting/patterning techniques, before or after the first portion 464 is wrapped and secured in a cylindrical shape.

FIG. 65A illustrates the third portion 468 in a laid-flat configuration. When laid flat, the third portion 468 can comprise an open circular shape, such as a C-shape or a backwards C-shape. Openings 482 can be formed in the first or radially inward edge portion 484A and in the second or radially outward edge portion 484B, as well as in at least one of the end portions 485A and/or 485B such that, in certain embodiments, the openings extend around the entire perimeter of the third portion 468. Referring to FIG. 65B, the edge portions 485A and 485B can be folded together and secured by a suture line 486 or other connection. When the edge portions 485A and 485B are folded together and secured, the third portion 468 can form a tapered, conical, or frustum shape with a relatively narrower or smaller diameter first or base portion formed by the radially inward edge portion 484A and a relatively wider or larger diameter second or top/upper portion formed by the radially outward edge portion 484B.

FIG. 66A illustrates the fourth portion 470 in a laid-flat configuration. In certain embodiments, the fourth portion 470 can be configured similarly to the first portion, at least initially, with openings 482 extending along first and second longitudinal edge portions 487A and 487B, and along end portions 488A and 488B. When the end portions 488A and 488B are folded together, they can be secured together at a suture line 489.

In certain embodiments, the various components of the sealing member 436 can be made from any of various materials, such as woven or non-woven fabrics, polymeric laminate materials, composite materials, etc. For example, in certain embodiments the various portions 464-470 of the sealing member can comprise, for example, woven fabrics comprising any of a variety of synthetic/polymeric and/or natural fiber materials, such as polyethylene terephthalate (PET) fabric (e.g., DACRON®), polyester fabric, polyamide fabric, Nylon, polytetrafluoroethylene (PTFE), expanded polytetrafluoroethylene (ePTFE), ultra-high molecular weight polyethylene (UHMWPE) (e.g., DYNEEMA®), polypropylene, cotton, combinations thereof, etc. In certain embodiments, any or all of the portions of the sealing member 436 can also comprise a film including any of a variety of crystalline or semi-crystalline polymeric materials, such as polytetrafluorethylene (PTFE), PET, polypropylene, polyamide, polyetheretherketone (PEEK), etc. In this manner, the sealing member 436 can be relatively thin and yet strong enough to allow it to be sutured to the frame, and to allow the prosthetic valve to be expanded against it, without tearing.

In embodiments in which the sealing member 436 comprises woven fabric, any or all of the portions 464-470 can comprise any of various weave patterns, such as gauze weave patterns, plain weave patterns, twill weave patterns, satin weave patterns, and/or their derivatives. In certain embodiments, the woven fabric can have a plurality of first threads/yarns/strands/filaments and second threads/yarns/strands/filaments interwoven with any specified thread count. For example, in certain embodiments the fabric can comprise 10 threads/strands/yarns/filaments per inch to about 200 threads/strands/yarns/filaments per inch, about 50 threads/strands/yarns/filaments per inch to about 200 threads/strands/yarns/filaments per inch, or about 100 threads/strands/yarns/filaments per inch to about 200 threads/strands/yarns/filaments per inch in the warp direction and/or in the weft direction. In certain embodiments, the threads/yarns/strands/filaments can have a denier of, for example, 7 dtex to 100 dtex. Any or all of the portions can also be knitted. In certain embodiments, the sealing member 436 can also comprise any of various non-woven fabrics, such as felt.

In certain embodiments, the threads/yarns/strands/filaments may be bulked or texturized, such as by twisting, heat setting, and untwisting the threads/yarns/strands/filaments such that they retain their deformed, twisted shape. The threads/yarns/strands/filaments can also be texturized by crimping, coiling, etc. In certain embodiments, the sealing member 436 can include such threads/yarns/strands/filaments, or other features such as frayed yarns or threads, to induce a biological response to the sealing member to aid in forming a seal between the frame and the surrounding anatomy, and/or between the frame and a prosthetic valve received in the valve seat.

In certain embodiments, the openings 482 can be formed by any of various processes, such as by laser-drilling, punching or stamping, cutting, weaving the openings into the fabric of the various sealing member portions, etc.

Figure 74:
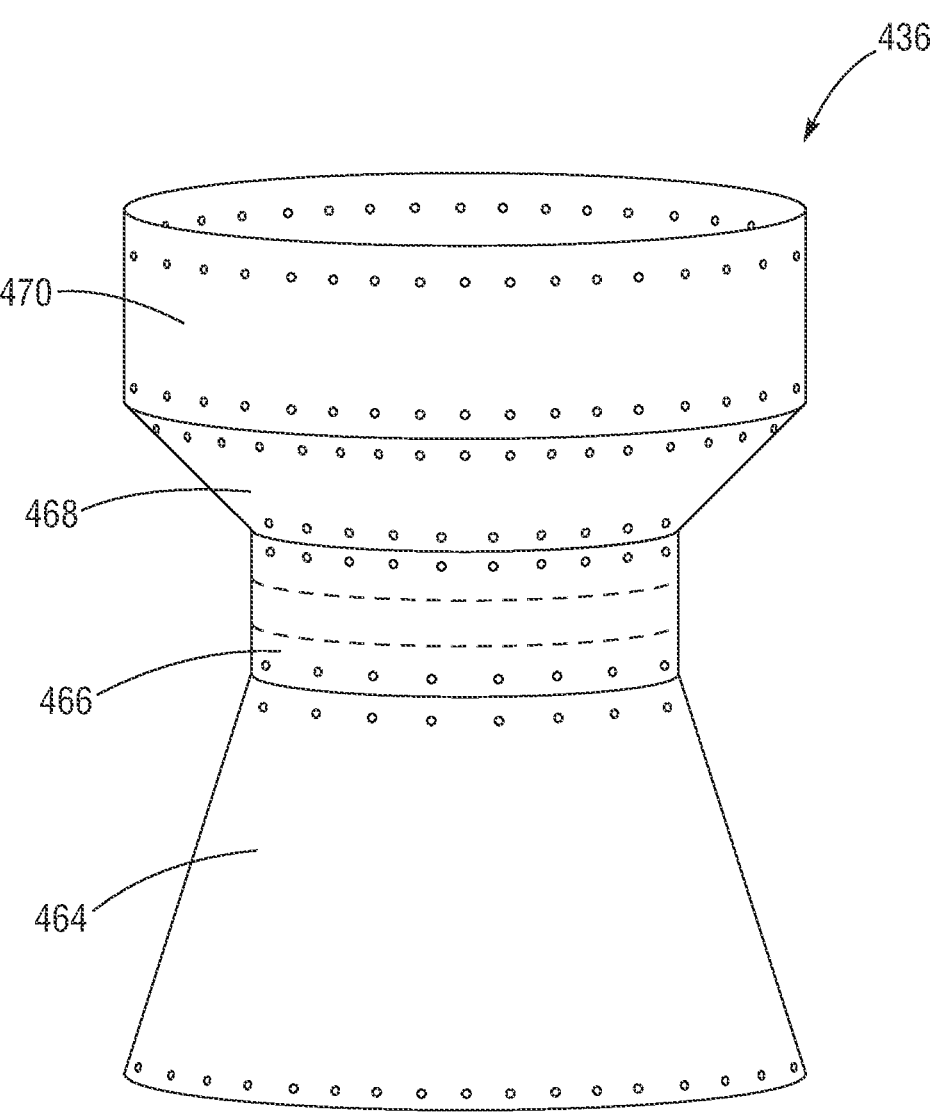
FIG. 74 illustrates a continuously woven tubular sealing member, according to another embodiment.

In certain embodiments, the various sealing member portions 464-470 can be assembled together, for example, by suturing, heating bonding, adhesive, or combinations thereof, and assembled onto the docking station frame. In certain examples, the sealing member 436 can be a unitary construction woven using any of various tubular weaving techniques. For example, with reference to FIG. 74, the various diameter portions of the sealing member 436 can be woven or knitted as a unitary body, which in certain embodiments can provide improved crimping profile, shorter assembly times, and/or improved manufacturability. The sealing member can also be formed by electrospinning. For example, a liquid polymer (e.g., a lubricious polymer such as PTFE, ePTFE, etc.) can be applied or electrospun on to the frame 402 and/or the valve seat 428 to form a sealing member or portions thereof.

Figure 75:
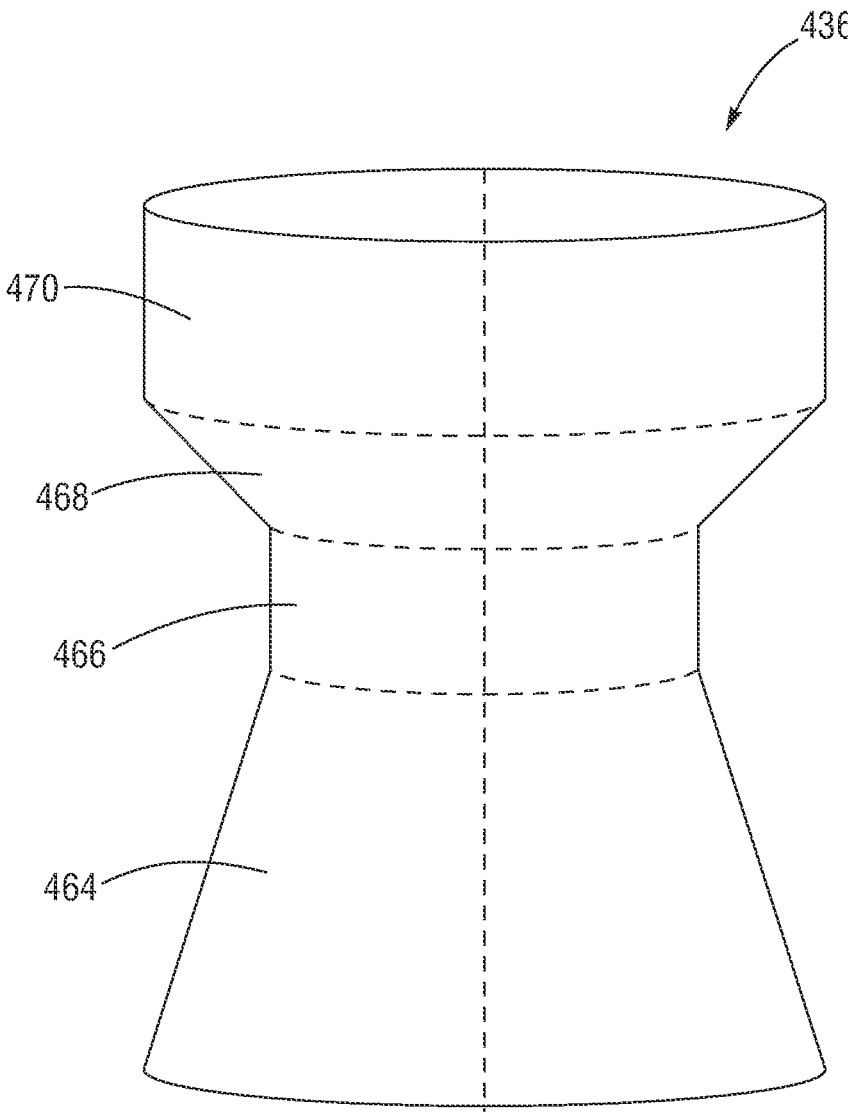
FIG. 75 is a perspective view of another embodiment of a sealing member.
Figure 76:
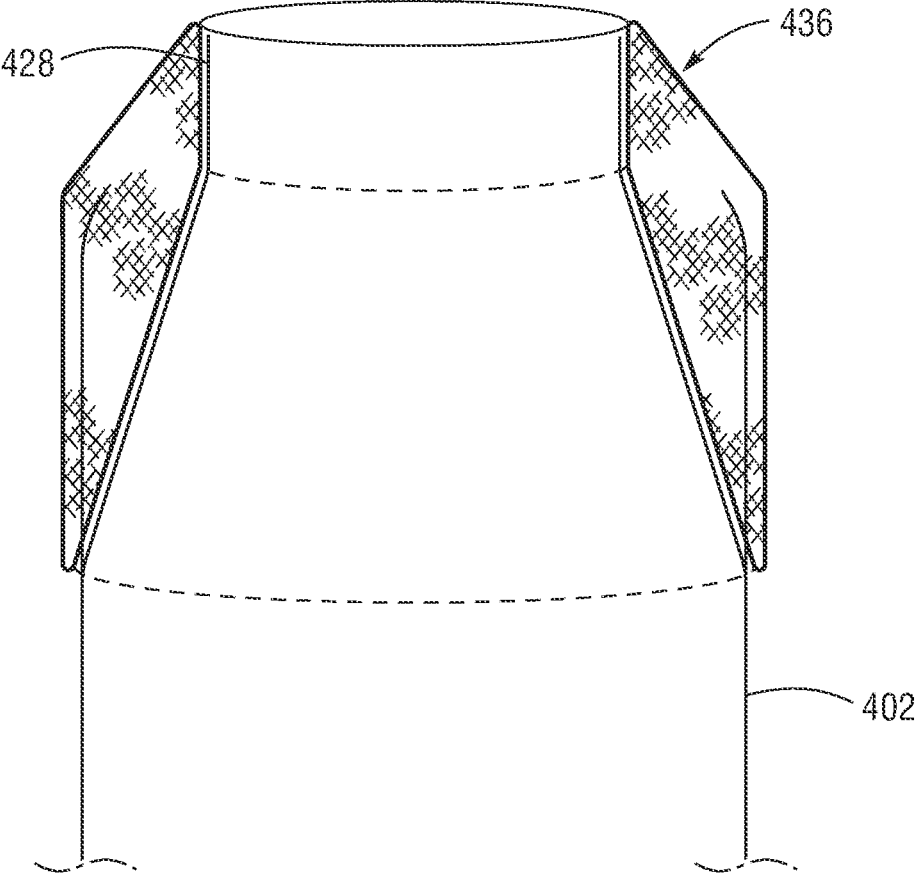
FIG. 76 illustrates the sealing member of FIG. 75 on a docking station frame.

FIG. 75 illustrates another embodiment of the sealing member 436 formed as a woven, knitted, and/or electrospun unitary tubular body without openings 482. FIG. 76 illustrates the sealing member 436 of FIG. 75 disposed on a docking stent frame 402. The sealing member 436 of FIG. 75 can also be used in combination with any of the other docking station frames described herein.

In certain embodiments, one or more portions of the sealing member 436 can comprise any of various coatings, such as anti-abrasive or lubricious coatings (e.g, PTFE, ePTFE, etc.), hydrophobic or water-repellant coatings, coatings for promoting a biological response such as tissue growth, clot formation, etc. In certain embodiments, there can be few if any mechanical loads on the sealing member during normal operation.

FIG. 67 illustrates the sealing member 436 partially assembled onto the frame 402 of FIG. 48. The first portion 464 can be positioned within the outflow end portion 406 of the frame, for example, with the longitudinal edge portion 476 adjacent the junctions 420 of the tenth row X of struts 410. The central portion 466 can be positioned within the valve seat 428 defined by the strut members 422, and the portions 468 and 470 can extend upwardly out of the frame 402.

Figure 68:
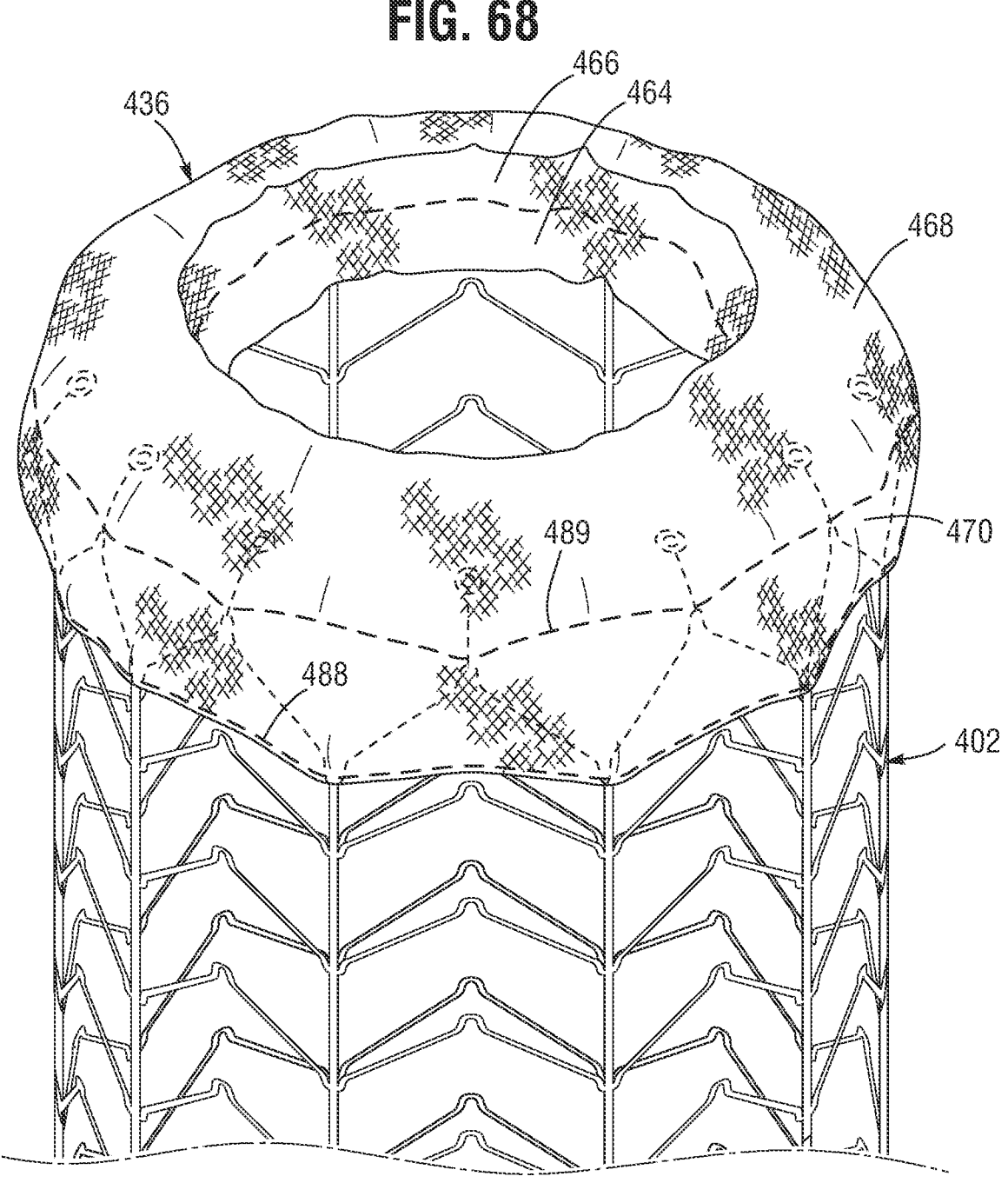
FIGS. 68-71 illustrate the sealing member of FIG. 62 assembled on the docking station frame of FIG. 48.
Figure 69:
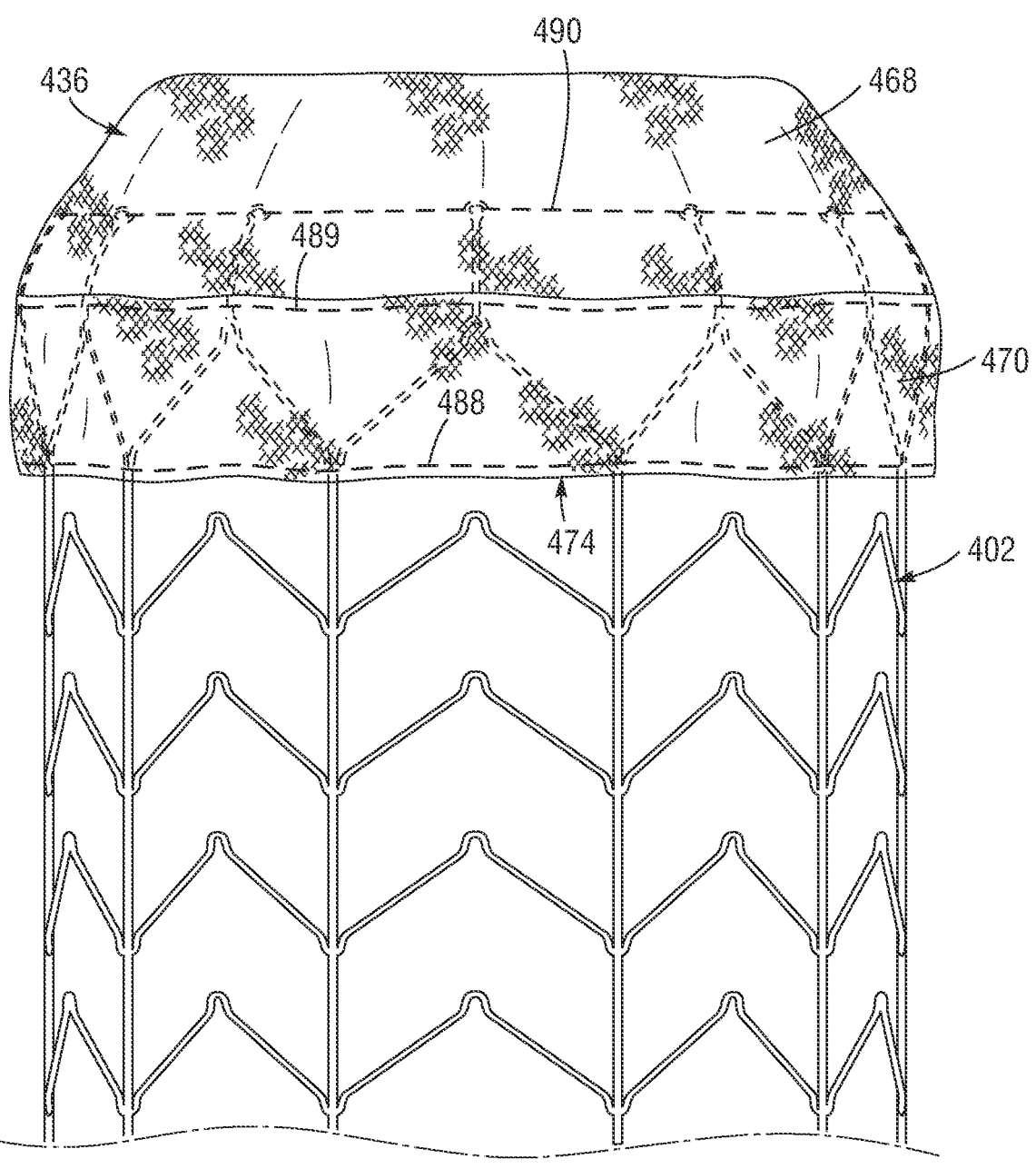

Referring to FIGS. 68 and 69, the sealing member 436 can be folded over the outer aspect of the frame 402 such that the sealing member extends over or covers the struts 422, the struts 434, the valve seat 428, and covers the eleventh row XI of struts 410. Thus, the portion 470 can be positioned against the radially outward surface of the frame 402. In certain embodiments, the portion 470 can be coupled to the frame by suturing 488 through the openings 462 (FIG. 48) of the longitudinal struts 408. In certain embodiments, the sealing member 436 can also be coupled by suturing 489 through the openings 419 (FIG. 48) of the free apices 418. The sealing member can also be coupled/attached to the frame by suturing 490 through the openings 435 of the struts 434. In certain embodiments, the radiopaque indicators/markers 457 can be positioned at or near the second end portion 474 (and/or the first edge portion 472) of the sealing member 436, which can correspond to the inflow edge portion of the sealing member when attached to the frame. In certain examples, the radiopaque indicators 457 can be 2 cm or less from the inflow edge portion 474 of the sealing member 436 along the longitudinal axis 412, 1 cm or less from the inflow edge portion 474 of the sealing member 436 along the longitudinal axis 412, 5 mm or less from the inflow edge portion 474 of the sealing member 436 along the longitudinal axis 412, etc. In this manner, the surgeon can use the radiopaque indicators/markers 457 to identify the location of the edge of the sealing member 436 during implantation, helping to avoid blockage of the hepatic veins and/or the renal vein with the sealing member. The inflow edge portion 474 may be upstream or downstream of the junctions 420 and the radiopaque markers 457. In certain embodiments, the surgeon can position the collapsed or partially collapsed docking station in the blood vessel by locating the radiopaque indicators/markers at a selected position relative to the hepatic veins and/or the renal vein (e.g., upstream or downstream) before expanding the docking station.

Figure 70:
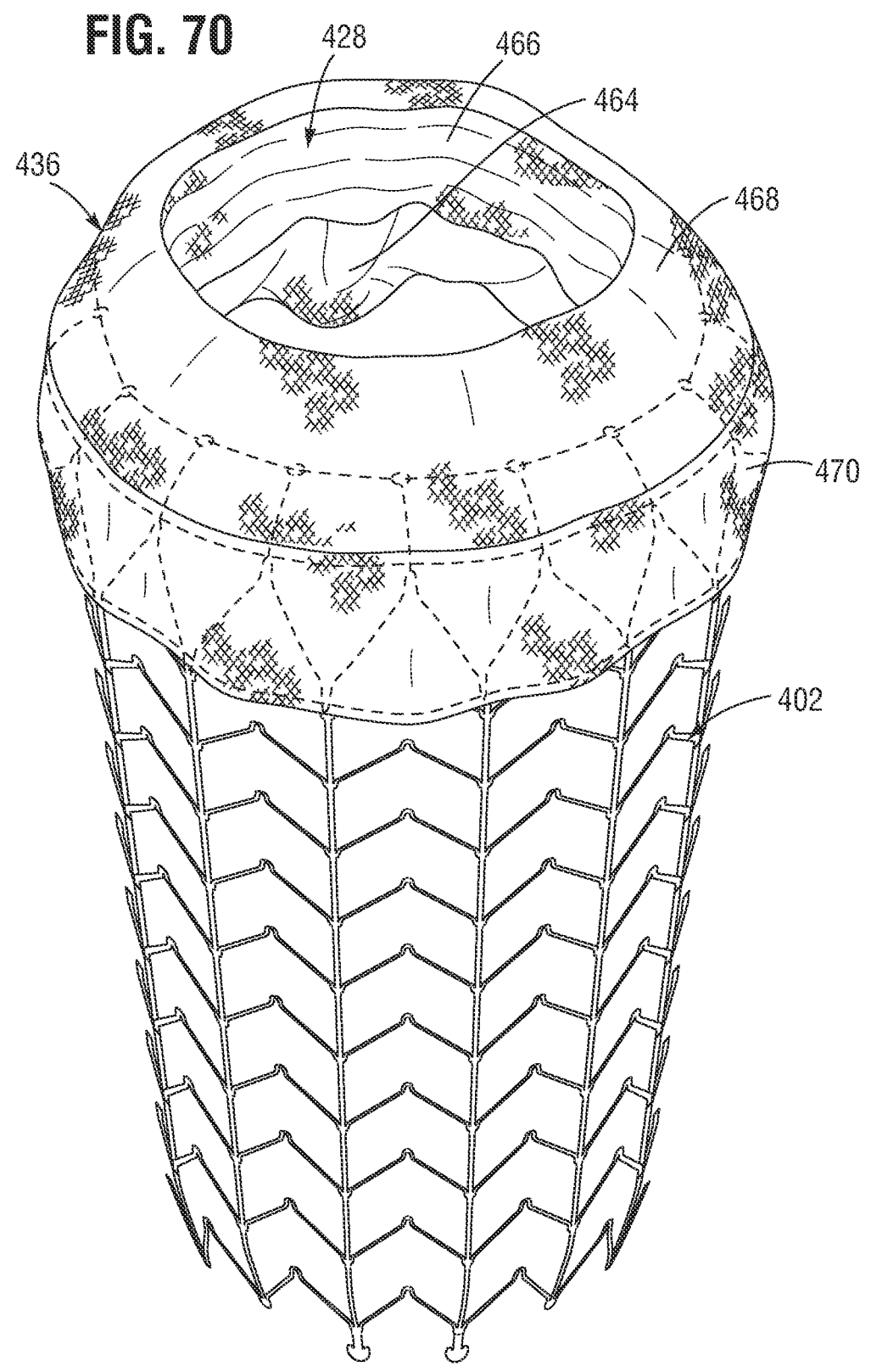
Figure 71:
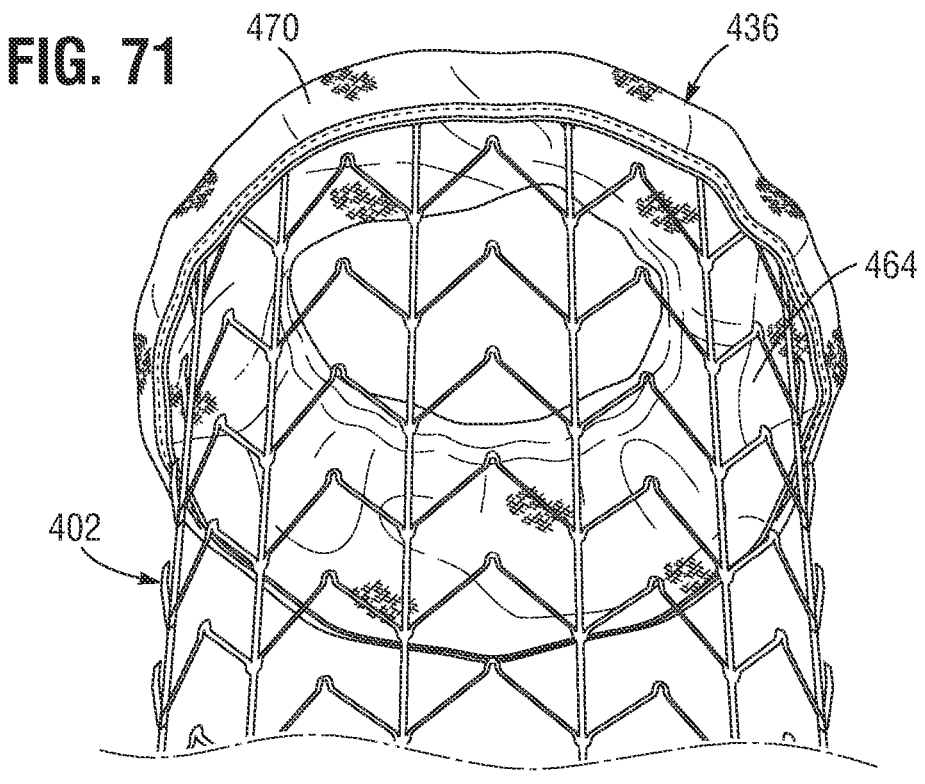

Referring to FIGS. 70 and 71, in certain embodiments the sealing member 436 can be configured such that the first portion 464 and/or the second portion 466 are loose, pleated, or billowy, with extra material draped within the lumen of the docking station at or below the level of the valve seat 428. In certain embodiments, the sealing member 436 is not stretched or taut, at least in the region above and/or below the valve seat 428, but hangs loosely. This can aid in forming a seal with the prosthetic valve, for example, because the extra material of the sealing member 436 can fill in gaps or spaces between the frame 402 and the prosthetic valve. In other embodiments, the sealing member may be stretched or taut around the valve seat and/or other portions of the frame.

Figure 72:
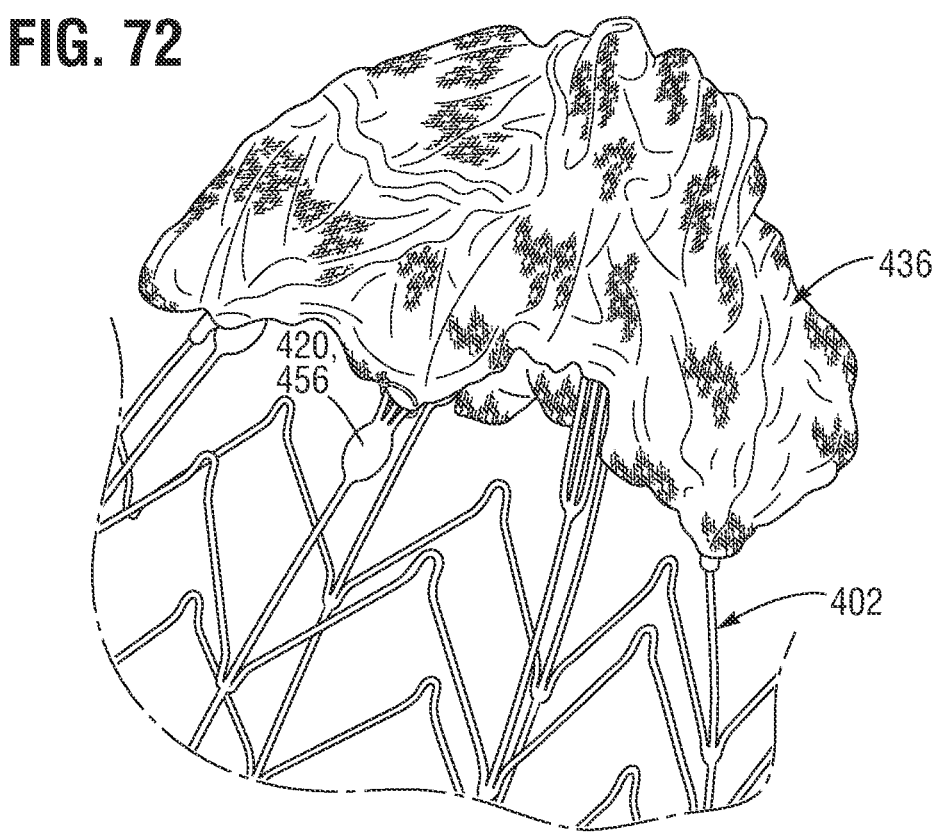
FIG. 72 illustrates the sealing member of FIG. 62 secured to the frame downstream of the radiopaque markers at the outflow end of the frame.

In certain embodiments, the sealing member 436 can also be sutured to the struts above or downstream of the junctions 420/openings 456 and radiopaque markers 457, as illustrated in FIG. 72.

Figure 73:
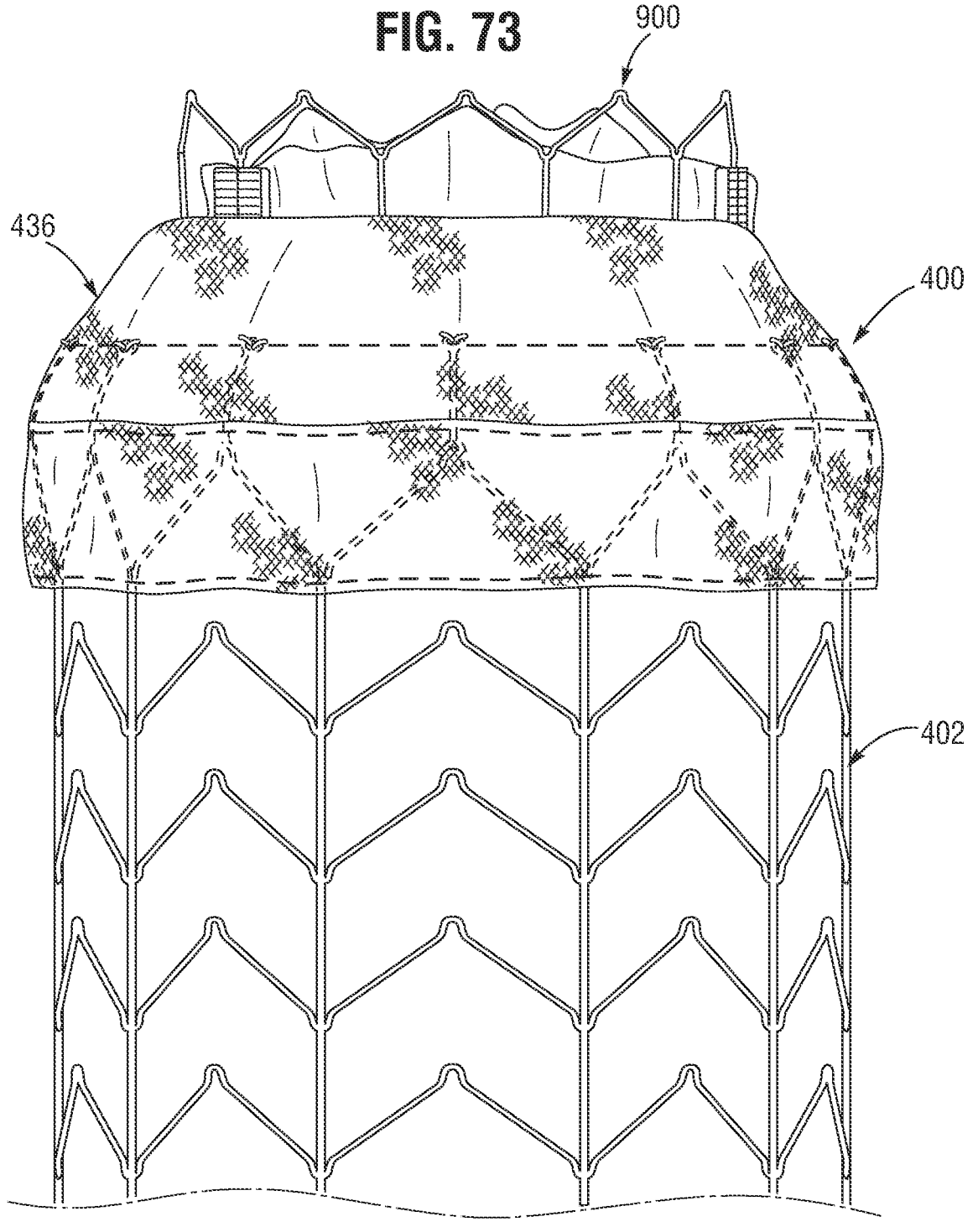
FIG. 73 is a side elevation view illustrating a prosthetic valve deployed in the docking station of FIG. 68.

FIG. 73 illustrates a prosthetic valve 900 deployed in a docking station 400 configured according to the embodiment of FIG. 48.

Figure 77:
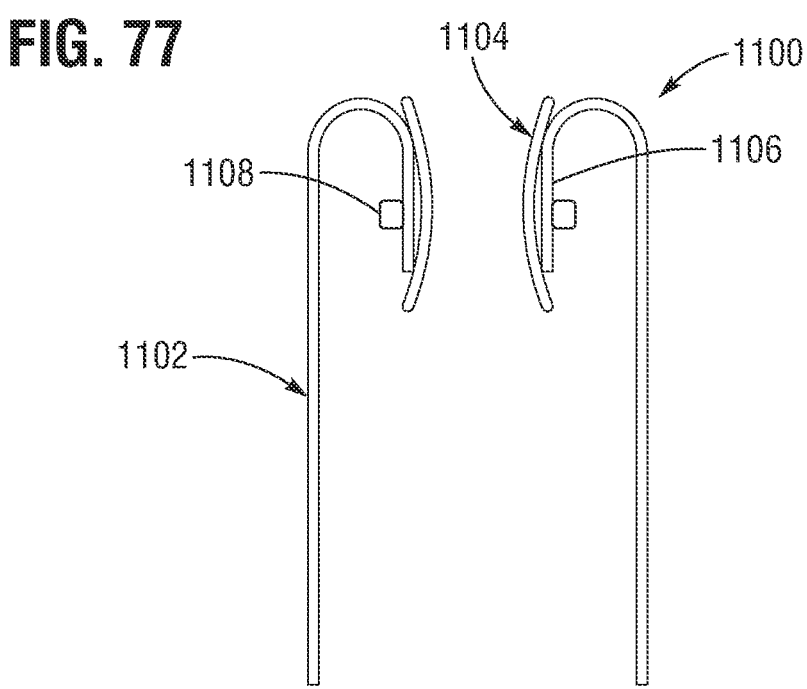
FIGS. 77 and 78 illustrate two docking station configurations including an annular member disposed around the valve seat, according to another embodiment.
Figure 78:
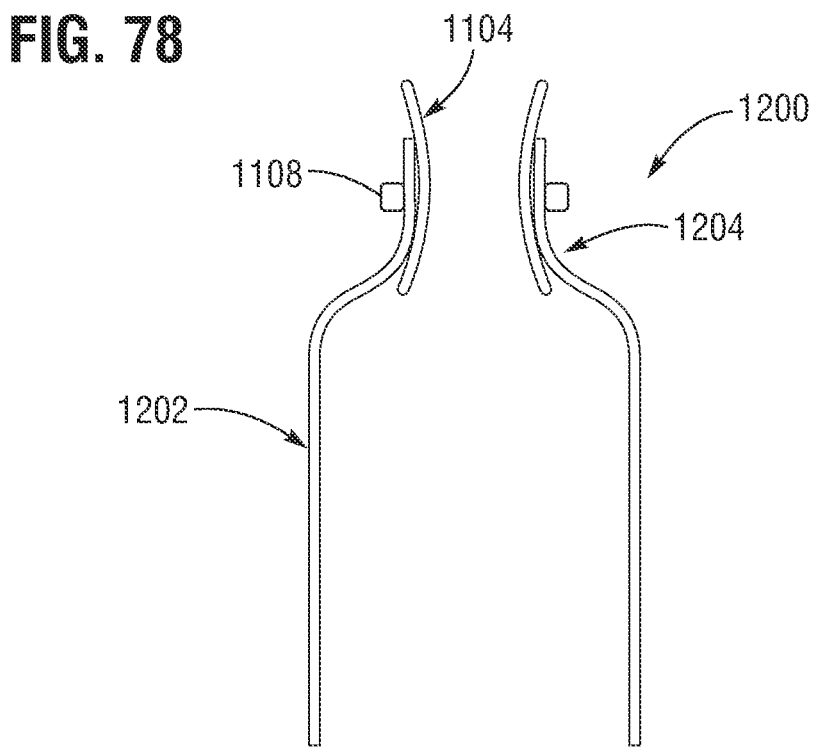

FIGS. 77 and 78 illustrate additional embodiments of docking stations including one or more circumferentially-extending annular members/bands configured as a restraint/clamp/constrictor/securing means/restraining means for limiting the diameter of the valve seat, and thereby the diameter of the expanded prosthetic valve. The annular member(s) can also influence the outer profile/shape of the prosthetic valve expanded in the valve seat. FIG. 77 schematically illustrates a docking station 1100 including a frame 1102 configured similarly to the frame 1002 of FIG. 47. A prosthetic valve 1104 is shown schematically positioned in the valve seat 1106. The frame 1102 can comprise an annular member 1108 positioned around the exterior of the valve seat. The annular member 1108 can be configured to limit or constrain radial expansion of at least a portion of the valve seat 1106 when the prosthetic valve 1104 is expanded in the valve seat. This, in turn, can limit radial expansion of the prosthetic valve at the location of the annular member 1108, facilitating expansion of the prosthetic valve to the hour-glass-shaped profile described above with reference to FIG. 23. FIG. 78 illustrates an annular member 1108 positioned around a valve seat 1204 of a frame 1202 of a docking station 1200 configured similarly to the docking station 200 and/or the docking station 400. A prosthetic valve 1104 is shown schematically positioned in the valve seat 1204 and urged into an hourglass shape by the constricting action of the annular member 1108 around the central portion of the prosthetic valve.

In certain embodiments, the annular member 1108 can be a separate member, or can be integrally formed with the docking station frame. In certain embodiments, the annular member 1108 can be an elastic member such as a ring comprising a metallic or polymeric material. As used herein, an "elastic member" refers to a member that returns to an initial state or form after deformation. In certain embodiments the annular member 1108 can comprise an expandable or elastic fabric or cloth member or ring wrapped around the valve seat, optionally including one or more sutures for attachment to the frame. In another example, the annular member 1108 can comprise a non-elastic cloth or fabric member/ring including one or more sutures or other securing means for coupling the annular member to the frame. As used herein, a "non-elastic member" refers to a member that does not return to an initial state or form after deformation, but remains substantially in the deformed state. In yet other examples, the circumference/diameter of the annular member 1108 can be adjustable, such as by a captive screw, ratchet, or other diameter adjustment means.

In particular examples, a docking station frame configured according to any of the embodiments described herein can have an outer diameter of 30 mm to 50 mm, such as 35 mm to 45 mm, or 40 mm. A typical diameter of the inferior vena cava in humans, superior to the hepatic veins, can be 28 mm to 35 mm. The docking station can have a length of 70 mm to 130 mm, such as 80 mm to 120 mm, 90 mm to 110 mm, or 100 mm in particular embodiments. The frame can comprise a nickel-titanium (NiTi) alloy stent. The sealing member can comprise a woven PET fabric ribbon skirt positioned on and secured to the outflow end portion of the frame by suturing, such as with FORCE FIBER® 5-0 sutures. The frame can include tantalum radiopaque markers at or near the inflow edge of the sealing member, such as at or incorporated into frame junctions near the outflow end portion of the frame as described above.

FIG. 80A shows a coupling member/connecting post 1302 of a frame (e.g., frame 402), according to another embodiment. FIGS. 80B-80D show the coupling member/connecting post 1302 being received by a retainer 1304, which can be similar to the retaining member 510 of FIGS. 30-33.

The coupling member/connecting post 1302 has an elongated arm 1306 and an enlarged head 1308 affixed to a proximal end of the arm 1306. The arm 1306 can bisect a distal edge 1310 of the head 1308 from the middle and divide it into two parts that are symmetric relative to a longitudinal axis of the arm 1306. In other embodiments, the arm 1306 can bisect the distal edge 1310 into two parts that are asymmetric about the longitudinal axis of the arm 1306.

In certain embodiments, the head 1308 has a wedge shape which tapers from a distal edge 1310 to a proximal edge 1312 of the head 1308. In addition, the head 1308 can have two opposing curved sides 1314 bulging outwardly relative to the proximal edge 1312 and the distal edge 1310. The curved sides 1314 can define a width (D) of the head 1308, which is the largest distance between the two opposing curved sides 1314 along a direction that is substantially perpendicular to the arm 1306.

The distal edge 1310 can have a substantially flat portion 1316 that is substantially perpendicular to the arm 1306, and the substantially flat portion 1316 can have a predefined length (L) (FIG. 80D). In the depicted embodiment, the distal edge 1310 has two substantially flat portions 1316 that are symmetrically positioned on opposite sides of the arm 1306. Thus, the total length of the substantially flat portions 1316 can be 2L. In other embodiments, the two substantially flat portions 1316 that are asymmetrically positioned on opposite sides of the arm 1306.

In some embodiments, the length (L) of a substantially flat portion 1316 can be configured to be a predefined percentage of the width (D) of the head 1308. For example, in some embodiments, the ratio L/D can range from about 10% to about 40%. In some embodiments, the ratio L/D can range from about 20% to about 30%.

In some embodiments, the length (L) of a substantially flat portion 1316 and the width (W) of the arm 1306 (W) can be configured to have a predefined ratio. For example, in some embodiments, the ratio L/D can range from about 0.2 to about 1.0. In some embodiments, the ratio L/D can range from about 0.4 to about 0.6.

The distal wall 1318 of the recess 1320 on the retainer 1304 can have a substantially flat portion 1322 that is configured to interface with each substantially flat portion 1316 on the distal edge 1310 of the head 1308 of the connecting post 1302. Specifically, when the head 1308 is disposed at the most distal position within the recess 1320 (as shown in FIGS. 80B-80D), the substantially flat portions 1316 on the connecting post 1306 can abut against the substantially flat portion 1322 of the distal wall 1318 on the retainer 1304.

Thus, when recapturing a partially expanded frame into a sheath or capsule as described above, the head 1308 of the connecting post 1302 can press against the retainer 1304 at the interface formed between the substantially flat portions 1316, 1322.

Optionally, as shown in FIGS. 80A-80D, the distal edge 1310 of the head 1308 can have a recessed portion 1324 (FIG. 80D) connecting each substantially flat portion 1316 of the distal edge 1310 and the proximal end of the arm 1306. Each recessed portion 1324 can extend proximally relative to the substantially flat portion 1316, and the depth of the recessed portion 1324 can be predefined. Thus, when the substantially flat portions 1316 on the connecting post 1302 abut against the substantially flat portion 1322 of the distal wall 1318, each recessed portion 1324 can avoid contact with the fillet 1326 (formed between the slot 1328 and the distal wall 1318), therefore not interfering with proper abutment between the substantially flat portions 1316, 1322.

The wedge-shaped connecting post head 1308 can have certain advantages. For example, the fillet 1326 is rounded, rather than perpendicular to the slot 1328. Further, the arc length of the fillet 1326 can be limited to a relatively small dimension due to the constraint of the corresponding arc angle. Thus, in some embodiments the force applied by the connecting post head on the fillet interface area can create uneven pressure and develop high stress on the fillet 1326, which may result in corrosion and material deformation at the fillet interface area, thereby potentially interfering with proper disengagement of the connecting post 1302 from the retainer 1304. In contrast, the connecting post head 1308 and the retainer 1304 of FIGS. 80A-80D can form an abutment between the substantially flat portions 1316, which are substantially perpendicular to the slot 1328. Further, the length (L) of the substantially flat portion 1316 can be configured to be much larger than the arc length of the fillet interface area. Thus, the pressure generated at the substantially flat portions 1316 can be more evenly distributed (i.e., mitigating the risk of generating concentrated stress at the interface region), thereby reducing the risk of corrosion or material deformation of the connecting post 1302 and/or the retainer 1304. Such material deformation can cause the connecting post to "sink" into the retainer material, thereby increasing the risk of fault detachment of the implant from the delivery apparatus (the implant not detaching from the delivery apparatus). By more evenly distributing the pressure and reducing concentrated stress, softer material (e.g., polymers) can be used for designing the connecting post and/or the retainer, thus reducing the cost of manufacturing such components without increasing the risk of corrosion.

The connecting post 1302 can be configured such that when the head 1308 is disposed at the most distal position within the recess 1320, any part of the head 1308 other than the substantially flat portion 1316 can be spaced apart from any wall (e.g., 1318, 1330) or boundary 1332 of the recess 1320.

Similarly, the top surface 1334 of the head 1308 can be substantially flat or curved, and the bottom surface 1336 of the head can also be substantially flat or curved. In some embodiments, the thickness of the head 1308 is about the same or smaller than a depth of the distal wall 1318 of the recess 1320. In some embodiments, the thickness of the head 1308 is slightly larger than (e.g., by a predefined percentage) a depth of the distal wall 1318 of the recess 1320. The coupling member/connecting post and retainer embodiments of FIGS. 80A-80D can be used in combination with any of the docking station frame and delivery system embodiments described herein. Further details regarding the coupling member/connecting post 1302 and the retainer 1304 of FIGS. 80A-80D can be found in U.S. Provisional Application No. 63/066,688, which is incorporated herein by reference.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A docking station, comprising: a radially expandable and collapsible frame comprising a first plurality of struts, the frame comprising an inflow end portion and an outflow end portion, and defining a longitudinal axis; a sealing member disposed on the outflow end portion and configured to form a seal between the docking station and a body lumen; and a valve seat coupled to the frame and configured to receive an expandable prosthetic valve, the valve seat comprising a second plurality of struts coupled to the frame extending in a downstream direction and angled inwardly toward the longitudinal axis of the frame.

Example 2. The docking station of any example herein, particularly example 1, wherein pairs of adjacent struts of the second plurality of struts are coupled together to form free apices, the free apices at least partially defining the valve seat.

Example 3. The docking station of any example herein, particularly example 2, wherein the second plurality of struts at least partially define cells of the frame of the docking station.

Example 4. The docking station of any example herein, particularly example 2 or example 3, wherein the free apices of the valve seat are offset from an outflow end of the frame in an upstream direction toward the inflow end portion of the frame.

Example 5. The docking station of any example herein, particularly example any one of examples 1-4, wherein the first plurality of struts comprises a plurality of circumferentially-arranged longitudinal struts extending between the inflow end portion and the outflow end portion of the frame.

Example 6. The docking station of any example herein, particularly example 5, wherein the first plurality of struts further comprises a plurality of angled struts extending between adjacent longitudinal struts.

Example 7. The docking station of any example herein, particularly example 6, wherein the plurality of angled struts form a plurality of cells of the frame.

Example 8. The docking station of any example herein, particularly example 7, wherein the cells are arranged in rows that are spaced apart from each other axially along the longitudinal axis of the frame.

Example 9. The docking station of any example herein, particularly any one of examples 6-8, wherein the angled struts of the frame define a plurality of free apices offset circumferentially from each other around a circumference of the frame and configured to resist movement of the docking station within a body lumen.

Example 10. The docking station of any example herein, particularly example 9, wherein the frame further comprises a third plurality of struts extending from free apices of the angled struts at the outflow end portion of the frame.

Example 11. The docking station of any example herein, particularly example 10, wherein free end portions of the third plurality of struts define openings.

Example 12. The docking station of any example herein, particularly example 10 or example 11, wherein the third plurality of struts are arranged in a circumferential arrangement radially outward of the second plurality of struts of the valve seat.

Example 13. The docking station of any example herein, particularly any one of examples 10-12, wherein struts of the third plurality of struts are curved radially inward toward the longitudinal axis of the frame.

Example 14. The docking station of any example herein, particularly any one of examples 5-13, wherein the longitudinal struts comprise flex-inducing portions.

Example 15. The docking station of any example herein, particularly example 14, wherein the flex-inducing portions are reduced thickness portions.

Example 16. The docking station of any example herein, particularly example 14, wherein the flex-inducing portions comprise a plurality of rings.

Example 17. The docking station of any example herein, particularly any one of examples 1-16, wherein: the outflow end portion of the frame comprises a plurality of outer frame cells; and the second plurality of struts define a plurality of valve seat frame cells positioned at least partially inward of the outer frame cells.

Example 18. The docking station of any example herein, particularly example 17, wherein struts of the outer frame cells and struts of the valve seat frame cells are coupled to common junctions of the frame.

Example 19. The docking station of any example herein, particularly any one of examples 1-18, wherein the frame further comprises at least one radiopaque marker.

Example 20. The docking station of any example herein, particularly example 19, wherein junctions between struts of the first plurality of struts and struts of the second plurality of struts comprise the radiopaque markers.

Example 21. The docking station of any example herein, particularly any one of examples 1-20, wherein the inflow end portion of the frame comprises a plurality of coupling members configured to engage a delivery apparatus.

Example 22. The docking station of any example herein, particularly example 21, wherein the coupling members comprise round members angled inwardly toward the longitudinal axis.

Example 23. The docking station of any example herein, particularly any one of examples 1-22, wherein free end portions of struts of the second plurality of struts define a downstream-most end of the frame of the docking station.

Example 24. The docking station of any example herein, particularly any one of examples 1-23, wherein the sealing member comprises a first portion coupled to the outflow end portion of the frame and a second portion radially inward of the first portion and coupled to the valve seat.

Example 25. The docking station of any example herein, particularly example 24, wherein: the outflow end portion of the frame comprises a first plurality of supports coupled to the sealing member; the valve seat comprises a second plurality of supports coupled to the sealing member; and the outflow end portion of the frame comprises more supports than the valve seat.

Example, 26. The docking station of any example herein, particularly example 25, wherein the supports of the outflow end portion of the frame comprise a plurality of apices defined by struts of the first plurality of struts.

Example 27. The docking station of any example herein, particularly any one of examples 1-26, wherein at least an outflow edge of the sealing member is disposed at an angle to the longitudinal axis of the frame to align with an outlet of a body lumen.

Example 28. The docking station of any example herein, particularly any one of examples 1-27, wherein struts of the second plurality of struts are coupled to the frame at frame junctions, and free end portions of the struts of the second plurality of struts are offset from the frame junctions in a downstream direction along the longitudinal axis.

Example 29. The docking station of any example herein, particularly example 28, wherein the struts of the second plurality of struts comprise a first portion that is angled inwardly toward the longitudinal axis of the frame, and a second portion that extends in the downstream direction along the longitudinal axis of the frame.

Example 30. The docking station of any example herein, particularly example 29, wherein the second portions of the struts of the second plurality of struts define at least one opening.

Example 31. The docking station of any example herein, particularly any one of examples 1-30, wherein the sealing member comprises a radiopaque material or a radiopaque marker.

Example 32. The docking station of any example herein, particularly any of examples 1-31, wherein the sealing member comprises a first portion disposed within the frame, a second portion disposed within the valve seat, and a third portion disposed on the exterior of the frame.

Example 33. The docking station of any example herein, particularly example 32, wherein a diameter of the second portion of the sealing member is less than a diameter of the first portion and the third portion.

Example 34. The docking station of any example herein, particularly example 33, wherein the diameter of the first portion decreases in a direction of the outflow end portion along the longitudinal axis of the frame.

Example 35. The docking station of any example herein, particularly example 33 or example 34, wherein the diameter of the third portion increases in a direction toward the inflow end portion along the longitudinal axis of the frame.

Example 36. The docking station of any example herein, particularly any one of examples 1-35, wherein the sealing member comprises a plurality of preformed openings configured to receive sutures.

Example 37. The docking station of any example herein, particularly example 37, wherein the openings are laser-drilled or cut.

Example 38. The docking station of any example herein, particularly example 36 or example 37, wherein the first portion comprises openings arranged around a perimeter of the first portion.

Example 39. The docking station of any example herein, particularly any one of examples 32 to 38, wherein the first portion comprises a scalloped edge portion.

Example 40. The docking station of any example herein, particularly any one of examples 1-39, wherein the sealing member comprises a woven or knitted fabric, or is formed by electrospinning.

Example 41. The docking station of any example herein, particularly example 40, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof.

Example 42. The docking station of any example herein, particularly example 40 or example 41, wherein the woven or knitted fabric is a woven fabric comprising a gauze weave, a plain weave, a twill weave, a satin weave, or combinations thereof.

Example 43. The docking station of any example herein, particularly any of examples 32-42, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 44. The docking station of any example herein, particularly any of examples 1-43, wherein the frame comprises a plurality of openings configured to receive sutures for attachment of the sealing member to the frame.

Example 45. The docking station of any example herein, particularly example 44, wherein the plurality of openings are in junctions of the frame.

Example 46. The docking station of any example herein, particularly example 45, wherein the frame further comprises a second plurality of openings defined in struts of the frame spaced apart from the junctions along the longitudinal axis.

Example 47. The docking station of any example herein, particularly any one of examples 1-46, further comprising an annular member disposed around the valve seat and configured to constrain expansion of a prosthetic heart valve when a prosthetic heart valve is deployed in the valve seat.

Example 48. The docking station of any example herein, particularly any one of examples 1-47, further comprising a prosthetic valve disposed in the valve seat, wherein the sealing member is configured to form a seal between the prosthetic valve and the valve seat.

Example 49. The docking station of any example herein, particularly example 48, wherein the prosthetic valve disposed in the valve seat comprises an hourglass-shaped outer profile.

Example 50. A method, comprising: advancing the docking station of any example herein, particularly any one of examples 1-49 to a treatment site in a radially collapsed state; expanding the docking station to anchor the docking station at the treatment site; and deploying a prosthetic valve in the valve seat of the docking station such that the prosthetic valve regulates blood flow through the docking station.

Example 51. A system, comprising: a delivery apparatus, comprising: a first shaft comprising a delivery capsule at a distal end portion of the first shaft; and a second shaft disposed within the first shaft and comprising a retaining member at a distal end portion of the second shaft; and the docking station of any example herein, particularly any one of examples 1-49 disposed within the delivery capsule and coupled to the retaining member.

Example 52. The system of any example herein, particularly example 51, wherein: the docking station comprises coupling members; and the retaining member comprises a slot configured to engage and retain the coupling members of the docking station.

Example 53. The system of example 51 or example 52, wherein the delivery capsule is transparent.

Example 54. A docking station for a prosthetic valve, comprising: a radially expandable and collapsible frame comprising a plurality of struts, the frame comprising an inflow end portion and an outflow end portion and defining a longitudinal axis; and a valve seat coupled to the frame and configured to receive an expandable prosthetic valve; wherein the valve seat is at least partially defined by a plurality of valve seat struts coupled to the frame at frame junctions and comprising free end portions, the valve seat struts being angled radially inwardly from the frame of the docking station toward the longitudinal axis such that the free end portions are offset from the frame junctions in a downstream direction along the longitudinal axis.

Example 55. The docking station of any example herein, particularly example 54, wherein pairs of adjacent valve seat struts are coupled together to form free apices, the free apices at least partially defining the valve seat.

Example 56. The docking station of any example herein, particularly example 54, wherein the valve seat struts at least partially define cells of the frame of the docking station.

Example 57. The docking station of any example herein, particularly any one of examples 54-56, wherein the free end portions of the valve seat struts are offset from an outflow edge of the frame in an upstream direction toward the inflow end portion of the frame.

Example 58. The docking station of any example herein, particularly any one of examples 54-57, wherein the frame comprises a plurality of circumferentially-arranged longitudinal struts extending between the inflow end portion and the outflow end portion of the frame.

Example 59. The docking station of any example herein, particularly example 58, wherein the frame further comprises a plurality of angled struts extending between adjacent longitudinal struts.

Example 60. The docking station of any example herein, particularly example 59, wherein the plurality of angled struts form a plurality of cells of the frame.

Example 61. The docking station of any example herein, particularly example 59 or example 60, wherein the angled struts of the frame define a plurality of free apices offset circumferentially from each other around a circumference of the frame and configured to resist movement of the docking station within a body lumen.

Example 62. The docking station of any example herein, particularly example 61, wherein the plurality of struts of the frame are a first plurality of struts, the valve seat struts are a second plurality of struts, and the frame further comprises a third plurality of struts extending from free apices of the angled struts at the outflow end portion of the frame.

Example 63. The docking station of any example herein, particularly example 62, wherein free end portions of the third plurality of struts define openings.

Example 64. The docking station of any example herein, particularly example 62 or example 63, wherein the third plurality of struts are arranged in a circumferential arrangement radially outward of the second plurality of struts of the valve seat.

Example 65. The docking station of any example herein, particularly any one of examples 62-64, wherein struts of the third plurality of struts are curved radially inward toward the longitudinal axis of the frame.

Example 66. The docking station of any example herein, particularly any one of examples 58-65, wherein the longitudinal struts comprise flex-inducing portions.

Example 67. The docking station of any example herein, particularly example 66, wherein the flex-inducing portions are reduced thickness portions.

Example 68. The docking station of any example herein, particularly example 66, wherein the flex-inducing portions comprise a plurality of rings.

Example 69. The docking station of any example herein, particularly any one of examples 54-68, wherein: the outflow end portion of the frame comprises a plurality of outer frame cells; and the valve seat struts define a plurality of valve seat frame cells positioned at least partially inward of the outer frame cells.

Example 70. The docking station of any example herein, particularly example 69, wherein struts of the outer frame cells and the valve seat struts are coupled to common junctions of the frame.

Example 71. The docking station of any example herein, particularly any one of examples 54-70, wherein the frame further comprises at least one radiopaque marker.

Example 72. The docking station of any example herein, particularly example 71, wherein junctions between struts of the frame and the valve seat struts comprise the radiopaque markers.

Example 73. The docking station of any example herein, particularly any one of examples 54-72, wherein the inflow end portion of the frame comprises a plurality of coupling members configured to engage a delivery apparatus.

Example 74. The docking station of any example herein, particularly example 73, wherein the coupling members comprise round members angled inwardly toward the longitudinal axis.

Example 75. The docking station of any example herein, particularly any one of examples 54-74, wherein the free end portions of the valve seat struts define a downstream-most end of the frame of the docking station.

Example 76. The docking station of any example herein, particularly any one of examples 54-75, wherein the docking station further comprises a sealing member disposed on the outflow end portion of the frame, the sealing member comprising a first portion coupled to the outflow end portion of the frame and a second portion radially inward of the first portion and coupled to the valve seat.

Example 77. The docking station of any example herein, particularly example 76, wherein: the outflow end portion of the frame comprises a first plurality of supports coupled to the sealing member; the free end portions of the valve seat struts comprise a second plurality of supports coupled to the sealing member; and the outflow end portion of the frame comprises more supports than the valve seat.

Example 78. The docking station of any example herein, particularly example 77, wherein the supports of the outflow end portion of the frame comprise a plurality of apices defined by struts of the frame.

Example 79. The docking station of any example herein, particularly any one of examples 76-78, wherein at least an outflow edge of the sealing member is disposed at an angle to the longitudinal axis of the frame to align with an outlet of a body lumen.

Example 80. The docking station of any example herein, particularly any one of examples 76-79, wherein the sealing member comprises a radiopaque material or a radiopaque marker.

Example 81. The docking station of any example herein, particularly any one of examples 76-80, wherein the sealing member comprises a first portion disposed within the frame, a second portion disposed within the valve seat, and a third portion disposed on the exterior of the frame.

Example 82. The docking station of any example herein, particularly example 81, wherein a diameter of the second portion of the sealing member is less than a diameter of the first portion and the third portion.

Example 83. The docking station of any example herein, particularly example 82, wherein the diameter of the first portion decreases in a direction of the outflow end portion along the longitudinal axis of the frame.

Example 84. The docking station of any example herein, particularly example 81 or example 82, wherein the diameter of the third portion increases in a direction toward the inflow end portion along the longitudinal axis of the frame.

Example 85. The docking station of any example herein, particularly any one of examples 76-84, wherein the sealing member comprises a plurality of preformed openings configured to receive sutures.

Example 86. The docking station of any example herein, particularly example 85, wherein the openings are laser-drilled or cut.

Example 87. The docking station of any example herein, particularly example 85 or example 86, wherein the first portion comprises openings arranged around a perimeter of the first portion.

Example 88. The docking station of any example herein, particularly any one of examples 81-87, wherein the first portion comprises a scalloped edge portion.

Example 89. The docking station of any example herein, particularly any one of examples 76-88, wherein the sealing member comprises a woven or knitted fabric, or is formed by electrospinning.

Example 90. The docking station of any example herein, particularly example 89, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 91. The docking station of any example herein, particularly example 89 or example 90, wherein the woven or knitted fabric is a woven fabric comprising a gauze weave, a plain weave, a twill weave, satin weave, or combinations thereof.

Example 92. The docking station of any example herein, particularly any one of examples 76-91, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 93. The docking station of any example herein, particularly any one of examples 76-92, wherein the frame comprises a plurality of openings configured to receive sutures for attachment of the sealing member to the frame.

Example 94. The docking station of any example herein, particularly example 92, wherein the plurality of openings are in junctions of the frame.

Example 95. The docking station of any example herein, particularly example 94, wherein the frame further comprises a second plurality of openings defined in struts of the frame spaced apart from the junctions along the longitudinal axis.

Example 96. The docking station of any example herein, particularly any one of examples 54-95, further comprising an annular member disposed around the valve seat and configured to constrain expansion of a prosthetic heart valve when a prosthetic heart valve is deployed in the valve seat.

Example 97. The docking station of any example herein, particularly any one of examples 54-96, wherein the valve seat struts comprise a first portion that is angled inwardly toward the longitudinal axis of the frame, and a second portion that extends in the downstream direction along the longitudinal axis of the frame.

Example 98. The docking station of any example herein, particularly example 97, wherein the second portions of the valve seat struts define at least one opening.

Example 99. A docking station for a prosthetic valve, comprising: a radially expandable and collapsible frame comprising: a plurality of longitudinally-extending first struts circumferentially arranged about a longitudinal axis of the frame and extending between an inflow end portion and an outflow end portion of the frame; and a plurality of angled second struts extending between adjacent first struts; and a valve seat coupled to the frame and configured to receive an expandable prosthetic valve.

Example 100. The docking station of any example herein, particularly example 99, wherein pairs of adjacent second struts are coupled together to form free apices, the free apices at least partially defining the valve seat.

Example 101. The docking station of any example herein, particularly example 100, wherein the second struts at least partially define cells of the frame of the docking station.

Example 102. The docking station of any example herein, particularly example 100 or example 101, wherein the free apices of the valve seat are offset from an outflow end of the frame in an upstream direction toward the inflow end portion of the frame.

Example 103. The docking station of any example herein, particularly example 101, wherein the cells are arranged in rows that are spaced apart from each other axially along the longitudinal axis of the frame.

Example 104. The docking station of any example herein, particularly any one of examples 99-103, wherein the first struts comprise flex-inducing portions.

Example 105. The docking station of any example herein, particularly example 104, wherein the flex-inducing portions are reduced thickness portions.

Example 106. The docking station of any example herein, particularly example 104, wherein the flex-inducing portions comprise a plurality of rings.

Example 107. The docking station of any example herein, particularly any one of examples 99-106, wherein: the outflow end portion of the frame comprises a plurality of outer frame cells; and the second struts define a plurality of valve seat frame cells positioned at least partially inward of the outer frame cells.

Example 108. The docking station of any example herein, particularly example 107, wherein struts of the outer frame cells and struts of the valve seat frame cells are coupled to common junctions of the frame.

Example 109. The docking station of any example herein, particularly any one of examples 99-108, wherein the frame further comprise at least one radiopaque marker.

Example 110. The docking station of any example herein, particularly any one of examples 99-109, wherein the inflow end portion of the frame comprises a plurality of coupling members configured to engage a delivery apparatus.

Example 111. The docking station of any example herein, particularly example 110, wherein the coupling members comprise round members angled inwardly toward the longitudinal axis.

Example 112. The docking station of any example herein, particularly any one of examples 99-111, wherein free end portions of second struts define a downstream-most end of the frame of the docking station.

Example 113. The docking station of any example herein, particularly any one of examples 99-112, further comprising a sealing member coupled to the frame, the sealing member comprising a first portion coupled to the outflow end portion of the frame and a second portion radially inward of the first portion and coupled to the valve seat.

Example 114. The docking station of any example herein, particularly example 113, wherein: the outflow end portion of the frame comprises a first plurality of supports coupled to the sealing member; the valve seat comprises a second plurality of supports coupled to the sealing member; and the outflow end portion of the frame comprises more supports than the valve seat.

Example 115. The docking station of any example herein, particularly example 114, wherein the supports of the outflow end portion of the frame comprise a plurality of apices defined by first struts of the frame.

Example 116. The docking station of any example herein, particularly any one of examples 99-115, wherein at least an outflow edge of the sealing member is disposed at an angle to the longitudinal axis of the frame to align with an outlet of a body lumen.

Example 117. The docking station of any example herein, particularly any one of examples 99-116, wherein the second struts are coupled to the frame at frame junctions, and free end portions of the second struts are offset from the frame junctions in a downstream direction along the longitudinal axis.

Example 118. The docking station of any example herein, particularly any one of examples 113-117, wherein the sealing member comprises a radiopaque material or a radiopaque marker.

Example 119. The docking station of any example herein, particularly any one of examples 113-118, wherein the sealing member comprises a first portion disposed within the frame, a second portion disposed within the valve seat, and a third portion disposed on the exterior of the frame.

Example 120. The docking station of any example herein, particularly example 119, wherein a diameter of the second portion of the sealing member is less than a diameter of the first portion and the third portion.

Example 121. The docking station of any example herein, particularly example 120, wherein the diameter of the first portion decreases in a direction of the outflow end portion along the longitudinal axis of the frame.

Example 122. The docking station of any example herein, particularly example 120 or 121, wherein the diameter of the third portion increases in a direction toward the inflow end portion along the longitudinal axis of the frame.

Example 123. The docking station of any example herein, particularly any one of examples 113-122, wherein the sealing member comprises a plurality of preformed openings configured to receive sutures.

Example 124. The docking station of any example herein, particularly example 123, wherein the openings are laser-drilled or cut.

Example 125. The docking station of any example herein, particularly example 123 or example 124, wherein the first portion comprises openings arranged around a perimeter of the first portion.

Example 126. The docking station of any example herein, particularly any one of examples 119 to 125, wherein the first portion comprises a scalloped edge portion.

Example 127. The docking station of any example herein, particularly any one of examples 113-126, wherein the sealing member comprises a woven or knitted fabric, or is formed by electrospinning.

Example 128. The docking station of any example herein, particularly example 127, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 129. The docking station of any example herein, particularly example 127 or example 128, wherein the woven or knitted fabric comprises a woven fabric comprising a gauze weave, a plain weave, a twill weave, satin weave, or combinations thereof.

Example 130. The docking station of any example herein, particularly example 129, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 131. The docking station of any example herein, particularly any one of examples 99-130, wherein the frame comprises a plurality of openings configured to receive sutures for attachment of the sealing member to the frame.

Example 132. The docking station of any example herein, particularly example 131, wherein the plurality of openings are in junctions of the frame.

Example 133. The docking station of any example herein, particularly example 132, wherein the frame further comprises a second plurality of openings defined in struts of the frame spaced apart from the junctions along the longitudinal axis.

Example 134. The docking station of any example herein, particularly any one of examples 99-133, further comprising an annular member disposed around the valve seat and configured to constrain expansion of a prosthetic heart valve when a prosthetic heart valve is deployed in the valve seat.

Example 135. The docking station of any example herein, particularly any one of examples 99-134, further comprising a prosthetic valve disposed in the valve seat, a sealing member disposed on the docking station, and wherein the sealing member is configured to form a seal between the prosthetic valve and the valve seat.

Example 136. The docking station of any example herein, particularly example 135, wherein the prosthetic valve disposed in the valve seat comprises an hourglass-shaped outer profile.

Example 137. A method, comprising: advancing the docking station of any example herein, particularly any one of examples 99-136, to a treatment site in a radially collapsed state; expanding the docking station to anchor the docking station at the treatment site; and deploying a prosthetic valve in the valve seat of the docking station such that the prosthetic valve regulates blood flow through the docking station.

Example 138. A docking station for a prosthetic valve, comprising: a radially expandable and collapsible frame comprising a plurality of struts, the frame comprising an inflow end portion and an outflow end portion, and defining a longitudinal axis; a sealing member disposed on the outflow end portion and configured to form a seal between the docking station and a body lumen; and a valve seat coupled to the frame and configured to receive an expandable prosthetic valve; wherein the struts of the frame define a plurality of free apices offset circumferentially from each other around a circumference of the frame and configured to resist movement of the docking station within a body lumen.

Example 139. The docking station of any example herein, particularly example 138, wherein pairs of adjacent struts of the plurality of struts are coupled together to form free apices, the free apices at least partially defining the valve seat.

Example 140. The docking station of any example herein, particularly example 139, wherein the plurality of struts at least partially define cells of the frame of the docking station.

Example 141. The docking station of any example herein, particularly example 139 or 140, wherein the free apices of the valve seat are offset from an outflow end of the frame in an upstream direction toward the inflow end portion of the frame.

Example 142. The docking station of any example herein, particularly any one of examples 138-141, wherein the plurality of struts are a second plurality of struts, and the frame further comprises a first plurality of circumferentially-arranged longitudinal struts extending between the inflow end portion and the outflow end portion of the frame.

Example 143. The docking station of any example herein, particularly example 142, wherein the second plurality of struts further comprises a plurality of angled struts extending between adjacent longitudinal struts.

Example 144. The docking station of any example herein, particularly example 143, wherein the plurality of angled struts form a plurality of cells of the frame.

Example 145. The docking station of any example herein, particularly example 144, wherein the cells are arranged in rows that are spaced apart from each other axially along the longitudinal axis of the frame.

Example 146. The docking station of any example herein, particularly any one of examples 142-145, wherein the longitudinal struts comprise flex-inducing portions.

Example 147. The docking station of any example herein, particularly example 146, wherein the flex-inducing portions are reduced thickness portions.

Example 148. The docking station of any example herein, particularly example 146, wherein the flex-inducing portions comprise a plurality of rings.

Example 149. The docking station of any example herein, particularly any one of examples 142-148, wherein: the outflow end portion of the frame comprises a plurality of outer frame cells; and the second plurality of struts define a plurality of valve seat frame cells positioned at least partially inward of the outer frame cells.

Example 150. The docking station of any example herein, particularly example 149, wherein struts of the outer frame cells and struts of the valve seat frame cells are coupled to common junctions of the frame.

Example 151. The docking station of any example herein, particularly any one of examples 138-150, wherein the frame further comprises at least one radiopaque marker.

Example 152. The docking station of any example herein, particularly any one of examples 138-151, wherein the inflow end portion of the frame comprises a plurality of coupling members configured to engage a delivery apparatus.

Example 153. The docking station of any example herein, particularly example 152, wherein the coupling members comprise round members angled inwardly toward the longitudinal axis.

Example 154. The docking station of any example herein, particularly any one of examples 142-153, wherein free end portions of struts of the second plurality of struts define a downstream-most end of the frame of the docking station.

Example 155. The docking station of any example herein, particularly any one of examples 138-154, wherein the sealing member comprises a first portion coupled to the outflow end portion of the frame and a second portion radially inward of the first portion and coupled to the valve seat.

Example 156. The docking station of any example herein, particularly example 155, wherein: the outflow end portion of the frame comprises a first plurality of supports coupled to the sealing member; the valve seat comprises a second plurality of supports coupled to the sealing member; and the outflow end portion of the frame comprises more supports than the valve seat.

Example 157. The docking station of any example herein, particularly example 156, wherein the supports of the outflow end portion of the frame comprise a plurality of apices defined by struts of the first plurality of struts.

Example 158. The docking station of any example herein, particularly any one of examples 138-157, wherein at least an outflow edge of the sealing member is disposed at an angle to the longitudinal axis of the frame to align with an outlet of a body lumen.

Example 159. The docking station of any example herein, particularly any one of examples 142-158, wherein the second plurality of struts are coupled to the frame at frame junctions, and free end portions of the second plurality of struts are offset from the frame junctions in a downstream direction along the longitudinal axis.

Example 160. The docking station of any example herein, particularly any one of examples 138-159, wherein the sealing member comprises a radiopaque material or a radiopaque marker.

Example 161. The docking station of any example herein, particularly any one of examples 138-160, wherein the sealing member comprises a first portion disposed within the frame, a second portion disposed within the valve seat, and a third portion disposed on the exterior of the frame.

Example 162. The docking station of any example herein, particularly example 161, wherein a diameter of the second portion of the sealing member is less than a diameter of the first portion and the third portion.

Example 163. The docking station of any example herein, particularly example 162, wherein the diameter of the first portion decreases in a direction of the outflow end portion along the longitudinal axis of the frame.

Example 164. The docking station of any example herein, particularly example 162 or example 163, wherein the diameter of the third portion increases in a direction toward the inflow end portion along the longitudinal axis of the frame.

Example 165. The docking station of any example herein, particularly any one of examples 162 to 164, wherein the first portion comprises a scalloped edge portion.

Example 166. The docking station of any example herein, particularly any one of examples 161-165, wherein the sealing member comprises a plurality of preformed openings configured to receive sutures.

Example 167. The docking station of any example herein, particularly example 166, wherein the openings are laser-drilled or cut.

Example 168. The docking station of any example herein, particularly example 166 or example 167, wherein the first portion comprises openings arranged around a perimeter of the first portion.

Example 169. The docking station of any example herein, particularly any one of examples 138-168, wherein the sealing member comprises a woven or knitted fabric, or is formed by electrospinning.

Example 170. The docking station of any example herein, particularly example 169, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 171. The docking station of any example herein, particularly example 169 or example 170, wherein the woven or knitted fabric is a woven fabric comprising a gauze weave, a plain weave, a twill weave, satin weave, or combinations thereof.

Example 172. The docking station of any example herein, particularly any one of examples 138-171, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 173. The docking station of any example herein, particularly any one of examples 138-172, wherein the frame comprises a plurality of openings configured to receive sutures for attachment of the sealing member to the frame.

Example 174. The docking station of any example herein, particularly example 173, wherein the plurality of openings are in junctions of the frame.

Example 175. The docking station of any example herein, particularly example 174, wherein the frame further comprises a second plurality of openings defined in struts of the frame spaced apart from the junctions along the longitudinal axis.

Example 176. The docking station of any example herein, particularly any one of examples 138-175, further comprising an annular member disposed around the valve seat and configured to constrain expansion of a prosthetic heart valve when a prosthetic heart valve is deployed in the valve seat.

Example 177. The docking station of any example herein, particularly any one of examples 138-176, further comprising a prosthetic valve disposed in the valve seat, wherein the sealing member is configured to form a seal between the prosthetic valve and the valve seat.

Example 178. The docking station of any example herein, particularly example 177, wherein the prosthetic valve disposed in the valve seat comprises an hourglass-shaped outer profile.

Example 179. A method, comprising: advancing the docking station of any example herein, particularly any one of examples 138-178 to a treatment site in a radially collapsed state; expanding the docking station to anchor the docking station at the treatment site; and deploying a prosthetic valve in the valve seat of the docking station such that the prosthetic valve regulates blood flow through the docking station.

Example 180. A system, comprising: a delivery apparatus, comprising: a first shaft comprising a delivery capsule at a distal end portion of the first shaft; and a second shaft disposed within the first shaft and comprising a retaining member at a distal end portion of the second shaft; and the docking station of any example herein, particularly any one of examples 138-178 disposed within the delivery capsule and coupled to the retaining member.

Example 181. The system of any example herein, particularly example 180, wherein: the docking station comprises coupling members; and the retaining member comprises a slot configured to engage and retain the coupling members of the docking station.

Example 182. They system of any example herein, particularly example 180 or example 181, wherein the delivery capsule is transparent.

Example 183. A docking station for a prosthetic valve, comprising: a radially expandable and collapsible frame comprising a plurality of struts, the frame comprising an inflow end portion and an outflow end portion and defining a longitudinal axis; a sealing member disposed on the outflow end portion and configured to form a seal between the docking station and a body lumen; and a valve seat within the frame and configured to receive an expandable prosthetic valve, the valve seat comprising an inflow end portion coupled to the frame and a free outflow end portion, the free outflow end portion being downstream of the inflow end portion of the valve seat and upstream of the outflow end of the frame of the docking station.

Example 184. The docking station of any example herein, particularly example 183, wherein pairs of adjacent struts of the plurality of struts are coupled together to form free apices, the free apices at least partially defining the valve seat.

Example 185. The docking station of any example herein, particularly example 184, wherein the plurality of struts at least partially define cells of the frame of the docking station.

Example 186. The docking station of any example herein, particularly any one of examples 184-185, wherein the plurality of struts are a second plurality of struts, and the frame further comprises a first plurality of circumferentially-arranged longitudinal struts extending between the inflow end portion and the outflow end portion of the frame.

Example 187. The docking station of any example herein, particularly example 186, wherein the second plurality of struts further comprises a plurality of angled struts extending between adjacent longitudinal struts.

Example 188. The docking station of any example herein, particularly example 187, wherein the plurality of angled struts form a plurality of cells of the frame.

Example 189. The docking station of any example herein, particularly example 188, wherein the cells are arranged in rows that are spaced apart from each other axially along the longitudinal axis of the frame.

Example 190. The docking station of any example herein, particularly any one of examples 186-189, wherein the longitudinal struts comprise flex-inducing portions.

Example 191. The docking station of any example herein, particularly example 190, wherein the flex-inducing portions are reduced thickness portions.

Example 192. The docking station of any example herein, particularly example 191, wherein the flex-inducing portions comprise a plurality of rings.

Example 193. The docking station of any example herein, particularly any one of examples 186-192, wherein: the outflow end portion of the frame comprises a plurality of outer frame cells; and the second plurality of struts define a plurality of valve seat frame cells positioned at least partially inward of the outer frame cells.

Example 194. The docking station of any example herein, particularly example 193, wherein struts of the outer frame cells and struts of the valve seat frame cells are coupled to common junctions of the frame.

Example 195. The docking station of any example herein, particularly any one of examples 183-194, wherein the frame further comprises at least one radiopaque marker.

Example 196. The docking station of any example herein, particularly any one of examples 183-195, wherein the inflow end portion of the frame comprises a plurality of coupling members configured to engage a delivery apparatus.

Example 197. The docking station of any example herein, particularly example 196, wherein the coupling members comprise round members angled inwardly toward the longitudinal axis.

Example 198. The docking station of any example herein, particularly any one of examples 186-197, wherein free end portions of struts of the second plurality of struts define a downstream-most end of the frame of the docking station.

Example 199. The docking station of any example herein, particularly any one of examples 183-198, wherein the sealing member comprises a first portion coupled to the outflow end portion of the frame and a second portion radially inward of the first portion and coupled to the valve seat.

Example 200. The docking station of any example herein, particularly any one of examples 186-199, wherein the second plurality of struts are coupled to the frame at frame junctions, and free end portions of the second plurality of struts are offset from the frame junctions in a downstream direction along the longitudinal axis.

Example 201. The docking station of any example herein, particularly example 200, wherein: the outflow end portion of the frame comprises a first plurality of supports coupled to the sealing member; the valve seat comprises a second plurality of supports coupled to the sealing member; and the outflow end portion of the frame comprises more supports than the valve seat.

Example 202. The docking station of any example herein, particularly example 201, wherein the supports of the outflow end portion of the frame comprise a plurality of apices defined by struts of the first plurality of struts.

Example 203. The docking station of any example herein, particularly any one of examples 183-202, wherein at least an outflow edge of the sealing member is disposed at an angle to the longitudinal axis of the frame to align with an outlet of a body lumen.

Example 204. The docking station of any example herein, particularly any one of examples 183-203, wherein the sealing member comprises a radiopaque material or a radiopaque marker.

Example 205. The docking station of any example herein, particularly any one of examples 183-204, wherein the sealing member comprises a first portion disposed within the frame, a second portion disposed within the valve seat, and a third portion disposed on the exterior of the frame.

Example 206. The docking station of any example herein, particularly example 205, wherein a diameter of the second portion of the sealing member is less than a diameter of the first portion and the third portion.

Example 207. The docking station of any example herein, particularly example 206, wherein the diameter of the first portion decreases in a direction of the outflow end portion along the longitudinal axis of the frame.

Example 208. The docking station of any example herein, particularly example 206 or example 207, wherein the diameter of the third portion increases in a direction toward the inflow end portion along the longitudinal axis of the frame.

Example 209. The docking station of any example herein, particularly any one of examples 206 to 208, wherein the first portion comprises a scalloped edge portion.

Example 210. The docking station of any example herein, particularly any of examples 183-209, wherein the sealing member comprises a plurality of preformed openings configured to receive sutures.

Examples 211. The docking station of any example herein, particularly example 210, wherein the openings are laser-drilled or cut.

Example 212. The docking station of any example herein, particularly example 210 or example 211, wherein the first portion comprises openings arranged around a perimeter of the first portion.

Example 213. The docking station of any example herein, particularly any one of examples 183-212, wherein the sealing member comprises a woven or knitted fabric, or is formed by electrospinning.

Example 214. The docking station of any example herein, particularly example 213, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 215. The docking station of any example herein, particularly example 213 or example 214, wherein the woven or knitted fabric is a woven fabric comprising a gauze weave, a plain weave, a twill weave, satin weave, or combinations thereof.

Example 216. The docking station of any example herein, particularly any one of examples 183-215, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 217. The docking station of any example herein, particularly any one of examples 183-216, wherein the frame comprises a plurality of openings configured to receive sutures for attachment of the sealing member to the frame.

Example 218. The docking station of any example herein, particularly example 217, wherein the plurality of openings are in junctions of the frame.

Example 219. The docking station of any example herein, particularly example 218, wherein the frame further comprises a second plurality of openings defined in struts of the frame spaced apart from the junctions along the longitudinal axis.

Example 220. The docking station of any example herein, particularly any one of examples 183-219, further comprising an annular member disposed around the valve seat and configured to constrain expansion of a prosthetic heart valve when a prosthetic heart valve is deployed in the valve seat.

Example 221. The docking station of any example herein, particularly any of examples 183-220, further comprising a prosthetic valve disposed in the valve seat, wherein the sealing member is configured to form a seal between the prosthetic valve and the valve seat.

Example 222. The docking station of any example herein, particularly example 221, wherein the prosthetic valve disposed in the valve seat comprises an hourglass-shaped outer profile.

Example 223. A method, comprising: advancing the docking station of any example herein, particularly any one of examples 183-222 to a treatment site in a radially collapsed state; expanding the docking station to anchor the docking station at the treatment site; and deploying a prosthetic valve in the valve seat of the docking station such that the prosthetic valve regulates blood flow through the docking station.

Example 224. A system, comprising: a delivery apparatus, comprising: a first shaft comprising a delivery capsule at a distal end portion of the first shaft; and a second shaft disposed within the first shaft and comprising a retaining member at a distal end portion of the second shaft; and the docking station of any example herein, particularly any one of examples 183-222 disposed within the delivery capsule and coupled to the retaining member.

Example 225. The system of any example herein, particularly example 224, wherein: the docking station comprises coupling members; and the retaining member comprises a slot configured to engage and retain the coupling members of the docking station.

Example 226. They system of any example herein, particularly example 224 or example 225, wherein the delivery capsule is transparent.

Example 227. A docking station for a prosthetic valve, comprising: a radially expandable and collapsible frame comprising a first plurality of struts, the frame comprising an inflow end portion and an outflow end portion, the outflow end portion of the frame comprising a plurality of supports defined by struts of the first plurality of struts, the frame defining a longitudinal axis; a sealing member disposed on the outflow end portion and configured to form a seal between the docking station and a body lumen, the sealing member being engaged by the plurality of supports of the outflow end of the frame; and a valve seat within the frame and configured to receive an expandable prosthetic valve, the valve seat comprising a second plurality of struts coupled to the frame and defining a plurality of supports; wherein the outflow end portion of the frame comprises more supports than the valve seat.

Example 228. The docking station of any example herein, particularly example 227, wherein pairs of adjacent struts of the second plurality of struts are coupled together to form free apices, the free apices at least partially defining the valve seat.

Example 229. The docking station of any example herein, particularly example 228, wherein the second plurality of struts at least partially define cells of the frame of the docking station.

Example 230. The docking station of any example herein, particularly example 228 or example 229, wherein the free apices of the valve seat are offset from an outflow end of the frame in an upstream direction toward the inflow end portion of the frame.

Example 231. The docking station of any example herein, particularly any one of examples 227-230, wherein the first plurality of struts comprises a plurality of circumferentially-arranged longitudinal struts extending between the inflow end portion and the outflow end portion of the frame.

Example 232. The docking station of any example herein, particularly example 231, wherein the first plurality of struts further comprises a plurality of angled struts extending between adjacent longitudinal struts.

Example 233. The docking station of any example herein, particularly example 232, wherein the plurality of angled struts form a plurality of cells of the frame.

Example 234. The docking station of any example herein, particularly example 233, wherein the cells are arranged in rows that are spaced apart from each other axially along the longitudinal axis of the frame.

Example 235. The docking station of any example herein, particularly any one of examples 232-234, wherein the angled struts of the frame define a plurality of free apices offset circumferentially from each other around a circumference of the frame and configured to resist movement of the docking station within a body lumen.

Example 236. The docking station of any example herein, particularly any one of examples 231-235, wherein the longitudinal struts comprise flex-inducing portions.

Example 237. The docking station of any example herein, particularly example 236, wherein the flex-inducing portions are reduced thickness portions.

Example 238. The docking station of any example herein, particularly example 236, wherein the flex-inducing portions comprise a plurality of rings.

Example 239. The docking station of any example herein, particularly any one of examples 227-238, wherein: the outflow end portion of the frame comprises a plurality of outer frame cells; and the second plurality of struts define a plurality of valve seat frame cells positioned at least partially inward of the outer frame cells.

Example 240. The docking station of any example herein, particularly example 239, wherein struts of the outer frame cells and struts of the valve seat frame cells are coupled to common junctions of the frame.

Example 241. The docking station of any example herein, particularly any one of examples 227-240, wherein the frame further comprise at least one radiopaque marker.

Example 242. The docking station of any example herein, particularly any one of examples 227-241, wherein the inflow end portion of the frame comprises a plurality of coupling members configured to engage a delivery apparatus.

Example 243. The docking station of any example herein, particularly example 242, wherein the coupling members comprise round members angled inwardly toward the longitudinal axis.

Example 244. The docking station of any example herein, particularly any one of examples 227-243, wherein the sealing member comprises a first portion coupled to the outflow end portion of the frame and a second portion radially inward of the first portion and coupled to the valve seat.

Example 245. The docking station of any example herein, particularly any one of examples 227-244, wherein the supports of the outflow end portion of the frame comprise a plurality of apices defined by struts of the first plurality of struts.

Example 246. The docking station of any example herein, particularly any one of examples 227-245, wherein at least an outflow edge of the sealing member is disposed at an angle to the longitudinal axis of the frame to align with an outlet of a body lumen.

Example 247. The docking station of any example herein, particularly any one of examples 227-246, wherein the second plurality of struts are coupled to the frame at frame junctions, and free end portions of the second plurality of struts are offset from the frame junctions in a downstream direction along the longitudinal axis.

Example 248. The docking station of any example herein, particularly any one of examples 227-247, wherein the sealing member comprises a radiopaque material or a radiopaque marker.

Example 249. The docking station of any example herein, particularly any one of examples 227-248, wherein the sealing member comprises a first portion disposed within the frame, a second portion disposed within the valve seat, and a third portion disposed on the exterior of the frame.

Example 250. The docking station of any example herein, particularly example 249, wherein a diameter of the second portion of the sealing member is less than a diameter of the first portion and the third portion.

Example 251. The docking station of any example herein, particularly example 250, wherein the diameter of the first portion decreases in a direction of the outflow end portion along the longitudinal axis of the frame.

Example 252. The docking station of any example herein, particularly example 249 or example 250, wherein the diameter of the third portion increases in a direction toward the inflow end portion along the longitudinal axis of the frame.

Example 253. The docking station of any example herein, particularly any one of examples 227-252, wherein the sealing member comprises a plurality of preformed openings configured to receive sutures.

Example 254. The docking station of any example herein, particularly example 253, wherein the openings are laser-drilled or cut.

Example 255. The docking station of any example herein, particularly example 253 or example 254, wherein the first portion comprises openings arranged around a perimeter of the first portion.

Example 256. The docking station of any example herein, particularly any one of examples 249 to 255, wherein the first portion comprises a scalloped edge portion.

Example 257. The docking station of any example herein, particularly any one of examples 227-256, wherein the sealing member comprises a woven or knitted fabric, or is formed by electrospinning.

Example 258. The docking station of any example herein, particularly example 257, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 259. The docking station of any example herein, particularly example 257 or example 258, wherein the woven or knitted fabric is a woven fabric comprising a gauze weave, a plain weave, a twill weave, satin weave, or combinations thereof.

Example 260. The docking station of any example herein, particularly any one of examples 227-259, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 261. The docking station of any example herein, particularly any one of examples 227-260, wherein the frame comprises a plurality of openings configured to receive sutures for attachment of the sealing member to the frame.

Example 262. The docking station of any example herein, particularly example 261, wherein the plurality of openings are in junctions of the frame.

Example 263. The docking station of any example herein, particularly example 262, wherein the frame further comprises a second plurality of openings defined in struts of the frame spaced apart from the junctions along the longitudinal axis.

Example 264. The docking station of any example herein, particularly example any one of examples 227-263, further comprising an annular member disposed around the valve seat and configured to constrain expansion of a prosthetic heart valve when a prosthetic heart valve is deployed in the valve seat.

Example 265. The docking station of any example herein, particularly any one of examples 227-264, further comprising a prosthetic valve disposed in the valve seat, wherein the sealing member is configured to form a seal between the prosthetic valve and the valve seat.

Example 266. The docking station of any example herein, particularly example 265, wherein the prosthetic valve disposed in the valve seat comprises an hourglass-shaped outer profile.

Example 267. The docking station of any example herein, particularly any one of examples 227-266, wherein the supports of the outflow end portion of the frame comprise a plurality of apices defined by struts of the first plurality of struts.

Example 268. A method, comprising: advancing the docking station of any example herein, particularly any one of examples 227-267 to a treatment site in a radially collapsed state; expanding the docking station to anchor the docking station at the treatment site; and deploying a prosthetic valve in the valve seat of the docking station such that the prosthetic valve regulates blood flow through the docking station.

Example 269. A system, comprising: a delivery apparatus, comprising: a first shaft comprising a delivery capsule at a distal end portion of the first shaft; and a second shaft disposed within the first shaft and comprising a retaining member at a distal end portion of the second shaft; and the docking station of any example herein, particularly any one of examples 227-267 disposed within the delivery capsule and coupled to the retaining member.

Example 270. The system of any example herein, particularly example 269, wherein: the docking station comprises coupling members; and the retaining member comprises a slot configured to engage and retain the coupling members of the docking station.

Example 271. They system of any example herein, particularly example 269 or example 270, wherein the delivery capsule is transparent.

Example 272. A docking station for a prosthetic valve, comprising: a radially expandable and collapsible frame comprising a plurality of struts, the frame comprising an inflow end portion and an outflow end portion, and defining a longitudinal axis; a sealing member disposed on the outflow end portion and configured to form a seal between the docking station and a body lumen; and a valve seat coupled to the frame and configured to receive an expandable prosthetic valve; wherein at least an outflow edge of the sealing member is disposed at an angle to the longitudinal axis of the frame to align with an outlet of the body lumen.

Example 273. The docking station of any example herein, particularly example 272, wherein pairs of adjacent struts of the plurality of struts are coupled together to form free apices, the free apices at least partially defining the valve seat.

Example 274. The docking station of any example herein, particularly example 273, wherein the plurality of struts at least partially define cells of the frame of the docking station.

Example 275. The docking station of any example herein, particularly any one of examples 272-274, wherein the plurality of struts are a second plurality of struts, and the frame further comprises a first plurality of circumferentially-arranged longitudinal struts extending between the inflow end portion and the outflow end portion of the frame.

Example 276. The docking station of any example herein, particularly example 275, wherein the second plurality of struts further comprises a plurality of angled struts extending between adjacent longitudinal struts.

Example 277. The docking station of any example herein, particularly example 276, wherein the plurality of angled struts form a plurality of cells of the frame.

Example 278. The docking station of any example herein, particularly example 277, wherein the cells are arranged in rows that are spaced apart from each other axially along the longitudinal axis of the frame.

Example 279. The docking station of any example herein, particularly any one of examples 272-278, wherein the longitudinal struts comprise flex-inducing portions.

Example 280. The docking station of any example herein, particularly example 279, wherein the flex-inducing portions are reduced thickness portions.

Example 281. The docking station of any example herein, particularly example 280, wherein the flex-inducing portions comprise a plurality of rings.

Example 282. The docking station of any example herein, particularly any one of examples 277-281, wherein: the outflow end portion of the frame comprises a plurality of outer frame cells; and the second plurality of struts define a plurality of valve seat frame cells positioned at least partially inward of the outer frame cells.

Example 283. The docking station of any example herein, particularly example 282, wherein struts of the outer frame cells and struts of the valve seat frame cells are coupled to common junctions of the frame.

Example 284. The docking station of any example herein, particularly any one of examples 275-283, wherein the second plurality of struts are coupled to the frame at frame junctions, and free end portions of the second plurality of struts are offset from the frame junctions in a downstream direction along the longitudinal axis.

Example 285. The docking station of any example herein, particularly any one of examples 272-284, wherein the frame further comprises at least one radiopaque marker.

Example 286. The docking station of any example herein, particularly any one of examples 272-285, wherein the inflow end portion of the frame comprises a plurality of coupling members configured to engage a delivery apparatus.

Example 287. The docking station of any example herein, particularly example 286, wherein the coupling members comprise round members angled inwardly toward the longitudinal axis.

Example 288. The docking station of any example herein, particularly any one of examples 272-287, wherein free end portions of struts of the second plurality of struts define a downstream-most end of the frame of the docking station.

Example 289. The docking station of any example herein, particularly any one of examples 272-288, wherein the sealing member comprises a first portion coupled to the outflow end portion of the frame and a second portion radially inward of the first portion and coupled to the valve seat.

Example 290. The docking station of any example herein, particularly any one of examples 272-289, wherein: the outflow end portion of the frame comprises a first plurality of supports coupled to the sealing member; the valve seat comprises a second plurality of supports coupled to the sealing member; and the outflow end portion of the frame comprises more supports than the valve seat.

Example 291. The docking station of any example herein, particularly example 290, wherein the supports of the outflow end portion of the frame comprise a plurality of apices defined by struts of the first plurality of struts.

Example 292. The docking station of any example herein, particularly any one of examples 272-291, wherein the sealing member comprises a radiopaque material or a radiopaque marker.

Example 293. The docking station of any example herein, particularly any one of examples 272-292, wherein the sealing member comprises a first portion disposed within the frame, a second portion disposed within the valve seat, and a third portion disposed on the exterior of the frame.

Example 294. The docking station of any example herein, particularly example 293, wherein a diameter of the second portion of the sealing member is less than a diameter of the first portion and the third portion.

Example 295. The docking station of any example herein, particularly example 294, wherein the diameter of the first portion decreases in a direction of the outflow end portion along the longitudinal axis of the frame.

Example 296. The docking station of any example herein, particularly example 294 or example 295, wherein the diameter of the third portion increases in a direction toward the inflow end portion along the longitudinal axis of the frame.

Example 297. The docking station of any example herein, particularly any one of examples 293 to 296, wherein the first portion comprises a scalloped edge portion.

Example 298. The docking station of any example herein, particularly any one of examples 272-297, wherein the sealing member comprises a plurality of preformed openings configured to receive sutures.

Example 299. The docking station of any example herein, particularly example 298, wherein the openings are laser-drilled or cut.

Example 300. The docking station of any example herein, particularly example 298 or example 299, wherein the first portion comprises openings arranged around a perimeter of the first portion.

Example 301. The docking station of any example herein, particularly any one of examples 272-300, wherein the sealing member comprises a woven or knitted fabric, or is formed by electrospinning.

Example 302. The docking station of any example herein, particularly example 301, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 303. The docking station of any example herein, particularly example 301 or example 302, wherein the woven or knitted fabric is a woven fabric comprising a gauze weave, a plain weave, a twill weave, satin weave, or combinations thereof.

Example 304. The docking station of any example herein, particularly any one of examples 272-303, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

Example 305. The docking station of any example herein, particularly any one of examples 272-304, wherein the frame comprises a plurality of openings configured to receive sutures for attachment of the sealing member to the frame.

Example 306. The docking station of any example herein, particularly example 305, wherein the plurality of openings are in junctions of the frame.

Example 307. The docking station of any example herein, particularly example 306, wherein the frame further comprises a second plurality of openings defined in struts of the frame spaced apart from the junctions along the longitudinal axis.

Example 308. The docking station of any example herein, particularly any one of examples 272-307, further comprising an annular member disposed around the valve seat and configured to constrain expansion of a prosthetic heart valve when a prosthetic heart valve is deployed in the valve seat.

Example 309. The docking station of any example herein, particularly any one of examples 272-308, further comprising a prosthetic valve disposed in the valve seat, wherein the sealing member is configured to form a seal between the prosthetic valve and the valve seat.

Example 310. The docking station of any example herein, particularly example 309, wherein the prosthetic valve disposed in the valve seat comprises an hourglass-shaped outer profile.

Example 311. The docking station of any example herein, particularly any one of examples 272-310, wherein: a diameter of the valve seat is less than a diameter of a main body of the frame; and struts of the outflow end portion of the frame are angled inwardly to form a shoulder portion upstream of the valve seat.

Example 312. A method, comprising: advancing the docking station of any example herein, particularly any one of examples 272-311 to a treatment site in a radially collapsed state; expanding the docking station to anchor the docking station at the treatment site; and deploying a prosthetic valve in the valve seat of the docking station such that the prosthetic valve regulates blood flow through the docking station.

Example 313. A system, comprising: a delivery apparatus, comprising: a first shaft comprising a delivery capsule at a distal end portion of the first shaft; and a second shaft disposed within the first shaft and comprising a retaining member at a distal end portion of the second shaft; and the docking station of any example herein, particularly any one of examples 272-311 disposed within the delivery capsule and coupled to the retaining member.

Example 314. The system of any example herein, particularly example 313, wherein: the docking station comprises coupling members; and the retaining member comprises a slot configured to engage and retain the coupling members of the docking station.

Example 315. The system of any example herein, particularly example 313 or example 314, wherein the delivery capsule is transparent.

Example 316. A docking station for a prosthetic valve, comprising: a radially expandable and collapsible frame comprising a plurality of longitudinal struts extending between an inflow end portion and an outflow end portion of the frame, the frame further comprising a plurality of angled struts arranged circumferentially to form a plurality of cylindrical, spaced apart frame portions interconnected by the longitudinal struts; and a valve seat at the outflow end portion of the frame.

Example 317. The docking station of any example herein, particularly example 316, further comprising a sealing member according to any of the sealing member embodiments described herein coupled to the outflow end portion of the frame.

Example 318. A sealing member for a prosthetic implant, comprising a tubular main body having an hourglass-shaped outer profile.

Example 319. The sealing member of any example herein, particularly example 318, wherein the sealing member comprises a plurality of openings.

Example 320. The sealing member of any example herein, particularly example 319, wherein the openings are laser-drilled or cut.

Example 321. The sealing member of any example herein, particularly example 319 or 320, wherein the openings are arranged in circumferentially-extending rows.

Example 322. The sealing member of any example herein, particularly any one of examples 318-321, wherein the tubular main body is a unitary construction.

Example 323. The sealing member of any example herein, particularly any one of examples 318-322, wherein the sealing member comprises: a first tubular portion which tapers along a longitudinal axis from a first diameter to a second diameter less than the first diameter; and a second tubular portion coupled to the first tubular portion and comprising the second diameter.

Example 324. The sealing member of any example herein, particularly example 323, further comprising a third tubular portion coupled to the second tubular portion such that the second tubular portion is between the first tubular portion and the third tubular portion, the third tubular portion having a diameter which increases from the second diameter toward the first diameter in a direction along the longitudinal axis.

Example 325. The sealing member of any example herein, particularly example 323 or example 324, wherein the first portion comprises a scalloped edge portion.

Example 326. The sealing member of any example herein, particularly any one of examples 323 to 325, wherein the first portion comprises openings arranged around a perimeter of the first portion.

Example 327. The sealing member of any example herein, particularly any one of examples 318 to 326, wherein the sealing member comprises a woven or knitted fabric, or is formed by electrospinning.

Example 328. The sealing member of any example herein, particularly example 327, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 329. The sealing member of any example herein, particularly example 327 or example 328, wherein the woven or knitted fabric is a woven fabric comprising a gauze weave, a plain weave, a twill weave, satin weave, or combinations thereof.

Example 330. A docking station including the sealing member of any example herein, particularly any one of examples 318 to 329.

Example 331. The docking station of any example herein, particularly example 330, wherein the docking station includes a radiopaque marker, and an inflow edge portion of the sealing member is 2 cm or less from the radiopaque marker along a longitudinal axis of the docking station, 1 cm or less from the radiopaque marker along the longitudinal axis of the docking station, or 5 mm or less from the radiopaque marker along the longitudinal axis of the docking station.

Example 332. A docking station configured according to any of the examples described herein including the sealing member of any example herein, particularly any of examples 318 to 329.

Example 333. A sealing member, comprising: a first tubular portion which tapers along a longitudinal axis from a first diameter to a second diameter less than the first diameter; a second tubular portion coupled to the first tubular portion and comprising the second diameter; and a third tubular portion coupled to the second tubular portion such that the second tubular portion is between the first tubular portion and the third tubular portion, the third tubular portion having a diameter which increases from the second diameter toward the first diameter in a direction along the longitudinal axis.

Example 334. The sealing member of any example herein, particularly example 333, wherein the sealing member comprises a plurality of openings.

Example 335. The sealing member of any example herein, particularly example 334, wherein the openings are laser-drilled or cut.

Example 336. The sealing member of any example herein, particularly example 334 or 335, wherein the openings are arranged in circumferentially-extending rows.

Example 337. The sealing member of any example herein, particularly any one of examples 333 to 336, wherein the sealing member is a unitary construction.

Example 338. The sealing member of any example herein, particularly any one of examples 332 to 337 wherein the first portion comprises a scalloped edge portion.

Example 339. The sealing member of any example herein, particularly any one of examples 332 to 338, wherein the first portion comprises openings arranged around a perimeter of the first portion.

Example 340. The sealing member of any example herein, particularly any one of examples 332 to 339, wherein the sealing member comprises a woven or knitted fabric, or is formed by electrospinning.

Example 341. The sealing member of any example herein, particularly example 340, wherein the woven or knitted fabric comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof or any combination thereof.

Example 342. The sealing member of any example herein, particularly example 340 or example 341, wherein the woven or knitted fabric is a woven fabric comprising a gauze weave, a plain weave, a twill weave, satin weave, or combinations thereof.

Example 343. The sealing member of any example herein, particularly any one of examples 332 to 342, wherein the sealing member has an hourglass-shaped outer profile.

Example 344. A docking station configured according to any of the embodiments described herein.

Example 345. A sealing member configured according to any of the embodiments described herein.

Example 346. A docking station, comprising: a radially expandable and collapsible frame comprising a first plurality of struts, the frame comprising an inflow end portion and an outflow end portion, and defining a longitudinal axis; a sealing member disposed on the outflow end portion and configured to form a seal between the docking station and a body lumen; and a valve seat within the frame and configured to receive an expandable prosthetic valve, the valve seat comprising a second plurality of struts coupled to the frame and angled inwardly toward the longitudinal axis of the frame.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope and spirit of these claims.

The invention claimed is:

1. A docking station, comprising:
a radially expandable and collapsible frame comprising an inflow end portion and an outflow end portion and defining a longitudinal axis, the frame comprising a first plurality of struts including a plurality of circumferentially-arranged longitudinal struts and a plurality of angled struts extending between adjacent longitudinal struts, the longitudinal struts extending between the inflow end portion and the outflow end portion of the frame;
a sealing member disposed on the outflow end portion and configured to form a seal between the docking station and a body lumen; and
a valve seat coupled to the frame and configured to receive an expandable prosthetic valve, the valve seat comprising a second plurality of struts coupled to the frame extending in a downstream direction and inwardly toward the longitudinal axis of the frame;
wherein the angled struts of the first plurality of struts define a plurality of free apices offset circumferentially from each other around a circumference of the frame and configured to resist movement of the docking station within a body lumen; and
wherein the frame further comprises a third plurality of struts extending from free apices of the angled struts at the outflow end portion of the frame, and the third plurality of struts are arranged in a circumferential arrangement radially outward of the second plurality of struts of the valve seat.

2. The docking station of claim 1, wherein struts of the third plurality of struts are curved radially inward toward the longitudinal axis of the frame.

3. The docking station of claim 1, wherein the inflow end portion of the frame comprises a plurality of coupling members configured to engage a delivery apparatus.

4. The docking station of claim 3, wherein the coupling members comprise round members angled inwardly toward the longitudinal axis.

5. The docking station of claim 1, wherein free end portions of struts of the second plurality of struts define a downstream-most end of the frame of the docking station.

6. The docking station of claim 1, wherein struts of the second plurality of struts are coupled to the frame at frame junctions, and free end portions of the struts of the second plurality of struts are offset from the frame junctions in a downstream direction along the longitudinal axis.

7. The docking station of claim 6, wherein the struts of the second plurality of struts comprise a first portion that is angled inwardly toward the longitudinal axis of the frame, and a second portion that extends in the downstream direction along the longitudinal axis of the frame.

8. The docking station of claim 1, wherein the sealing member comprises a first portion disposed within the frame, a second portion disposed within the valve seat, and a third portion disposed on an exterior of the frame.

9. The docking station of claim 8, wherein a diameter of the second portion of the sealing member is less than a diameter of the first portion and the third portion.

10. The docking station of claim 9, wherein:
the diameter of the first portion decreases in a direction of the outflow end portion along the longitudinal axis of the frame; and
the diameter of the third portion increases in a direction toward the inflow end portion along the longitudinal axis of the frame.

11. The docking station of claim 1, wherein the sealing member comprises a woven or knitted fabric, or is formed by electrospinning, and comprises polyethylene terephthalate (PET), polyester, polyamide, Nylon, polytetrafluoroethylene (PTFE), expanded polytetrafluoroethylene (ePTFE), ultra-high molecular weight polyethylene (UHMWPE), polypropylene, or any combination thereof.

12. The docking station of claim 1, wherein the docking station includes a radiopaque marker, and an inflow edge portion of the sealing member is 2 cm or less from the radiopaque marker along the longitudinal axis of the frame, 1 cm or less from the radiopaque marker along the longitudinal axis of the frame, or 5 mm or less from the radiopaque marker along the longitudinal axis of the frame.

13. The docking station of claim 1, wherein the frame comprises a plurality of openings configured to receive sutures for attachment of the sealing member to the frame.

14. The docking station of claim 13, wherein the openings are in junctions of the frame.

15. A system, comprising:
a delivery apparatus, comprising:
a first shaft comprising a delivery capsule at a distal end portion of the first shaft; and
a second shaft disposed within the first shaft and comprising a retaining member at a distal end portion of the second shaft; and
the docking station of claim 1 disposed within the delivery capsule and coupled to the retaining member.

16. A docking station, comprising:
a radially expandable and collapsible frame comprising a first plurality of struts, the frame comprising an inflow end portion and an outflow end portion, and defining a longitudinal axis;
a sealing member disposed on the outflow end portion and configured to form a seal between the docking station and a body lumen; and
a valve seat coupled to the frame and configured to receive an expandable prosthetic valve, the valve seat comprising a second plurality of struts coupled to the frame extending in a downstream direction and inwardly toward the longitudinal axis of the frame; and
wherein the frame comprises a plurality of junctions, and the junctions define openings configured to receive sutures for attachment of the sealing member to the frame.

17. The docking station of claim 16, wherein the first plurality of struts comprises:
a plurality of circumferentially-arranged longitudinal struts extending between the inflow end portion and the outflow end portion of the frame; and
a plurality of angled struts extending between adjacent longitudinal struts and defining a plurality of free apices offset circumferentially from each other around a circumference of the frame and configured to resist movement of the docking station within a body lumen.

18. The docking station of claim 17, wherein the frame further comprises a third plurality of struts extending from free apices of the angled struts at the outflow end portion of the frame, and the third plurality of struts are arranged in a circumferential arrangement radially outward of the second plurality of struts of the valve seat.

19. The docking station of claim 16, wherein free end portions of struts of the second plurality of struts define a downstream-most end of the frame of the docking station.

20. The docking station of claim 16, wherein struts of the second plurality of struts are coupled to the frame at respective frame junctions, and free end portions of the struts of the second plurality of struts are offset from the frame junctions in a downstream direction along the longitudinal axis.

21. The docking station of claim 20, wherein the struts of the second plurality of struts comprise a first portion that is angled inwardly toward the longitudinal axis of the frame and a second portion that extends in the downstream direction along the longitudinal axis of the frame.

\* \* \* \* \*